United States Patent
Berger et al.

(10) Patent No.: US 10,925,876 B2
(45) Date of Patent: *Feb. 23, 2021

(54) METHODS FOR USING TRIAZOLO-PYRAZINYL SOLUBLE GUANYLATE CYCLASE ACTIVATORS IN FIBROTIC DISORDERS

(71) Applicant: Merck Sharp & Dohme Corp., Rahway, NJ (US)

(72) Inventors: Raphaelle Berger, New York, NY (US); Guizhen Dong, Dayton, NJ (US); Subharekha Raghavan, Teaneck, NJ (US); Zhiqiang Yang, Westfield, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/301,936

(22) PCT Filed: May 12, 2017

(86) PCT No.: PCT/US2017/032310
§ 371 (c)(1),
(2) Date: Nov. 15, 2018

(87) PCT Pub. No.: WO2017/200857
PCT Pub. Date: Nov. 23, 2017

(65) Prior Publication Data
US 2019/0282579 A1   Sep. 19, 2019

Related U.S. Application Data

(60) Provisional application No. 62/338,076, filed on May 18, 2016.

(51) Int. Cl.
| | |
|---|---|
| *A61K 31/519* | (2006.01) |
| *A61K 45/06* | (2006.01) |
| *C07D 519/00* | (2006.01) |
| *C07D 235/00* | (2006.01) |
| *A61K 31/505* | (2006.01) |
| *C07D 249/16* | (2006.01) |

(52) U.S. Cl.
CPC .......... *A61K 31/519* (2013.01); *A61K 31/505* (2013.01); *A61K 45/06* (2013.01); *C07D 235/00* (2013.01); *C07D 249/16* (2013.01); *C07D 519/00* (2013.01)

(58) Field of Classification Search
CPC .... A61K 31/519; A61K 31/505; A61K 45/06; C07D 235/00; C07D 249/16; C07D 519/00
See application file for complete search history.

(56) References Cited

U.S. PATENT DOCUMENTS

| | | |
|---|---|---|
| 6,743,798 B1 | 6/2004 | Berkmann |
| 7,173,037 B2 | 2/2007 | Alonso-Alija et al. |
| 8,420,656 B2 | 4/2013 | Follmann et al. |
| 8,455,638 B2 | 6/2013 | Bittner et al. |
| 8,507,512 B2 | 8/2013 | Kim et al. |
| 8,741,910 B2 | 6/2014 | Brockunier et al. |
| 8,859,569 B2 | 10/2014 | Follmann et al. |
| 8,895,583 B2 | 11/2014 | Tan et al. |
| 9,023,849 B2 | 5/2015 | Follmann et al. |
| 9,090,610 B2 | 7/2015 | Follmann et al. |

(Continued)

FOREIGN PATENT DOCUMENTS

| | | |
|---|---|---|
| DE | 19744027 A1 | 10/1997 |
| EP | 908456 B1 | 9/1998 |

(Continued)

OTHER PUBLICATIONS

Allanore, Y., et al, "Advances in Cohort Enrichment Shape Future of Trial Design", Nature Reviews Rheumatology, 2015, pp. 72-74, vol. 11, No. 2.
Beyer, C., et al, "Stimulation of the Soluble Guanylate Cyclase (sGC) Inhibits Fibrosis by Blocking Non-Canonical TGFB Signalling", Ann Rheum Dis, 2015, pp. 1408-1416, vol. 74.
Buchwald, Stephen L., et al, "Selective Monoarylation of Acetate Esters and Aryl Methyl Ketones Using Aryl Chlorides", Organic Letters, 2009, pp. 1773-1775, vol. 11, No. 8.
Vesely, D.L., et al, "Phencyclidine Stimulates Guanylate Cyclase Activity", Biochem. Ciophys. Res. Comm., 1979, pp. 1244-1248, vol. 88.
Davies, I.W., et al..,, "Preparation of 2-Chloro-1,3 Bis(Dimethylamino)Trimethinium Hexafluorophosphate", Organic Syntheses, 2003, pp. 200-206, vol. 80.

(Continued)

*Primary Examiner* — Kortney L. Klinkel
*Assistant Examiner* — William Y Lee
(74) *Attorney, Agent, or Firm* — Eric A. Meade; John C. Todaro

(57) ABSTRACT

Provided are methods for treating or preventing a fibrotic disease selected from systemic sclerosis, cystic fibrosis, non-alcoholic steatohepatitis, Peyronie's disease, or interstitial lung disease; the method comprising administering a therapeutically effective amount of a compound of Formula (I) (wherein $R^1$, $R^2$, $R^3$, $R^4$, and $R^5$ are as herein described) or a pharmaceutically acceptable salt thereof, to a patient in need of such therapy.

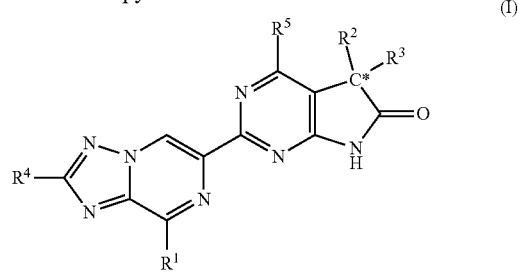

9 Claims, No Drawings

(56) References Cited

U.S. PATENT DOCUMENTS

| | | | |
|---|---|---|---|
| 9,216,978 | B2 | 12/2015 | Follmann et al. |
| 9,284,301 | B2 | 3/2016 | Schmidt et al. |
| 9,365,574 | B2 | 6/2016 | Raghavan et al. |
| 9,611,278 | B2 | 4/2017 | Han et al. |
| 9,783,552 | B2 | 10/2017 | Han et al. |
| 9,796,733 | B2 | 10/2017 | Campbell et al. |
| 9,822,130 | B2 * | 11/2017 | Berger .............. A61K 45/06 |
| 10,030,027 | B2 | 7/2018 | Berger et al. |
| 10,213,429 | B2 * | 2/2019 | Garfunkle .......... A61P 15/10 |
| 2011/0218202 | A1 | 9/2011 | Brockunier et al. |
| 2013/0072492 | A1 | 3/2013 | Raghavan et al. |
| 2014/0171434 | A1 | 6/2014 | Follmann et al. |
| 2014/0228366 | A1 | 8/2014 | Follmann et al. |
| 2014/0357637 | A1 | 12/2014 | Follmann et al. |
| 2014/0371218 | A1 | 12/2014 | Hoveyda et al. |
| 2016/0145272 | A1 | 5/2016 | Berger et al. |
| 2018/0147208 | A1 | 5/2018 | Garfunkle et al. |
| 2018/0193343 | A1 | 7/2018 | Garfunkle et al. |
| 2018/0305366 | A1 | 10/2018 | Berger et al. |

FOREIGN PATENT DOCUMENTS

| | | |
|---|---|---|
| WO | 2010065275 A1 | 6/2010 |
| WO | 2015187470 A1 | 12/2015 |
| WO | 2017200857 A1 | 11/2017 |

OTHER PUBLICATIONS

Dees, C., et al, "Stimulators of Soluble Guanylate Cyclase (sGC) Ihibit Experimental Skin Fibrosis of Different Aetiologies", Ann Rheum Dis, 2015, pp. 1621-1625, vol. 74.

Desbois, C.A., et al..,, "Systemic Sclerosis: An Update in 2016", Autoimmuity Reviews, 2016, pp. 417-426, vol. 15.

Follmann, N. et al., "The Chemistry and Biology of Soluble Guanylate Cyclase Stimulators and Activators", Angewandte Chemie-International Edition, 2013, pp. 9442-9462,vol. 52, No. 36.

Garigipati, Ravi S., "An Efficient Conversion of Nitriles To Amidines", Tetrahedron Letters, 1990, pp. 1969-1972, vol. 31, No. 14.

Hagiwara, K., et al, "An Improved Synthesis of Ethyl 2-(Dicyanomethylene)Propanoate", Synthesis, 1974, pp. 669-670, vol. 9.

Ignarro, L.J. "Regulation of Cytosolic Guanylyl Cyclase by Porphirins and Metalloporphyrins", Adv. Pharmacol. 1994, pp. 35-65, vol. 26.

International Search Report and Written Opinion for PCT/US2017/032310, dated Jul. 19, 2017, 10 pages.

Ko, F.N., et al, "YC-1 a novel activator of platelet guanylate cyclase", Blood, 1994, pp. 4226-4233, vol. 84.

Masuyama, H., et al..,, "Pressure Independent Effects of Pharmacological Stimulation of Soluble Guanylate Cyclase on Fibrosis in Pressure-Overloaded Rat Heart", Hypertension Research, 2009, pp. 597-603, vol. 32.

Pattanaik, D., et al.,, "Pathogenesis of Systemic Sclerosis", Frontiers in Immunology, 2015, pp. 1-40, vol. 6, No. 272.

Pettibone, et al., "A Structurally Novel Stimulator of Guanylate Cyclase With Long-Lasting Hypotensive Activity in the Dog", Eur J. Pharmacol., 1985, pp. 307-312, vol. 116.

Pinner, A., et al, "Umwandlung Der Nirile In Imide", Ber. Dtsch. Chem Ges., 1877, pp. 1889-1897, vol. 10.

Prokopenko, V.V., et al.,, "Synthesis and Chemical Transformations of 2-Cyclopropyl-2-Diazoacetates", Russian Chemical Bulletin, 2007, pp. 1515-1521, vol. 56, No. 8.

Sentman, R.C., et al, "Dimethyl 1,1-Dicyanoethene-2,2-dicarboxylate, A New Electrophilic Olefin", American Dancer Society, 1982, pp. 4572-4577, vol. 47.

Shen, H.C., et al, "a-Heteroarylation of Esters, Lactones, Amides, and Lactams by Nucleophilic Aroatic Substitution", Organic Letters, 2006, pp. 1447-1450, vol. 8, No. 7.

Stasch, J.P., et al.,, "Renal Effects of Soluble Guanylate Cyclase Stimulators and Activators: A Review of the Preclinical Evidence", Current Opinion in Pharmacology, 2015, pp. 95-104, vol. 21.

Vesely, D.L., et al, "B Complex Vitamins Activate Rat Guanylate Cyclase and Increase Cyclic GMP Levels", Eur. J. Clin. Invest., 1985, pp. 258-262, vol. 15.

Wu, C.C., et al., "YC-1 Inhibited Human Platelet Aggregation Through No-Independent Activation of Soluble Guyanylate Cyclase", Brit J. Pharmacol., 1995, pp. 1973-1978, vol. 116.

Yu, S.M., et al., Vasorelaxant Effect of Isoliquiritigenin, A Novel Soluble Guanylate Cyclase Activator, In Rat Aorta, Brit. J. Pharmacol., 1995, pp. 1587-1594, vol. 114.

Yu, S.M.., "Mechanism of Anti-Proliferation Caused by YC-1, An Indazole Derivative, In Cultured Rat A10 Vascular Smooth Cells", Biochem. J., 1995, pp. 787-792, vol. 306.

European Search Report, Application No. 17799909.1, dated Jan. 27, 2020, 5 pages.

GSur, Serap et al., Drugs of the future for Peyronies disease, Medical Hypotheses, 2011, 305-311, 78(2).

\* cited by examiner

METHODS FOR USING TRIAZOLO-PYRAZINYL SOLUBLE GUANYLATE CYCLASE ACTIVATORS IN FIBROTIC DISORDERS

CROSS REFERENCE TO RELATED APPLICATIONS

This application is a U.S. National Phase application under 35 U.S.C. § 371 of PCT Application No. PCT/US2017/032310, filed May 12, 2017, which claims the priority of U.S. provisional Application No. 62/338,076, filed May 18, 2016.

BACKGROUND OF THE INVENTION

Cyclic GMP (cGMP) is an important intracellular messenger which triggers a multitude of different effects via the modulation of cGMP-dependent protein kinases, phosphodiesterases and ion channels. Examples are the relaxation of smooth muscles, the inhibition of thrombocyte activation and the inhibition of the proliferation of smooth-muscle cells and of leukocyte adhesion. cGMP is produced by particulate and soluble guanylate cyclases as a response to a number of extracellular and intracellular stimuli. In the case of the particulate guanylate cyclases, stimulation is essentially effected by peptidic messengers, such as the atrial natriuretic peptide or the cerebral natriuretic peptide. The soluble guanylate cyclases ("sGC"), which are cytosolic heterodimeric heme proteins, in contrast, are essentially regulated by a family of low-molecular-weight factors which are formed enzymatically. The most important stimulant is nitrogen monoxide ("NO") or a closely related species. The function of other factors such as carbon monoxide or the hydroxyl radical is still largely unclear. The binding of NO to the heme with formation of a penta-coordinate heme-nitrosyl complex is proposed as the mechanism of the activation by NO. The associated release of the histidine which is bound in the basal state to the iron converts the enzyme into the active conformation.

Active soluble guanylate cyclases are each composed of an α and a β subunit. Several subunit subtypes have been described which differ from one another with respect to sequence, tissue-specific distribution and expression in different development stages. The subtypes $\alpha_1$ and $\beta_1$ are mainly expressed in brain and lung, while $\beta_2$ is found in particular in liver and kidney. The subtype $\alpha_2$ was shown to be present in human fetal brain. The subunits referred to as $\alpha_3$ and $\beta_3$ were isolated from human brain and are homologous to $\alpha_1$ and $\beta_1$. More recent works indicate an $\alpha_{2i}$ subunit which contains an insert in the catalytic domain. All subunits show great homologies in the region of the catalytic domain. The enzymes presumably contain one heme per heterodimer, which is bound via $\beta_1$-Cys-78 and/or $\beta_1$-His-105 and is part of the regulatory center.

Under pathologic conditions, the formation of guanylate-cyclase-activating factors can be reduced, or their degradation may be promoted owing to the increased occurrence of free radicals. The resulting reduced activation of the sGC leads, via a weakening of the respective cGMP-mediated cellular response, for example to an increase of the blood pressure, to platelet activation or to increased cell proliferation and cell adhesion. As a consequence, formation of endothelial dysfunction, atherosclerosis, hypertension, stable or unstable angina pectoris, thrombosis, myocardial infarction, strokes or erectile dysfunction results. Pharmacological stimulation of sGC offers a possibility to normalize cGMP production and therefore may make possible the treatment and/or prevention of such disorders.

Stimulating sGC function may improve microvascular dysfunction, inhibit inflammation and inhibit fibrosis, all of which are key components in the pathogenesis of systemic sclerosis (SSc). SSc is classified as either limited cutaneous (lSSc; ~60% of cases) or diffuse cutaneous (dSSc; ~40% of cases) based on the array of fibrotic changes and internal organ involvement; whereby lSSc is typically restricted to the hands and forearms with some internal organ involvement with a slower development paradigm and a better prognosis (Desbois et al., *Autoimmun. Rev.* 15(5), pp. 417-246, 2016; Allanore et al., *Nature Reviews Rheumatology* 11(2), pp. 72-74, 2015). In contrast, dSSc spreads beyond the hands and forearms and involves the trunk with significant internal organ involvement (lung, gastrointestinal tract, kidney and heart). Associated mortality is primarily due to pulmonary fibrosis (35%), primary hypertension (26%), and heart involvement (26%) (Desbois et al., *Autoimmun. Rev.* 15(5), pp. 417-246, 2016). Although the exact cause of increased fibrosis in SSc is unknown, data indicates that endothelial dysfunction contributes to the microvascular dysfunction resulting in inflammation that drives the fibrotic processes (Allanore et al., *Nature Reviews Rheumatology* 11(2), pp. 72-74, 2015; Pattanaik et al., *Frontiers in Immunology*, vol. 6, 2015). Beneficial effects with sGC stimulation on pathologic conditions involving endothelial dysfunction, inflammatory mediators and pro-fibrotic signaling have been demonstrated through pre-clinical studies and clinically through improvements in vascular tone and outcomes in patients with primary hypertension. Pre-clinical studies support the anti-fibrotic role of sGC. In a recent report, sGC stimulators inhibited the production of collagen and TGF-β1 signaling via a non-canonical pathway and inhibited the differentiation of fibroblasts to myofibroblasts (cells primarily responsible for production of newly synthesized collagen) (Beyer et al., *Ann. Rheum. Dis.*, 74(7), pp. 1408-1416, 2014). In support of these findings, in vivo studies with riociguat inhibited fibrosis in several skin sclerosis models (cGvHD mouse, TSK mouse and bleomycin mouse) (Dees et al., *Ann. Rheum. Dis.*, 74(8), pp. 1621-1625, 2015). Furthermore, sGC modulators inhibited fibrosis in target organs affected by dSSc (i.e., heart, lung, kidney and gastrointestinal tract) (Masuyama et al., *Hypertension Research* 32(7), pp. 597-603, 2009; Dees et al., *Ann. Rheum. Dis.*, 74(8), pp. 1621-1625, 2015; Stasch et al., *Current Opinion in Pharmacology* 21, pp. 95-104, 2015; Evgenov et al., *European Respiratory Journal*, 38 (Sup. 55), 2011).

For the pharmacological stimulation of the sGC, use has been made of compounds whose activity is based on an intermediate NO release, for example organic nitrates. The drawback of this treatment is the development of tolerance and a reduction of activity, and the higher dosage which is required because of this.

Various sGC stimulators which do not act via NO release were described by Vesely in a series of publications. However, the compounds, most of which are hormones, plant hormones, vitamins or natural compounds such as, for example, lizard poisons, predominantly only have weak effects on the cGMP formation in cell lysates. D. L. Vesely, *Eur. J. Clin. Invest.*, vol. 15, 1985, p. 258; D. L. Vesely, *Biochem. Biophys. Res. Comm.*, vol. 88, 1979, p. 1244. A stimulation of heme-free guanylate cyclase by protoporphyrin IX was demonstrated by Ignarro et al., *Adv. Pharmacol.*, vol. 26, 1994, p. 35. Pettibone et al., *Eur. J. Pharmacol.*, vol. 116, 1985 p. 307, described an antihypertensive action of diphenyliodonium hexafluorophosphate and attributed this to a stimulation of sGC. According to Yu et al., *Brit. J. Pharmacol*, vol. 114, 1995, p. 1587, isoliquiritigenin, which has a relaxing action on isolated rat aortas, also activates sGC. Ko et al., *Blood* vol. 84, 1994, p. 4226, Yu et al., *Biochem. J.* vol. 306, 1995, p. 787, and Wu et al., *Brit. J. Pharmacol*. vol. 116, 1995, p. 1973, demonstrated a sGC-stimulating activity of 1-benzyl-3-(5-hydroxymethyl-2-furyl)indazole and demonstrated an antiproliferative and thrombocyte-inhibiting action. Pyrazoles and fused pyrazoles which exhibit a sGC-stimulating activity are described in European Patent No. 908,456 and German Patent Application No. 19,744,027.

The compounds described herein effect a strong activation of soluble guanylate cyclase and are therefore may be suitable for the therapy and prophylaxis of disorders which are associated with a low cGMP level, such as fibrotic diseases.

SUMMARY OF THE INVENTION

The present invention relates to a method of treating or preventing a fibrotic disease selected from systemic sclerosis, cystic fibrosis, non-alcoholic steatohepatitis, Peyronie's disease, or interstitial lung disease; the method comprising administering a therapeutically effective amount of a compound having structural Formula I

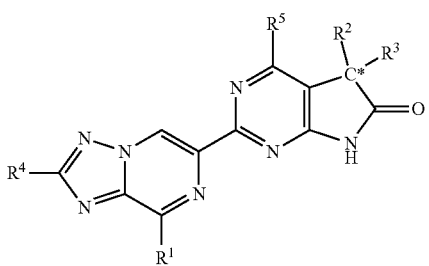

to a patient in need of such therapy. The compounds of Formula I are capable of modulating the body's production of cyclic guanosine monophosphate ("cGMP") and may be suitable for the therapy and prophylaxis of diseases which are associated with a disturbed cGMP balance, such as the fibrotic diseases described above. The invention furthermore relates to medical uses for the compounds of Formula I or pharmaceutically acceptable salts thereof, to the use of such compounds for the therapy and prophylaxis of the above mentioned diseases and for preparing pharmaceuticals for this purpose. The invention also relates to use of the compounds of Formula I or pharmaceutically acceptable salts thereof in the manufacture of a medicament for the therapy and prophylaxis of the above mentioned diseases.

DETAILED DESCRIPTION OF THE INVENTION

The present invention is directed to methods for the treatment or prevention of a fibrotic disease selected from systemic sclerosis, cystic fibrosis, non-alcoholic steatohepatitis, Peyronie's disease, or interstitial lung disease comprising administering a therapeutically effective amount of a compound having structural Formula I:

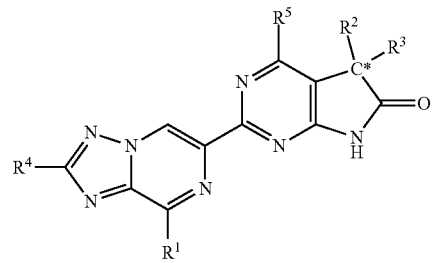

or a pharmaceutically acceptable salt thereof to a patient in need of such therapy, wherein:
C* indicates a potential chiral carbon atom;
$R^1$ is
  (1) hydrogen,
  (2) $(C_{1-6})$alkyl,
  (3) halo$(C_{1-6})$alkyl,
  (4) $(C_{1-6})$alkyl-O—,
  (5) halo$(C_{1-6})$alkyl-O—,
  (6) $(C_{1-6})$alkyl-NH—,
  (7) halo$(C_{1-6})$alkyl-NH—,
  (8) —$(C_{1-3})$alkyl-$(C_{3-7})$cycloalkyl,
  (9) —$(C_{1-3})$alkyl-aryl, wherein aryl is unsubstituted or substituted by one, two, or three $R^7$,
  (10) aryl unsubstituted or substituted by one, two, or three $R^7$,
  (11) $(C_{3-7})$cycloalkyl, or
  (12) —$(C_{1-3})$alkyl-heteroaryl wherein the heteroaryl is a 5- or 6-membered ring containing one, two, or three heteroatoms independently selected from the group consisting of N, O, and S, wherein heteroaryl is unsubstituted or substituted by one, two, or three $R^7$;
$R^2$ is
  (1) $(C_{1-3})$alkyl, or
  (2) $(C_{3-7})$cycloalkyl;
$R^3$ is
  (1) aryl unsubstituted or substituted by one, two, or three $R^6$,
  (2) five- or six-membered heteroaryl containing one, two or three heteroatoms independently selected from the group consisting of N, O and S, wherein heteroaryl is unsubstituted or substituted one, two, or three $R^6$,
  (3) $(C_{1-3})$alkyl, or
  (4) $(C_{3-7})$cycloalkyl;
$R^4$ is
  (1) hydrogen,
  (2) $(C_{1-3})$alkyl,
  (3) halo$(C_{1-3})$alkyl, or
  (4) $(C_{3-7})$cycloalkyl;
$R^5$ is
  (1) hydrogen,
  (2) hydroxy,
  (3) —N($R^{8a}$)($R^{8b}$),
  (4) —COOH,
  (5) —C(O)NH$_2$,
  (6) $(C_{1-3})$alkyl,
  (7) $(C_{3-7})$cycloalkyl, or
  (8) four- to six-membered monocyclic heterocyclyl containing 1 N hetero atom, wherein the heterocyclyl is unsubstituted or substituted by one to two $R^9$;
each $R^6$ is independently
  (1) $(C_{1-3})$alkyl,
  (2) halo$(C_{1-3})$alkyl,
  (3) $(C_{1-3})$alkoxy, (4) halo($C_{1-3}$)alkoxy,
(5) ($C_{3-7}$)cycloalkyl, unsubstituted or substituted by halo,
(6) halo,
(7) cyano,
(8) hydroxy,
(9) —$NH_2$,
(10) —($C_{1-6}$)alkyl-COOH, or
(11) —($C_{1-6}$)alkyl-COO($C_{1-4}$)alkyl;

each $R^7$ is independently
(1) ($C_{1-3}$)alkoxy,
(2) halo,
(3) hydroxy, or
(4) ($C_{1-3}$)alkyl;

$R^{8a}$ and $R^{8b}$ are independently
(1) hydrogen,
(2) ($C_{1-3}$)alkyl, or
(3) ($C_{3-7}$)cycloalkyl; and $R^9$ is
(1) ($C_{1-3}$)alkyl,
(2) halo($C_{1-3}$)alkyl, or
(3) hydroxy.

In one embodiment, the present invention is drawn to the above-described method for treating a fibrotic disease wherein
$R^3$ is
(1) aryl unsubstituted or substituted by one, two, or three $R^6$, or
(2) five- or six-membered heteroaryl containing one, two or three heteroatoms independently selected from the group consisting of N, O and S, wherein heteroaryl is unsubstituted or substituted one, two, or three $R^6$
in the compound administered to the patient.

In one embodiment, $R^1$ is hydrogen, ($C_{1-6}$)alkyl, halo ($C_{1-6}$)alkyl, ($C_{1-3}$)alkyl-aryl, wherein aryl is unsubstituted or substituted by one, two, or three $R^7$; $R^2$ is ($C_{1-3}$)alkyl or ($C_{3-7}$)cycloalkyl; $R^3$ is aryl unsubstituted or substituted by one, two, or three $R^6$, or five- or six-membered heteroaryl containing one, two, or three heteroatoms independently selected from the group consisting of N, O and S, wherein heteroaryl is unsubstituted or substituted one, two, or three $R^6$; $R^4$ is hydrogen or ($C_{1-3}$)alkyl; $R^5$ is hydrogen, —$NH_2$, hydroxy, or C(O)$NH_2$; each $R^6$ ($C_{1-3}$)alkyl, halo($C_{1-3}$)alkyl, ($C_{1-3}$)alkoxy, halo, hydroxy, ($C_{3-7}$)cycloalkyl, unsubstituted or substituted by halo or cyano; and $R^7$ is ($C_{1-3}$)alkoxy, halo, or hydroxyl in the compound or pharmaceutically acceptable salt administered to the patient.

In one embodiment, $R^1$ is hydrogen, ($C_{1-6}$)alkyl, halo ($C_{1-6}$)alkyl, or —($C_{1-3}$)alkyl-aryl, wherein aryl is unsubstituted or substituted by one, two, or three $R^7$ in the compound or pharmaceutically acceptable salt administered to the patient. In one embodiment, $R^1$ is ($C_{1-6}$)alkyl or halo($C_{1-6}$)alkyl in the compound or pharmaceutically acceptable salt administered to the patient.

In one embodiment, $R^1$ is ($C_{1-6}$)alkyl, halo($C_{1-6}$)alkyl, or —($C_{1-3}$)alkyl-aryl, wherein aryl is unsubstituted or substituted by one, two, or three $R^7$ in the compound or pharmaceutically acceptable salt administered to the patient.

In one embodiment, $R^1$ is hydrogen in the compound or pharmaceutically acceptable salt administered to the patient. In one class of this embodiment, $R^3$ is aryl unsubstituted or substituted by one, two, or three $R^6$ in the compound or pharmaceutically acceptable salt administered to the patient. In one class of this embodiment, $R^3$ is five- or six-membered heteroaryl containing one, two, or three heteroatoms independently selected from the group consisting of N, O and S, wherein heteroaryl is unsubstituted or substituted by one, two, or three $R^6$ in the compound or pharmaceutically acceptable salt administered to the patient.

In one embodiment, $R^1$ is ($C_{1-6}$)alkyl in the compound or pharmaceutically acceptable salt administered to the patient. In one class of this embodiment, $R^3$ is aryl unsubstituted or substituted by one, two, or three $R^6$ in the compound or pharmaceutically acceptable salt administered to the patient. In one class of this embodiment, $R^3$ is five- or six-membered heteroaryl containing one, two, or three heteroatoms independently selected from the group consisting of N, O and S, wherein heteroaryl is unsubstituted or substituted by one, two, or three $R^6$ in the compound or pharmaceutically acceptable salt administered to the patient.

In one embodiment, $R^1$ is halo($C_{1-6}$)alkyl in the compound or pharmaceutically acceptable salt administered to the patient. In one class of this embodiment, $R^3$ is aryl unsubstituted or substituted by one, two, or three $R^6$ in the compound or pharmaceutically acceptable salt administered to the patient. In one class of this embodiment, $R^3$ is five- or six-membered heteroaryl containing one, two, or three heteroatoms independently selected from N, O and S, wherein heteroaryl is unsubstituted or substituted by one, two, or three $R^6$ in the compound or pharmaceutically acceptable salt administered to the patient.

In one embodiment, $R^1$ is ($C_{1-6}$)alkyl-O— in the compound or pharmaceutically acceptable salt administered to the patient. In one class of this embodiment, $R^3$ is aryl unsubstituted or substituted by one, two, or three $R^6$ in the compound or pharmaceutically acceptable salt administered to the patient. In one class of this embodiment, $R^3$ is five- or six-membered heteroaryl containing one, two, or three heteroatoms independently selected from N, O and S, wherein heteroaryl is unsubstituted or substituted by one, two, or three $R^6$ in the compound or pharmaceutically acceptable salt administered to the patient.

In one embodiment, $R^1$ is halo($C_{1-6}$)alkyl-O— in the compound or pharmaceutically acceptable salt administered to the patient. In one class of this embodiment, $R^3$ is aryl unsubstituted or substituted by one, two, or three $R^6$ in the compound or pharmaceutically acceptable salt administered to the patient. In one class of this embodiment, $R^3$ is five- or six-membered heteroaryl containing one, two, or three heteroatoms independently selected from N, O and S, wherein heteroaryl is unsubstituted or substituted by one, two, or three $R^6$ in the compound or pharmaceutically acceptable salt administered to the patient.

In one embodiment, $R^1$ is ($C_{1-6}$)alkyl-NH— in the compound or pharmaceutically acceptable salt administered to the patient. In one class of this embodiment, $R^3$ is aryl unsubstituted or substituted by one, two, or three $R^6$ in the compound or pharmaceutically acceptable salt administered to the patient. In one class of this embodiment, $R^3$ is five- or six-membered heteroaryl containing one, two, or three heteroatoms independently selected from N, O and S, wherein heteroaryl is unsubstituted or substituted by one, two, or three $R^6$ in the compound or pharmaceutically acceptable salt administered to the patient.

In one embodiment, $R^1$ is halo($C_{1-6}$)alkyl-NH— in the compound or pharmaceutically acceptable salt administered to the patient. In one class of this embodiment, $R^3$ is aryl unsubstituted or substituted by one, two, or three $R^6$ in the compound or pharmaceutically acceptable salt administered to the patient. In one class of this embodiment, $R^3$ is five- or six-membered heteroaryl containing one, two, or three heteroatoms independently selected from N, O and S, wherein heteroaryl is unsubstituted or substituted by one, two, or three $R^6$ in the compound or pharmaceutically acceptable salt administered to the patient.

In one embodiment, $R^1$ is —$(C_{1-3})$alkyl-$(C_{3-7})$cycloalkyl in the compound or pharmaceutically acceptable salt administered to the patient. In one class of this embodiment, $R^3$ is aryl unsubstituted or substituted by one, two, or three $R^6$ in the compound or pharmaceutically acceptable salt administered to the patient. In one class of this embodiment, $R^3$ is five- or six-membered heteroaryl containing one, two, or three heteroatoms independently selected from N, O and S, wherein heteroaryl is unsubstituted or substituted by one, two, or three $R^6$ in the compound or pharmaceutically acceptable salt administered to the patient.

In one embodiment, $R^1$ is —$(C_{1-3})$alkyl-aryl, wherein aryl is unsubstituted or substituted by one, two, or three $R^7$ in the compound or pharmaceutically acceptable salt administered to the patient. In one class of this embodiment, $R^3$ is aryl unsubstituted or substituted by one, two, or three $R^6$ in the compound or pharmaceutically acceptable salt administered to the patient. In one class of this embodiment, $R^3$ is five- or six-membered heteroaryl containing one, two, or three heteroatoms independently selected from N, O and S, wherein heteroaryl is unsubstituted or substituted by one, two, or three $R^6$ in the compound or pharmaceutically acceptable salt administered to the patient.

In one embodiment, $R^1$ is aryl unsubstituted or substituted by one, two, or three $R^7$ in the compound or pharmaceutically acceptable salt administered to the patient. In one class of this embodiment, $R^3$ is aryl unsubstituted or substituted by one, two, or three $R^6$ in the compound or pharmaceutically acceptable salt administered to the patient. In one class of this embodiment, $R^3$ is five- or six-membered heteroaryl containing one, two, or three heteroatoms independently selected from the group consisting of N, O and S, wherein heteroaryl is unsubstituted or substituted by one, two, or three $R^6$ in the compound or pharmaceutically acceptable salt administered to the patient.

In one embodiment, $R^1$ is $(C_{3-7})$cycloalkyl in the compound or pharmaceutically acceptable salt administered to the patient. In one class of this embodiment, $R^3$ is aryl unsubstituted or substituted by one, two, or three $R^6$ in the compound or pharmaceutically acceptable salt administered to the patient. In one class of this embodiment, $R^3$ is five- or six-membered heteroaryl containing one, two, or three heteroatoms independently selected from N, O and S, wherein heteroaryl is unsubstituted or substituted by one, two, or three $R^6$ in the compound or pharmaceutically acceptable salt administered to the patient.

In one embodiment, $R^1$ is —$(C_{1-3})$alkyl-heteroaryl wherein the heteroaryl is a 5- or 6-membered ring containing one, two, or three heteroatoms independently selected from N, O, and S, wherein heteroaryl is unsubstituted or substituted by one, two, or three $R^7$ in the compound or pharmaceutically acceptable salt administered to the patient. In one class of this embodiment, $R^3$ is aryl unsubstituted or substituted by one, two, or three $R^6$ in the compound or pharmaceutically acceptable salt administered to the patient. In one class of this embodiment, $R^3$ is five- or six-membered heteroaryl containing one, two, or three heteroatoms independently selected from the group consisting of N, O and S, wherein heteroaryl is unsubstituted or substituted by one, two, or three $R^6$ in the compound or pharmaceutically acceptable salt administered to the patient.

In one embodiment, $R^1$ is hydrogen,

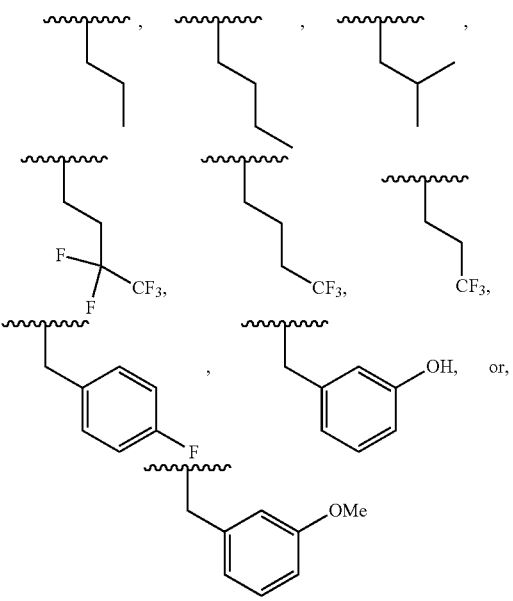

in the compound or pharmaceutically acceptable salt administered to the patient.

In one class of this embodiment, $R^2$ is methyl or cyclopropyl in the compound or pharmaceutically acceptable salt administered to the patient.

In one subclass of this class, $R^3$ is

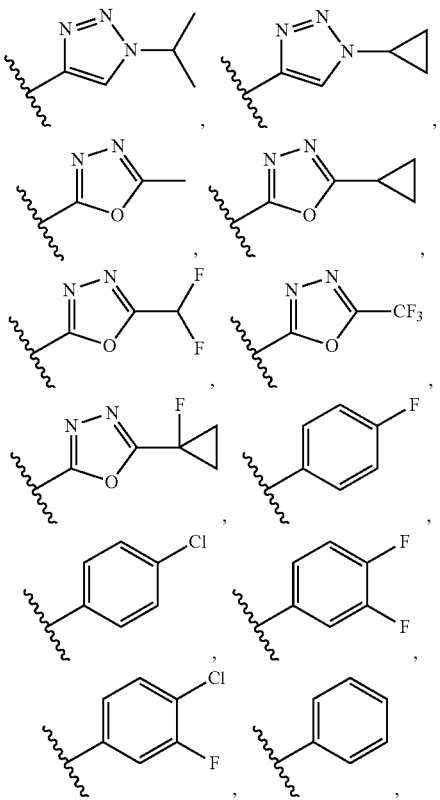

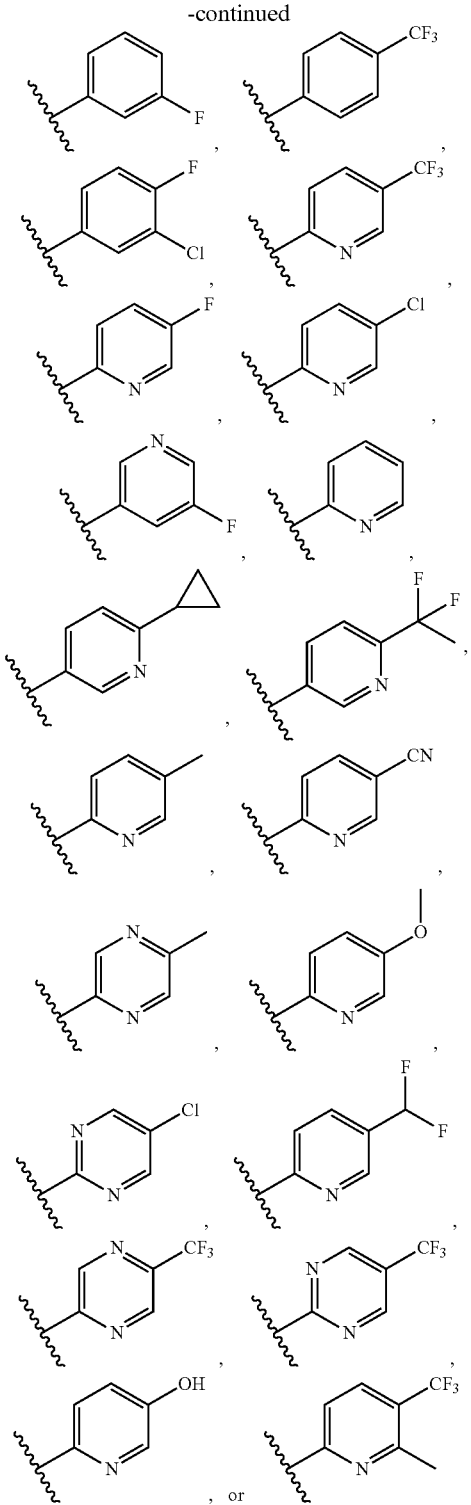

in the compound or pharmaceutically acceptable salt administered to the patient.

In one sub-subclass of this subclass, R⁵ is hydroxy or —NH₂, hydrogen, or —C(O)NH₂ in the compound or pharmaceutically acceptable salt administered to the patient.

In one sub-sub-subclass of this sub-subclass, R⁴ is hydrogen or methyl in the compound or pharmaceutically acceptable salt administered to the patient.

In one class of this embodiment, R¹ is

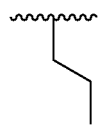

in the compound or pharmaceutically acceptable salt administered to the patient. In one class of this embodiment, R¹ is

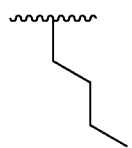 [SMILES: *CCCC]

in the compound or pharmaceutically acceptable salt administered to the patient. In one class of this embodiment, R¹ is

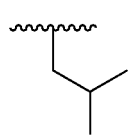

in the compound or pharmaceutically acceptable salt administered to the patient. In one class of this embodiment, R¹ is

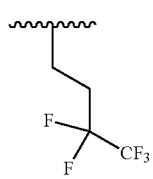

in the compound or pharmaceutically acceptable salt administered to the patient. In one class of this embodiment, R¹ is

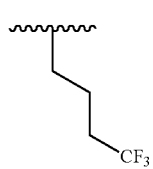

in the compound or pharmaceutically acceptable salt administered to the patient. In one class of this embodiment, R¹ is

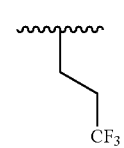 [SMILES: *CCC(F)(F)F]

in the compound or pharmaceutically acceptable salt administered to the patient. In one class of this embodiment, $R^1$ is

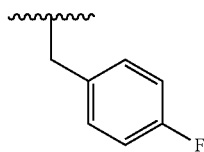 [SMILES: *Cc1ccc(F)cc1]

in the compound or pharmaceutically acceptable salt administered to the patient. In one class of this embodiment, $R^1$ is

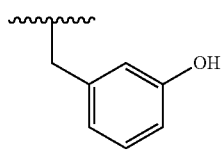 [SMILES: *Cc1cccc(O)c1]

in the compound or pharmaceutically acceptable salt administered to the patient. In one class of this embodiment, $R^1$ is

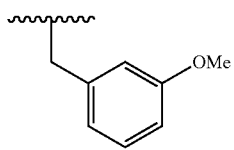 [SMILES: *Cc1cccc(OC)c1]

in the compound or pharmaceutically acceptable salt administered to the patient.

In one embodiment $R^2$ is $(C_{1-3})$alkyl in the compound or pharmaceutically acceptable salt administered to the patient. In one class of this embodiment, $R^2$ is methyl in the compound or pharmaceutically acceptable salt administered to the patient.

In one embodiment $R^2$ is $(C_{3-7})$cycloalkyl in the compound or pharmaceutically acceptable salt administered to the patient. In one class of this embodiment, $R^2$ is cyclopropyl in the compound or pharmaceutically acceptable salt administered to the patient.

In one embodiment, $R^3$ is

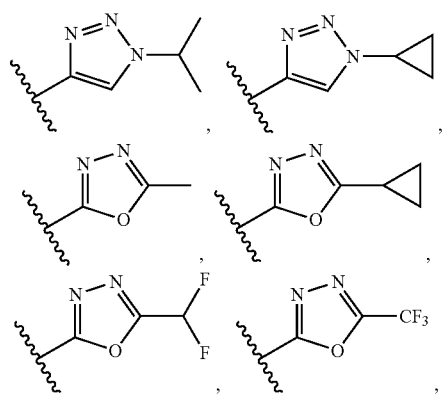

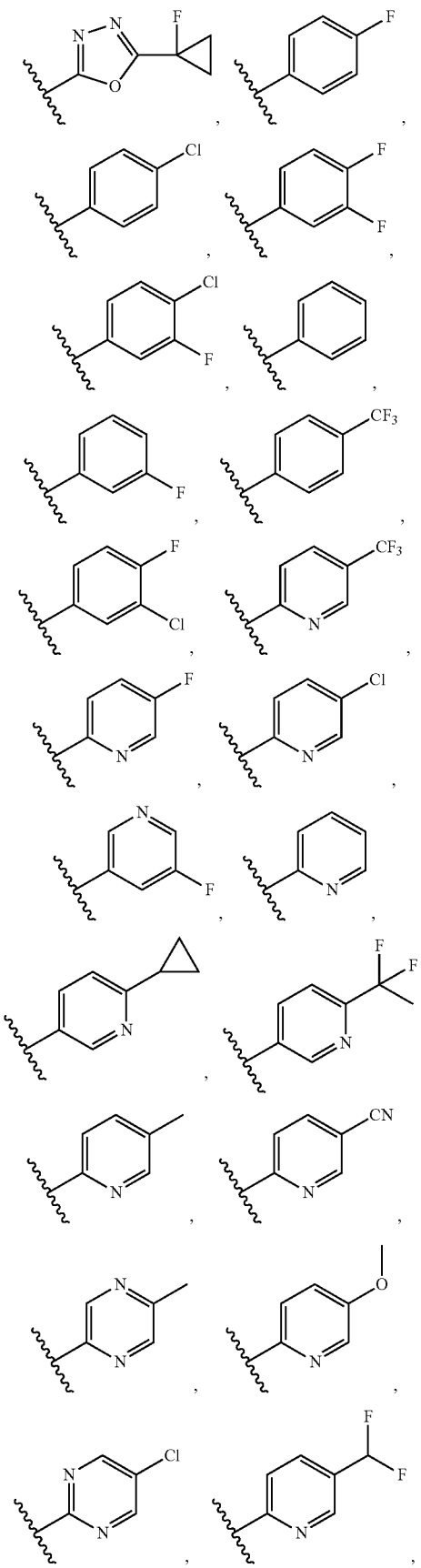

[Structures shown: pyrazine-CF3, pyrimidine-CF3, pyridine-OH, pyridine-CF3-methyl]

, or in the compound or pharmaceutically acceptable salt administered to the patient.

In one embodiment, $R^3$ is aryl unsubstituted or substituted by one, two, or three $R^6$ in the compound or pharmaceutically acceptable salt administered to the patient.

In one class of this embodiment, $R^5$ is $N(R^{8a})(R^{8b})$ in the compound or pharmaceutically acceptable salt administered to the patient.

In one subclass of this class, $R^1$ is hydrogen in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is $(C_{1-6})$alkyl in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is halo$(C_{1-6})$alkyl in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is —$(C_{1-3})$alkyl-$(C_{3-7})$cycloalkyl in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is —$(C_{1-3})$alkyl-aryl, wherein aryl is unsubstituted or substituted by one, two, or three $R^7$ in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is aryl unsubstituted or substituted by one, two, or three $R^7$ in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is $(C_{3-7})$cycloalkyl in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is —$(C_{1-3})$alkyl-heteroaryl wherein the heteroaryl is a 5- or 6-membered ring containing one, two, or three heteroatoms independently selected from N, O, and S, wherein heteroaryl is unsubstituted or substituted by one, two, or three $R^7$ in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one class of this embodiment, $R^5$ is hydroxyl in the compound or pharmaceutically acceptable salt administered to the patient.

In one subclass of this class, $R^1$ is hydrogen in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is $(C_{1-6})$alkyl in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is halo$(C_{1-6})$alkyl in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is —$(C_{1-3})$alkyl-$(C_{3-7})$cycloalkyl in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is —$(C_{1-3})$alkyl-aryl, wherein aryl is unsubstituted or substituted $R^7$ in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is aryl unsubstituted or substituted by one, two, or three $R^7$ in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is $(C_{3-7})$cycloalkyl in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is $(C_{1-3})$alkyl-heteroaryl wherein the heteroaryl is a 5- or 6-membered ring containing one, two, or three heteroatoms independently selected from N, O, and S, wherein heteroaryl is unsubstituted or substituted by one, two, or three $R^7$ in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one class of this embodiment, $R^5$ is hydrogen in the compound or pharmaceutically acceptable salt administered to the patient.

In one subclass of this class, $R^1$ is hydrogen in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is $(C_{1-6})$alkyl in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is halo$(C_{1-6})$alkyl in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is —$(C_{1-3})$alkyl-$(C_{3-7})$cycloalkyl in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is —$(C_{1-3})$alkyl-aryl, wherein aryl is unsubstituted or substituted by one, two, or three $R^7$ in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is aryl unsubstituted or substituted by one, two, or three $R^7$ in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is $(C_{3-7})$cycloalkyl in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is —$(C_{1-3})$alkyl-heteroaryl wherein the heteroaryl is a 5- or 6-membered ring containing one, two, or three heteroatoms independently selected from N, O, and S, wherein heteroaryl is unsubstituted or substituted by one, two, or three $R^7$ in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one class of this embodiment, $R^5$ is COOH or —C(O)NH$_2$ in the compound or pharmaceutically acceptable salt administered to the patient.

In one subclass of this class, $R^1$ is hydrogen in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is $(C_{1-6})$alkyl in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is halo$(C_{1-6})$alkyl in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is —$(C_{1-3})$alkyl-$(C_{3-7})$cycloalkyl in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is —$(C_{1-3})$alkyl-aryl, wherein aryl is unsubstituted or substituted by one, two, or three $R^7$ in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is aryl unsubstituted or substituted by one, two, or three $R^7$. In one sub-subclass of this subclass, $R^2$ is $(C_{1-3})$alkyl. In one sub-subclass of this subclass, $R^2$ is $(C_{3-7})$cycloalkyl.

In one subclass of this class, $R^1$ is $(C_{3-7})$cycloalkyl in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is —$(C_{1-3})$alkyl-heteroaryl wherein the heteroaryl is a 5- or 6-membered ring containing one, two, or three heteroatoms independently selected from N, O, and S, wherein heteroaryl is unsubstituted or substituted by one, two, or three $R^7$ in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one class of this embodiment, $R^5$ is $(C_{1-3})$alkyl in the compound or pharmaceutically acceptable salt administered to the patient.

In one subclass of this class, $R^1$ is hydrogen in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is $(C_{1-6})$alkyl in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is halo$(C_{1-6})$alkyl in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is —$(C_{1-3})$alkyl-$(C_{3-7})$cycloalkyl in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is —$(C_{1-3})$alkyl-aryl, wherein aryl is unsubstituted or substituted by one, two, or three $R^7$ in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is aryl unsubstituted or substituted by one, two, or three $R^7$ in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is $(C_{3-7})$cycloalkyl in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is —$(C_{1-3})$alkyl-heteroaryl wherein the heteroaryl is a 5- or 6-membered ring containing one, two, or three heteroatoms independently selected from N, O, and S, wherein heteroaryl is unsubstituted or substituted by one, two, or three $R^7$ in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one class of this embodiment, $R^5$ is $(C_{3-7})$cycloalkyl in the compound or pharmaceutically acceptable salt administered to the patient.

In one subclass of this class, $R^1$ is hydrogen in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is $(C_{1-6})$alkyl in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is halo$(C_{1-6})$alkyl in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is —$(C_{1-3})$alkyl-$(C_{3-7})$cycloalkyl in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is —$(C_{1-3})$alkyl-aryl, wherein aryl is unsubstituted or substituted by one, two, or three $R^7$ in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is aryl unsubstituted or substituted by one, two, or three $R^7$ in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is $(C_{3-7})$cycloalkyl in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is $(C_{1-3})$alkyl-heteroaryl wherein the heteroaryl is a 5- or 6-membered ring containing one, two, or three heteroatoms independently selected from the group consisting of N, O, and S, wherein heteroaryl is unsubstituted or substituted by one, two, or three $R^7$ in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one class of this embodiment, $R^5$ is four- or six-membered monocyclic heterocyclyl containing 1 N heteroatom, wherein the heterocyclyl is unsubstituted or substituted by one to two $R^9$ in the compound or pharmaceutically acceptable salt administered to the patient.

In one subclass of this class, $R^1$ is hydrogen in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is $(C_{1-6})$alkyl in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is halo$(C_{1-6})$alkyl in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is —$(C_{1-3})$alkyl-$(C_{3-7})$cycloalkyl in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is —$(C_{1-3})$alkyl-aryl, wherein aryl is unsubstituted or substituted by one, two, or three $R^7$ in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is aryl unsubstituted or substituted by one, two, or three $R^7$ in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is $(C_{3-7})$cycloalkyl in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is —$(C_{1-3})$alkyl-heteroaryl wherein the heteroaryl is a 5- or 6-membered ring containing one, two, or three heteroatoms independently selected from N, O, and S heteroatoms, wherein heteroaryl is unsubstituted or substituted by one, two, or three $R^7$ in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one embodiment, $R^3$ is phenyl unsubstituted or substituted by one, two, or three $R^6$ in the compound or pharmaceutically acceptable salt administered to the patient.

In one class of this embodiment, $R^5$ is —N($R^{8a}$)($R^{8b}$) in the compound or pharmaceutically acceptable salt administered to the patient.

In one subclass of this class, $R^1$ is hydrogen in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is $(C_{1-6})$alkyl in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is halo$(C_{1-6})$alkyl in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is —$(C_{1-3})$alkyl-$(C_{3-7})$cycloalkyl in the compound or pharmaceutically acceptable salt administered to the patient. In one sub-subclass of this subclass, $R^2$ is $(C_{1-3})$alkyl in the compound or pharmaceutically acceptable salt administered to the patient.

In one sub-subclass of this subclass, $R^2$ is $(C_{3-7})$cycloalkyl in the compound or pharmaceutically acceptable salt administered to the patient.

In one subclass of this class, $R^1$ is —$(C_{1-3})$alkyl-aryl, wherein aryl is unsubstituted or substituted by one, two, or three $R^7$ in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is aryl unsubstituted or substituted by one, two, or three $R^7$ in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is ($C_{3-7}$)cycloalkyl in the compound or pharmaceutically acceptable salt administered to the patient.

In one subclass of this class, $R^1$ is ($C_{3-7}$)cycloalkyl in the compound or pharmaceutically acceptable salt administered to the patient. In one sub-subclass of this subclass, $R^2$ is ($C_{1-3}$)alkyl in the compound or pharmaceutically acceptable salt administered to the patient. In one sub-subclass of this subclass, $R^2$ is ($C_{3-7}$)cycloalkyl in the compound or pharmaceutically acceptable salt administered to the patient.

In one subclass of this class, $R^1$ is —($C_{1-3}$)alkyl-heteroaryl wherein the heteroaryl is a 5- or 6-membered ring containing one, two, or three heteroatoms independently selected from N, O, and S heteroatoms, wherein heteroaryl is unsubstituted or substituted by one, two, or three $R^7$ in the compound or pharmaceutically acceptable salt administered to the patient. In one sub-subclass of this subclass, $R^2$ is ($C_{1-3}$)alkyl in the compound or pharmaceutically acceptable salt administered to the patient. In one sub-subclass of this subclass, $R^2$ is ($C_{3-7}$)cycloalkyl in the compound or pharmaceutically acceptable salt administered to the patient.

In one class of this embodiment, $R^5$ is hydroxy in the compound or pharmaceutically acceptable salt administered to the patient.

In one subclass of this class, $R^1$ is hydrogen in the compound or pharmaceutically acceptable salt administered to the patient. In one sub-subclass of this subclass, $R^2$ is ($C_{1-3}$)alkyl in the compound or pharmaceutically acceptable salt administered to the patient. In one sub-subclass of this subclass, $R^2$ is ($C_{3-7}$)cycloalkyl in the compound or pharmaceutically acceptable salt administered to the patient.

In one subclass of this class, $R^1$ is ($C_{1-6}$)alkyl in the compound or pharmaceutically acceptable salt administered to the patient. In one sub-subclass of this subclass, $R^2$ is ($C_{1-3}$)alkyl in the compound or pharmaceutically acceptable salt administered to the patient. In one sub-subclass of this subclass, $R^2$ is ($C_{3-7}$)cycloalkyl in the compound or pharmaceutically acceptable salt administered to the patient.

In one subclass of this class, $R^1$ is halo($C_{1-6}$)alkyl in the compound or pharmaceutically acceptable salt administered to the patient. In one sub-subclass of this subclass, $R^2$ is ($C_{1-3}$)alkyl in the compound or pharmaceutically acceptable salt administered to the patient. In one sub-subclass of this subclass, $R^2$ is ($C_{3-7}$)cycloalkyl in the compound or pharmaceutically acceptable salt administered to the patient.

In one subclass of this class, $R^1$ is —($C_{1-3}$)alkyl-($C_{3-7}$)cycloalkyl in the compound or pharmaceutically acceptable salt administered to the patient. In one sub-subclass of this subclass, $R^2$ is ($C_{1-3}$)alkyl in the compound or pharmaceutically acceptable salt administered to the patient. In one sub-subclass of this subclass, $R^2$ is ($C_{3-7}$)cycloalkyl in the compound or pharmaceutically acceptable salt administered to the patient.

In one subclass of this class, $R^1$ is —($C_{1-6}$)alkyl-aryl, wherein aryl is unsubstituted or substituted by one, two, or three $R^7$ in the compound or pharmaceutically acceptable salt administered to the patient. In one sub-subclass of this subclass, $R^2$ is ($C_{1-3}$)alkyl in the compound or pharmaceutically acceptable salt administered to the patient. In one sub-subclass of this subclass, $R^2$ is ($C_{3-7}$)cycloalkyl in the compound or pharmaceutically acceptable salt administered to the patient.

In one subclass of this class, $R^1$ is aryl unsubstituted or substituted by one, two, or three $R^7$ in the compound or pharmaceutically acceptable salt administered to the patient. In one sub-subclass of this subclass, $R^2$ is ($C_{1-3}$)alkyl in the compound or pharmaceutically acceptable salt administered to the patient. In one sub-subclass of this subclass, $R^2$ is ($C_{3-7}$)cycloalkyl in the compound or pharmaceutically acceptable salt administered to the patient.

In one subclass of this class, $R^1$ is ($C_{3-7}$)cycloalkyl in the compound or pharmaceutically acceptable salt administered to the patient. In one sub-subclass of this subclass, $R^2$ is ($C_{1-3}$)alkyl in the compound or pharmaceutically acceptable salt administered to the patient. In one sub-subclass of this subclass, $R^2$ is ($C_{3-7}$)cycloalkyl in the compound or pharmaceutically acceptable salt administered to the patient.

In one subclass of this class, $R^1$ is ($C_{1-3}$)alkyl-heteroaryl wherein the heteroaryl is a 5- or 6-membered ring containing one, two, or three heteroatoms independently selected from N, O, and S heteroatoms, wherein heteroaryl is unsubstituted or substituted by one, two, or three $R^7$ in the compound or pharmaceutically acceptable salt administered to the patient. In one sub-subclass of this subclass, $R^2$ is ($C_{1-3}$)alkyl in the compound or pharmaceutically acceptable salt administered to the patient. In one sub-subclass of this subclass, $R^2$ is ($C_{3-7}$)cycloalkyl in the compound or pharmaceutically acceptable salt administered to the patient.

In one class of this embodiment, $R^5$ is hydrogen in the compound or pharmaceutically acceptable salt administered to the patient.

In one subclass of this class, $R^1$ is hydrogen in the compound or pharmaceutically acceptable salt administered to the patient. In one sub-subclass of this subclass, $R^2$ is ($C_{1-3}$)alkyl in the compound or pharmaceutically acceptable salt administered to the patient. In one sub-subclass of this subclass, $R^2$ is ($C_{3-7}$)cycloalkyl in the compound or pharmaceutically acceptable salt administered to the patient.

In one subclass of this class, $R^1$ is ($C_{1-6}$)alkyl in the compound or pharmaceutically acceptable salt administered to the patient. In one sub-subclass of this subclass, $R^2$ is ($C_{1-3}$)alkyl in the compound or pharmaceutically acceptable salt administered to the patient. In one sub-subclass of this subclass, $R^2$ is ($C_{3-7}$)cycloalkyl in the compound or pharmaceutically acceptable salt administered to the patient.

In one subclass of this class, $R^1$ is halo($C_{1-6}$)alkyl in the compound or pharmaceutically acceptable salt administered to the patient. In one sub-subclass of this subclass, $R^2$ is ($C_{1-3}$)alkyl in the compound or pharmaceutically acceptable salt administered to the patient. In one sub-subclass of this subclass, $R^2$ is ($C_{3-7}$)cycloalkyl in the compound or pharmaceutically acceptable salt administered to the patient.

In one subclass of this class, $R^1$ is —($C_{1-3}$)alkyl-($C_{3-7}$)cycloalkyl in the compound or pharmaceutically acceptable salt administered to the patient. In one sub-subclass of this subclass, $R^2$ is ($C_{1-3}$)alkyl in the compound or pharmaceutically acceptable salt administered to the patient. In one sub-subclass of this subclass, $R^2$ is ($C_{3-7}$)cycloalkyl in the compound or pharmaceutically acceptable salt administered to the patient.

In one subclass of this class, $R^1$ is —($C_{1-3}$)alkyl-aryl, wherein aryl is unsubstituted or substituted by one, two, or three $R^7$ in the compound or pharmaceutically acceptable salt administered to the patient. In one sub-subclass of this subclass, $R^2$ is ($C_{1-3}$)alkyl in the compound or pharmaceutically acceptable salt administered to the patient. In one sub-subclass of this subclass, $R^2$ is ($C_{3-7}$)cycloalkyl in the compound or pharmaceutically acceptable salt administered to the patient.

In one subclass of this class, $R^1$ is aryl unsubstituted or substituted by one, two, or three $R^7$ in the compound or pharmaceutically acceptable salt administered to the patient. In one sub-subclass of this subclass, $R^2$ is ($C_{1-3}$)alkyl in the compound or pharmaceutically acceptable salt administered to the patient. In one sub-subclass of this subclass, $R^2$ is ($C_{3-7}$)cycloalkyl in the compound or pharmaceutically acceptable salt administered to the patient.

In one subclass of this class, $R^1$ is ($C_{3-7}$)cycloalkyl in the compound or pharmaceutically acceptable salt administered to the patient. In one sub-subclass of this subclass, $R^2$ is ($C_{1-3}$)alkyl in the compound or pharmaceutically acceptable salt administered to the patient. In one sub-subclass of this subclass, $R^2$ is ($C_{3-7}$)cycloalkyl in the compound or pharmaceutically acceptable salt administered to the patient.

In one subclass of this class, $R^1$ is —($C_{1-3}$)alkyl-heteroaryl wherein the heteroaryl is a 5- or 6-membered ring containing one, two, or three heteroatoms independently selected from the group N, O, and S, wherein heteroaryl is unsubstituted or substituted by one, two, or three $R^7$ in the compound or pharmaceutically acceptable salt administered to the patient. In one sub-subclass of this subclass, $R^2$ is ($C_{1-3}$)alkyl in the compound or pharmaceutically acceptable salt administered to the patient. In one sub-subclass of this subclass, $R^2$ is ($C_{3-7}$)cycloalkyl in the compound or pharmaceutically acceptable salt administered to the patient.

In one class of this embodiment, $R^5$ is COOH or —C(O)NH$_2$ in the compound or pharmaceutically acceptable salt administered to the patient.

In one subclass of this class, $R^1$ is hydrogen in the compound or pharmaceutically acceptable salt administered to the patient. In one sub-subclass of this subclass, $R^2$ is ($C_{1-3}$)alkyl in the compound or pharmaceutically acceptable salt administered to the patient. In one sub-subclass of this subclass, $R^2$ is ($C_{3-7}$)cycloalkyl in the compound or pharmaceutically acceptable salt administered to the patient.

In one subclass of this class, $R^1$ is ($C_{1-6}$)alkyl in the compound or pharmaceutically acceptable salt administered to the patient. In one sub-subclass of this subclass, $R^2$ is ($C_{1-3}$)alkyl in the compound or pharmaceutically acceptable salt administered to the patient. In one sub-subclass of this subclass, $R^2$ is ($C_{3-7}$)cycloalkyl in the compound or pharmaceutically acceptable salt administered to the patient.

In one subclass of this class, $R^1$ is halo($C_{1-6}$)alkyl in the compound or pharmaceutically acceptable salt administered to the patient. In one sub-subclass of this subclass, $R^2$ is ($C_{1-3}$)alkyl in the compound or pharmaceutically acceptable salt administered to the patient. In one sub-subclass of this subclass, $R^2$ is ($C_{3-7}$)cycloalkyl in the compound or pharmaceutically acceptable salt administered to the patient.

In one subclass of this class, $R^1$ is —($C_{1-3}$)alkyl-($C_{3-7}$)cycloalkyl in the compound or pharmaceutically acceptable salt administered to the patient. In one sub-subclass of this subclass, $R^2$ is ($C_{1-3}$)alkyl in the compound or pharmaceutically acceptable salt administered to the patient. In one sub-subclass of this subclass, $R^2$ is ($C_{3-7}$)cycloalkyl in the compound or pharmaceutically acceptable salt administered to the patient.

In one subclass of this class, $R^1$ is —($C_{1-3}$)alkyl-aryl, wherein aryl is unsubstituted or substituted by one, two, or three $R^7$ in the compound or pharmaceutically acceptable salt administered to the patient. In one sub-subclass of this subclass, $R^2$ is ($C_{1-3}$)alkyl in the compound or pharmaceutically acceptable salt administered to the patient. In one sub-subclass of this subclass, $R^2$ is ($C_{3-7}$)cycloalkyl in the compound or pharmaceutically acceptable salt administered to the patient.

In one subclass of this class, $R^1$ is aryl unsubstituted or substituted by one, two, or three $R^7$ in the compound or pharmaceutically acceptable salt administered to the patient. In one sub-subclass of this subclass, $R^2$ is ($C_{1-3}$)alkyl in the compound or pharmaceutically acceptable salt administered to the patient. In one sub-subclass of this subclass, $R^2$ is ($C_{3-7}$)cycloalkyl in the compound or pharmaceutically acceptable salt administered to the patient.

In one subclass of this class, $R^1$ is ($C_{3-7}$)cycloalkyl in the compound or pharmaceutically acceptable salt administered to the patient. In one sub-subclass of this subclass, $R^2$ is ($C_{1-3}$)alkyl in the compound or pharmaceutically acceptable salt administered to the patient. In one sub-subclass of this subclass, $R^2$ is ($C_{3-7}$)cycloalkyl in the compound or pharmaceutically acceptable salt administered to the patient.

In one subclass of this class, $R^1$ is —($C_{1-3}$)alkyl-heteroaryl wherein the heteroaryl is a 5- or 6-membered ring containing one, two, or three heteroatoms independently selected from the group consisting of N, O, and S, wherein heteroaryl is unsubstituted or substituted by one, two, or three $R^7$ in the compound or pharmaceutically acceptable salt administered to the patient. In one sub-subclass of this subclass, $R^2$ is ($C_{1-3}$)alkyl in the compound or pharmaceutically acceptable salt administered to the patient. In one sub-subclass of this subclass, $R^2$ is ($C_{3-7}$)cycloalkyl in the compound or pharmaceutically acceptable salt administered to the patient.

In one class of this embodiment, $R^5$ is ($C_{1-3}$)alkyl in the compound or pharmaceutically acceptable salt administered to the patient.

In one subclass of this class, $R^1$ is hydrogen in the compound or pharmaceutically acceptable salt administered to the patient. In one sub-subclass of this subclass, $R^2$ is ($C_{1-3}$)alkyl in the compound or pharmaceutically acceptable salt administered to the patient. In one sub-subclass of this subclass, $R^2$ is ($C_{3-7}$)cycloalkyl in the compound or pharmaceutically acceptable salt administered to the patient.

In one subclass of this class, $R^1$ is ($C_{1-6}$)alkyl in the compound or pharmaceutically acceptable salt administered to the patient. In one sub-subclass of this subclass, $R^2$ is ($C_{1-3}$)alkyl in the compound or pharmaceutically acceptable salt administered to the patient. In one sub-subclass of this subclass, $R^2$ is ($C_{3-7}$)cycloalkyl in the compound or pharmaceutically acceptable salt administered to the patient.

In one subclass of this class, $R^1$ is halo($C_{1-6}$)alkyl in the compound or pharmaceutically acceptable salt administered to the patient. In one sub-subclass of this subclass, $R^2$ is ($C_{1-3}$)alkyl in the compound or pharmaceutically acceptable salt administered to the patient. In one sub-subclass of this subclass, $R^2$ is ($C_{3-7}$)cycloalkyl in the compound or pharmaceutically acceptable salt administered to the patient.

In one subclass of this class, $R^1$ is —($C_{1-3}$)alkyl-($C_{3-7}$)cycloalkyl in the compound or pharmaceutically acceptable salt administered to the patient. In one sub-subclass of this subclass, $R^2$ is ($C_{1-3}$)alkyl in the compound or pharmaceutically acceptable salt administered to the patient. In one sub-subclass of this subclass, $R^2$ is ($C_{3-7}$)cycloalkyl in the compound or pharmaceutically acceptable salt administered to the patient.

In one subclass of this class, $R^1$ is —($C_{1-3}$)alkyl-aryl, wherein aryl is unsubstituted or substituted by one, two, or three $R^7$ in the compound or pharmaceutically acceptable salt administered to the patient. In one sub-subclass of this subclass, $R^2$ is ($C_{1-3}$)alkyl in the compound or pharmaceutically acceptable salt administered to the patient. In one sub-subclass of this subclass, $R^2$ is ($C_{3-7}$)cycloalkyl in the compound or pharmaceutically acceptable salt administered to the patient.

In one subclass of this class, $R^1$ is aryl unsubstituted or substituted by one, two, or three $R^7$ in the compound or pharmaceutically acceptable salt administered to the patient. In one sub-subclass of this subclass, $R^2$ is ($C_{1-3}$)alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is $(C_{3-7})$cycloalkyl in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is —$(C_{1-3})$alkyl-heteroaryl wherein the heteroaryl is a 5- or 6-membered ring containing one, two, or three heteroatoms independently selected from the group consisting of N, O, and S, wherein heteroaryl is unsubstituted or substituted by one, two, or three $R^7$ in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one class of this embodiment, $R^5$ is $(C_{3-7})$cycloalkyl in the compound or pharmaceutically acceptable salt administered to the patient.

In one subclass of this class, $R^1$ is hydrogen. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is $(C_{1-6})$alkyl in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is halo$(C_{1-6})$alkyl in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is —$(C_{1-3})$alkyl-$(C_{3-7})$cycloalkyl in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is —$(C_{1-3})$alkyl-aryl, wherein aryl is unsubstituted or substituted by one, two, or three $R^7$ in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is aryl unsubstituted or substituted by one, two, or three $R^7$ in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is $(C_{3-7})$cycloalkyl in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is —$(C_{1-3})$alkyl-heteroaryl wherein the heteroaryl is a 5- or 6-membered ring containing one, two, or three heteroatoms independently selected from the group consisting of N, O, and S, wherein heteroaryl is unsubstituted or substituted by one, two, or three $R^7$ in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one class of this embodiment, $R^5$ is four- to six-membered monocyclic heterocyclyl containing 1 N heteroatom, wherein the heterocyclyl is unsubstituted or substituted by one to two $R^9$ in the compound or pharmaceutically acceptable salt administered to the patient.

In one subclass of this class, $R^1$ is hydrogen in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is $(C_{1-6})$alkyl in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is halo$(C_{1-6})$alkyl in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is —$(C_{1-3})$alkyl-$(C_{3-7})$cycloalkyl in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is —$(C_{1-3})$alkyl-aryl, wherein aryl is unsubstituted or substituted by one, two, or three $R^7$ in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is aryl unsubstituted or substituted by one, two, or three $R^7$ in the compound or pharmaceutically acceptable salt administered to the patient.

In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is $(C_{3-7})$cycloalkyl in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is —$(C_{1-3})$alkyl-heteroaryl wherein the heteroaryl is a 5- or 6-membered ring containing one, two, or three heteroatoms independently selected from the group consisting of N, O, and S, wherein heteroaryl is unsubstituted or substituted by one, two, or three $R^7$ in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one embodiment, $R^3$ is five- or six-membered heteroaryl containing one, two, or three heteroatoms independently selected from the group consisting of N, O and S, wherein heteroaryl is unsubstituted or substituted by one, two, or three $R^6$ in the or pharmaceutically acceptable salt administered to the patient.

In one class of this embodiment, $R^5$ is —$N(R^{8a})(R^{8b})$ in the compound or pharmaceutically acceptable salt administered to the patient.

In one subclass of this class, $R^1$ is hydrogen in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is $(C_{1-6})$alkyl in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is halo$(C_{1-6})$alkyl in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is —$(C_{1-3})$alkyl-$(C_{3-7})$cycloalkyl in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is —$(C_{1-3})$alkyl-aryl, wherein aryl is unsubstituted or substituted by one, two, or three $R^7$ in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is aryl unsubstituted or substituted by one, two, or three $R^7$ in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is $(C_{3-7})$cycloalkyl in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is —$(C_{1-3})$alkyl-heteroaryl wherein the heteroaryl is a 5- or 6-membered ring containing one, two, or three heteroatoms independently selected from the group consisting of N, O, and S, wherein heteroaryl is unsubstituted or substituted by one, two, or three $R^7$ in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one class of this embodiment, $R^5$ is hydroxy in the compound or pharmaceutically acceptable salt administered to the patient.

In one subclass of this class, $R^1$ is hydrogen in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is $(C_{1-6})$alkyl in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is halo$(C_{1-6})$alkyl in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is —$(C_{1-3})$alkyl-$(C_{3-7})$cycloalkyl in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is $(C_{1-3})$alkyl-aryl, wherein aryl is unsubstituted or substituted by one, two, or three $R^7$ in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is aryl unsubstituted or substituted by one, two, or three $R^7$ in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is $(C_{3-7})$cycloalkyl in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is —$(C_{1-3})$alkyl-heteroaryl wherein the heteroaryl is a 5- or 6-membered ring containing one, two, or three heteroatoms independently selected from the group consisting of N, O, and S, wherein heteroaryl is unsubstituted or substituted by one, two, or three $R^7$ in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one class of this embodiment, $R^5$ is hydrogen in the compound or pharmaceutically acceptable salt administered to the patient.

In one subclass of this class, $R^1$ is hydrogen in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is $(C_{1-6})$alkyl in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is halo$(C_{1-6})$alkyl in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is —$(C_{1-3})$alkyl-$(C_{3-7})$cycloalkyl in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is —$(C_{1-3})$alkyl-aryl, wherein aryl is unsubstituted or substituted by one, two, or three $R^7$ in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is —$(C_{1-3})$alkyl-heteroaryl wherein the heteroaryl is a 5- or 6-membered ring containing one, two, or three heteroatoms independently selected from the group consisting of N, O, and S, wherein heteroaryl is unsubstituted or substituted by one, two, or three $R^7$ in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one class of this embodiment, $R^5$ is COOH or —C(O)NH$_2$ in the compound or pharmaceutically acceptable salt administered to the patient.

In one subclass of this class, $R^1$ is hydrogen in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is $(C_{1-6})$alkyl in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is halo$(C_{1-6})$alkyl in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is —$(C_{1-3})$alkyl-$(C_{3-7})$cycloalkyl in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is —$(C_{1-3})$alkyl-aryl, wherein aryl is unsubstituted or substituted by one, two, or three $R^7$ in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is aryl unsubstituted or substituted by one, two, or three $R^7$ in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is $(C_{3-7})$cycloalkyl in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is —$(C_{1-3})$alkyl-heteroaryl wherein the heteroaryl is a 5- or 6-membered ring containing one, two, or three heteroatoms independently selected from the group consisting of N, O, and S, wherein heteroaryl is unsubstituted or substituted by one, two, or three $R^7$ in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one class of this embodiment, $R^5$ is $(C_{1-3})$alkyl in the compound or pharmaceutically acceptable salt administered to the patient.

In one subclass of this class, $R^1$ is hydrogen in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is $(C_{1-6})$alkyl in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is halo$(C_{1-6})$alkyl in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is —$(C_{1-3})$alkyl-$(C_{3-7})$cycloalkyl in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is —$(C_{1-3})$alkyl-aryl, wherein aryl is unsubstituted or substituted by one, two, or three $R^7$ in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is aryl unsubstituted or substituted by one, two, or three $R^7$ in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is $(C_{3-7})$cycloalkyl in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is —$(C_{1-3})$alkyl-heteroaryl wherein the heteroaryl is a 5- or 6-membered ring containing one, two, or three heteroatoms independently selected from the group consisting of N, O, and S, wherein heteroaryl is unsubstituted or substituted by one, two, or three $R^7$ in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one class of this embodiment, $R^5$ is $(C_{3-7})$cycloalkyl in the compound or pharmaceutically acceptable salt administered to the patient.

In one subclass of this class, $R^1$ is hydrogen in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is $(C_{1-6})$alkyl in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is halo$(C_{1-6})$alkyl in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3-7})$cycloalkyl in the compound or pharmaceutically acceptable salt administered to the patient.

In one subclass of this class, $R^1$ is —$(C_{1-3})$alkyl-$(C_{3-7})$cycloalkyl in the compound or pharmaceutically acceptable salt administered to the patient. In one sub-subclass of this subclass, $R^2$ is $(C_{1-3})$alkyl in the compound or pharmaceutically acceptable salt administered to the patient. In one sub-subclass of this subclass, $R^2$ is $(C_{3\text{-}7})$cycloalkyl in the compound or pharmaceutically acceptable salt administered to the patient.

In one subclass of this class, $R^1$ is —$(C_{1\text{-}3})$alkyl-aryl, wherein aryl is unsubstituted or substituted by one, two, or three $R^7$ in the compound or pharmaceutically acceptable salt administered to the patient. In one sub-subclass of this subclass, $R^2$ is $(C_{1\text{-}3})$alkyl in the compound or pharmaceutically acceptable salt administered to the patient. In one sub-subclass of this subclass, $R^2$ is $(C_{3\text{-}7})$cycloalkyl in the compound or pharmaceutically acceptable salt administered to the patient.

In one subclass of this class, $R^1$ is aryl unsubstituted or substituted by one, two, or three $R^7$ in the compound or pharmaceutically acceptable salt administered to the patient. In one sub-subclass of this subclass, $R^2$ is $(C_{1\text{-}3})$alkyl in the compound or pharmaceutically acceptable salt administered to the patient. In one sub-subclass of this subclass, $R^2$ is $(C_{3\text{-}7})$cycloalkyl in the compound or pharmaceutically acceptable salt administered to the patient.

In one subclass of this class, $R^1$ is $(C_{3\text{-}7})$cycloalkyl in the compound or pharmaceutically acceptable salt administered to the patient. In one sub-subclass of this subclass, $R^2$ is $(C_{1\text{-}3})$alkyl in the compound or pharmaceutically acceptable salt administered to the patient. In one sub-subclass of this subclass, $R^2$ is $(C_{3\text{-}7})$cycloalkyl in the compound or pharmaceutically acceptable salt administered to the patient.

In one subclass of this class, $R^1$ is $(C_{1\text{-}3})$alkyl-heteroaryl wherein the heteroaryl is a 5- or 6-membered ring containing one, two, or three heteroatoms independently selected from the group consisting of N, O, and S, wherein heteroaryl is unsubstituted or substituted by one, two, or three $R^7$ in the compound or pharmaceutically acceptable salt administered to the patient. In one sub-subclass of this subclass, $R^2$ is $(C_{1\text{-}3})$alkyl in the compound or pharmaceutically acceptable salt administered to the patient. In one sub-subclass of this subclass, $R^2$ is $(C_{3\text{-}7})$cycloalkyl in the compound or pharmaceutically acceptable salt administered to the patient.

In one embodiment, $R^4$ is $(C_{1\text{-}3})$alkyl in the compound or pharmaceutically acceptable salt administered to the patient. In one class of this embodiment, $R^4$ is methyl in the compound or pharmaceutically acceptable salt administered to the patient. In one embodiment, $R^4$ is halo$(C_{1\text{-}3})$alkyl in the compound or pharmaceutically acceptable salt administered to the patient. In one embodiment, $R^4$ is hydrogen in the compound or pharmaceutically acceptable salt administered to the patient. In one embodiment, $R^4$ is $(C_{3\text{-}7})$cycloalkyl in the compound or pharmaceutically acceptable salt administered to the patient.

In one embodiment, $R^5$ is —$N(R^{8a})(R^{8b})$ in the compound or pharmaceutically acceptable salt administered to the patient.

In one class of this embodiment, $R^2$ is $(C_{1\text{-}3})$alkyl in the compound or pharmaceutically acceptable salt administered to the patient. In one subclass of this class, $R^4$ is $(C_{1\text{-}3})$alkyl in the compound or pharmaceutically acceptable salt administered to the patient. In one subclass of this class, $R^4$ is hydrogen in the compound or pharmaceutically acceptable salt administered to the patient. In one subclass of this class, $R^4$ is $(C_{3\text{-}7})$cycloalkyl in the compound or pharmaceutically acceptable salt administered to the patient.

In one class of this embodiment, $R^2$ is $(C_{3\text{-}7})$cycloalkyl in the compound or pharmaceutically acceptable salt administered to the patient. In one subclass of this class, $R^4$ is $(C_{1\text{-}3})$alkyl in the compound or pharmaceutically acceptable salt administered to the patient. In one subclass of this class, $R^4$ is hydrogen in the compound or pharmaceutically acceptable salt administered to the patient. In one subclass of this class, $R^4$ is $(C_{3\text{-}7})$cycloalkyl in the compound or pharmaceutically acceptable salt administered to the patient.

In one embodiment, $R^5$ is hydroxyl in the compound or pharmaceutically acceptable salt administered to the patient.

In one class of this embodiment, $R^2$ is $(C_{1\text{-}3})$alkyl in the compound or pharmaceutically acceptable salt administered to the patient. In one subclass of this class, $R^4$ is $(C_{1\text{-}3})$alkyl in the compound or pharmaceutically acceptable salt administered to the patient. In one subclass of this class, $R^4$ is hydrogen in the compound or pharmaceutically acceptable salt administered to the patient. In one subclass of this class, $R^4$ is $(C_{3\text{-}7})$cycloalkyl in the compound or pharmaceutically acceptable salt administered to the patient.

In one class of this embodiment, $R^2$ is $(C_{3\text{-}7})$cycloalkyl in the compound or pharmaceutically acceptable salt administered to the patient. In one subclass of this class, $R^4$ is $(C_{1\text{-}3})$alkyl in the compound or pharmaceutically acceptable salt administered to the patient. In one subclass of this class, $R^4$ is hydrogen in the compound or pharmaceutically acceptable salt administered to the patient. In one subclass of this class, $R^4$ is $(C_{3\text{-}7})$cycloalkyl in the compound or pharmaceutically acceptable salt administered to the patient.

In one embodiment, $R^5$ is hydrogen in the compound administered to the patient in the compound or pharmaceutically acceptable salt administered to the patient.

In one class of this embodiment, $R^2$ is $(C_{1\text{-}3})$alkyl in the compound or pharmaceutically acceptable salt administered to the patient. In one subclass of this class, $R^4$ is $(C_{1\text{-}3})$alkyl in the compound or pharmaceutically acceptable salt administered to the patient. In one subclass of this class, $R^4$ is hydrogen in the compound or pharmaceutically acceptable salt administered to the patient. In one subclass of this class, $R^4$ is $(C_{3\text{-}7})$cycloalkyl in the compound or pharmaceutically acceptable salt administered to the patient.

In one class of this embodiment, $R^2$ is $(C_{3\text{-}7})$cycloalkyl in the compound or pharmaceutically acceptable salt administered to the patient. In one subclass of this class, $R^4$ is $(C_{1\text{-}3})$alkyl in the compound or pharmaceutically acceptable salt administered to the patient. In one subclass of this class, $R^4$ is hydrogen in the compound or pharmaceutically acceptable salt administered to the patient. In one subclass of this class, $R^4$ is $(C_{3\text{-}7})$cycloalkyl in the compound or pharmaceutically acceptable salt administered to the patient.

In one embodiment, $R^5$ is COOH or —$C(O)NH_2$ in the compound or pharmaceutically acceptable salt administered to the patient.

In one class of this embodiment, $R^2$ is $(C_{1\text{-}3})$alkyl in the compound or pharmaceutically acceptable salt administered to the patient. In one subclass of this class, $R^4$ is $(C_{1\text{-}3})$alkyl in the compound or pharmaceutically acceptable salt administered to the patient. In one subclass of this class, $R^4$ is hydrogen in the compound or pharmaceutically acceptable salt administered to the patient. In one subclass of this class, $R^4$ is $(C_{3\text{-}7})$cycloalkyl in the compound or pharmaceutically acceptable salt administered to the patient.

In one embodiment, $R^5$ is $(C_{1\text{-}3})$alkyl in the compound or pharmaceutically acceptable salt administered to the patient.

In one class of this embodiment, $R^2$ is $(C_{1\text{-}3})$alkyl in the compound or pharmaceutically acceptable salt administered to the patient. In one subclass of this class, $R^4$ is $(C_{1\text{-}3})$alkyl in the compound or pharmaceutically acceptable salt administered to the patient. In one subclass of this class, $R^4$ is hydrogen in the compound or pharmaceutically acceptable salt administered to the patient. In one subclass of this class, $R^4$ is $(C_{3\text{-}7})$cycloalkyl in the compound or pharmaceutically acceptable salt administered to the patient.

In one class of this embodiment, $R^2$ is $(C_{3-7})$cycloalkyl in the compound or pharmaceutically acceptable salt administered to the patient. In one subclass of this class, $R^4$ is $(C_{1-3})$alkyl in the compound or pharmaceutically acceptable salt administered to the patient. In one subclass of this class, $R^4$ is hydrogen in the compound or pharmaceutically acceptable salt administered to the patient. In one subclass of this class, $R^4$ is $(C_{3-7})$cycloalkyl in the compound or pharmaceutically acceptable salt administered to the patient.

In one embodiment, $R^5$ is $(C_{3-7})$cycloalkyl in the compound or pharmaceutically acceptable salt administered to the patient.

In one class of this embodiment, $R^2$ is $(C_{1-3})$alkyl in the compound or pharmaceutically acceptable salt administered to the patient. In one subclass of this class, $R^4$ is $(C_{1-3})$alkyl in the compound or pharmaceutically acceptable salt administered to the patient. In one subclass of this class, $R^4$ is hydrogen in the compound or pharmaceutically acceptable salt administered to the patient. In one subclass of this class, $R^4$ is $(C_{3-7})$cycloalkyl in the compound or pharmaceutically acceptable salt administered to the patient.

In one class of this embodiment, $R^2$ is $(C_{3-7})$cycloalkyl in the compound or pharmaceutically acceptable salt administered to the patient. In one subclass of this class, $R^4$ is $(C_{1-3})$alkyl in the compound or pharmaceutically acceptable salt administered to the patient. In one subclass of this class, $R^4$ is hydrogen in the compound or pharmaceutically acceptable salt administered to the patient. In one subclass of this class, $R^4$ is $(C_{3-7})$cycloalkyl in the compound or pharmaceutically acceptable salt administered to the patient.

In one embodiment, $R^5$ is four- to six-membered monocyclic heterocyclyl containing 1 N heteroatom, wherein the heterocyclyl is unsubstituted or substituted by one to two $R^9$ in the compound or pharmaceutically acceptable salt administered to the patient.

In one class of this embodiment, $R^2$ is $(C_{1-3})$alkyl in the compound or pharmaceutically acceptable salt administered to the patient. In one subclass of this class, $R^4$ is $(C_{1-3})$alkyl in the compound or pharmaceutically acceptable salt administered to the patient. In one subclass of this class, $R^4$ is hydrogen in the compound or pharmaceutically acceptable salt administered to the patient. In one subclass of this class, $R^4$ is $(C_{3-7})$cycloalkyl in the compound or pharmaceutically acceptable salt administered to the patient.

In one class of this embodiment, $R^2$ is $(C_{3-7})$cycloalkyl in the compound or pharmaceutically acceptable salt administered to the patient. In one subclass of this class, $R^4$ is $(C_{1-3})$alkyl in the compound or pharmaceutically acceptable salt administered to the patient. In one subclass of this class, $R^4$ is hydrogen in the compound or pharmaceutically acceptable salt administered to the patient. In one subclass of this class, $R^4$ is $(C_{3-7})$cycloalkyl in the compound or pharmaceutically acceptable salt administered to the patient.

In one embodiment, $R^6$ is chloro, fluoro, hydroxy, trifluoromethyl, difluoromethyl, 1,1-difluoroethyl, cyano, methyl, isopropyl, methoxy, cyclopropyl, or fluoro-cyclopropyl in the compound or pharmaceutically acceptable salt administered to the patient.

In one embodiment, $R^7$ is fluoro, hydroxy, or methoxy in the compound or pharmaceutically acceptable salt administered to the patient. In one embodiment, $R^7$ is halo in the compound or pharmaceutically acceptable salt administered to the patient. In one class of this embodiment, $R^7$ is fluoro in the compound or pharmaceutically acceptable salt administered to the patient. In one embodiment, $R^7$ is hydroxy in the compound or pharmaceutically acceptable salt administered to the patient. In one embodiment, $R^7$ is $(C_{1-3})$alkoxy in the compound or pharmaceutically acceptable salt administered to the patient. In one class of this embodiment, $R^7$ is methoxy in the compound or pharmaceutically acceptable salt administered to the patient.

In one embodiment, $R^3$ is phenyl, pyridinyl, triazolyl, pyrazinyl, pyrimidinyl, or oxadiazolyl, each unsubstituted or substituted by one, two, or three $R^6$ in the compound or pharmaceutically acceptable salt administered to the patient.

In one class of this embodiment, $R^2$ is methyl in the compound or pharmaceutically acceptable salt administered to the patient.

In one subclass of this class, $R^5$ is hydroxy or —$NH_2$, hydrogen, or —$C(O)NH_2$ in the compound or pharmaceutically acceptable salt administered to the patient. In one subclass of this class, $R^5$ is hydroxy or —$NH_2$ in the compound or pharmaceutically acceptable salt administered to the patient. In one subclass of this class, $R^5$ is hydroxy in the compound or pharmaceutically acceptable salt administered to the patient. In one subclass of this class, $R^5$ is —$NH_2$ in the compound or pharmaceutically acceptable salt administered to the patient. In one subclass of this class, $R^5$ is hydrogen in the compound or pharmaceutically acceptable salt administered to the patient. In one subclass of this class, $R^5$ is —$C(O)NH_2$ in the compound or pharmaceutically acceptable salt administered to the patient.

In one class of this embodiment, $R^2$ is cyclopropyl in the compound or pharmaceutically acceptable salt administered to the patient.

In one subclass of this class, $R^5$ is hydroxy or —$NH_2$, hydrogen, or —$C(O)NH_2$ in the compound or pharmaceutically acceptable salt administered to the patient. In one subclass of this class, $R^5$ is hydroxy or —$NH_2$ in the compound or pharmaceutically acceptable salt administered to the patient. In one subclass of this class, $R^5$ is hydroxy in the compound or pharmaceutically acceptable salt administered to the patient. In one subclass of this class, $R^5$ is —$NH_2$ in the compound or pharmaceutically acceptable salt administered to the patient. In one subclass of this class, $R^5$ is hydrogen in the compound or pharmaceutically acceptable salt administered to the patient. In one subclass of this class, $R^5$ is —$C(O)NH_2$ in the compound or pharmaceutically acceptable salt administered to the patient.

In one embodiment, $R^3$ is phenyl unsubstituted or substituted by one, two, or three $R^6$ in the compound or pharmaceutically acceptable salt administered to the patient.

In one class of this embodiment, $R^2$ is methyl in the compound or pharmaceutically acceptable salt administered to the patient.

In one subclass of this class, $R^5$ is hydroxy or —$NH_2$, hydrogen, or —$C(O)NH_2$ in the compound or pharmaceutically acceptable salt administered to the patient. In one subclass of this class, $R^5$ is hydroxy or —$NH_2$ in the compound or pharmaceutically acceptable salt administered to the patient. In one subclass of this class, $R^5$ is hydroxy in the compound or pharmaceutically acceptable salt administered to the patient. In one subclass of this class, $R^5$ is —$NH_2$ in the compound or pharmaceutically acceptable salt administered to the patient. In one subclass of this class, $R^5$ is hydrogen in the compound or pharmaceutically acceptable salt administered to the patient. In one subclass of this class, $R^5$ is —$C(O)NH_2$ in the compound or pharmaceutically acceptable salt administered to the patient.

In one class of this embodiment, $R^2$ is cyclopropyl in the compound or pharmaceutically acceptable salt administered to the patient.

In one subclass of this class, $R^5$ is hydroxy or —$NH_2$, hydrogen, or —$C(O)NH_2$ in the compound or pharmaceutically acceptable salt administered to the patient. In one subclass of this class, $R^5$ is hydroxy or —$NH_2$ in the compound or pharmaceutically acceptable salt administered to the patient. In one subclass of this class, $R^5$ is hydroxy in the compound or pharmaceutically acceptable salt administered to the patient. In one subclass of this class, $R^5$ is —$NH_2$ in the compound or pharmaceutically acceptable salt administered to the patient. In one subclass of this class, $R^5$ is hydrogen in the compound or pharmaceutically acceptable salt administered to the patient. In one subclass of this class, $R^5$ is —$C(O)NH_2$ in the compound or pharmaceutically acceptable salt administered to the patient.

In one embodiment, $R^3$ is pyridinyl unsubstituted or substituted by one, two, or three $R^6$ in the compound or pharmaceutically acceptable salt thereof administered to the patient.

In one class of this embodiment, $R^2$ is methyl in the compound or pharmaceutically acceptable salt administered to the patient.

In one subclass of this class, $R^5$ is hydroxy or —$NH_2$, hydrogen, or —$C(O)NH_2$ in the compound or pharmaceutically acceptable salt administered to the patient. In one subclass of this class, $R^5$ is hydroxy or —$NH_2$ in the compound or pharmaceutically acceptable salt administered to the patient. In one subclass of this class, $R^5$ is hydroxy in the compound or pharmaceutically acceptable salt administered to the patient. In one subclass of this class, $R^5$ is —$NH_2$ in the compound or pharmaceutically acceptable salt administered to the patient. In one subclass of this class, $R^5$ is hydrogen in the compound or pharmaceutically acceptable salt administered to the patient. In one subclass of this class, $R^5$ is —$C(O)NH_2$ in the compound or pharmaceutically acceptable salt administered to the patient.

In one class of this embodiment, $R^2$ is cyclopropyl in the compound or pharmaceutically acceptable salt administered to the patient.

In one subclass of this class, $R^5$ is hydroxy or —$NH_2$, hydrogen, or —$C(O)NH_2$ in the compound or pharmaceutically acceptable salt administered to the patient. In one subclass of this class, $R^5$ is hydroxy or —$NH_2$ in the compound or pharmaceutically acceptable salt administered to the patient. In one subclass of this class, $R^5$ is hydroxy in the compound or pharmaceutically acceptable salt administered to the patient. In one subclass of this class, $R^5$ is —$NH_2$ in the compound or pharmaceutically acceptable salt administered to the patient. In one subclass of this class, $R^5$ is hydrogen in the compound or pharmaceutically acceptable salt administered to the patient. In one subclass of this class, $R^5$ is —$C(O)NH_2$ in the compound or pharmaceutically acceptable salt administered to the patient.

In one embodiment, $R^3$ is triazolyl unsubstituted or substituted by one, two, or three $R^6$ in the compound administered to the patient in the compound or pharmaceutically acceptable salt administered to the patient.

In one class of this embodiment, $R^2$ is methyl in the compound or pharmaceutically acceptable salt administered to the patient.

In one subclass of this class, $R^5$ is hydroxy or —$NH_2$, hydrogen, or —$C(O)NH_2$ in the compound or pharmaceutically acceptable salt administered to the patient. In one subclass of this class, $R^5$ is hydroxy or —$NH_2$ in the compound or pharmaceutically acceptable salt administered to the patient. In one subclass of this class, $R^5$ is hydroxy in the compound or pharmaceutically acceptable salt administered to the patient. In one subclass of this class, $R^5$ is —$NH_2$ in the compound or pharmaceutically acceptable salt administered to the patient. In one subclass of this class, $R^5$ is hydrogen in the compound or pharmaceutically acceptable salt administered to the patient. In one subclass of this class, $R^5$ is —$C(O)NH_2$ in the compound or pharmaceutically acceptable salt administered to the patient.

In one class of this embodiment, $R^2$ is cyclopropyl in the compound or pharmaceutically acceptable salt administered to the patient.

In one subclass of this class, $R^5$ is hydroxy or —$NH_2$, hydrogen, or —$C(O)NH_2$ in the compound or pharmaceutically acceptable salt administered to the patient. In one subclass of this class, $R^5$ is hydroxy or —$NH_2$ in the compound or pharmaceutically acceptable salt administered to the patient. In one subclass of this class, $R^5$ is hydroxy in the compound or pharmaceutically acceptable salt administered to the patient. In one subclass of this class, $R^5$ is —$NH_2$ in the compound or pharmaceutically acceptable salt administered to the patient. In one subclass of this class, $R^5$ is hydrogen in the compound or pharmaceutically acceptable salt administered to the patient. In one subclass of this class, $R^5$ is —$C(O)NH_2$ in the compound or pharmaceutically acceptable salt administered to the patient.

In one embodiment, $R^3$ is pyrazinyl unsubstituted or substituted by one, two, or three $R^6$ in the compound or pharmaceutically acceptable salt administered to the patient.

In one class of this embodiment, $R^2$ is methyl in the compound or pharmaceutically acceptable salt administered to the patient.

In one subclass of this class, $R^5$ is hydroxy or —$NH_2$, hydrogen, or —$C(O)NH_2$ in the compound or pharmaceutically acceptable salt administered to the patient. In one subclass of this class, $R^5$ is hydroxy or —$NH_2$ in the compound or pharmaceutically acceptable salt administered to the patient. In one subclass of this class, $R^5$ is hydroxy in the compound or pharmaceutically acceptable salt administered to the patient. In one subclass of this class, $R^5$ is —$NH_2$ in the compound or pharmaceutically acceptable salt administered to the patient. In one subclass of this class, $R^5$ is hydrogen in the compound or pharmaceutically acceptable salt administered to the patient. In one subclass of this class, $R^5$ is —$C(O)NH_2$ in the compound or pharmaceutically acceptable salt administered to the patient.

In one class of this embodiment, $R^2$ is cyclopropyl in the compound or pharmaceutically acceptable salt administered to the patient.

In one subclass of this class, $R^5$ is hydroxy or —$NH_2$, hydrogen, or —$C(O)NH_2$ in the compound or pharmaceutically acceptable salt administered to the patient. In one subclass of this class, $R^5$ is hydroxy or —$NH_2$ in the compound or pharmaceutically acceptable salt administered to the patient. In one subclass of this class, $R^5$ is hydroxy in the compound or pharmaceutically acceptable salt administered to the patient. In one subclass of this class, $R^5$ is —$NH_2$ in the compound or pharmaceutically acceptable salt administered to the patient. In one subclass of this class, $R^5$ is hydrogen in the compound or pharmaceutically acceptable salt administered to the patient. In one subclass of this class, $R^5$ is —$C(O)NH_2$ in the compound or pharmaceutically acceptable salt administered to the patient.

In one embodiment, $R^3$ is pyrimidinyl unsubstituted or substituted by one, two, or three $R^6$ in the compound or pharmaceutically acceptable salt administered to the patient.

In one class of this embodiment, $R^2$ is methyl in the compound or pharmaceutically acceptable salt administered to the patient.

In one subclass of this class, $R^5$ is hydroxy or —$NH_2$, hydrogen, or —$C(O)NH_2$ in the compound or pharmaceutically acceptable salt administered to the patient. In one subclass of this class, $R^5$ is hydroxy or —$NH_2$ in the compound or pharmaceutically acceptable salt administered to the patient. In one subclass of this class, $R^5$ is hydroxy in the compound or pharmaceutically acceptable salt administered to the patient. In one subclass of this class, $R^5$ is —$NH_2$ in the compound or pharmaceutically acceptable salt administered to the patient. In one subclass of this class, $R^5$ is hydrogen in the compound or pharmaceutically acceptable salt administered to the patient. In one subclass of this class, $R^5$ is —$C(O)NH_2$ in the compound or pharmaceutically acceptable salt administered to the patient.

In one class of this embodiment, $R^2$ is cyclopropyl in the compound or pharmaceutically acceptable salt administered to the patient.

In one subclass of this class, $R^5$ is hydroxy or —$NH_2$, hydrogen, or —$C(O)NH_2$ in the compound or pharmaceutically acceptable salt administered to the patient. In one subclass of this class, $R^5$ is hydroxy or —$NH_2$ in the compound or pharmaceutically acceptable salt administered to the patient. In one subclass of this class, $R^5$ is hydroxy in the compound or pharmaceutically acceptable salt administered to the patient. In one subclass of this class, $R^5$ is —$NH_2$ in the compound or pharmaceutically acceptable salt administered to the patient. In one subclass of this class, $R^5$ is hydrogen in the compound or pharmaceutically acceptable salt administered to the patient. In one subclass of this class, $R^5$ is —$C(O)NH_2$ in the compound or pharmaceutically acceptable salt administered to the patient.

In one embodiment, $R^3$ is oxadiazolyl unsubstituted or substituted by one, two, or three $R^6$ in the compound or pharmaceutically acceptable salt administered to the patient.

In one class of this embodiment, $R^2$ is methyl in the compound or pharmaceutically acceptable salt administered to the patient.

In one subclass of this class, $R^5$ is hydroxy or —$NH_2$, hydrogen, or —$C(O)NH_2$ in the compound or pharmaceutically acceptable salt administered to the patient. In one subclass of this class, $R^5$ is hydroxy or —$NH_2$ in the compound or pharmaceutically acceptable salt administered to the patient. In one subclass of this class, $R^5$ is hydroxy in the compound or pharmaceutically acceptable salt administered to the patient. In one subclass of this class, $R^5$ is —$NH_2$ in the compound or pharmaceutically acceptable salt administered to the patient. In one subclass of this class, $R^5$ is hydrogen in the compound or pharmaceutically acceptable salt administered to the patient. In one subclass of this class, $R^5$ is —$C(O)NH_2$ in the compound or pharmaceutically acceptable salt administered to the patient.

In one class of this embodiment, $R^2$ is cyclopropyl in the compound or pharmaceutically acceptable salt administered to the patient.

In one subclass of this class, $R^5$ is hydroxy or —$NH_2$, hydrogen, or —$C(O)NH_2$ in the compound or pharmaceutically acceptable salt administered to the patient. In one subclass of this class, $R^5$ is hydroxy or —$NH_2$ in the compound or pharmaceutically acceptable salt administered to the patient. In one subclass of this class, $R^5$ is hydroxy in the compound or pharmaceutically acceptable salt administered to the patient. In one subclass of this class, $R^5$ is —$NH_2$ in the compound or pharmaceutically acceptable salt administered to the patient. In one subclass of this class, $R^5$ is hydrogen in the compound or pharmaceutically acceptable salt administered to the patient. In one subclass of this class, $R^5$ is —$C(O)NH_2$ in the compound or pharmaceutically acceptable salt administered to the patient.

In one embodiment, $R^2$ is methyl or cycloalkyl in the compound or pharmaceutically acceptable salt administered to the patient. In one class of this embodiment, $R^2$ is methyl in the compound or pharmaceutically acceptable salt administered to the patient. In one class of this embodiment, $R^2$ is cycloalkyl in the compound or pharmaceutically acceptable salt administered to the patient. In one subclass of this class, $R^2$ is cyclopropyl in the compound or pharmaceutically acceptable salt administered to the patient.

In one embodiment of the method, the compounds of use in the above described methods are of Formula I-a:

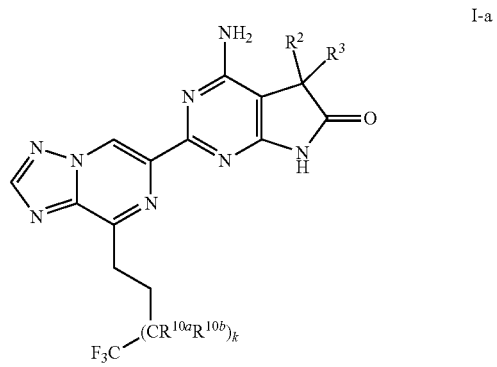

or a pharmaceutically acceptable salt thereof, wherein k is 0 or 1; $R^{10a}$ and $R^{10b}$ are independently hydrogen or fluoro; and $R^2$, and $R^3$ are as previously defined.

In one embodiment of the method, the compounds of use in the above described methods are of Formula I-b:

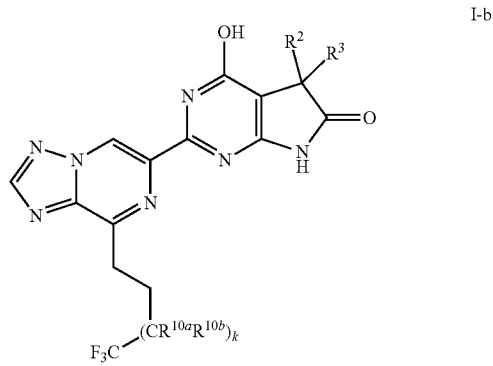

or a pharmaceutically acceptable salt thereof, wherein k is 0 or 1; $R^{10a}$ and $R^{10b}$ are independently hydrogen or fluoro; and $R^2$, $R^3$, $R^4$ and $R^5$ are as previously defined.

In one embodiment of the method, the compounds of use in the above described methods are of Formula I-c:

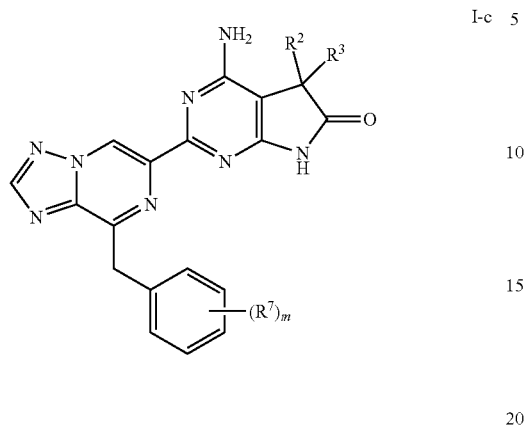

I-c or a pharmaceutically acceptable salt thereof, wherein m is 0, 1, 2, or 3; and $R^2$, $R^3$, and $R^7$ are as previously defined.

In one embodiment of the method, the compounds of use in the above described methods are of Formula I-d:

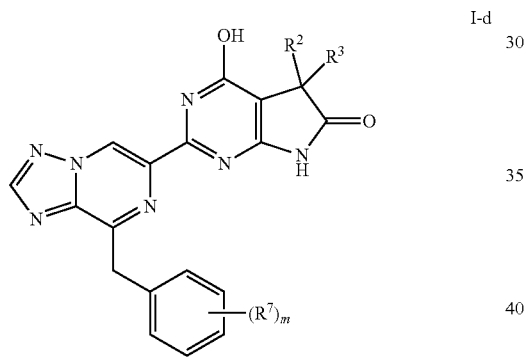

I-d or a pharmaceutically acceptable salt thereof, wherein m is 0, 1, 2, or 3; and $R^2$, $R^3$, and $R^7$ are as previously defined.

As will be apparent to those of skill in the art, compounds of Formula I-b and I-d can exist in alternative tautomeric forms, with the ratio between the tautomeric forms varying depending on conditions. For instance, the tautomeric forms of the compound of Formula I-b are shown below.

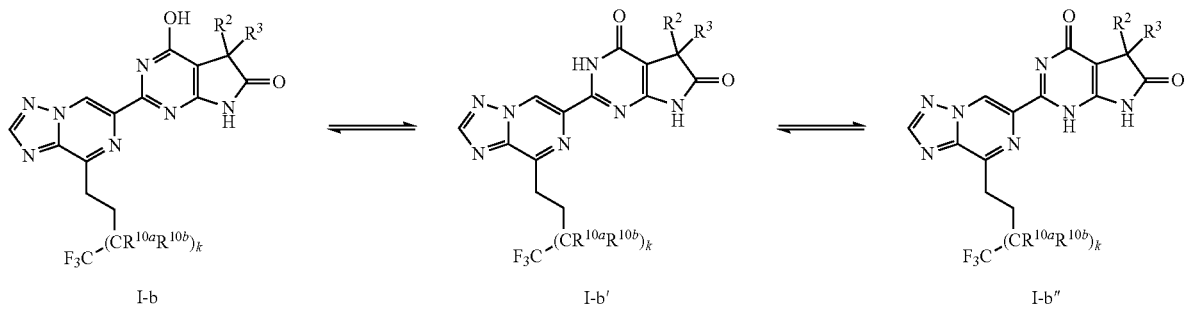

The tautomeric forms of the compound of Formula I-d are shown below.

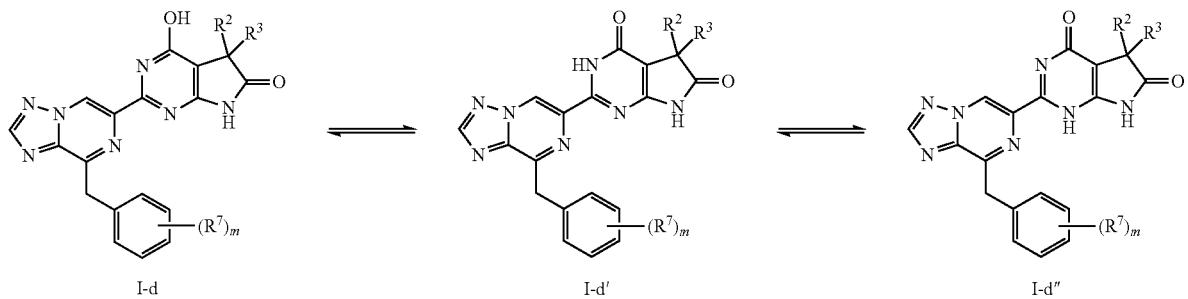

In one embodiment of the inventive method, the compounds administered are compounds of Formula I, wherein the compounds exist as S and R enantiomers with respect to C*. In one class of this embodiment, the compounds of Formula I exist as an S enantiomer with respect to C*. In one class of this embodiment, the compounds of Formula I exist as R enantiomer with respect to C*.

One embodiment of this method is directed to the use as described herein which comprises administration of one of the following compounds:

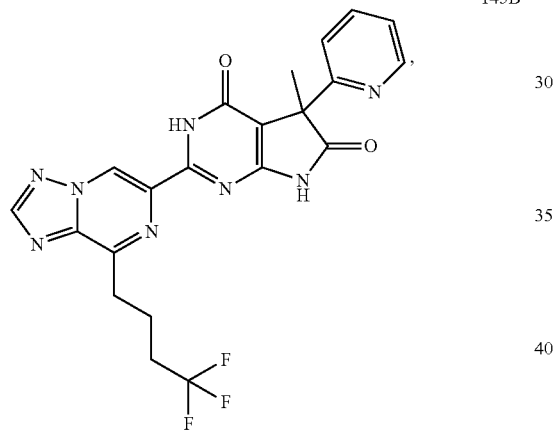

145B 5-methyl-5-(pyridin-2-yl)-2-[8-(4,4,4-trifluorobutyl) [1,2,4]triazolo[1,5-a]pyrazin-6-yl]-5,7-dihydro-1H-pyrrolo[2,3-d]pyrimidine-4,6-dione

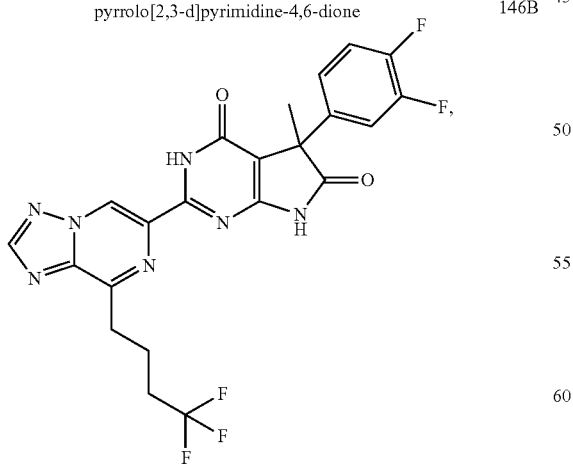

146B 5-(3,4-difluorophenyl)-5-methyl-2-[8-(4,4,4-trifluorobutyl) [1,2,4]triazolo[1,5-a]pyrazin-6-yl]-5,7-dihydro-1H-pyrrolo[2,3-d]pyrimidine-4,6-dione

147B

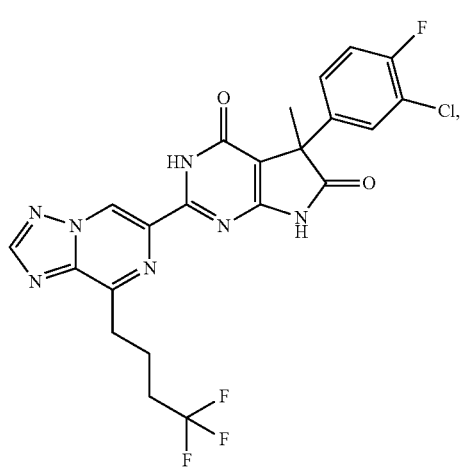

5-(3-chloro-4-fluorophenyl)-5-methyl-2-[8-(4,4,4-trifluorobutyl)[1,2,4]triazolo[1,5-a]pyrazin-6-yl]-5,7-dihydro-1H-pyrrolo[2,3-d]pyrimidine-4,6-dione

148A

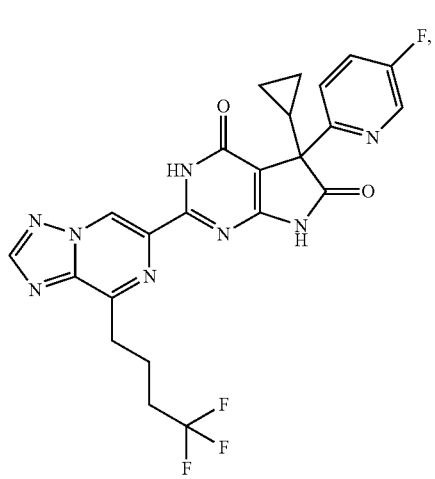

5-(5-methoxypyridin-2-yl)-5-methyl-2-[8-(4,4,4-trifluorobutyl)[1,2,4]triazolo[1,5-a]pyrazin-6-yl]-5,7-dihydro-1H-pyrrolo[2,3-d]pyrimidine-4,6-dione

149B

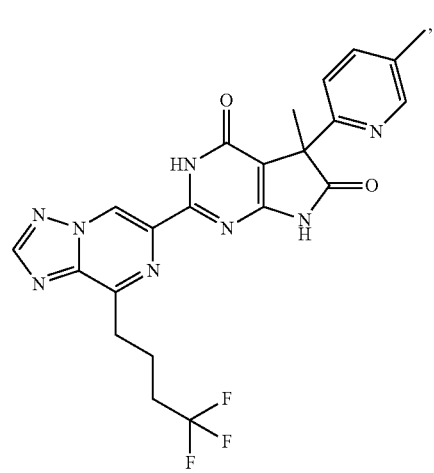

5-methyl-5-(5-methylpyridin-2-yl)-2-[8-(4,4,4-trifluorobutyl)[1,2,4]triazolo[1,5-a]pyrazin-6-yl]-5,7-dihydro-1H-pyrrolo[2,3-d]pyrimidine-4,6-dione

150A

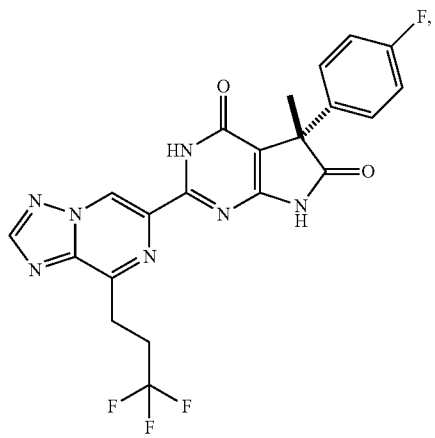

5-cyclopropyl-5-(5-fluoropyridin-2-yl)-2-[8-(4,4,4-trifluorobutyl)[1,2,4]triazolo[1,5-a]pyrazin-6-yl]-5,7-dihydro-1H-pyrrolo[2,3-d]pyrimidine-4,6-dione

151A

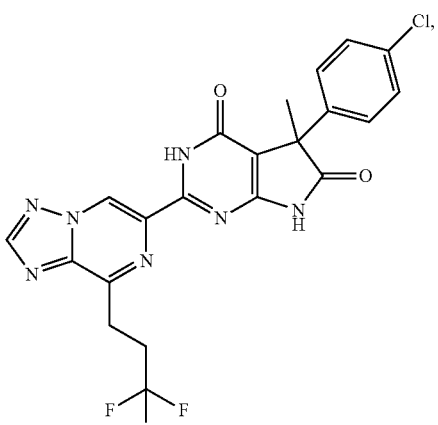

(5S)-5-(4-fluorophenyl)-5-methyl-2-[8-(3,3,3-trifluoropropyl)[1,2,4]triazolo[1,5-a]pyrazin-6-yl]-5,7-dihydro-1H-pyrrolo[2,3-d]pyrimidine-4,6-dione

152A 5-(4-cyclophenyl)-5-methyl-2-[8-(3,3,3-trifluoropropyl)[1,2,4]triazolo[1,5-a]pyrazin-6-yl]-5,7-dihydro-1H-pyrrolo[2,3-d]pyrimidine-4,6-dione

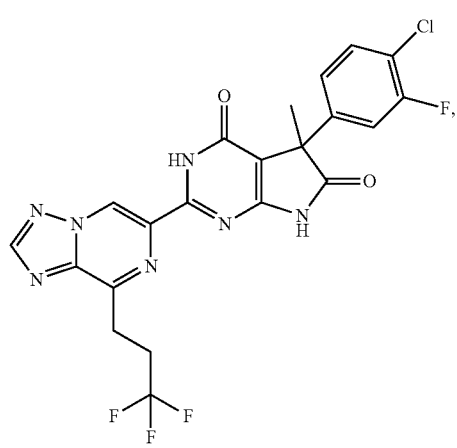

5-(4-chloro-3-fluorophenyl)-5-methyl-2-
[8-(3,3,3-trifluoropropyl)
[1,2,4]triazolo[1,5-a]pyrazin-6-yl]-5,7-dihydro-1H-
pyrrolo[2,3-d]pyrimidine-4,6-dione

153B

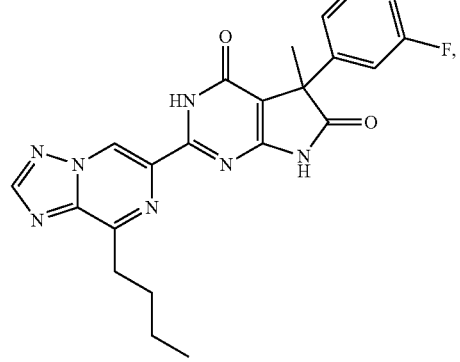

2-[8-butyl-[1,2,4]triazolo[1,5-a]pyrazin-6-yl]-5-(4-
chloro-3-fluorophenyl)-5-methyl-5,7-dihydro-1H-
pyrrolo[2,3-d]pyrimidine-4,6-dione

156B

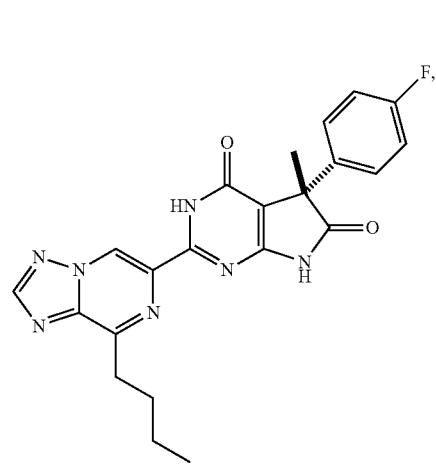

(5S)-2-[8-butyl-[1,2,4]triazolo[1,5-a]pyrazin-6-yl]-
5-(4-fluorophenyl)-5-methyl-5,7-dihydro-1H-
pyrrolo[2,3-d]pyrimidine-4,6-dione

154A

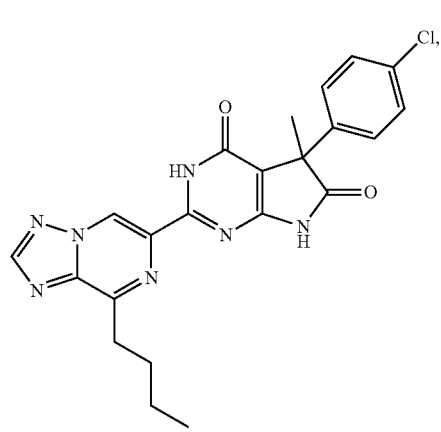

2-[8-butyl-[1,2,4]triazolo[1,5-a]pyrazin-6-yl]-5-(4-
chlorophenyl)-5-methyl-5,7-dihydro-1H-
pyrrolo[2,3-d]pyrimidine-4,6-dione

157A

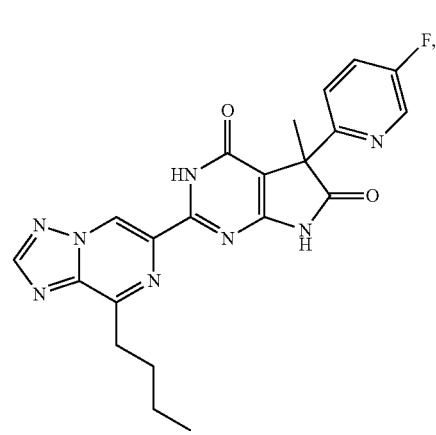

2-[8-butyl-[1,2,4]triazolo[1,5-a]pyrazin-6-yl]-5-(5-
fluoropyridin-2-yl)-5-methyl-5,7-dihydro-1H-
pyrrolo[2,3-d]pyrimidine-4,6-dione

155B

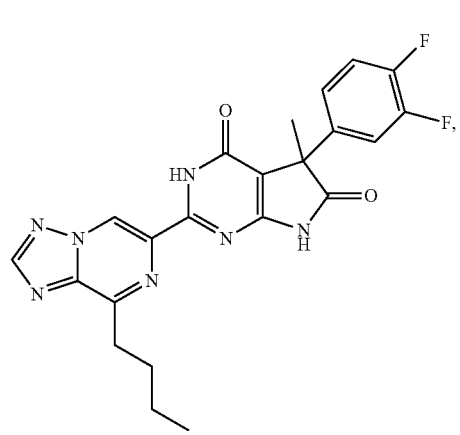

2-[8-butyl-[1,2,4]triazolo[1,5-a]pyrazin-6-yl]-5-(3,4-
difluorophenyl)-5-methyl-5,7-dihydro-1H-
pyrrolo[2,3-d]pyrimidine-4,6-dione

158B

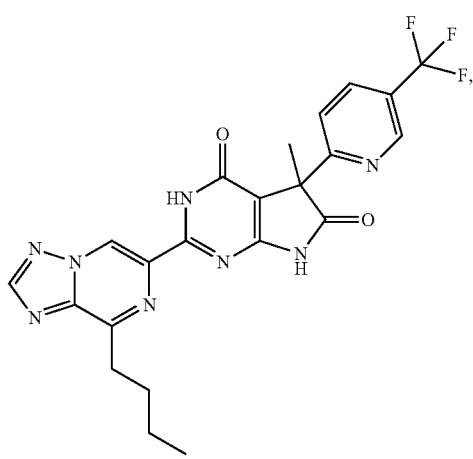

2-[8-butyl-[1,2,4]triazolo[1,5-a]pyrazin-6-yl]-5-methyl-5-(5-(trifluoromethyl)pyridin-2-yl)-5,7-dihydro-1H-pyrrolo[2,3-d]pyrimidine-4,6-dione

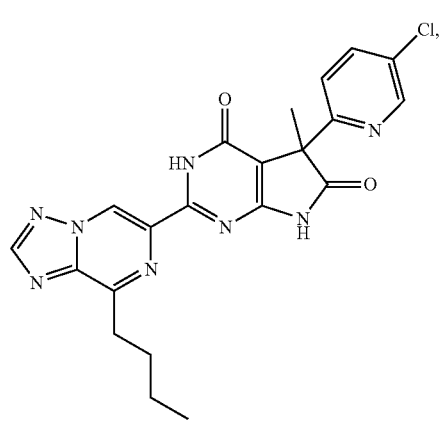

2-[8-butyl-[1,2,4]triazolo[1,5-a]pyrazin-6-yl]-5-(5-chloropyridin-2-yl)-5-methyl-5,7-dihydro-1H-pyrrolo[2,3-d]pyrimidine-4,6-dione

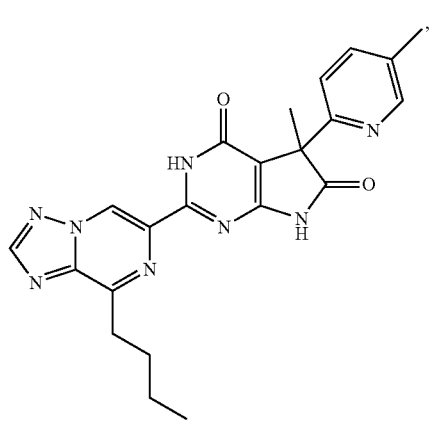

2-[8-butyl-[1,2,4]triazolo[1,5-a]pyrazin-6-yl]-5-methyl-5-(5-methylpyridin-2-yl)-5,7-dihydro-1H-pyrrolo[2,3-d]pyrimidine-4,6-dione

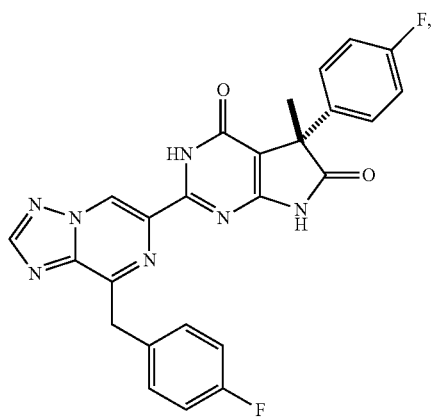

(5S)-2-[8-(4-fluorobenzyl)[1,2,4]triazolo[1,5-a]pyrazin-6-yl]-5-(4-fluorophenyl)-5-methyl-5,7-dihydro-1H-pyrrolo[2,3-d]pyrimidine-4,6-dione

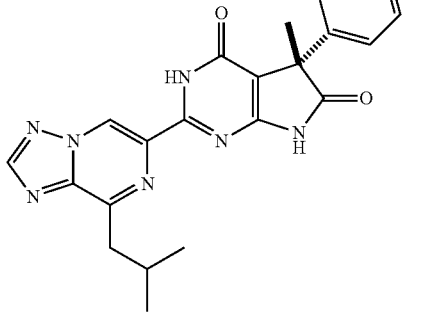

(5S)-5-(4-fluorobenzyl)-2-[8-isobutyl-[1,2,4]triazolo[1,5-a]pyrazin-6-yl]-5-methyl-5,7-dihydro-1H-pyrrolo[2,3-d]pyrimidine-4,6-dione

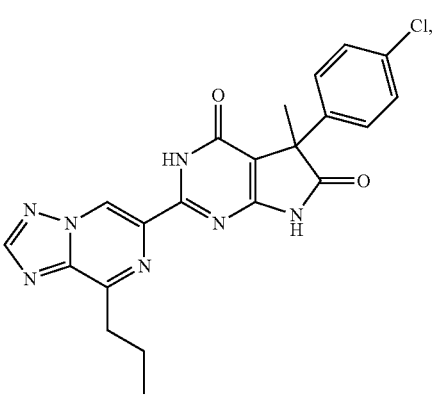

5-(4-chlorophenyl)-5-methyl-2-[8-propyl-[1,2,4]triazolo[1,5-a]pyrazin-6-yl]-5,7-dihydro-1H-pyrrolo[2,3-d]pyrimidine-4,6-dione

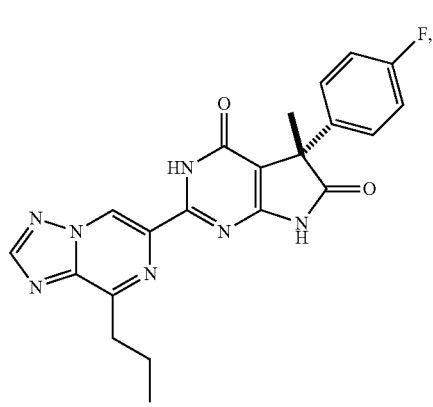

(5S)-5-(4-fluorophenyl)-5-methyl-2-[8-propyl-
[1,2,4]triazolo[1,5-a]pyrazin-6-yl]-5,7-dihydro-1H-
pyrrolo[2,3-d]pyrimidine-4,6-dione

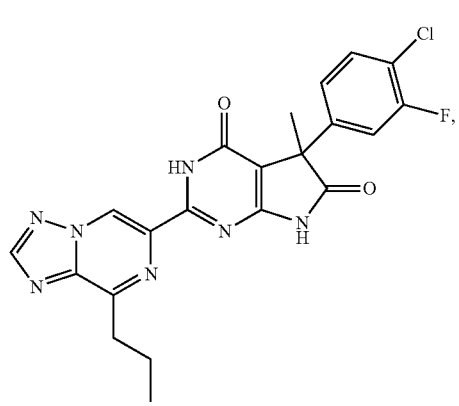

5-(4-chloro-3-fluorophenyl)-5-methyl-2-[8-propyl-
[1,2,4]triazolo[1,5-a]pyrazin-6-yl]-5,7-dihydro-1H-
pyrrolo[2,3-d]pyrimidine-4,6-dione

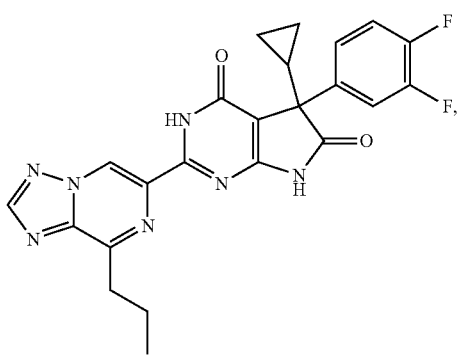

5-cyclopropyl-5-(3,4-difluorophenyl)-2-[8-propyl-
[1,2,4]triazolo[1,5-a]pyrazin-6-yl]-5,7-dihydro-1H-
pyrrolo[2,3-d]pyrimidine-4,6-dione

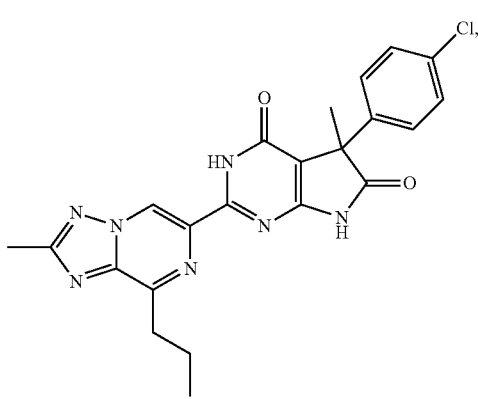

5-(4-chlorophenyl)-5-methyl-2-[2-methyl-8-propyl-
[1,2,4]triazolo[1,5-a]pyrazin-6-yl]-5,7-dihydro-1H-
pyrrolo[2,3-d]pyrimidine-4,6-dione

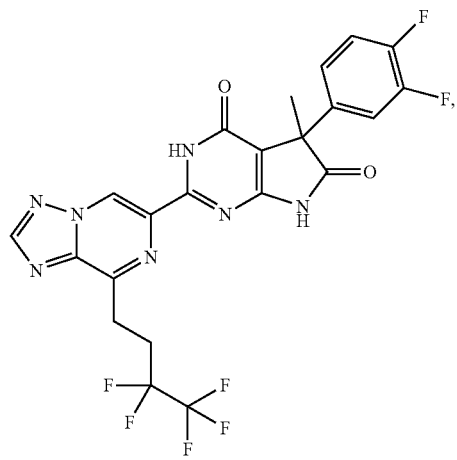

5-(3,4-difluorophenyl)-5-methyl-2-[8-(3,3,4,4,4-
pentafluorobutyl)[1,2,4]triazolo[1,5-a]pyrazin-6-yl]-
5,7-dihydro-1H-
pyrrolo[2,3-d]pyrimidine-4,6-dione

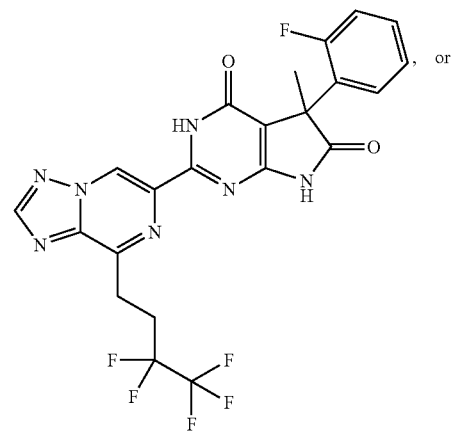

5-(2-fluorophenyl)-5-methyl-2-[8-(3,3,4,4,4-
pentafluorobutyl)[1,2,4]triazolo[1,5-a]pyrazin-6-yl]-
5,7-dihydro-1H-pyrrolo[2,3-d]pyrimidine-4,6-dione

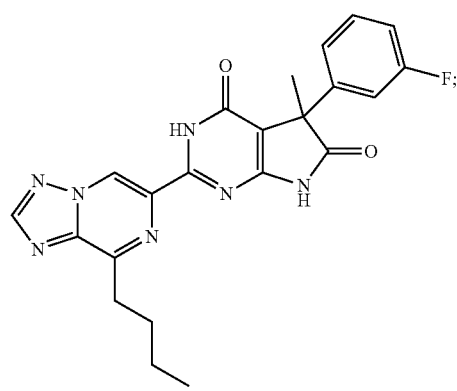

2-[8-butyl-[1,2,4]triazolo[1,5-a]pyrazin-6-yl]-
5-(3-fluorophenyl)-5-methyl-5,7-dihydro-1H-pyrrolo
[2,3-d]pyrimidine-4,6-dione

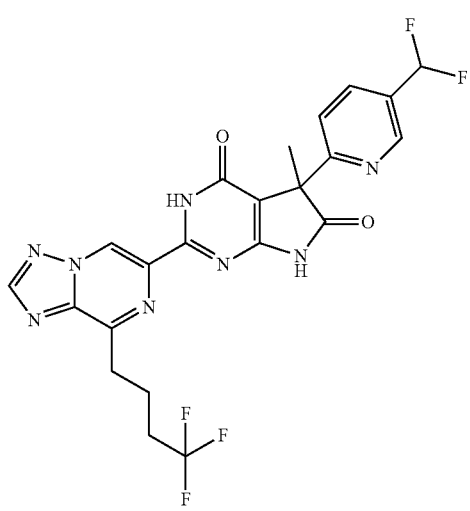

5-(5-(difluoromethyl)pyridin-2-yl)-5-methyl-2-
[8-(4,4,4-trifluorobutyl)[1,2,4]triazolo[1,5-a]pyrazin-6-yl]-
5,7-dihydro-1H-pyrrolo[2,3-d]pyrimidine-4,6-dione

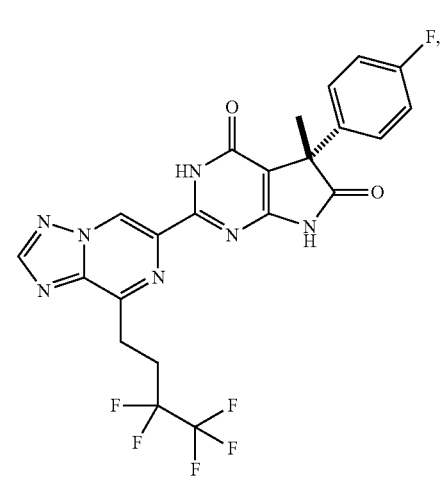

(5S)-5-(4-fluorophenyl)-5-methyl-2-[8-(3,3,4,4,4-
pentafluorobutyl)[1,2,4]triazolo[1,5-a]pyrazin-6-yl]-
5,7-dihydro-1H-pyrrolo[2,3-d]pyrimidine-4,6-dione

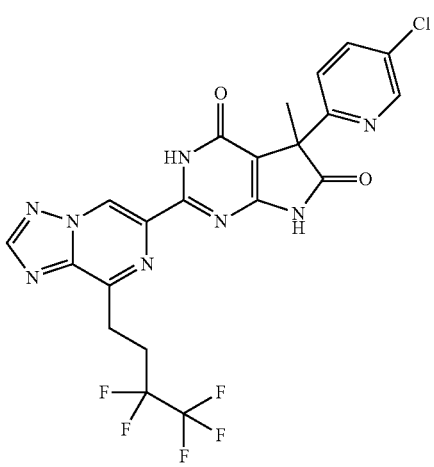

5-(5-chloropyridin-2-yl)-5-methyl-2-[8-(3,3,4,4,4-
pentafluorobutyl)[1,2,4]triazolo[1,5-a]pyrazin-6-yl]-
5,7-dihydro-1H-pyrrolo[2,3-d]pyrimidine-4,6-dione

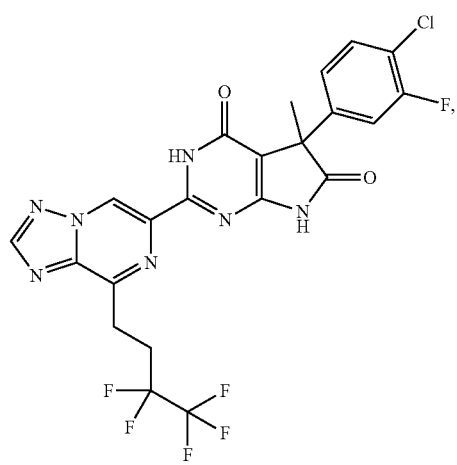

5-(4-chloro-3-fluorophenyl)-5-methyl-2-[8-(3,3,4,4,4-
pentafluorobutyl)[1,2,4]triazolo[1,5-a]pyrazin-6-yl]-
5,7-dihydro-1H-pyrrolo[2,3-d]pyrimidine-4,6-dione

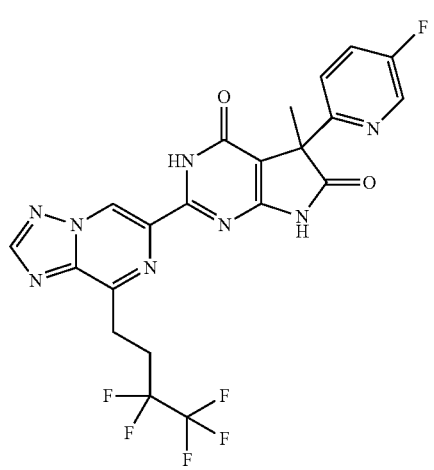

5-(5-fluoropyridin-2-yl)-5-methyl-2-[8-(3,3,4,4,4-
pentafluorobutyl)[1,2,4]triazolo[1,5-a]pyrazin-6-yl]-
5,7-dihydro-1H-pyrrolo[2,3-d]pyrimidine-4,6-dione

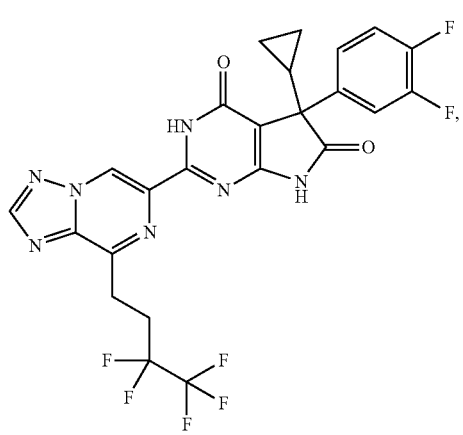

5-cyclopropyl-5-(3,4-difluorophenyl)-2-[8-(3,3,4,4,4-pentafluorobutyl)[1,2,4]triazolo[1,5-a]pyrazin-6-yl]-5,7-dihydro-1H-pyrrolo[2,3-d]pyrimidine-4,6-dione

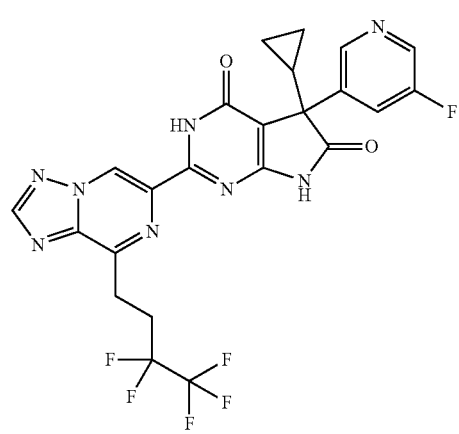

5-cyclopropyl-5-(5-fluoropyridin-3-yl)-2-[8-(3,3,4,4,4-pentafluorobutyl)[1,2,4]triazolo[1,5-a]pyrazin-6-yl]-5,7-dihydro-1H-pyrrolo[2,3-d]pyrimidine-4,6-dione

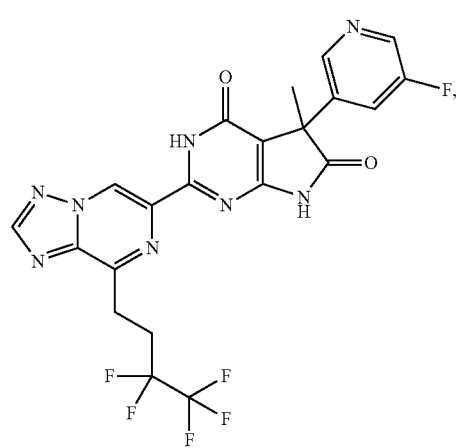

5-(5-fluoropyridin-3-yl)-5-methyl-2-[8-(3,3,4,4,4-pentafluorobutyl)[1,2,4]triazolo[1,5-a]pyrazin-6-yl]-5,7-dihydro-1H-pyrrolo[2,3-d]pyrimidine-4,6-dione

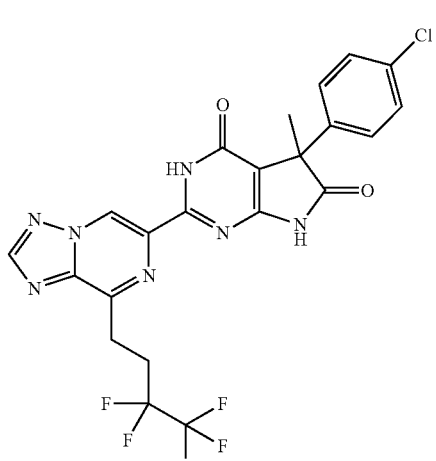

5-(4-chlorophenyl)-5-methyl-2-[8-(3,3,4,4,4-pentafluorobutyl)[1,2,4]triazolo[1,5-a]pyrazin-6-yl]-5,7-dihydro-1H-pyrrolo[2,3-d]pyrimidine-4,6-dione

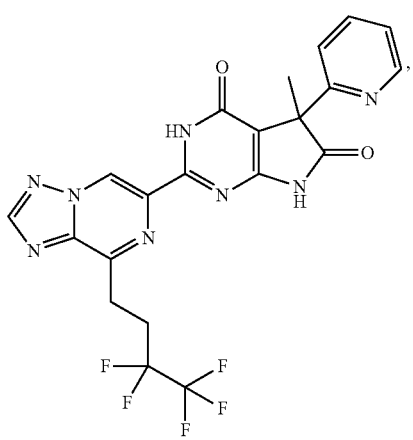

5-methyl-2-[8-(3,3,4,4,4-pentafluorobutyl)[1,2,4]triazolo[1,5-a]pyrazin-6-yl]-5-(pyridin-2-yl)-5,7-dihydro-1H-pyrrolo[2,3-d]pyrimidine-4,6-dione

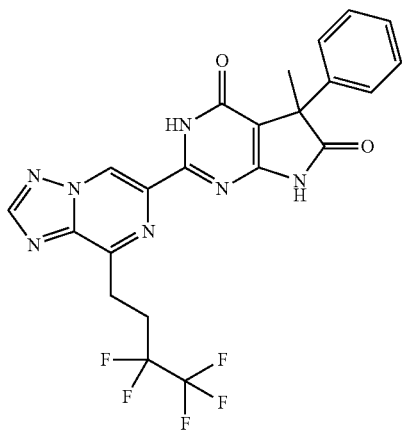

5-methyl-2-[8-(3,3,4,4,4-pentafluorobutyl)[1,2,4]triazolo[1,5-a]pyrazin-6-yl]-5-phenyl-5,7-dihydro-1H-pyrrolo[2,3-d]pyrimidine-4,6-dione

129B

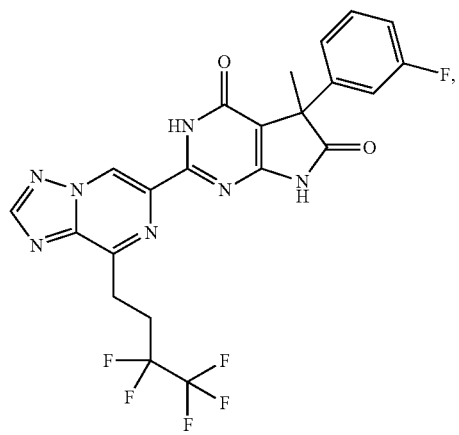

5-(3-fluorophenyl)-5-methyl-2-[8-(3,3,4,4,4-pentafluorobutyl)[1,2,4]triazolo[1,5-a]pyrazin-6-yl]-5,7-dihydro-1H-pyrrolo[2,3-d]pyrimidine-4,6-dione

130B

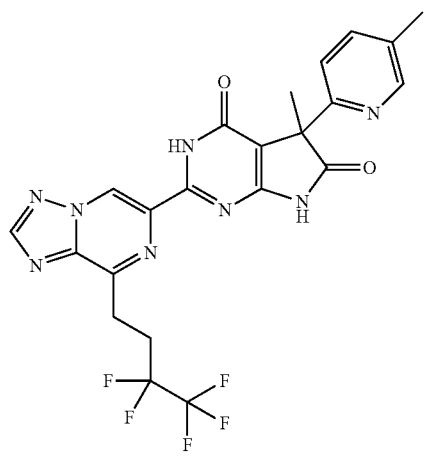

5-methyl-5-(5-methylpyridin-2-yl)-2-[8-(3,3,4,4,4-pentafluorobutyl)[1,2,4]triazolo[1,5-a]pyrazin-6-yl]-5,7-dihydro-1H-pyrrolo[2,3-d]pyrimidine-4,6-dione

131A

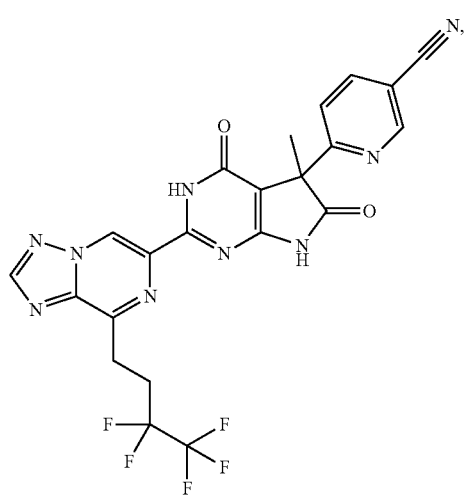

6-(5-methyl-4,6-dioxo-2-[8-(3,3,4,4,4-pentafluorobutyl)[1,2,4]triazolo[1,5-a]pyrazin-6-yl]-4,5,6,7-tetrahydro-1H-pyrrolo[2,3-d]pyrimidin-5-yl)nicotinonitrile

132B

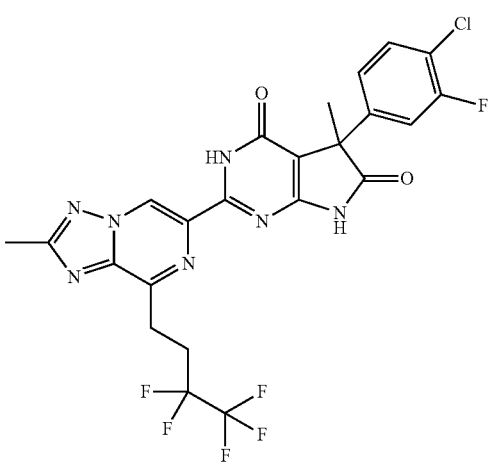

5-(4-chloro-3-fluorophenyl)-5-methyl-2-[2-methyl-8-(3,3,4,4,4-pentafluorobutyl)[1,2,4]triazolo[1,5-a]pyrazin-6-yl]-5,7-dihydro-1H-pyrrolo[2,3-d]pyrimidine-4,6-dione

133B

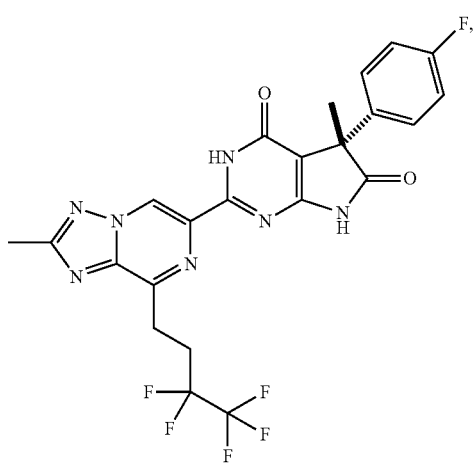

(5S)-5-(4-fluorophenyl)-5-methyl-2-[2-methyl-8-(3,3,4,4,4-pentafluorobutyl)[1,2,4]triazolo[1,5-a]pyrazin-6-yl]-5,7-dihydro-1H-pyrrolo[2,3-d]pyrimidine-4,6-dione

134A

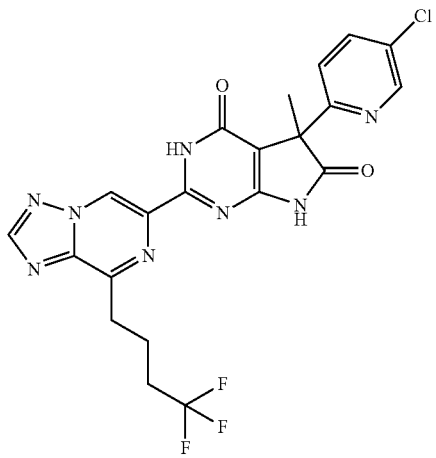

5-(5-chloropyridin-2-yl)-5-methyl-2-[8-(4,4,4-trifluorobutyl)[1,2,4]triazolo[1,5-a]pyrazin-6-yl]-5,7-dihydro-1H-pyrrolo[2,3-d]pyrimidine-4,6-dione

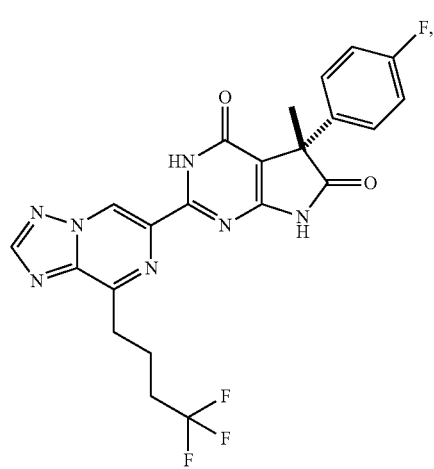

(5S)-5-(4-fluorophenyl)-5-methyl-2-[8-(4,4,4-trifluorobutyl)[1,2,4]triazolo[1,5-a]pyrazin-6-yl]-5,7-dihydro-1H-pyrrolo[2,3-d]pyrimidine-4,6-dione

135A

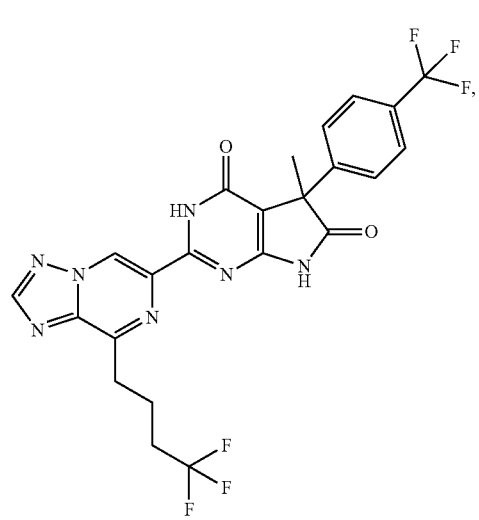

5-methyl-2-[8-(4,4,4-trifluorobutyl)[1,2,4]triazolo[1,5-a]pyrazin-6-yl]-5-(4-trifluoromethyl)phenyl)-5,7-dihydro-1H-pyrrolo[2,3-d]pyrimidine-4,6-dione

137B

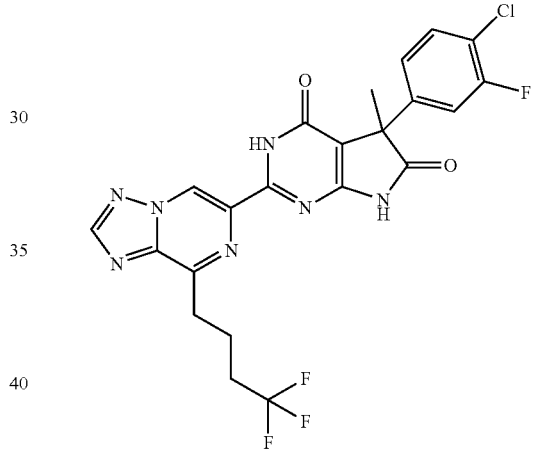

5-(4-chloro-3-fluorophenyl)-5-methyl-2-[8-(4,4,4-trifluorobutyl)[1,2,4]triazolo[1,5-a]pyrazin-6-yl]-5,7-dihydro-1H-pyrrolo[2,3-d]pyrimidine-4,6-dione

138B

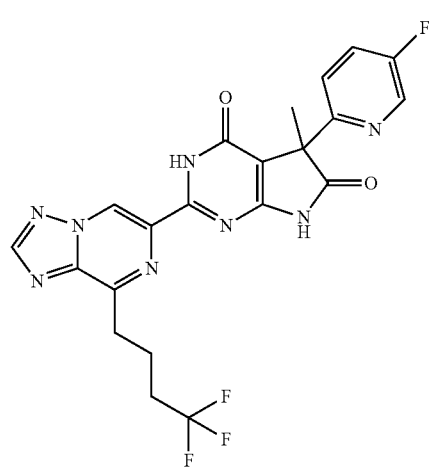

5-(5-fluoropyridin-2-yl)-5-methyl-2-[8-(4,4,4-trifluorobutyl)[1,2,4]triazolo[1,5-a]pyrazin-6-yl]-5,7-dihydro-1H-pyrrolo[2,3-d]pyrimidine-4,6-dione

136B

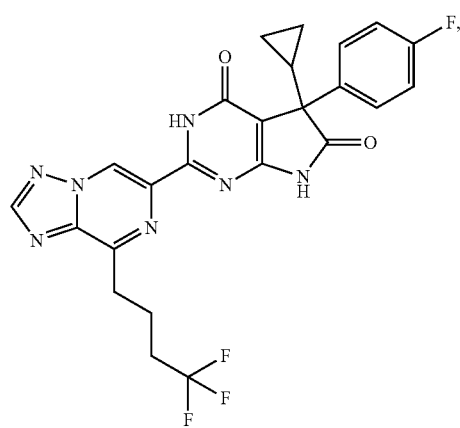

5-cyclopropyl-5-(4-fluorophenyl)-2-[8-(4,4,4-trifluorobutyl)[1,2,4]triazolo[1,5-a]pyrazin-6-yl]-5,7-dihydro-1H-pyrrolo[2,3-d]pyrimidine-4,6-dione

139B

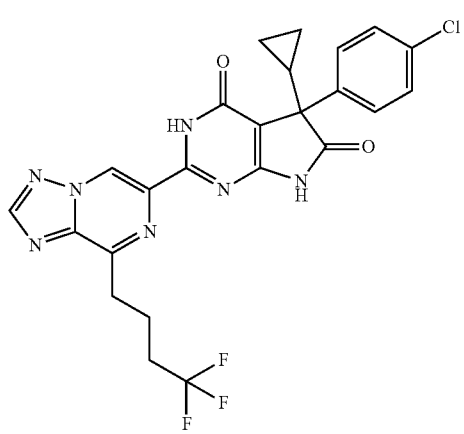

5-(4-chlorophenyl)-5-cyclopropyl-2-[8-(4,4,4-trifluorobutyl)[1,2,4]triazolo[1,5-a]pyrazin-6-yl]-5,7-dihydro-1H-pyrrolo[2,3-d]pyrimidine-4,6-dione

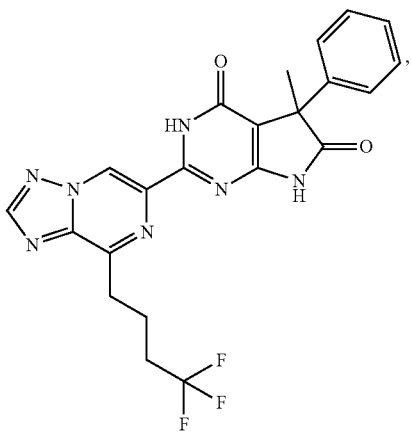

5-methyl-5-phenyl-2-[8-(4,4,4-trifluorobutyl)[1,2,4]triazolo[1,5-a]pyrazin-6-yl]-5,7-dihydro-1H-pyrrolo[2,3-d]pyrimidine-4,6-dione

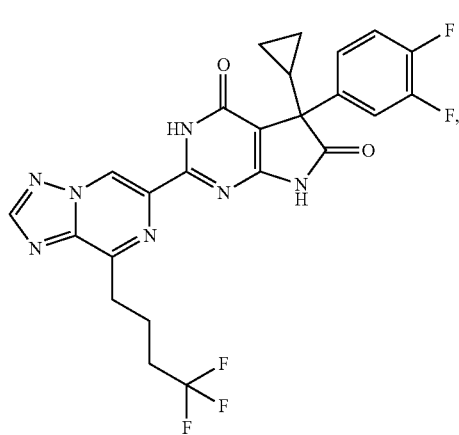

5-cyclopropyl-5-(3,4-difluorophenyl)-2-[8-(4,4,4-trifluorobutyl)[1,2,4]triazolo[1,5-a]pyrazin-6-yl]-5,7-dihydro-1H-pyrrolo[2,3-d]pyrimidine-4,6-dione

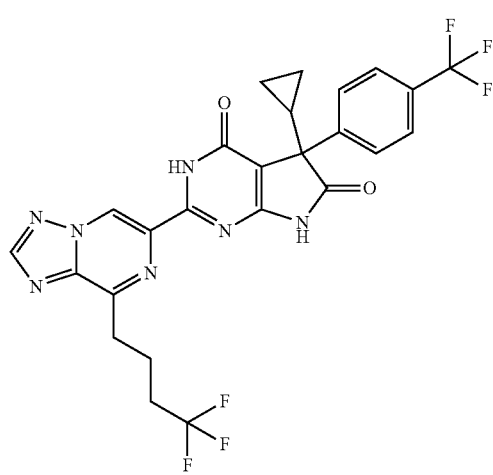

5-cyclopropyl-2-[8-(4,4,4-trifluorobutyl)[1,2,4]triazolo[1,5-a]pyrazin-6-yl]-5-(4-trifluoromethyl)phenyl)-5,7-dihydro-1H-pyrrolo[2,3-d]pyrimidine-4,6-dione

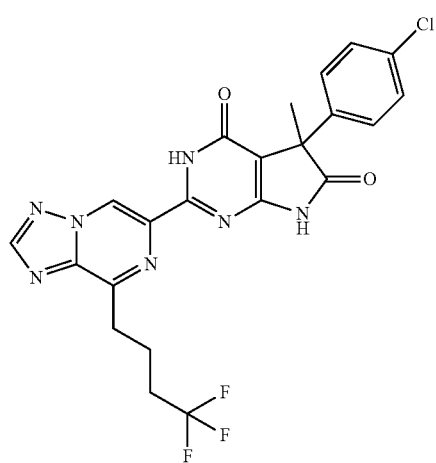

5-(4-chlorophenyl)-5-methyl-2-[8-(4,4,4-trifluorobutyl)[1,2,4]triazolo[1,5-a]pyrazin-6-yl]-5,7-dihydro-1H-pyrrolo[2,3-d]pyrimidine-4,6-dione or a pharmaceutically acceptable salt thereof.

In one embodiment of the invention, the fibrotic disease to be treated or prevented is systemic sclerosis, which is a multi-system autoimmune disease affecting the connective tissue of the skin, blood vessel and internal organs. In one embodiment, the patient is in need of treatment or prevention for limited systemic sclerosis (lSSc) where sclerosis is restricted to the patient's distal extremities. In another embodiment, the patient is in need of treatment or prevention for diffuse systemic sclerosis (sSSc), where sclerosis is more pronounced throughout the body.

In another embodiment of the invention, the fibrotic disease to be treated or prevented is cystic fibrosis.

In still another embodiment of the invention, the fibrotic disease to be treated or prevented is non-alcoholic steatohepatitis (NASH), which can lead to cirrhosis.

In another embodiment of the invention, the fibrotic disease to be treated or prevented is Peyronie's disease.

In yet another embodiment of the invention, the fibrotic disease to be treated or prevented is interstitial lung disease. In one embodiment, the patient is in need of treatment or prevention for idiopathic interstitial pneumonia (IIP). In another embodiment, the patient is in need of treatment or prevention for idiopathic pulmonary fibrosis.

Prevention and treatment as described herein constitute distinct embodiments of the present invention.

All structural Formulas, embodiments and classes thereof described herein include the pharmaceutically acceptable salts of the compounds defined therein. Reference to the compounds of structural Formula I includes the compounds of other generic structural Formulas and embodiments that fall within the scope of Formula I, including but not limited to Formula Ia to I-d.

"Alkyl", as well as other groups having the prefix "alk", such as alkoxy, and the like, means carbon chains which may be linear or branched, or combinations thereof, containing the indicated number of carbon atoms. If no number is specified, 1-6 carbon atoms are intended for linear and 3-7 carbon atoms for branched alkyl groups. Examples of alkyl groups include methyl, ethyl, propyl, isopropyl, butyl, sec- and tert-butyl, pentyl, hexyl, heptyl, octyl, nonyl and the like.

"Alkoxy" and "alkyl-O—" are used interchangeably and refer to an alkyl group linked to oxygen.

"Alkyl-NH—" refers to an alkyl group linked to an NH group. Examples of alkyl-NH-include methyl-amino or methyl-NH— and ethyl-amino or ethyl-NH—.

"Aryl" means phenyl or naphthyl.

"Haloalkyl" include mono-substituted as well as multiple halo substituted alkyl groups, up to perhalo substituted alkyl. For example, halomethyl, 1,1-difluoroethyl, trifluoromethyl or 1,1,1,2,2-pentafluorobutyl are included.

"Haloalkoxy" and "haloalkyl-O" are used interchangeably and refer to halo substituted alkyl groups or "haloalkyl" linked through the oxygen atom. Haloalkoxy include mono-substituted as well as multiple halo substituted alkoxy groups, up to perhalo substituted alkoxy. For example, trifluoromethoxy is included.

"Cycloalkyl" means a saturated cyclic hydrocarbon radical having the number of carbon atoms designated if no number of atoms is specified, 3-7 carbon atoms are intended, forming 1-3 carbocyclic rings that are fused. "Cycloalkyl" also includes monocyclic rings fused to an aryl group in which the point of attachment is on the non-aromatic portion. Examples of cycloalkyl include cyclopropyl, cyclobutyl, cyclopentyl, cyclohexyl, cycloheptyl, tetrahydronaphthyl, decahydronaphthyl, indanyl and the like.

"Cycloalkoxy" and "cycloalkyl-O" are used interchangeably and refer to a cycloalkyl group, as defined above, linked to oxygen.

"Heterocyclyl" "heterocycle" or "heterocyclic" refers to nonaromatic cyclic ring structures in which one or more atoms in the ring, the heteroatom(s), is an element other than carbon. Heteroatoms are typically 0, S or N atoms. Examples of heterocyclyl groups include: piperidine, piperazinyl, morpholinyl, pyrrolidinyl, tetrahydrofuranyl, azetidinyl, oxiranyl, or aziridinyl, and the like.

"Heteroaryl" refers to an aromatic cyclic ring structures in which one or more atoms in the ring, the heteroatom(s), is an element other than carbon. Heteroatoms are typically O, S, or N atoms. Examples of heteroaromatic groups include: pyridinyl, pyrimidinyl, pyrrolyl, pyridazinyl, isoxazolyl, indolyl, or imidazolyl.

"Halogen" (or "halo") unless otherwise indicated, includes fluorine (fluoro), chlorine (chloro), bromine (bromo) and iodine (iodo). In one embodiment, halo is fluoro (—F) or chloro (—Cl).

When any variable (e.g., $R^1$, $R^2$, etc.) occurs more than one time in any constituent or in Formula I or other generic formulas herein, its definition on each occurrence is independent of its definition at every other occurrence. Combinations of substituents and/or variables are permissible only if such combinations result in stable compounds. In choosing compounds to be used in the present invention, one of ordinary skill in the art will recognize that the various substituents, i.e., $R^1$, $R^2$, etc., are to be chosen in conformity with well-known principles of chemical structure connectivity and stability. Unless expressly stated to the contrary, substitution by a named substituent is permitted on any atom in a ring (e.g., aryl, a heteroaryl ring, or a saturated heterocyclic ring) provided such ring substitution is chemically allowed and results in a stable compound. A "stable" compound is a compound which can be prepared and isolated and whose structure and properties remain or can be caused to remain essentially unchanged for a period of time sufficient to allow use of the compound for the purposes described herein (e.g., therapeutic or prophylactic administration to a subject).

The term "substituted" shall be deemed to include multiple degrees of substitution by a named substituent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

Unless expressly depicted or described otherwise, variables depicted in a structural formula with a "floating" bond, such as $R^7$ in Formulas I-c and I-d, are permitted on any available carbon atom in the ring to which the variable is attached. When a moiety is noted as being "optionally substituted" in Formulas I to Id or any embodiment thereof, it means that Formula I or the embodiment thereof encompasses compounds that contain the noted substituent (or substituents) on the moiety and also compounds that do not contain the noted substituent (or substituents) on the moiety.

Compounds of structural Formulas I to I-d may contain one or more asymmetric centers and can thus occur as racemates and racemic mixtures, single enantiomers, diastereoisomeric mixtures and individual diastereoisomers. Centers of asymmetry that are present in the compounds of Formula I can all independently of one another have S configuration or R configuration. The compounds of use in this invention include all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The present invention is meant to comprehend the use of all such stereo-isomeric forms of the compounds of structural Formulas I to I-d.

Compounds of structural Formulas I to I-d may be separated into their individual diastereoisomers by, for example, fractional crystallization from a suitable solvent, for example methanol or ethyl acetate or a mixture thereof, or via chiral chromatography using an optically active stationary phase. Absolute stereochemistry may be determined by X-ray crystallography of crystalline products or crystalline intermediates which are derivatized, if necessary, with a reagent containing an asymmetric center of known absolute configuration. Alternatively, any stereoisomer or isomers of a compound of Formulas I to I-d may be obtained by stereospecific synthesis using optically pure starting materials or reagents of known absolute configuration.

If desired, racemic mixtures of the compounds may be separated so that the individual enantiomers are isolated and utilized in the methods disclosed herein. The separation can be carried out by methods well known in the art, such as the coupling of a racemic mixture of compounds to an enantiomerically pure compound to form a diastereoisomeric mixture, followed by separation of the individual diastereoisomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

For compounds of Formulas I to I-d described herein which contain olefinic double bonds, unless specified otherwise, they are meant to include both E and Z geometric isomers.

Some of the compounds described herein may exist as tautomers which have different points of attachment of hydrogen accompanied by one or more double bond shifts. For example, a ketone and its enol form are keto-enol tautomers. The individual tautomers as well as mixtures thereof are encompassed with compounds of Formulas I to I-d of the present invention.

In the compounds of structural Formulas I to I-d, the atoms may exhibit their natural isotopic abundances, or one or more of the atoms may be artificially enriched in a particular isotope having the same atomic number, but an atomic mass or mass number different from the atomic mass or mass number predominately found in nature. The present invention as described and claimed herein is meant to encompass the use of all suitable isotopic variations of the compounds of structural Formulas I to I-d and embodiments thereof. For example, different isotopic forms of hydrogen (H) include protium ($^1$H) and deuterium ($^2$H, also denoted herein as D). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within structural Formulas I to I-d, can be prepared without undue experimentation by conventional techniques well known to those skilled in the art or by processes analogous to those described in the Schemes and Examples herein using appropriate isotopically-enriched reagents and/or intermediates.

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Preferred are the ammonium, calcium, magnesium, potassium and sodium salts. Salts prepared from pharmaceutically acceptable organic non-toxic bases include salts of primary, secondary, and tertiary amines derived from both naturally occurring and synthetic sources. Pharmaceutically acceptable organic non-toxic bases from which salts can be formed include, for example, arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, dicyclohexylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids. If the compounds of Formulas I to I-d simultaneously contain acidic and basic groups in the molecule the invention also includes, in addition to the salt forms mentioned, inner salts or betaines (zwitterions). Salts can be obtained from the compounds of Formulas I to I-d by customary methods which are known to the person skilled in the art, for example by combination with an organic or inorganic acid or base in a solvent or dispersant, or by anion exchange or cation exchange from other salts.

Furthermore, compounds used in the present invention may exist in amorphous form and/or one or more crystalline forms, and as such all amorphous and crystalline forms and mixtures thereof of the compounds of Formula I, including the Examples, are intended to be included within the scope of the present invention. In addition, some of the compounds of used in the instant invention may form solvates with water (i.e., a hydrate) or common organic solvents such as but not limited to ethyl acetate. Use of such solvates and hydrates, particularly the pharmaceutically acceptable solvates and hydrates, of the instant compounds are likewise encompassed within the scope of this invention, along with unsolvated and anhydrous forms.

Any pharmaceutically acceptable pro-drug modification of a compound of this invention which results in conversion in vivo to a compound within the scope of this invention is also within the scope of this invention. For example, esters can optionally be made by esterification of an available carboxylic acid (—COOH) group or by formation of an ester on an available hydroxy group in a compound. Similarly, labile amides can be made. Pharmaceutically acceptable esters or amides of the compounds of this invention may be prepared to act as pro-drugs which can be hydrolyzed back to an acid (or —COO— depending on the pH of the fluid or tissue where conversion takes place) or hydroxy form particularly in vivo and as such are encompassed within the scope of this invention. Included are those esters and acyl groups known in the art for modifying the solubility or hydrolysis characteristics for use as sustained-release or prodrug formulations. Also, in the case of a carboxylic acid (—COOH) or alcohol group being present in the compounds used in the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be employed.

The compounds of Formulas I to I-d according to the invention effect an increase of cGMP concentration via the activation of the soluble guanylate cyclase (sGC), and they therefore may additionally be useful agents for the therapy and prophylaxis of disorders which are associated with a low or decreased cGMP level or which are caused thereby, or for whose therapy or prophylaxis an increase of the present cGMP level is desired. The activation of the sGC by the compounds of Formulas I to I-d can be examined, for example, in the activity assay described herein.

The terms "therapeutically effective (or efficacious) amount" and similar descriptions such as "an amount efficacious for treatment" are intended to mean that amount of a pharmaceutical drug that will elicit the biological or medical response of a tissue, a system, animal or human that is being sought by a researcher, veterinarian, medical doctor or other clinician in the treatment of the fibrotic disease selected from systemic sclerosis, cystic fibrosis, non-alcoholic steatohepatitis, Peyronie's disease, or interstitial lung disease. The terms "prophylactically effective (or efficacious) amount" and similar descriptions such as "an amount efficacious for prevention" are intended to mean that amount of a pharmaceutical drug that will prevent or reduce the risk of occurrence of the biological or medical event that is sought to be prevented in a tissue, a system, animal or human by a researcher, veterinarian, medical doctor or other clinician in the prevention of the fibrotic disease selected from systemic sclerosis, cystic fibrosis, non-alcoholic steatohepatitis, Peyronie's disease, or interstitial lung disease. As an example, the dosage a patient receives can be selected so as to achieve the desired reduction in symptoms of the fibrotic disease; the dosage a patient receives may also be titrated over time in order to reach the desired relief. The dosage regimen utilizing a compound of the instant invention is selected in accordance with a variety of factors including type, species, age, weight, sex and medical condition of the patient; the severity of the condition to be treated; the potency of the compound chosen to be administered; the route of administration; and the renal and hepatic function of the patient. A consideration of these factors is well within the purview of the ordinarily skilled clinician for the purpose of determining the therapeutically effective or prophylactically effective dosage amount needed to prevent, counter, or arrest the progress of the condition. It is understood that a specific daily dosage amount can simultaneously be both a therapeutically effective amount, e.g., for treatment of the fibrotic disease, and a prophylactically effective amount, e.g., for prevention of the fibrotic disease.

The compounds of Formulas I to I-d and their pharmaceutically acceptable salts can be administered to animals, preferably to mammals, and in particular to humans, as pharmaceuticals by themselves, in mixtures with one another or in the form of pharmaceutical compositions. The term "patient" includes animals, preferably mammals and especially humans, who use the instant active agents for the prevention or treatment of a medical condition which is a fibrotic disease selected from systemic sclerosis, cystic fibrosis, non-alcoholic steatohepatitis, Peyronie's disease, or interstitial lung disease. Administering of the drug to the patient includes both self-administration and administration to the patient by another person. The patient may be in need of, or desire, treatment for an existing disease or medical condition as described above, or may be in need of or desire prophylactic treatment to prevent or reduce the risk of occurrence of said disease or medical condition. As used herein, a patient "in need" of treatment of an existing condition or of prophylactic treatment for a fibrotic disease selected from systemic sclerosis, cystic fibrosis, non-alcoholic steatohepatitis, Peyronie's disease, or interstitial lung disease encompasses both a determination of need by a medical professional as well as the desire of a patient for such treatment.

Subjects of the present invention therefore also are the use of compounds of Formulas I to I-d and their pharmaceutically acceptable salts in the therapy and prophylaxis of the above mentioned syndromes as well as their use for preparing medicaments for these purposes.

Furthermore, a subject of the present invention is the use of a pharmaceutical composition which comprises as an active component an effective dose of at least one compound of Formulas I to I-d and/or a pharmaceutically acceptable salt thereof and a customary pharmaceutically acceptable carrier, i.e., one or more pharmaceutically acceptable carrier substances and/or additives for treating or preventing a fibrotic disease selected from systemic sclerosis, cystic fibrosis, non-alcoholic steatohepatitis, Peyronie's disease, or interstitial lung disease.

Thus, a subject of the invention is, for example, use of a pharmaceutical composition which comprises as an active component an effective dose of a compound of Formulas I to I-d and/or a pharmaceutically acceptable salt thereof and a customary pharmaceutically acceptable carrier, in the therapy or prophylaxis of the abovementioned syndromes as well as their use for preparing medicaments for these purposes.

The pharmaceutical compositions according to the invention can be administered orally, for example in the form of pills, tablets, lacquered tablets, sugar-coated tablets, granules, hard and soft gelatin capsules, aqueous, alcoholic or oily solutions, syrups, emulsions or suspensions, or rectally, for example in the form of suppositories. Administration can also be carried out parenterally, for example subcutaneously, intramuscularly or intravenously in the form of solutions for injection or infusion. Other suitable administration forms are, for example, percutaneous or topical administration, for example in the form of ointments, tinctures, sprays or transdermal therapeutic systems, or the inhalative administration in the form of nasal sprays or aerosol mixtures, or, for example, microcapsules, implants or rods. The preferred administration form depends, for example, on the disease to be treated and on its severity.

The amount of active compound of Formulas I to I-d and/or its pharmaceutically acceptable salts in the pharmaceutical composition normally is from 0.1 to 200 mg, preferably from 1 to 200 mg, per dose, but depending on the type of the pharmaceutical composition it can also be higher. The pharmaceutical compositions usually comprise 0.5 to 90 percent by weight of the compounds of Formulas I to I-d and/or their pharmaceutically acceptable salts. The preparation of the pharmaceutical compositions can be carried out in a manner known per se. For this purpose, one or more compounds of Formulas I to I-d and/or their pharmaceutically acceptable salts, together with one or more solid or liquid pharmaceutical carrier substances and/or additives (or auxiliary substances) and, if desired, in combination with other pharmaceutically active compounds having therapeutic or prophylactic action, are brought into a suitable administration form or dosage form which can then be used as a pharmaceutical in human or veterinary medicine.

For the production of pills, tablets, sugar-coated tablets and hard gelatin capsules, it is possible to use, for example, lactose, starch, for example maize starch, or starch derivatives, talc, stearic acid or its salts, etc. Carriers for soft gelatin capsules and suppositories are, for example, fats, waxes, semisolid and liquid polyols, natural or hardened oils, etc. Suitable carriers for the preparation of solutions, for example of solutions for injection, or of emulsions or syrups are, for example, water, physiologically acceptable sodium chloride solution, alcohols such as ethanol, glycerol, polyols, sucrose, invert sugar, glucose, mannitol, vegetable oils, etc. It is also possible to lyophilize the compounds of Formulas I to I-d and their pharmaceutically acceptable salts and to use the resulting lyophilisates, for example, for preparing preparations for injection or infusion. Suitable carriers for microcapsules, implants or rods are, for example, copolymers of glycolic acid and lactic acid.

Besides the active compounds and carriers, the pharmaceutical compositions can also contain customary additives, for example fillers, disintegrants, binders, lubricants, wetting agents, stabilizers, emulsifiers, dispersants, preservatives, sweeteners, colorants, flavorings, aromatizers, thickeners, diluents, buffer substances, solvents, solubilizers, agents for achieving a depot effect, salts for altering the osmotic pressure, coating agents or antioxidants.

The dosage of the active compound of Formulas I to I-d and/or of a pharmaceutically acceptable salt thereof to be administered depends on the individual case and is, as is customary, to be adapted to the individual circumstances to achieve an optimum effect. Thus, it depends on the nature and the severity of the disorder to be treated, and also on the sex, age, weight and individual responsiveness of the human or animal to be treated, on the efficacy and duration of action of the compounds used, on whether the therapy is acute or chronic or prophylactic, or on whether other active compounds are administered in addition to compounds of Formulas I to I-d. In general, a daily dose of approximately 0.01 to 100 mg/kg, preferably 0.01 to 10 mg/kg, in particular 0.3 to 5 mg/kg (in each case mg per kg of bodyweight) is appropriate for administration to an adult weighing approximately 75 kg in order to obtain the desired results. The daily dose can be administered in a single dose or, in particular when larger amounts are administered, be divided into several, for example two, three or four individual doses. In some cases, depending on the individual response, it may be necessary to deviate upwards or downwards from the given daily dose. A single daily dose is preferred.

One or more additional pharmacologically active agents may be administered in combination with a compound of Formulas I to I-d. An additional active agent (or agents) is intended to mean a pharmaceutically active agent (or agents) that is active in the body, including pro-drugs that convert to pharmaceutically active form after administration, which are different from the compound of Formulas I to I-d, and also includes free-acid, free-base and pharmaceutically acceptable salts of said additional active agents. Generally, any suitable additional active agent or agents, including but not limited to anti-hypertensive agents, anti-atherosclerotic agents such as camphor, menthol, a topical emollient, a corticosteroid (e.g., prednisone, dexamethasone) methotrexate, chlorambucil, mycophenolate mofetil, cyclosporine, FK506 (tacrolimus), cyclophosphamide, a statin (e.g., atorvastatin, rosuvastatin, pravastatin, fluvastatin, simvastatin, lovastatin), a tyrosine kinase inhibitor such as imatinib mesylate or nintedanib, an angiotensin converting enzyme inhibitor (e.g., alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril), an angiotensin II receptor antagonist (e.g., losartan valsartan, candesartan, olmesartan, telmesartan), a calcium channel blocker (e.g., amlodipine, nifedipine, veraparmil, diltiazem, gallopamil, niludipine, nimodipins, nicardipine), omeprazole, D-penicillamine, interferon alfa, interferon gamma, aspirin, pancrealipase, a fat soluble vitamin, pulmozyme, ivacaftor, vacaftor, gentamycin, aztreonam, colistin, tobramycin, a fluoroquinoline such as ciprofloxacin, piperacillin, chloramphenicol, sulfamethoxazole, trimethoprim, cephalexin, ceftazidime, nintedanib, N-acetylcysteine, azathioprine, toclizumab, and pirfenidone.

In some embodiments, wherein the patient is in need of treatment for systemic sclerosis, the additional active agent is camphor, menthol, a topical emollient, a corticosteroid (e.g., prednisone, dexamethasone) methotrexate, chlorambucil, mycophenolate mofetil, cyclosporine, FK506 (tacrolimus), cyclophosphamide, a statin (e.g., atorvastatin, rosuvastatin, pravastatin, fluvastatin, simvastatin, lovastatin), a tyrosine kinase inhibitor such as imatinib mesylate or nintedanib, an angiotensin converting enzyme inhibitor (e.g., alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril), an angiotensin II receptor antagonist (e.g., losartan valsartan, candesartan, olmesartan, telmesartan), a calcium channel blocker (e.g., amlodipine, nifedipine, veraparmil, diltiazem, gallopamil, niludipine, nimodipins, nicardipine), omeprazole, D-penicillamine, interferon alfa, interferon gamma, aspirin, tocilizumab, or pirfenidone.

In other embodiments, wherein the patient is in need of treatment for cystic fibrosis, the additional active agent is pancrealipase, a fat soluble vitamin, pulmozyme, ivacaftor, vacaftor, gentamycin, aztreonam, colistin, tobramycin, a fluoroquinoline, piperacillin, chloramphenicol, sulfamethoxazole, trimethoprim, cephalexin, or ceftazidime.

In still other embodiments, wherein the patient is in need of treatment for idiopathic pulmonary fibrosis, the additional active agent is nintedanib, N-acetylcysteine, azathioprine, or pirfenidone.

In vivo studies with the compounds of Formula I or pharmaceutically acceptable salts thereof may be used to assess the compounds' abilities to inhibit fibrosis in several skin sclerosis models. For instance, tight-skin mice, mice having skin fibrosis induced by bleomycin, and sclerodermatous chronic graft-versus-host disease-affected mice may serve as the study subjects for evaluating the test compounds. Skin fibrosis may be assessed by evaluating dermal thickening and hydroxyproline content, and by measuring the number of α-smooth muscle actin-positive myofibroblasts. Dees et al. in *Ann. Rheum. Dis.*, 74(8), pp. 1621-1625, 2015 discloses several of these models useful for assessing the compounds' antifibrotic properties.

The following examples are provided so that the invention might be more fully understood. Unless otherwise indicated, the starting materials are commercially available. They should not be construed as limiting the invention in any way.

Several methods for preparing the compounds used in this invention are described in the following Schemes and Examples. Starting materials and intermediates are purchased, made from known procedures, or as otherwise illustrated. Some frequently applied routes to the compounds of Formula S-I are also described by the Schemes as follows. In some cases the order of carrying out the steps of reaction schemes may be varied to facilitate the reaction or to avoid unwanted reaction products. The "R" and "X" groups in the Schemes correspond to the variables defined in Formula S-I at the same positions on the structures.

SCHEME 1

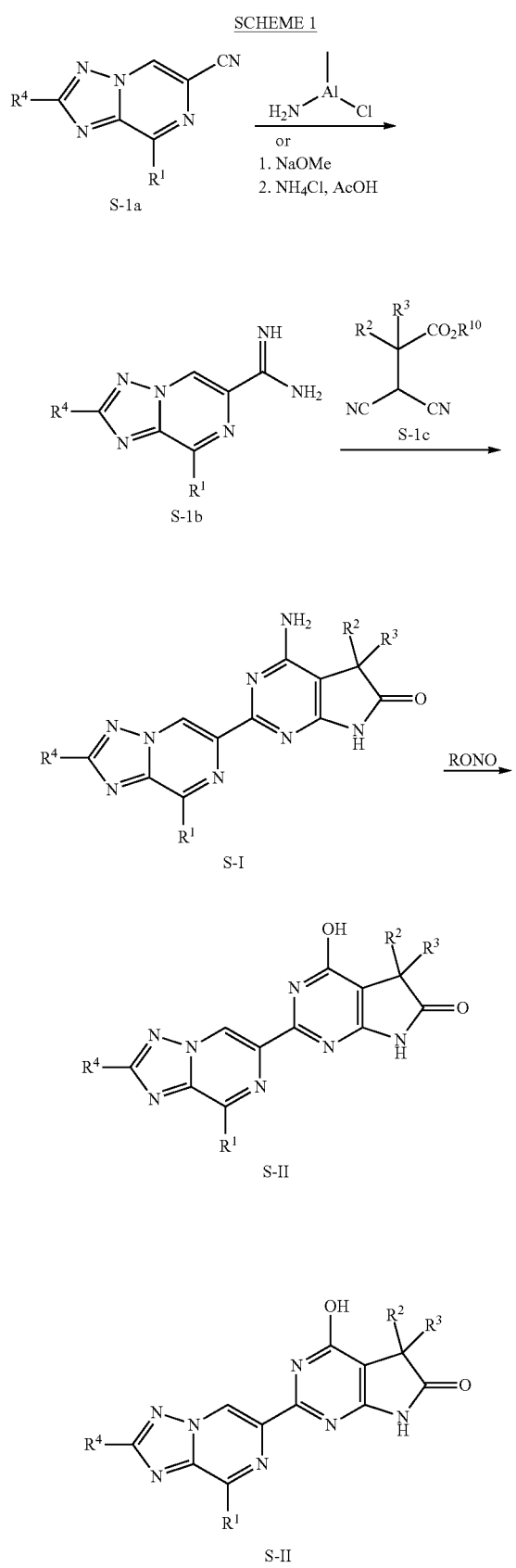

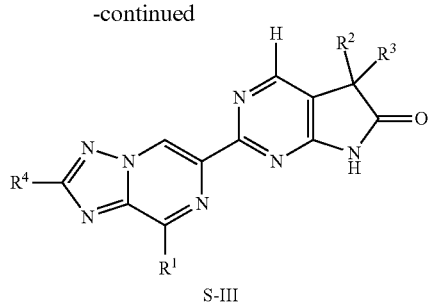

Compounds of Formula S-I, S-II and S-III can be prepared according to the sequence as depicted in Scheme 1. Conversion of the triazolo[1,5-a]pyrazine nitrile S-1a to the amidine intermediate S-1b can be accomplished with a reagent such as amino(chloro)methylaluminum, prepared from trimethylaluminum and NH$_4$Cl, in a non-polar solvent such as toluene at elevated temperature as described by Garigipati, R. S. et al *Tetrahedron Letters* 1990, 31, 1969. The nitrile S-1a can also be converted to the amidine S-1b by using NaOMe in MeOH to form the imidate, which can then be transformed to the amidine S-1b using NH$_4$Cl and acetic acid as described by Pinner, A. et al, *Ber. Dtsch. Chem. Ges.* 1877, 10, 1889. Treatment of the amidine S-1b with a suitable malononitrile intermediate S-1c in an alcoholic solvent, such as t-BuOH, and a suitable base such as NaHCO$_3$, KHCO$_3$, or Na$_2$CO$_3$ at elevated temperature provides compounds of Formula S-I. The reactions leading to compounds of Formula S-I in Scheme 1 may also be carried out using the corresponding methyl, ethyl, or propyl esters (R$^{10}$) of compound S-1c. Treatment of compounds of Formula S-I with a suitable diazotizing reagent such as tert-butyl nitrite, isopentyl nitrite, or sodium nitrite in a solvent such as 1,2-DCE, DMA, DMF, MeCN, or THF at elevated temperature provides compounds with Formula S-II and S-III. The ratio of S-II and S-III varies depending on the structure of Formula S-I and water content in the reaction.

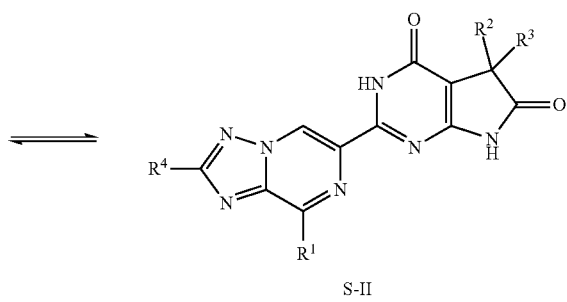

FIG. 1

Compounds of Formula S-II can be drawn in both tautomeric forms as shown in FIG. 1. Although the compounds are drawn in the alcohol form throughout, the compounds can also be drawn in the keto form. For example, Example 170A is drawn in the alcohol form. However, Example 170A could have been drawn in the keto form.

FIG. 2

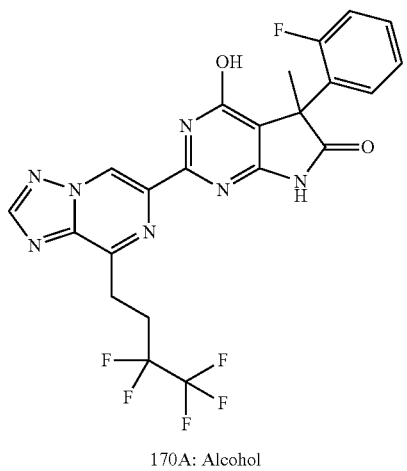

170A: Alcohol

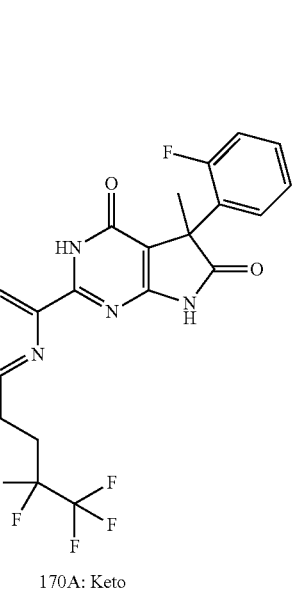

170A: Keto

SCHEME 2

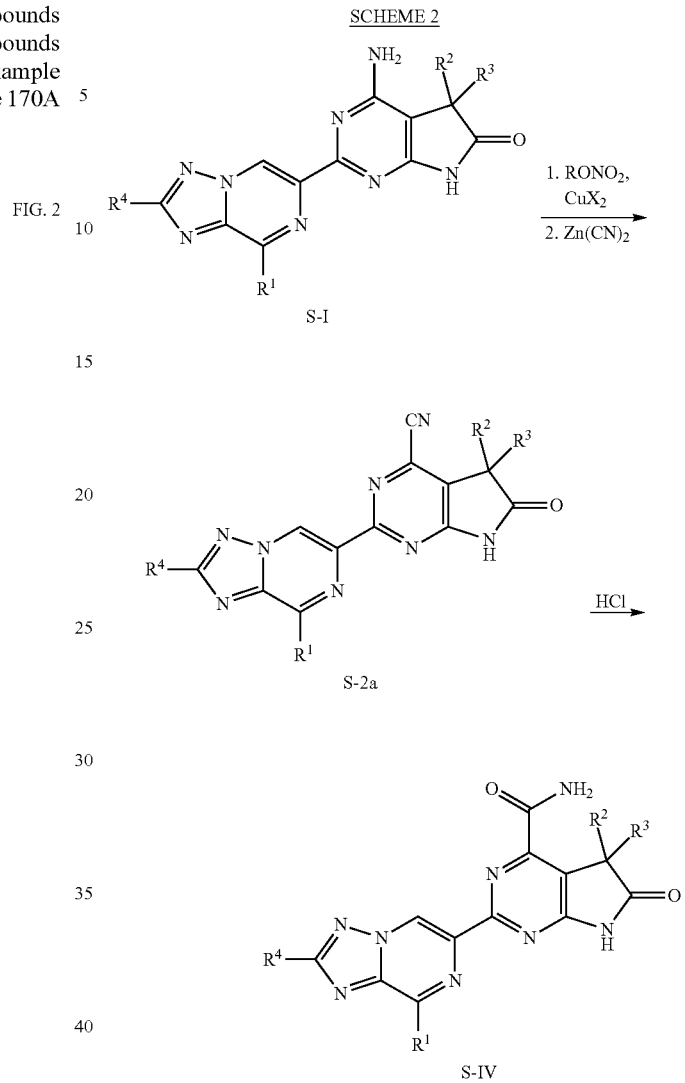

Compounds of Formula S-IV, can be prepared according to sequence as depicted in Scheme 2. Treatment of compounds of Formula S-I with a suitable diazotizing reagent such as tert-butyl nitrite, in presence of a copper (II) salt such as $CuCl_2$ or $CuBr_2$ can afford halogenated intermediate which can be transformed into the nitrile intermediate S-2a using $Zn(CN)_2$ and a palladium catalyst such as $Pd(dppf)Cl_2$ at an elevated temperature. Compounds of Formula S-IV can be obtained by the treatment of compound S-2a with an aq. HCl solution.

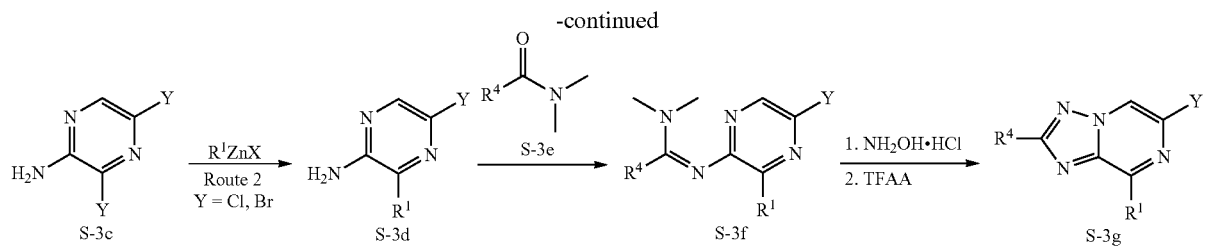

The nitrile intermediate S-1a can be prepared by two different routes as depicted in Scheme 3. In the first route 6,8-dibromo-[1,2,4]triazolo[1,5-a]pyrazine S-3a can be selectively coupled to an alkylzinc reagent, R¹ZnX, using a palladium catalyst such as Pd(PPh₃)₂Cl₂ to give compound S-3b, which can be transformed into the nitrile intermediate S-1a using Zn(CN)₂ and a palladium catalyst such as Pd(dppf)Cl₂ at an elevated temperature. Alternatively, nitrile intermediate S-1a can be obtained from 3,5-dihalopyrazin-2-amine S-3c such as 3,5-dichloropyrazin-2-amine or 3,5-dibromopyrazin-2-amine, via route 2. Treatment of S-3c with an alkylzinc reagent, R₁ZnX, using a palladium catalyst such as Pd(PPh₃)₂Cl₂ affords S-3d, which can be transformed into compound S-3f by condensation with amide S-3e. Treatment of compound S-3f with hydroxylamine hydrochloride followed by trifluoroacetic anhydride (TFAA) affords the triazolo[1,5-a]pyrazine S-3g. Compound S-3g can be transformed into the nitrile intermediate S-1a using Zn(CN)₂ and a palladium catalyst such as Pd(dppf)Cl₂ at an elevated temperature.

SCHEME 4

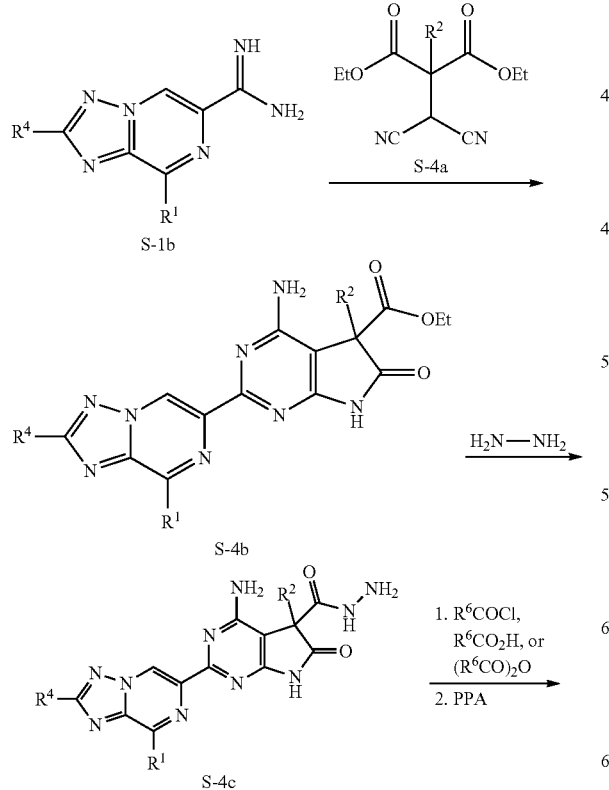

-continued

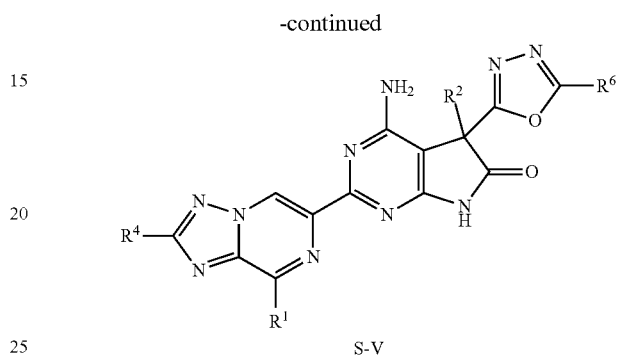

In one embodiment of the present invention, compounds with Formula S-V may be prepared by the sequence depicted in Scheme 4. The amidine intermediate S-1b from Scheme 1 can be cyclized with a suitable diester-malononitrile intermediate (S-4a) to afford compound S-4b. Treatment of the ester intermediate S-4b with hydrazine affords the acyl hydrazide intermediate S-4c, which can be acylated with a suitable acylating reagent bearing the desired R⁶ substitution and subsequently can be cyclized in the presence of a suitable condensing reagent such as polyphosphoric acid (PPA) to form a 1,3,4-oxadiazole Formula S-V.

SCHEME 5

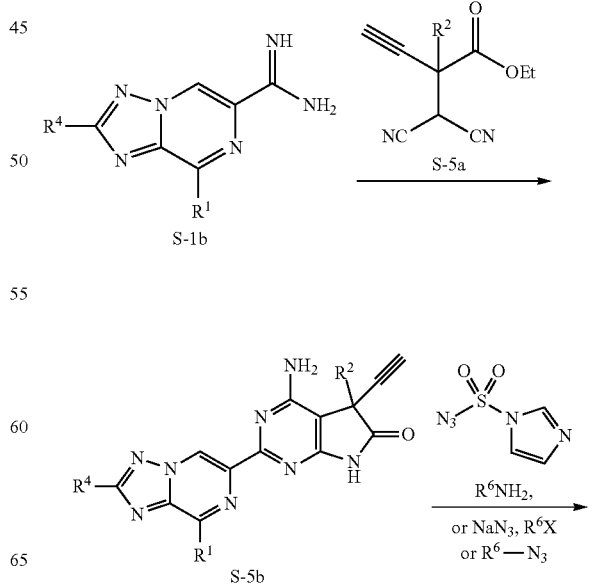

-continued

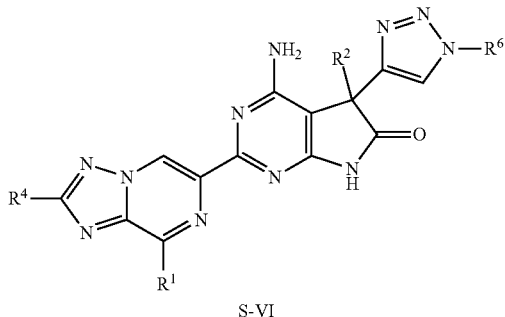

S-VI

In one embodiment of the present invention, compounds with Formula S-VI may be prepared by the sequence outlined in Scheme 5. The amidine intermediate S-1b from Scheme 1 can be treated with a suitable malononitrile reagent S-5a under similar conditions described for Scheme 1 to afford the alkyne intermediate S-5b. The alkyne intermediate S-5b can be further transformed into 1,2,3-triazoles with Formula S-VI by treatment with a suitable alkyl azide that is either commercially available or formed in situ from sodium azide and an alkyl bromide or an alkyl amine and imidazole-1-sulfonyl azide hydrochloride in the presence of a suitable copper source such as copper(II) sulfate.

SCHEME 6

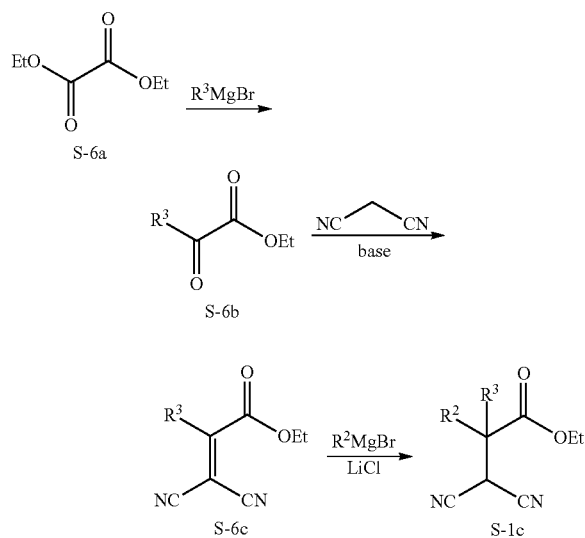

The preparation of compound S-1c is outlined in Scheme 6. Treatment of diethyl oxalate with a suitable aryl magnesium bromide (with or without LiCl additive) or the lithiate of heteroaryl reagents derived via metal-halogen exchange in a suitable solvent such as THF affords compound S-6b. Treatment of compound S-6b with malononitrile and a suitable base such as piperidine in a solvent such as EtOH at elevated temperature affords compound S-6c. Compound S-6c, upon treatment with a suitable alkyl magnesium bromide (with or without LiCl additive) in a solvent such as THF affords compound S-1c.

SCHEME 7

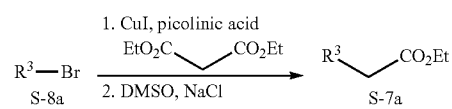

In addition to the method described in Scheme 6, intermediates S-1c, may also be prepared as shown in Scheme 7. Deprotonation of ester S-7a using a suitable base such as LiHMDS, NaHMDS, NaH or LDA in a solvent such as THF or DMF followed by treatment with an alkyl iodide affords the intermediate S-7b. Treatment of intermediate S-7b with a suitable brominating reagent such as NBS and AIBN in a solvent such as carbon tetrachloride at refluxing temperatures affords intermediate S-7c. Intermediate S-7c can be transformed to compound S-1c by reaction with malononitrile in the presence of a suitable base such as NaH, t-BuOK, $K_2CO_3$ or DBU in a solvent such as THF or DMF at RT or at elevated temperatures. The synthetic sequence depicted in Scheme 7 can be used to prepare the corresponding methyl, ethyl or propyl esters ($R^{10}$) of compound S-1c.

SCHEME 8

The ester S-7a can be prepared according to Scheme 8 from the corresponding carboxylic acid by one skilled in the art. The ester S-7a may also be prepared by the α-arylation/heteroarylation of esters as described by Buchwald, S. L. et al Organic Letters 2009, 11, 1773; or by Shen, H. C. et al Organic Letters 2006, 8, 1447. Commercially available aryl bromides S-8a can be converted to compound S-7a (depicted as the ethyl ester) by the reaction with diethyl malonate in the presence of a suitable catalyst system such as CuI and picolinic acid, followed by decarboxylation at elevated temperatures.

Compounds used in the present invention possess an asymmetric center at the carbon bearing the $R^2/R^3$ substituent which can be either R or S configuration. These enantiomeric mixtures may be separated or resolved to single enantiomers using methods familiar to those skilled in the art. For example, compounds used in the present invention may be resolved to the pure isomers by using chiral SFC chromatography. Racemic material can be resolved to enantiomerically pure compounds whenever possible and at any step in the route. Characterization data may be of the chiral or racemic material.

The independent synthesis of diastereomers and enantiomers or their chromatographic separations may be achieved using methods familiar to those skilled in the art and by appropriate modification of the methodology disclosed herein. Their absolute stereochemistry may be determined by X-ray crystallography of crystalline products or crystalline intermediates which are derivatized, if necessary, with a reagent containing an asymmetric center of known absolute stereochemistry, or by vibrational circular dichroism (VCD) spectroscopy.

Throughout the synthetic schemes and examples, abbreviations and acronyms may be used with the following meanings unless otherwise indicated:

AcOH=acetic acid; AIBN=2,2'-azobisisobutyronitrile; Anhydr.=Anhydrous; Aq.=aqueous; bp, b.p.=boiling point; br s=broad singlet; Bu=butyl; t-Bu=tert-butyl; BuLi=butyllithium; tBuOH, tert-BuOH=tert-butanol; tBuOK=potassium tert-butoxide; $CDCl_3$=deuterated chloroform; $CD_3OD$=Tetradeuteromethanol; CELITE=diatomaceous earth; $CF_3$=trifluoromethyl; cGMP=cyclic guanosine monophosphate; conc, conc.=concentrated, concentrate, concentrates; DBU=1,8-Diazabicyclo[4.3.0]undec-7-ene; DCM=dichloromethane; 1,2-DCE, DCE=1,2-dichloroethane; DIEA=diisopropylethylamine; DMA, DMAC=N,N-dimethylacetamide; DMF=N,N-dimethylformamide; DMF-DMA=N,N-Dimethylformamide dimethyl acetal; DMSO=dimethylsulfoxide; dppf=1,1'-bis(diphenylphosphino)ferrocene; EAB=egg albumin; EBSS=Earle's balanced salt solution; equiv, eq.=equivalent(s); Et=ethyl; $Et_3N$=triethylamine; EtOAc=ethyl acetate; EtOH=ethanol; GTP=guanosine triphosphate; h, hr=hour; HATU=1-[bis(dimethylamino)methylene]-1H-1,2,3-triazolo[4,5-b]pyridinium 3-oxid hexafluorophosphate; HCl=hydrogen chloride; HOBt=Hydroxybenzotriazole; HPLC=High pressure liquid chromatography; Int.=intermediate; iPr=isopropyl; IPA, i-PrOH=Isopropanol; LCMS, LC/MS=liquid chromatography-mass spectrometry; LDA=lithium diisopropylamide; LiHMDS, LHMDS=lithium bis(trimethylsilyl)amide; min, min.=minute; M=Molar; Me=methyl; MeCN=acetonitrile; MeI=methyl iodide; MeOH=methanol; mp, m.p.=melting point; mpk=milligrams per kilogram; N=Normal; $N_2$=nitrogen; NaOMe=sodium methoxide; NCS=N-chloro succinimide; NMP=N-methylpyrrolidone; NBS=N-bromo succinimide; NaHMDS=sodium bis(trimethylsilyl)amide; NMR=nuclear magnetic resonance; N.D.=not determined; PDA=photodiode array; Pd(dppf)$CL_2$=dichloro((1,1'-bis(diphenylphosphino)ferrocene) palladium (II); Pd(PPh$_3$)$_2$CL$_2$=dichlorobis(triphenylphosphine)palladium(II) or bis(triphenylphosphine) palladium (II) chloride; Pd$_2$(dba)$_3$=tris(dibenzylideneacetone)dipalladium (0); Ph=phenyl; PPA=polyphosphoric acid; Pr=propyl; psig=pounds per square inch gauge; PTFE=polytetrafluoroethylene; PTLC, prep TLC=preparative thin layer chromatography; PyBOP=(benzotriazol-1-yloxy) tripyrrolidinophosphonium hexafluorophosphate; rac=racemic; rt=retention time; RP-HPLC=reverse phase HPLC; RT=room temperature; sat., sat'd=saturated; SFC=supercritical fluid chromatography; sGC=soluble guanylate cyclase; TFA=trifluoroacetic acid; TFAA=trifluoroacetic anhydride; TLC=thin layer chromatography; THF=tetrahydrofuran; VCD=vibrational circular dichroism; v, v/v=volume, volume to volume; w, w/w=weight, weight to weight.

The following examples are provided to more fully illustrate the present invention, and shall not be construed as limiting the scope in any manner. Unless stated otherwise, the following conditions were employed. All operations were carried out at room or ambient temperature (RT), that is, at a temperature in the range 18-25° C. Reactions are generally done using commercially available anhydrous solvents under an inert atmosphere, either nitrogen or argon. Microwave reactions were done using a BIOTAGE Initiator™ or CEM EXPLORER® system. Evaporation of solvent was carried out using a rotary evaporator under reduced pressure (4.5-30 mmHg) with a bath temperature of up to 50° C. The course of reactions was followed by thin layer chromatography (TLC) and/or tandem high performance liquid chromatography (HPLC) followed by electron spray mass spectroscopy (MS), herein termed LCMS, and any reaction times are given for illustration only. The structure of all final compounds was assured by at least one of the following techniques: MS or proton nuclear magnetic resonance ($^1$H NMR) spectrometry, and the purity was assured by at least one of the following techniques: TLC or HPLC. $^1$H NMR spectra were recorded on either a Varian Unity or a Varian Inova instrument at 300, 400, 500 or 600 MHz using the indicated solvent. When line-listed, NMR data are in the form of delta values for major diagnostic protons, given in parts per million (ppm) relative to residual solvent peaks (multiplicity and number of hydrogens). Conventional abbreviations used for signal shape are: s. singlet; d. doublet (apparent); t. triplet (apparent); m. multiplet; br. broad; etc. MS data were recorded on a Waters Micromass unit, interfaced with a Hewlett-Packard (AGILENT 1100) HPLC instrument, and operating on MASSLYNX/OpenLynx software. Electrospray ionization was used with positive (ES+) or negative ion (ES-) detection; and diode array detection. Purification of compounds by preparative reverse phase HPLC was performed on a GILSON system using a YMC-Pack Pro C18 column (150×20 mm i.d.) eluting at 20 mL/min with a water/acetonitrile (0.1% TFA) gradient (typically 5% acetonitrile to 95% acetonitrile) using a SUNFIRE Prep C18 OBD 5 µM column (100×30 mm i.d.) eluting at 50 mL/min with a water/acetonitrile (0.1% TFA) gradient. Purification of compounds by preparative thin layer chromatography (PTLC) was conducted on 20×20 cm glass plates coated with silica gel, commercially available from Analtech; or E. Merck. Flash column chromatography was carried out on a glass silica gel column using Kieselgel 60, 0.063-0.200 mm ($SiO_2$), or on a BIOTAGE $SiO_2$ cartridge system using the BIOTAGE Horizon and BIOTAGE SP-1 systems; or a Teledyne Isco $SiO_2$ cartridge using the COMBIFLASH Rf system. Chemical symbols have their usual meanings, and the following abbreviations have also been used: h or hr (hours), min (minutes), v (volume), w (weight), b.p. (boiling point), m.p. (melting point), L (litre(s)), mL (millilitres), g (gram(s)), mg (milligrams(s)), mol (moles), mmol (millimoles), eq or equiv (equivalent(s)), µM (micromolar), nM (nanomolar), ca (circa/about).

The following are representative procedures for the preparation of intermediates used to prepare the final products described in the Examples that follow thereafter. These examples are provided for the purpose of further illustration only and are not intended to be limitations on the disclosed invention.

It is understood that a chiral center in a compound may exist in the "S" or "R" stereo-configurations, or as a mixture of both. In some of the examples for intermediate compounds and final compounds, such compounds having a racemic chiral center were separated into individual stereoisomers, for example, referred to as isomer A (or enantiomer A or the like), which refers to the observed faster eluting isomer, and isomer B (or enantiomer B or the like), which refers to the observed slower eluting isomer, and each such isomer may be noted in the example as either the fast or slow eluting isomer. When a single "A" or "B" isomer intermediate is used to prepare a downstream compound, the downstream compound may take the "A" or "B" designation that corresponds to the previously used intermediate.

Any Intermediates described below may be referred to herein by their number preceded by "I-." For illustration, the racemic parent title compound would be referred to as Intermediate 39 (I-39, or rac I-39), and the separated stereoisomers are noted as Intermediates 39A and 39B (or I-39A and I-39B). In some examples, compounds having a chiral center were derived synthetically from a single isomer intermediate; e.g., Example 63 was made using stereoisomer I-2A. Absolute stereochemistry (R or S) of each of the separated isomers was not determined, unless specifically described. An asterisk (*) may be used in a chemical structure drawing that indicates the location of a chiral center.

Absolute stereochemistry of separate stereoisomers in the Examples and Intermediates was not determined unless stated otherwise in an Example or Intermediate synthesis.

Intermediate 1, 1A and 1B and the S and R Isomers

Ethyl 3,3-dicyano-2-(4-fluorophenyl)-2-methylpropanoate

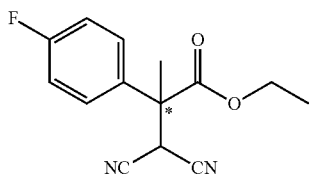 [SMILES: CCOC(=O)C(C)(c1ccc(F)cc1)C(C#N)C#N]

Step A—Ethyl 2-(4-fluorophenyl)-2-oxoacetate

Into a flask was placed a solution of diethyl oxalate (28.5 g, 195 mmol) in THF (300 mL) which was cooled at −78° C. 4-fluorophenylmagnesium bromide (150 mL, 1.0 M in THF) was added dropwise, and the resulting solution was stirred for 1.5 h with warming to RT. The reaction was quenched by the addition of sat. aq. NH$_4$Cl. The resulting solution was extracted with EtOAc (3×) and the organic layers were combined, dried over anhydr. Na$_2$SO$_4$, and filtered. The filtrate was conc. in vacuo to dryness. The residue was purified by silica gel chromatography with EtOAc:petroleum ether (1%) to afford the title compound.

Step B—Ethyl 3,3-dicyano-2-(4-fluorophenyl)acrylate

Into a flask was placed the intermediate from Step A (28.0 g, 143 mmol), malononitrile (37.7 g, 571 mmol), piperidine (2.5 mL), and EtOH (125 mL). The resulting solution was stirred at reflux for 16 h. Upon completion, the resulting mixture was conc. in vacuo. The residue was purified by silica gel chromatography with EtOAc:petroleum ether (10%) to afford the title compound.

Step C—Ethyl 3,3-dicyano-2-(4-fluorophenyl)-2-methylpropanoate

Into a flask was placed the intermediate from Step B (3.0 g, 12 mmol), THF (50 mL), and lithium chloride (1.0 g, 23.6 mmol) which was cooled at 0° C. Subsequently, methylmagnesium bromide (7 mL) was added dropwise, and the resulting solution was stirred for 1 h at 0° C. The reaction was then quenched by the addition of water. The resulting solution was extracted with EtOAc (2×). The organic layers were combined, dried over anhydr. Na$_2$SO$_4$, and filtered. The filtrate was conc. in vacuo to dryness. The residue was purified by silica gel chromatography with EtOAc:petroleum ether (25%) to afford the racemic title compound I-1. The racemic material was resolved using chiral SFC (OJ column) to afford isomers I-1A (faster eluting) and I-1B (slower eluting) of the title compound. $^1$H NMR (300 MHz, CDCl$_3$): δ 7.40-7.33 (2H, m), 7.17-7.09 (2H, m), 4.45 (1H, s), 4.30 (2H, q, J=7.2 Hz), 1.99 (3H, s), 1.26 (3H, t, J=7.2 Hz).

Using a similar procedure to that described in Intermediate 1, the following compounds in Table 1 were prepared using either commercial starting reagents or from compounds known in the literature.

TABLE 1

| Int | Chiral Resolution Column | R$_3$ | m/z (M + H) or $^1$H NMR |
|---|---|---|---|
| I-2A and 2B | CHIRALCEL OJ | —C$_6$H$_4$—Cl (para) | 275 [M − 1]$^-$ |
| I-3A and 3B | CHIRALPAK AD | —C$_6$H$_4$—CF$_3$ (para) | $^1$H NMR (400 MHz, DMSO-d$_6$): δ 7.89 (2H, d, J = 8.4 Hz), 7.67 (2H, d, J = 8.4 Hz) 5.83 (1H, s), 4.28 (2H, q, J = 7.2 Hz), 1.89 (3H, s), 1.19 (3H, t, J = 7.2 Hz) |

TABLE 1-continued

| Int | Chiral Resolution Column | $R_3$ | m/z (M + H) or $^1$H NMR |
|---|---|---|---|
| I-4A and B | CHIRALPAK AD | 2-F, 4-Cl phenyl | 293 [M − 1]⁻ |
| I-5A and B | CHIRALPAK AD | 2-F, 4-F phenyl | $^1$H NMR (300 MHz, CDCl$_3$): δ 7.31-7.12 (3H, m), 4.46 (1H, s), 4.31 (2H, q, J = 7.2 Hz), 1.99 (3H, s), 1.28 (3H, t, J = 7.2 Hz) |
| I-6A and B | PHENOMENEX LUX 5U CELLULOSE-3 | 2-Cl, 4-F phenyl | 293 [M − 1]⁻ |
| I-7A and B | CHIRALPAK IA | 3-F phenyl | $^1$H NMR (500 MHz, CDCl$_3$): δ 7.43 (1 H, td, J = 8.11, 5.97 Hz), 7.07-7.16 (3 H, m), 4.49 (1 H, s), 3.82 (3 H, s), 2.00 (3 H, s). |

Intermediate 8, 8A and 8B

Ethyl 3,3-dicyano-2-(5-fluoropyridin-2-yl)-2-Methylpropanoate and S and R Isomers Thereof

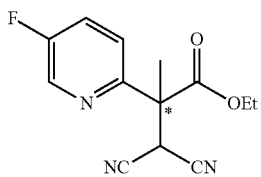 [SMILES: CCOC(=O)C(C)(c1ccc(F)cn1)C(C#N)C#N]

Step A—Diethyl 2-(5-fluoropyridin-2-yl)malonate

Into a flask was placed 2-bromo-5-fluoropyridine (20.0 g, 114 mmol), 1,3-diethyl propanedioate (54.5 g, 340 mmol), picolinic acid (5.6 g, 45 mmol), Cs$_2$CO$_3$ (143 g, 438 mmol), CuI (4.3 g, 23 mmol), and 1,4-dioxane (500 mL). The resulting solution was stirred for 12 h at 100° C. The mixture was quenched by the addition of water (300 mL). The resulting solution was extracted with EtOAc (2×), the organic layers combined and dried over anhydr. Na$_2$SO$_4$, and conc. in vacuo to dryness. The residue was purified by silica gel chromatography using EtOAc:petroleum ether (0-20%) to afford the title compound.

Step B—Ethyl 2-(5-fluoropyridin-2-yl)acetate

Into a flask was placed the intermediate from Step A (46 g, crude), NaCl (20 g, 342 mmol), water (6 mL), and DMSO (90 mL). The mixture was stirred for 3 h at 180° C. Upon completion, the resulting solution was diluted with EtOAc, washed with water (5×) and the organic layer was dried over anhydr. Na$_2$SO$_4$ and conc. in vacuo to dryness. The residue was purified by silica gel chromatography using EtOAc:petroleum ether (0-20%) to afford the title compound.

Step C—Ethyl 2-(5-fluoropyridin-2-yl)propanoate

Into a flask was placed THF (200 mL) and LiHMDS (45 mL, 1.0 M). This was followed by dropwise addition of the intermediate from Step B (7.5 g, 41 mmol) with stirring at 0° C. After stirring the resulting solution for 1 h, a solution of iodomethane (5.8 g, 41 mmol) in THF (10 mL) was added dropwise. The resulting solution was stirred for 3 h at 0° C. The reaction was then quenched by the addition of water. The resulting mixture was extracted with EtOAc (3×), the organic layers combined and dried over anhydr. Na$_2$SO$_4$, and conc. in vacuo to dryness. The residue was purified by silica gel chromatography using EtOAc:petroleum ether (0-20%) to afford the title compound.

Step D—Ethyl 2-bromo-2-(5-fluoropyridin-2-yl)propanoate

Into a flask was added the intermediate from Step C (1 g, 5 mmol) and THF (50 mL). This was followed by the addition of LiHMDS (5 mL, 1.0 M) dropwise with stirring at −78° C. The resulting solution was stirred for 30 min at −78° C. before NBS (1.2 g, 7.1 mmol) in THF (10 mL) was added, and the solution was warmed to RT and stirred for 1 h. The reaction was then quenched by the addition of water.

The resulting solution was extracted with EtOAc (3×) and the organic layers combined and dried over anhydr. Na$_2$SO$_4$. The solid was filtered and the filtrate was conc. in vacuo to dryness. The residue was purified by silica gel chromatography using EtOAc:petroleum ether (0-10%) to afford the title compound.

Step E—Ethyl 3,3-dicyano-2-(5-fluoropyridin-2-yl)-2-methylpropanoate

Into a flask was placed DMF (20 mL) and sodium hydride (260 mg, 6.50 mmol, 60%). This was followed by the addition of malononitrile (460 mg, 6.96 mmol) with stirring at 0° C. The resulting solution was stirred for 30 min at 0° C. To this was added the intermediate from Step D (950 mg, 3.44 mmol) in DMF dropwise with stirring at 0° C. The resulting solution was stirred for 1 h at RT. Upon completion, the resulting solution was quenched with water, and extracted with EtOAc. The organic layer was dried over anhydr. Na$_2$SO$_4$ and conc. in vacuo to dryness. The residue was purified by silica gel chromatography using EtOAc:petroleum ether (0-20%). The racemic material was resolved using a chiral SFC (IA column) to afford isomers I-8A (faster eluting) and I-8B (slower eluting) of the title compound. $^1$H NMR (300 MHz, CDCl$_3$): δ 8.45-8.44 (1H, dd, J=0.9, 2.4 Hz), 7.57-7.47 (2H, m), 5.17 (1H, s), 4.29-4.19 (2H, m), 2.00 (3H, s), 1.27-1.22 (3H, t, J=6.9 Hz).

Using a similar procedure for the preparation of Intermediate 8, the following intermediates in Table 2 were prepared.

TABLE 2

| Int. | Chiral Resolution Column | R$_3$ | R | m/z (M + H) or $^1$H NMR |
|---|---|---|---|---|
| I-9A and 9B | CHIRALPAK IA | 5-chloropyridin-2-yl | Et | 278.2 |
| I-10A and 10B | CHIRALPAK AD-H | 5-methoxypyridin-2-yl | Et | 274.0 |
| I-11A and 11B | CHIRALPAK AD | phenyl | Me | $^1$H NMR (500 MHz, CDCl$_3$): δ 7.44-7.42 (3H, m), 7.38-7.36 (2H, m), 4.50 (1H, s), 3.80 (3H, s), 2.00 (3H, s). |
| I-12A and 12B | CHIRALPAK OJ | 2-fluorophenyl | Et | 259 [M − 1]$^-$ |
| I-13A and 13B | CHIRALPAK IA | 5-(trifluoromethyl)pyridin-2-yl | Et | 312.0 |
| I-14A and 14B | CHIRALPAK IA | 5-methylpyridin-2-yl | Et | 258 |
| I-15A and 15B | CHIRALPAK AS | 5-cyanopyridin-2-yl | Et | 269.1 |
| I-16A and 16B | PHENO LUX CELLULOSE-2 | 4-fluorophenyl | Me | 247.1 |

Intermediate 17, 17A and 17B and the S and R Isomers Thereof

Ethyl 3,3-dicyano-2-methyl-2-(5-(trifluoromethyl) pyrimidin-2-yl)

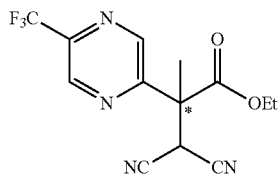 [SMILES: CCOC(=O)C(C)(c1cnc(C(F)(F)F)cn1)C(C#N)C#N]

Step A—Diethyl 2-(5-iodopyrazin-2-yl)malonate

To a flask was added 2-bromo-5-iodopyrazine (3.0 g, 10.53 mmol), diethyl malonate (3.5 g, 22.11 mmol), potassium carbonate (3.0 g, 21.59 mmol), and DMSO (20 mL). The resulting mixture was stirred for 16 h at 80° C., then cooled to RT and quenched by the addition of sat. aq. NH$_4$Cl. The mixture was extracted with EtOAc (3×). The organic layer was washed with brine, dried over anhydr. Na$_2$SO$_4$, and filtered. The filtrate was conc. in vacuo to dryness. The residue was purified by silica gel column chromatography with EtOAc:petroleum ether (10-20%) to afford the title compound.

Step B—Diethyl 2-(5-(trifluoromethyl)pyrazin-2-yl)malonate

To a flask, under an inert atmosphere of nitrogen, was added copper(I) iodide (6.15 g, 32.3 mmol), potassium fluoride (1.75 g, 30.1 mmol) (dried in vacuo at 200° C. for 30 min), trimethyl(trifluoromethyl)silane (3.45 g, 24.3 mmol), and N-methyl-2-pyrrolidinone (80 mL). The mixture was heated to 50° C. over 30 min and stirred for 5 min before diethyl 2-(5-iodopyrazin-2-yl)malonate (7.3 g, 14.0 mmol) in N-methyl-2-pyrrolidinone (10 mL) was added. The resulting mixture was stirred for 6 h at 50° C. The reaction mixture was cooled to RT and quenched by the addition of NH$_4$OH (10%). The mixture was extracted with EtOAc (3×). The organic layer was washed with NH$_4$OH (10%) and brine, dried over anhydr. Na$_2$SO$_4$, and filtered. The filtrate was conc. in vacuo. The residue was purified by silica gel column chromatography with EtOAc:petroleum ether (5-20%) to afford the title compound.

Step C—Synthesis of ethyl 2-(5-(trifluoromethyl)pyrazin-2-yl)acetate

To a flask, under an inert atmosphere of nitrogen, was added diethyl 2-(5-(trifluoromethyl)pyrazin-2-yl)malonate (3.8 g, 12.4 mmol), dimethyl sulfoxide (40 mL), water (0.34 mL, 18.6 mmol), and sodium chloride (1.09 mL, 18.6 mmol). The resulting mixture was stirred at 150° C. for 1 h, then allowed to cool down to RT. The resulting mixture was diluted with EtOAc, the organic layer was washed with brine (2×), dried over anhydr. Na$_2$SO$_4$, and filtered. The filtrate was conc. in vacuo. The residue was purified by silica gel column chromatography with EtOAc:petroleum ether (0-20%). The crude product was applied onto a C18 column with water:acetonitrile (with 0.05% ammonium bicarbonate) (30-70%). The residue was extracted with EtOAc (3×). The organic layer was dried over anhydr. Na$_2$SO$_4$, and filtered. The filtrate was conc. in vacuo, to afford the title compound.

Step D—Ethyl 2-(5-(trifluoromethyl)pyrazin-2-yl)propanoate

To a flask, under an inert atmosphere of nitrogen, was added ethyl 2-(5-(trifluoromethyl)pyrazin-2-yl)acetate (700 mg, 2.60 mmol) and THF (14 mL). The resulting mixture was cooled to 0° C., and bis(trimethylsilyl)amide (2.86 mL, 2.86 mmol) was added dropwise. The resulting mixture was stirred for 1 h at 0° C. before MeI (0.16 mL, 2.60 mmol) was added dropwise. The resulting mixture was stirred for 1 h at 0° C. then 3 h at RT. The reaction mixture was quenched by the addition of sat. aq. NH$_4$Cl. The mixture was extracted with EtOAc (3×). The organic layer was washed with brine, dried over anhydr. Na$_2$SO$_4$, and filtered. The filtrate was conc. in vacuo. The residue was purified by silica gel column chromatography with EtOAc:petroleum ether (0-10%) to afford the title compound.

Step E—Ethyl 2-bromo-2-(5-(trifluoromethyl) pyrazin-2-yl)propanoate

To a flask, under an inert atmosphere of nitrogen, was added ethyl 2-(5-(trifluoromethyl)pyrazin-2-yl)propanoate (280 mg, 0.98 mmol) and THF (8 mL). The resulting mixture was cooled to 0° C. and bis(trimethylsilyl)amide (1.47 mL, 1.47 mmol, 1.5 equiv) was added dropwise. The resulting mixture was stirred for 1 h at 0° C. before 1-bromopyrrolidine-2,5-dione (262 mg, 1.47 mmol) in THF (4 mL) RT and stirred for 1 h. The reaction mixture was quenched by the addition of sat. aq. NH$_4$Cl. The mixture was extracted with EtOAc (3×). The organic layer was washed with brine, dried over anhydr. Na$_2$SO$_4$, and filtered. The filtrate was conc. in vacuo. The residue was purified by silica gel column chromatography with EtOAc:petroleum ether (0-10%) to afford the title compound.

Step F—Ethyl 3,3-dicyano-2-methyl-2-(5-(trifluoromethyl)pyrazin-2-yl)propanoate To a flask, under an inert atmosphere of nitrogen, was added ethyl 2-bromo-2-(5-(trifluoromethyl)pyrazin-2-yl) propanoate (270 mg, 0.83 mmol), malononitrile (109 mg, 1.65 mmol), potassium carbonate (114 mg, 0.83 mmol) and DMSO (13 mL). The resulting mixture was stirred for 2 h at RT. The reaction mixture was quenched by the addition of water, extracted with EtOAc (3×). The organic layer was washed with brine, dried over anhydr. Na$_2$SO$_4$, and filtered. The filtrate was conc. in vacuo. The residue was purified by silica gel column chromatography with EtOAc:petroleum ether (0-20%) to afford the racemic title compound I-19. The racemic material was resolved using Chiral-Prep-HPLC (Chiralpak IA) to afford isomers I-17A (faster eluting) and I-17B (slower eluting). $^1$H NMR (400 MHz, DMSO-d$_6$) δ 9.32 (s, 1H), 9.23 (s, 1H), 5.88 (s, 1H), 4.25 (q, J=7.2 Hz, 2H), 1.96 (s, 3H), 1.18 (t, J=7.2 Hz, 3H); m/z=311 [M−1]$^-$.

Intermediate 18

Ethyl 3,3-dicyano-2-methyl-2-(5-(trifluoromethyl)pyrimidin-2-yl)propanoate

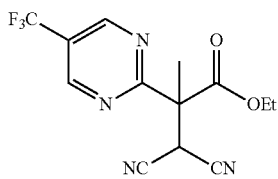 [SMILES: CCOC(=O)C(C)(c1ncc(C(F)(F)F)cn1)C(C#N)C#N]

Step A—N-(3-(dimethylamino)-2-(trifluoromethyl)allylidene)-N-methylmethanaminium hexafluorophosphate(V)

In a flask containing 3,3,3-trifluoropropanoic acid (7.4 g, 57.8 mmol) and DMF (37 mL) at 70° C. phosphoryl trichloride (26.6 g, 173.4 mmol) was added dropwise over 1 h. The resulting mixture was stirred at 70° C. for 1.5 h before the mixture was cooled to RT. The reaction mixture and a 5 N solution of NaOH (100 mL) were added concurrently into a mixture of 60% hydrogen hexafluorophosphate(V) (15.5 g, 63.7 mmol), a 5 N NaOH (18.5 mL) and water (67 mL) at a temperature below 10° C. The resulting mixture was aged for 1 h, filtered and washed with water. The filter cake was dried in vacuo below 40° C. to afford the title compound.

Step B—Ethyl 3-ethoxy-3-imino-2-methylpropanoate hydrochloride

In a flask containing ethyl 2-cyanopropanoate (10 g, 79 mmol) and EtOH (100 mL) at 0° C., was bubbled HCl (gas) for 30 min and the mixture was stirred at 0° C. for 4 h. The reaction mixture was conc. in vacuo at RT to afford the title compound.

Step C—Ethyl 3-amino-3-imino-2-methylpropanoate

In a flask containing ethyl 3-ethoxy-3-imino-2-methylpropanoate hydrochloride (7.0 g, 33.4 mmol) and EtOH (35 mL) at 0° C., was added a solution of ammonia in EtOH (22 mL, 3.34 N). The resulting mixture was stirred at 0° C. for 3 h then stirred for 16 h at RT. The reaction mixture was conc. in vacuo at RT to afford the title compound.

Step D—Ethyl 2-(5-(trifluoromethyl)pyrimidin-2-yl)propanoate

In a flask containing ethyl 3-amino-3-imino-2-methylpropanoate (2.0 g, 13.87 mmol), N-(3-(dimethylamino)-2-(trifluoromethyl)allylidene)-N-methylmethanaminium hexafluorophosphate(V) (4.7 g, 13.8 mmol) and acetonitrile (40 mL) was added triethylamine (2.81 g, 27.7 mmol). The resulting mixture was stirred at RT for 16 h. The reaction mixture was diluted with EtOAc, washed with brine (2×), the organic layer was dried over anhydr. $Na_2SO_4$, and filtered. The filtrate was conc. in vacuo. The residue was purified by silica gel column chromatography with EtOAc:petroleum ether (5-10%) to afford the title compound.

Step E—Ethyl 2-bromo-2-(5-(trifluoromethyl)pyrimidin-2-yl)propanoate

A flask, under an inert atmosphere of nitrogen, was charged with ethyl 2-(5-(trifluoromethyl)pyrimidin-2-yl)propanoate (1.0 g, 4.03 mmol) and THF (20 mL). To this was added lithium bis(trimethylsilyl)amide (4.83 mL, 4.83 mmol) dropwise at 0° C. The resulting mixture was stirred at RT for 30 min. Then the mixture was cooled to 0° C. and a solution of 1-bromopyrrolidine-2,5-dione (1.0 g, 5.64 mmol) in THF (10 mL) was added in one portion. The resulting mixture was stirred at RT for 1 h. The reaction mixture was quenched by the addition of sat. aq. $NH_4Cl$. The mixture was extracted with EtOAc (3×). The organic layer was washed with brine (2×), dried over anhydr. $Na_2SO_4$, and filtered. The filtrate was conc. in vacuo. The residue was purified by silica gel column chromatography with EtOAc:petroleum ether (5-10%) to afford the title compound.

Step F—Ethyl 3,3-dicyano-2-methyl-2-(5-(trifluoromethyl)pyrimidin-2-yl)propanoate To a flask containing ethyl 2-bromo-2-(5-(trifluoromethyl)pyrimidin-2-yl)propanoate (500 mg, 1.53 mmol), malononitrile (202 mg, 3.06 mmol), and DMSO (15 mL) was added potassium carbonate (215 mg, 1.56 mmol) in portions at RT during 1 h. The resulting mixture was stirred for 2 h at RT then quenched by the addition of sat. aq. $NH_4Cl$. The mixture was extracted with EtOAc (3×). The organic layer was washed with brine, dried over anhydr. $Na_2SO_4$, and filtered. The filtrate was conc. in vacuo. The residue was purified by silica gel column chromatography with EtOAc:petroleum ether (5-20%) to afford the title compound. $^1$H NMR ($CDCl_3$, 400 MHz): δ 9.07 (s, 2H), 5.02 (s, 1H), 4.31 (q, J=7.2 Hz, 2H), 2.08 (s, 3H), 1.28 (d, J=7.2 Hz, 3H); m/z=311 [M−1]$^-$.

Intermediate 19, 19A and 19B

Ethyl-2-(dicyanomethyl))-2-methylbut-3-ynoate and the S and R Isomers Thereof

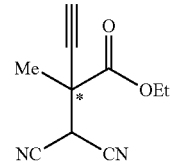

To a flask containing anhydr. LiCl (25.8 mg, 0.609 mmol) in THF (1 mL), was added a solution of ethynylmagnesium bromide (1.3 mL, 0.64 mmol, 0.5M in THF). The reaction was stirred at RT for 0.5 h. The resulting solution was then quickly added dropwise via syringe to a solution of ethyl 3,3-dicyano-2-methylprop-2-enoate (prepared according to Hagiware et. al. *Synthesis* 1974, 9, 669) (0.609 mL, 0.609 mmol, 1M solution in benzene) in THF (22.5 mL) at −10° C. The reaction was stirred for 10 min then quenched with sat. aq. $NH_4Cl$ and diluted with water and EtOAc. The layers were separated and the organic layer was dried over anhydr. $Na_2SO_4$, and conc. in vacuo to dryness. The residue was purified by silica gel chromatography using an EtOAc: hexanes gradient to afford the racemic title product 1-19. The racemic material was resolved using chiral SFC (OJ-H column) to afford isomers I-19A (faster eluting) and I-19B (slower eluting). $^1$H NMR (500 MHz, CDCl$_3$): δ 4.34 (2H, q, J=7.2 Hz), 4.31 (1H, s), 2.66 (1H, s), 1.80 (3H, s), 1.35 (3H, t, J=7.1 Hz).

Intermediate 20, 20A and 20B

Ethyl 3,3-dicyano-2-(5-(difluoromethyl)pyridin-2-yl)-2-methylpropanoate and the S and R Isomers Thereof

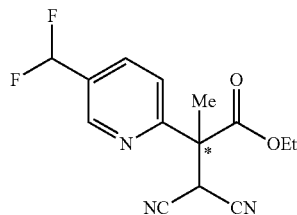 [SMILES: CCOC(=O)C(C)(c1ccc(C(F)F)cn1)C(C#N)C#N]

To a 3-necked flask, under an inert atmosphere of nitrogen, containing a solution of n-butyllithium (1.5 mL, 3.65 mmol) in toluene (25 mL), was added 2-bromo-5-(difluoromethyl)pyridine (760 mg, 3.65 mmol) in toluene (5 mL) dropwise at −78° C. After 30 min, ethyl 3,3-dicyano-2-methylprop-2-enoate (prepared according to Hagiware et. al. Synthesis 1974, 9, 669) (500 mg, 3.05 mmol) in THF (2 mL) was added in one portion at −78° C. The reaction was stirred for 1 h at −78° C., then quenched with sat. aq. NH$_4$Cl and diluted with water and EtOAc. The layers were separated and the organic layer was dried over anhydr. Na$_2$SO$_4$, and conc. in vacuo to dryness. The residue was purified by silica gel chromatography using an EtOAc/petroleum ether (10%-15%) gradient. The crude product was purified with C18 column with acetonitrile/water with 0.05% ammonium bicarbonate (30%-70%) to afford the racemic title product 20. The racemic material was resolved using Chiral-Prep-HPLC (Chiralpak IA) to afford isomers I-20A (faster eluting) and I-20B (slower eluting). $^1$H NMR (300 MHz, CDCl$_3$): δ 8.73 (s, 1H), 7.95 (d, J=8.4 Hz, 1H), 7.63 (d, J=8.4 Hz, 1H), 6.74 (t, J=55.5 Hz, 1H), 5.21 (s, 1H), 4.24 (q, J=7.2 Hz, 2H), 2.03 (s, 3H), 1.25 (t, J=7.2 Hz, 3H); m/z=292 [M−1]$^−$.

Using a similar procedure described for the synthesis of intermediate 19 and 20, the following compounds in Table 3 were prepared using either commercial starting reagents or from compounds known in the literature.

TABLE 3

| Int. | Chiral Resolution Column | R$_3$ | m/z (M + H) |
|---|---|---|---|
| I-21A and 21B | CHIRALPAK AS | 5-(2-cyclopropylpyridin-5-yl) | 284 |
| I-22A and 22B | CHIRALPAK IA | pyridin-2-yl | 243.9 |
| I-23 | Racemic | 5-(2-(1,1-difluoroethyl)pyridin-5-yl) | 308 |
| I-24A and 24B | CHIRALPAK AD | 5-fluoropyridin-3-yl | 262.2 |
| I-25 | Racemic | 6-(2-methyl-3-(trifluoromethyl)pyridin-6-yl) | 326.9 |

Intermediate 26, 26A and 26B

Ethyl 3,3-dicyano-2-(1-isopropyl-1H-1,2,3-triazol-4-yl)-2-methylpropanoate and the S and R Isomers Thereof

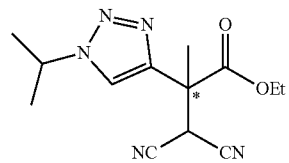 [SMILES: CCOC(=O)C(C)(c1cn(C(C)C)nn1)C(C#N)C#N]

A flask, under an inert atmosphere of nitrogen, was charged with ethyl-2-(dicyanomethyl))-2-methylbut-3-ynoate 1-19 (2 g, 10.32 mmol), bromotris(triphenylphosphine)copper(I) (0.192 g, 0.206 mmol) and DMSO (20 mL). To this was added 2-azidopropane (1.27 mL, 12.3 mmol) and the reaction was stirred at 50° C. for 18 h. The reaction mixture was diluted with EtOAc, and quenched by the addition of water. The mixture was extracted with EtOAc (3×). The organic layer was washed with brine (2×), dried over anhydr. magnesium sulfate, and filtered. The filtrate was conc. in vacuo. The residue was purified by silica gel column chromatography with EtOAc:hexane (0-50%) to afford the racemic title compound I-26. The racemic material was resolved using chiral SFC (CHIRALCEL ID) to afford isomers I-26A (faster eluting) and I-26B (slower eluting). $^1$H NMR (CHCl$_3$, 400 MHz): δ 7.66 (1H, s), 5.01 (1H, s), 4.88-4.83 (1H, m), 4.36-4.30 (2H, m), 1.99 (3H, s), 1.64 (6H, d, J=6.8 Hz), 1.34 (3H, t, J=7.1 Hz),). m/z 276.2 [M+H].

Intermediate 27, 27A and 27B and the S and R Isomers Thereof

Methyl 2-cyclopropyl-2-(dicyanomethyl)but-3-ynoate

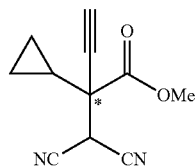

Step A—Methyl 3,3-dicyano-2-cyclopropylacrylate

A mixture of methyl 2-cyclopropyl-2-oxoacetate (prepared similarly to: Russian Chemical Bulletin 2007, 56, 1515-1521) (800 mg, 6.24 mmol) and malononitrile (516 mg, 7.80 mmol) was stirred for 2-3 min. A solution of beta-alanine (27.8 mg, 0.312 mmol) in water (540 µl) was added in small portions over ~5 min period. The reaction was cooled in an ice-bath and EtOH (350 µl) was added. The reaction was stirred at RT for 24 h. The reaction was diluted with water and extracted with ethyl ether. The ether layer was back extracted with water (2x). The organic layer was further diluted with EtOAc and dried over anhydr. $Na_2SO_4$. The combined organic layers were purified by silica gel column chromatography with EtOAc:hexanes (0-30%) to give the title compound.

Step B—Methyl 2-cyclopropyl-2-(dicyanomethyl)but-3-ynoate

To a flask containing anhydr. LiCl (144 mg, 3.41 mmol) in THF (2 mL) was added a solution of ethynylmagnesium bromide (6.8 mL, 3.41 mmol, 0.5 M in THF). The reaction was stirred at RT for 30 min. The resulting solution was cooled to −30° C. A solution of Methyl 3,3-dicyano-2-cyclopropylacrylate (0.500 g, 2.84 mmol) in THF (5 mL) was added. The reaction was stirred for 1 h in then raised to RT slowly. The mixture was quenched with sat. aq. $NH_4Cl$, and then diluted with water and EtOAc. The layers were separated and the organic layer was dried over anhydr. $Na_2SO_4$ and conc. in vacuo. Purification by silica gel column chromatography with EtOAc:hexanes (0-30%) gave the racemic title compound I-27. The racemic material was resolved using chiral SFC (CHIRALCEL OJ-H) to afford isomers I-27A (faster eluting) and I-27B (slower eluting). $^1$H NMR (500 MHz, $CDCl_3$): δ 4.41 (1H, s), 3.93 (3H, s), 2.63 (1H, s), 1.31-1.24 (1H, m), 1.03-0.96 (1H, m), 0.92-0.79 (2H, m), 0.77-0.67 (1H, m).

Intermediate 28, 28A and 28B and the S and R Isomers Thereof

Methyl 3,3-dicyano-2-cyclopropyl-2-(5-(trifluoromethyl)pyridin-2-yl)propanoate

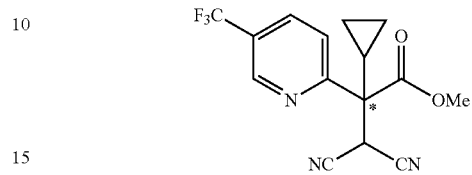

To a flask, under an inert atmosphere of nitrogen, was added toluene (300 mL) and n-butyl-lithium (14.8 mL, 36.9 mmol, 2.5M in hexane). 2-Bromo-5-(trifluoromethyl)pyridine (8.34 g, 36.9 mmol) in toluene (15 mL) was added dropwise with stirring at −78° C. The resulting mixture was stirred for 45 min at −78° C. To this was added Methyl 3,3-dicyano-2-cyclopropylacrylate (5 g, 28 mmol) in THF (20 mL). The resulting mixture was stirred for 0.5 h at −78° C. The reaction mixture was quenched by the addition of sat. aq. $NH_4Cl$. The mixture was extracted with EtOAc (3x). The organic layer was washed with brine, dried over anhydr. $Na_2SO_4$, and filtered. The filtrate was conc. in vacuo. The residue was purified by silica gel column chromatography with EtOAc:petroleum ether (5-30%). The major component was further purified by RP-HPLC with acetonitrile:water (0.3% ammonium bicarbonate) to afford the racemic title compound I-28. The racemic material was resolved using chiral SFC (CHIRALPAK AD-H) to afford isomers I-28A (faster eluting) and I-28B (slower eluting). $^1$H NMR (300 MHz, $CDCl_3$) (8.86 (s, 1H), 8.05 (dd, J=1.8, 8.4 Hz, 1H), 7.95 (d, J=8.4 Hz, 1H), 5.06 (s, 1H), 3.78 (s, 3H), 1.65-1.55 (m, 1H), 1.08-0.84 (m, 3H), 0.63-0.54 (m, 1H); m/z=322 [M−1]⁻.

Using a similar procedure to that described in Intermediates 27 & 28, the following compounds in Table 4 were prepared using either commercial starting reagents or from compounds known in the literature.

TABLE 4

| Int. | Chiral Resolution Column | $R_3$ | R | m/z (M + H) |
|---|---|---|---|---|
| I-29A and 29B | CHIRALPAK AS | 4-F-phenyl | Et | 285.0 [M − 1]⁻ |
| I-30A and 30B | CHIRALPAK IC | 4-Cl-phenyl | Et | 301.2 [M − 1]⁻ |

TABLE 4-continued

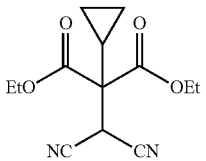

| Int. | Chiral Resolution Column | R₃ | R | m/z (M + H) |
|---|---|---|---|---|
| I-31A and 21B | CHIRALPAK OJ | 3-F, 4-Cl phenyl | Me | 305 [M − 1]⁻ |
| I-32A and 32B | CHIRALPAK OJ | 3-F, 4-F phenyl | Me | 289 [M − 1]⁻ |
| I-33A and 33B | CHIRALPAK OJ | 4-CF₃ phenyl | Me | 321 [M − 1]⁻ |
| I-34A and 34B | CHIRALPAK OJ | 5-F pyridin-2-yl | Me | 274 |
| I-35A and 35B | CHIRALPAK AD | 5-Cl pyridin-2-yl | Me | 290.1 |
| I-36A and 36B | CHIRALPAK OJ | 5-OMe pyridin-2-yl | Me | 286 |
| I-37 | Racemic | 5-Me pyridin-2-yl | Me | 270.0 |
| I-38 | Racemic | 5-CHF₂ pyridin-2-yl | Me | 304 [M − 1]⁻ |
| I-39A and 39B | CHIRALPAK AD | 5-F pyridin-3-yl | Me | 274.2 |
| I-40 | Racemic | 5-Me pyrazin-2-yl | Me | 268.9 [M − 1]⁻ |
| I-44 | Racemic | 5-CF₃ pyrazin-2-yl | Me | 322.9 [M − 1]⁻ |

Intermediate 41

Diethyl 2-cyclopropyl-2-(dicyanomethyl)malonate

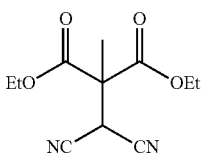

A THF (45.0 mL) solution of diethyl 2-(dicyanomethylene)malonate (prepared analogously to Sentman et. al. *J. Org. Chem.* 1982, 47, 4577) (4.50 mL, 4.50 mmol, 1M solution in benzene) was cooled to 0° C. and cyclopropylmagnesium bromide (9.00 mL, 4.50 mmol) and lithium chloride (0.191 g, 4.50 mmol) were added. The reaction was stirred at 0° C. for 2 hours and then warmed to RT while stirring for an additional 2 h. The reaction was diluted with EtOAc and quenched with sat. NH₄Cl. The layers were separated and the organic layer was dried over anhydr. MgSO₄, filtered, and conc. in vacuo to dryness. Purification by silica gel column chromatography using a EtOAc:hexanes gradient afforded the title compound. ¹H NMR (500 MHz, CDCl₃): δ 4.41 (1H, s), 4.38-4.26 (4H, m), 1.52-1.45 (1H, m), 1.33 (6H, t, J=7.1 Hz), 0.86-0.79 (2H, m), 0.71-0.66 (2H, m).

Intermediate 42

Diethyl 2-(dicyanomethyl)-2-methylmalonate

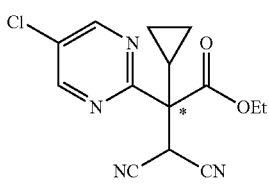 [SMILES: CCOC(=O)C(c1ncc(Cl)cn1)(C(C#N)C#N)C1CC1]

Using a similar procedure as described in intermediate 41, the following intermediate was prepared. ¹H NMR (500 MHz, CDCl₃): δ 4.55 (1H, s), 4.28-4.39 (4H, m), 1.82 (3H, s), 1.34 (6H, t, J=7.12 Hz).

Intermediate 43, 43A and 43B and the S and R Isomers Thereof

Ethyl 2-(5-chloropyrimidin-2-yl)-3,3-dicyano-2-cyclopropylpropanoate

Step A—Ethyl 2-cyano-2-cyclopropylacetate

To a flask, under an inert atmosphere of nitrogen, was added diethyl carbonate (29.1 g, 247 mmol), sodium hydride (15.3 g, 382 mmol), and toluene (80 mL). To this was added 2-cyclopropylacetonitrile (10 g, 123 mmol) in toluene (40 mL) dropwise with stirring at reflux, over a period of 30 min. The resulting mixture was stirred for 2 h at reflux, then cooled to 0° C. To this was added acetic acid (40 mL) dropwise at 0° C., followed by water (100 mL). The mixture was extracted with EtOAc (3×). The organic layer was washed with brine, dried over anhydr. Na$_2$SO$_4$, and filtered. The filtrate was conc. in vacuo and distillation at reduced pressure (86-90° C. at −10 mmHg) to afford the title compound.

Step B—Ethyl 2-cyclopropyl-3-imino-3-methoxypropanoate hydrochloride

In a flask containing ethyl 2-cyano-2-cyclopropylacetate (10.6 g, 69.2 mmol) and EtOH (100 mL) at 0° C. was introduced gaseous hydrogen chloride for 4 h. The reaction mixture was conc. in vacuo at RT to afford the title compound.

Step C—Ethyl 3-amino-2-cyclopropyl-3-iminopropanoate

In a flask containing ethyl 2-cyclopropyl-3-ethoxy-3-iminopropanoate hydrochloride (15.6 g, 66.2 mmol) and EtOH (50 mL) at 0° C. was added ammonia (70 mL, 206 mmol, 3 N). The resulting mixture was stirred for 3 h at 0° C., then stirred for 16 h at RT. The reaction mixture was conc. in vacuo at RT to afford the title compound.

Step D—Ethyl 2-(5-chloropyrimidin-2-yl)-2-cyclopropylacetate

To a flask, under an inert atmosphere of nitrogen, was added sodium (2.7 g, 117 mmol) and EtOH (200 mL), the resulting mixture was stirred for 1 h at RT. To this was added ethyl 3-amino-2-cyclopropyl-3-iminopropanoate (15.2 g, 62.5 mmol). The resulting mixture was stirred for 10 min at RT then cooled to 5° C. N-(2-chloro-3-(dimethylamino) allylidene)-N-methylmethanaminium hexafluorophosphate (V) (8.7 g, 28.4 mmol) (prepared according to Davis et. al. *Org. Synth.* 2003, 80, 200) was then added in portions over 45 min. The resulting mixture was stirred 2 h at RT. The reaction mixture was quenched by the addition of sat. aq. NH$_4$Cl. The mixture was extracted with EtOAc (3×). The organic layer was washed with brine, dried over anhydr. Na$_2$SO$_4$, and filtered. The filtrate was conc. in vacuo. The residue was purified by silica gel column chromatography with EtOAc:petroleum ether (5-10%) to afford the title compound.

Step E—Ethyl 2-bromo-2-(5-chloropyrimidin-2-yl)-2-cyclopropylacetate

A flask, under an inert atmosphere of nitrogen, was charged with ethyl 2-(5-chloropyrimidin-2-yl)-2-cyclopropylacetate (300 mg, 1.25 mmol) and THF (20 mL) and cooled to 0° C. To this was added lithium bis(trimethylsilyl)amide (1.50 mL, 1.50 mmol, 1M in THF) dropwise with stirring at 0° C. The resulting mixture was stirred for 1 h at 0° C. then NBS (333 mg, 1.87 mmol) was added and the mixture was allowed to stir for 2 h at RT. The reaction mixture was quenched by the addition of sat. aq. NH$_4$Cl. The mixture was extracted with EtOAc (3×). The organic layer was washed with brine, dried over anhydr. Na$_2$SO$_4$, and filtered. The filtrate was conc. in vacuo to dryness. The residue was purified by silica gel column chromatography with EtOAc:petroleum ether (0-10%) to afford the title compound.

Step F—Ethyl 2-(5-chloropyrimidin-2-yl)-3,3-dicyano-2-cyclopropylpropanoate

To a flask containing ethyl 2-bromo-2-(5-chloropyrimidin-2-yl)-2-cyclopropylacetate (250 mg, 0.78 mmol), malononitrile (258 mg, 3.91 mmol), and DMSO (10 mL) was added potassium carbonate (216 mg, 1.57 mmol) in portions at RT. The resulting mixture was stirred for 16 h at RT. The reaction mixture was quenched by the addition of sat. aq. NH$_4$Cl. The mixture was extracted with EtOAc (3×). The organic layer was washed with brine, dried over anhydr. Na$_2$SO$_4$, and filtered. The filtrate was conc. in vacuo to dryness. The residue was purified by silica gel column chromatography with EtOAc:petroleum ether (5-20%) to afford the racemic title compound I-43. The racemic material was resolved using Chiral-Prep-HPLC (CHIRALCEL OJ-H) to afford isomers I-43A (faster eluting) and I-43B (slower eluting). $^1$H NMR (400 MHz, CDCl$_3$) δ 8.76 (s, 2H), 4.78 (s, 1H), 4.36 (q, J=7.2 Hz, 2H), 1.81-1.75 (m, 1H), 1.31 (t, J=7.2 Hz, 3H), 0.72-0.75 (m, 2H), 0.57-0.44 (m, 2H); m/z=305 [M+1]$^+$

Intermediate A1

8-(4,4,4-Trifluorobutyl)-[1,2,4]triazolo[1,5-a]pyrazine-6-carboximidamide

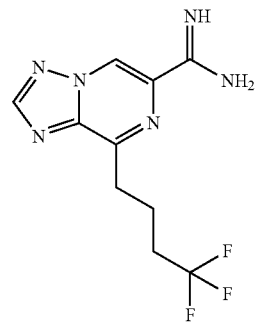 [SMILES: N=C(N)c1cn2ncnc2c(CCCC(F)(F)F)n1]

Step A—(4,4,4-Trifluorobutyl)zinc(II) bromide

Into a flask, under an inert atmosphere of nitrogen, was placed 1,1,1-trifluoro-4-iodobutane (6.7 g, 28 mmol), zinc metal (3.7 g, 56 mmol) and DMA (10 mL). This was followed by the dropwise addition of a solution of iodine (0.33 g, 1.3 mmol) in DMA (0.5 mL). The resulting mixture was stirred for 3 h at 80° C. The reaction was cooled and directly used in the next step.

Step B—6-Bromo-8-(4,4,4-trifluorobutyl)-[1,2,4]triazolo[1,5-a]pyrazine

Into a flask, under an inert atmosphere of nitrogen, was placed 6,8-dibromo-[1,2,4]triazolo[1,5-a]pyrazine (6.0 g, 22 mmol), Pd(PPh$_3$)$_2$Cl$_2$ (0.91 g, 1.3 mmol) and THF (80 mL). The resulting mixture was allowed to stir for 1 h at RT. The intermediate from Step A (11 mL, 28 mmol) was added and the resulting solution was stirred for 16 h at RT. The reaction was quenched by the addition of sat. aq. NH$_4$Cl. The resulting solution was extracted with EtOAc (3×) and the organic layers were combined, washed with brine, dried over anhydr. Na$_2$SO$_4$, and filtered. The filtrate was conc. in vacuo to dryness. The residue purified by silica gel chromatography with EtOAc:petroleum ether (0-20%) to afford the title compound.

Step C—8-(4,4,4-Trifluorobutyl)-[1,2,4]triazolo[1,5-a]pyrazine-6-carbonitrile Into a flask, under an inert atmosphere of nitrogen, was placed the intermediate from Step B (2.3 g, 7.4 mmol), zinc cyanide (1.14 g, 9.67 mmol), dppf (0.83 g, 1.5 mmol), Pd$_2$(dba)$_3$ (0.77 g, 0.74 mmol), zinc metal (0.243 g, 3.72 mmol) and DMF (25 mL). The resulting mixture was warmed at 120° C. for 1 h. The reaction was cooled to RT and quenched by the addition of water and EtOAc. The precipitate was filtered through CELITE and the filtrate was extracted with EtOAc (3×). The organic layers were combined, dried over anhydr. Na$_2$SO$_4$, filtered and the filtrate was conc. in vacuo to dryness. The residue was purified by silica gel chromatography with EtOAc:petroleum ether (5-25%) to afford the title compound.

Step D—8-(4,4,4-Trifluorobutyl)-[1,2,4]triazolo[1,5-a]pyrazine-6-carboximidamide Into a flask, under an inert atmosphere of nitrogen, was placed NH$_4$Cl (3.60 g, 67.3 mmol) and toluene (60 mL). This was followed by the dropwise addition of trimethyl aluminum (25.4 mL, 50.8 mmol, 2.0 M in toluene) with stirring at 0° C. The reaction was slowly warmed to RT over 1.5 h. To this was added a solution of the intermediate from Step C (1.62 g, 6.35 mmol) in toluene (10 mL). The resulting mixture was stirring for an additional 2 h at 100° C. The reaction mixture was cooled to 0° C., then quenched by the addition of MeOH:CH$_2$Cl$_2$ (1:1). The solid was filtered through CELITE and washed with MeOH:DCM (1:1). The combined filtrate was conc. in vacuo to dryness. The pH value was adjusted to 10 with NaOH (1 N). The resulting solution was extracted with EtOAc (3×), and the organic layers were combined, dried over anhydr. Na$_2$SO$_4$, filtered and the filtrate was conc. in vacuo to dryness to afford the title compound. $^1$H NMR (300 MHz, CDCl$_3$): δ 9.41 (1H, s), 8.50 (1H, s), 5.82 (3H, brs), 3.41 (2H, t, J=6.9 Hz), 2.34-2.21 (4H, m). m/z=309.0 (M+H).

Intermediate A2

8-(3,3,4,4,4-Pentafluorobutyl)-[1,2,4]triazolo[1,5-a]pyrazine-6-carboximidamide

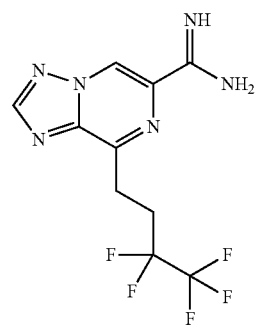 [SMILES: N=C(N)c1cn2ncnc2c(CCC(F)(F)C(F)(F)F)n1]

Step A—(3,3,4,4,4-Pentafluorobutyl)zinc(II) bromide

Into a flask, under an inert atmosphere of nitrogen, was placed 1,1,1,2,2-pentafluoro-4-iodobutane (21.7 g, 79 mmol), zinc metal (8.4 g, 128 mmol) and DMA (60 mL). This was followed by the dropwise addition of a solution of iodine (0.77 g, 3.05 mmol) in DMA (4 mL). The resulting mixture was stirred for 3 h at 80° C. The reaction was cooled and directly used in the next step.

Step B—5-Chloro-3-(3,3,4,4,4-pentafluorobutyl)pyrazin-2-amine

In a flask, under an inert atmosphere of argon, was added 3,5-dichloropyrazin-2-amine (10.0 g, 61.0 mmol) and Pd(PPh$_3$)$_2$Cl$_2$ (4.3 g, 6.1 mmol). The resulting mixture was allowed to stir for 1 h at RT. The intermediate from Step A (65 mL, 79 mmol) was added and the resulting solution was warmed at 45° C. for 3 h. The reaction was then quenched by the addition of sat. aq. NH$_4$Cl. The resulting solution was extracted with EtOAc (3×), and the organic layers combined, washed with brine, dried over anhydr. Na$_2$SO$_4$, and filtered. The filtrate was conc. in vacuo to dryness. The residue was purified RP-HPLC with acetonitrile:water (0.2% TFA) to afford the title compound.

Step C—N'-(5-Chloro-3-(3,3,4,4,4-pentafluorobutyl)pyrazin-2-yl)-N,N-dimethylformimidamide In a flask was placed the intermediate from Step B (3.0 g, 11 mmol), DMF-DMA (1.75 mL, 13.1 mmol) and EtOH (30 mL). The resulting mixture was warmed at 90° C. for 2 h. The resulting solution was conc. in vacuo to afford the title compound, which was used without further purification.

Step D—N-(5-Chloro-3-(3,3,4,4,4-pentafluorobutyl)pyrazin-2-yl)-N'-hydroxyformimidamide In a flask was placed the intermediate from Step C (3.5 g, 11 mmol), hydroxylamine hydrochloride (1.1 g, 15 mmol) and MeOH (20 mL). The resulting mixture was stirred at RT for 18 h. The precipitate was filtered, and the filtrate was conc. in vacuo. The residue was purified by silica gel chromatography with MeOH:DCM (10%) to afford the title compound.

Step E—6-Chloro-8-(3,3,4,4,4-pentafluorobutyl)-[1,2,4]triazolo[1,5-a]pyrazine In a flask, under an inert atmosphere of nitrogen, was placed the intermediate from Step D (2.5 g, 7.9 mmol), 2,2,2-trifluoroacetic anhydride (8.1 mL, 57 mmol) and toluene (12.5 mL). The resulting mixture was warmed at 90° C. for 2 h. The reaction was conc. in vacuo. Then sat. aq. NaHCO$_3$ was added to adjust the pH to 8. The resulting mixture was extracted with EtOAc (3×). The organic layers were combined, washed with brine, dried over anhydr. Na$_2$SO$_4$, filtered, and conc. in vacuo. The residue was purified by silica gel chromatography with EtOAc:petroleum ether (0-30%) to afford the title compound.

Step F—8-(3,3,4,4,4-Pentafluorobutyl)-[1,2,4]triazolo[1,5-a]pyrazine-6-carbonitrile Into a flask, under an inert atmosphere of nitrogen, was placed the intermediate from Step E (1.0 g, 3.3 mmol), Pd$_2$(dba)$_3$ (0.34 g, 0.33 mmol), dppf (0.37 g, 0.67 mmol), zinc cyanide (0.51 g, 4.32 mmol), zinc metal (0.11 g, 1.7 mmol) and DMF (15 mL). The resulting mixture was warmed at 120° C. for 5 h. The reaction was cooled to RT, quenched by the addition of brine and EtOAc and the precipitate was filtered. The filtrate was extracted with EtOAc (3×). The organic layers were combined, washed with brine, dried over anhydr. Na$_2$SO$_4$, filtered, and conc. in vacuo. The residue was purified by silica gel chromatography with EtOAc:petroleum ether (0-20%) to afford the title compound.

Step G—8-(3,3,4,4,4-Pentafluorobutyl)-[1,2,4]triazolo[1,5-a]pyrazine-6-carboximidamide In a flask, under an inert atmosphere of nitrogen, was placed NH$_4$Cl (1.46 g, 27.3 mmol) and toluene (20 mL). This was followed by the dropwise addition of trimethyl aluminum (14 mL, 2.0 M in toluene) at 0° C. The resulting mixture was stirred for 1 h at RT. To this was added the intermediate from Step F (750 mg, 2.58 mmol). The resulting mixture was warmed at 100° C. for 4 h. The reaction mixture was cooled to 0° C., and quenched by the addition of MeOH:DCM (1:1). The solid was filtered through CELITE. The eluent was conc. in vacuo. The residue was dissolved in EtOAc. The pH value of the solution was adjusted to pH 10 with NaOH (1 N). The resulting solution was extracted with EtOAc (3×), and the organic layers were combined, dried over anhydr. Na$_2$SO$_4$, filtered and the filtrate was conc. in vacuo to dryness to afford the title compound. $^1$H NMR (300 MHz, DMSO-d$_6$): δ 9.44 (1H, s), 8.80 (1H, s), 6.94 (2H, brs), 3.51 (2H, t, J=7.8 Hz), 3.08-2.90 (m, 2H). m/z=309.0 (M+H).

Intermediate A3

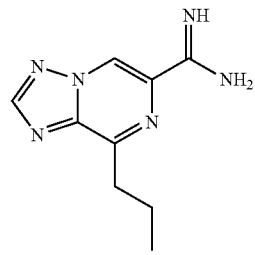

Step A—Propylzinc(II) iodide

Into a flask, under an inert atmosphere of nitrogen, was placed 1-iodopropane (10.9 g, 64.0 mmol), zinc metal (8.4 g, 128 mmol) and N,N-dimethylpropionamide (28 mL). This was followed by the dropwise addition of a solution of iodine (0.1 g, 0.43 mmol) in N,N-dimethylpropionamide (2 mL) at 0° C. The resulting mixture was stirred for 3 h at 80° C. The reaction was cooled and directly used in the next step.

Step B—5-chloro-3-propylpyrazin-2-amine

In a flask, under an inert atmosphere of argon, was added 3,5-dichloropyrazin-2-amine (7.0 g, 42.7 mmol), bis(triphenylphosphine)palladium(II) dichloride (3.0 g, 4.27 mmol) and THF (240 mL). The resulting mixture was allowed to stir for 1 h at RT. The intermediate from Step A (30 mL, 64 mmol) was added and the resulting solution was warmed at 35° C. for 2 days. The reaction was then quenched by the addition of brine. The resulting solution was extracted with EtOAc (3×) and the organic layers combined, washed with brine, dried over anhydr. Na$_2$SO$_4$, and filtered. The residue was purified by silica gel chromatography with EtOAc:petroleum ether (5-20%) to afford the title compound.

Step C—N'-(5-chloro-3-propylpyrazin-2-yl)-N,N-dimethylacetimidamide

In a flask was placed 5-chloro-3-propylpyrazin-2-amine (6.0 g, 35.0 mmol), 1,1-dimethoxy-N,N-dimethylethanamine (5.6 g, 42.0 mmol) and ethanol (60 mL). The resulting mixture was stirred for 3 h at 90° C. The ethanol was removed in vacuo. The residue was diluted with EtOAc, washed with brine, dried over anhydr. Na$_2$SO$_4$, filtered, and conc. in vacuo. The residue was purified by silica gel chromatography with EtOAc:petroleum ether (5-20%) to afford the title compound.

Step D—N-(5-chloro-3-propylpyrazin-2-yl)-N'-hydroxyacetimidamide

Into a flask was placed N'-(5-chloro-3-propylpyrazin-2-yl)-N,N-dimethylacetimidamide (6.4 g, 26.6 mmol), MeOH (60 mL) and hydroxylamine hydrochloride (2.7 g, 38.3 mmol). The resulting mixture was stirred for 16 h at RT, then conc. in vacuo to dryness. The residue was purified by silica gel chromatography with EtOAc:petroleum ether (5-30%) to afford the title compound.

Step E—6-chloro-2-methyl-8-propyl-[1,2,4]triazolo[1,5-a]pyrazine

Into a flask was placed N'-(5-chloro-3-propylpyrazin-2-yl)-N-hydroxyacetimidamide (6.0 g, 26.2 mmol), toluene (60 mL) and 2,2,2-trifluoroacetic anhydride (40.2 g, 192 mmol). The resulting mixture was stirred for 2 days at 90° C. The reaction was conc. in vacuo. Then sat. aq. Na$_2$HCO$_3$ was added to adjust the pH to 8. The resulting mixture was extracted with EtOAc (3×), and the organic layers combined, washed with brine, dried over anhydr. Na$_2$SO$_4$, and filtered. The residue was purified by silica gel chromatography with EtOAc:petroleum ether (5-30%) to afford the title compound.

Step F—Synthesis of 2-methyl-8-propyl-[1,2,4]triazolo[1,5-a]pyrazine-6-carbonitrile In a flask, under an inert atmosphere of argon, was added 6-chloro-2-methyl-8-propyl-[1,2,4]triazolo[1,5-a]pyrazine (4.6 g, 21.8 mmol), tris(dibenzylideneacetone)dipalladium-chloroform adduct (2.3 g, 2.18 mmol), 1,1'-bis(diphenylphosphino)ferrocene (2.4 g, 4.37 mmol), zinc metal (0.7 g, 10.92 mmol), zinc cyanide (3.3 g, 28.40 mmol) and DMA (50 mL). The resulting mixture was stirred for 6 h at 120° C. then cooled to RT and diluted with EtOAc (50 mL), MeOH (50 mL) and DCM (50 mL). The solid was filtered through CELITE. The combined filtrate was conc. in vacuo to dryness. The residue was dissolved in EtOAc, washed with brine, dried over anhydr. $Na_2SO_4$, and filtered. The residue was purified by silica gel chromatography with EtOAc:petroleum ether (15-60%) to afford the title compound.

Step G—2-methyl-8-propyl-[1,2,4]triazolo[1,5-a]pyrazine-6-carboximidamide

In a flask, under an inert atmosphere of argon, was added $NH_4Cl$ (11.0 g, 205 mmol) and toluene (200 mL), the resulting mixture was cooled to 0° C. and trimethyl aluminum (78 mL, 155 mmol) was added dropwise. The resulting mixture was stirred for 1 h at RT before 2-methyl-8-propyl-[1,2,4]triazolo[1,5-a]pyrazine-6-carbonitrile (3.9 g, 19.38 mmol) was added. The resulting mixture was stirred for additional 3 h at 100° C. then cooled to 0° C. and quenched by the addition of DCM:MeOH in a ratio of 1:1 (200 mL). The precipitate was removed by filtration through CELITE. The resulting filtrate was conc. in vacuo. The residue was dissolved in EtOAc. The pH value of the solution was adjusted to pH 10 with NaOH (1 N). The resulting solution was extracted with a mixture DCM:MeOH (10:1, 6×), and the organic layers were combined, dried over anhydr. $Na_2SO_4$, filtered and conc. in vacuo to dryness affording the title compound. $^1H$ NMR (300 MHz, DMSO-$d_6$) δ 9.27 (s, 1H), 6.90-6.72 (br, 3H), 3.15 (t, J=7.2 Hz, 2H), 2.57 (s, 3H), 1.94-1.84 (m, 2H), 0.98 (t, J=7.2 Hz, 3H); m/z=219.2 $[M+1]^+$.

Using a similar procedure to that described in Intermediate A1, A2 and A3, the following compounds in Table 5 were prepared using either commercial starting reagents or from compounds known in the literature.

TABLE 5

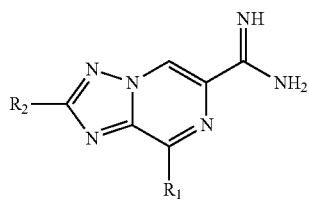

| Int. | $R_1$ | $R_2$ | m/z (M + H) |
|---|---|---|---|
| I-A4 | 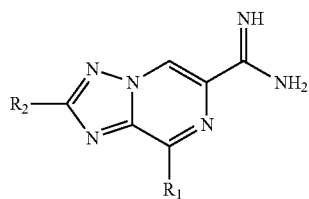 | H | 205 |
| I-A5 | | H | 219.2 |
| I-A6 | | H | 219.2 |
| I-A7 | | H | 259.0 |
| I-A8 | | H | 271.1 |
| I-A9 | | H | 283.1 |
| I-A10 | | Me | 285.1 |
| I-A11 | | Me | 323.0 |

Intermediate A12

[1,2,4]Triazolo[1,5-a]pyrazine-6-carboximidamide

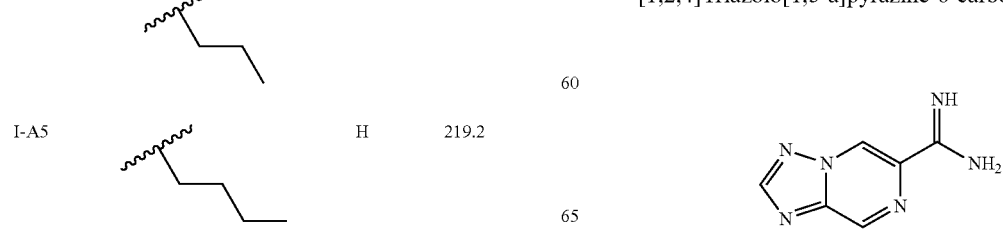

Step A—[1,2,4]triazolo[1,5-a]pyrazine-6-carbonitrile

Into a flask, under an inert atmosphere of nitrogen, was placed 6-bromo-[1,2,4]triazolo[1,5-a]pyrazine (1.0 g, 5.02 mmol), $Pd_2(dba)_3$ (460 mg, 0.50 mmol), dppf (557 mg, 1.00 mmol), zinc cyanide (649 mg, 5.53 mmol), zinc metal (164 mg, 2.51 mmol) and DMA (20 mL). The resulting mixture was warmed at 100° C. for 4 h. The reaction was cooled to RT, quenched by the addition of brine and EtOAc and the precipitate was filtered. The filtrate was extracted with EtOAc (3×). The organic layers were combined, washed with brine, dried over anhydr. $Na_2SO_4$, filtered, and conc. in vacuo. The residue was purified by silica gel chromatography with EtOAc:petroleum ether (0-50%) to afford the title compound.

Step-B—[1,2,4]Triazolo[1,5-a]pyrazine-6-carboximidamide

In a flask, under an inert atmosphere of nitrogen, was placed [1,2,4]triazolo[1,5-a]pyrazine-6-carbonitrile (440 mg, 3.03 mmol) and MeOH (10 mL). This was followed by the addition of NaOMe (30% in MeOH) (0.626 mL, 3.34 mmol) at RT. The resulting mixture was stirred for 2 h at RT. To this was added $NH_4Cl$ (178 mg, 3.34 mmol) and AcOH (1.73 mL, 30.3 mmol). The resulting mixture was warmed at 70° C. for 4 h. The reaction mixture was cooled to RT and was conc. in vacuo to dryness. The resulting solid was azeotroped with EtOAc and toluene to afford the title compound.

Example 1A (S)-4-Amino-5-(4-fluorophenyl)-5-methyl-2-(8-(3,3,4,4,4-pentafluorobutyl)-[1,2,4]triazolo[1,5-a]pyrazin-6-yl)-5H-pyrrolo[2,3-d]pyrimidin-6(7H)-one

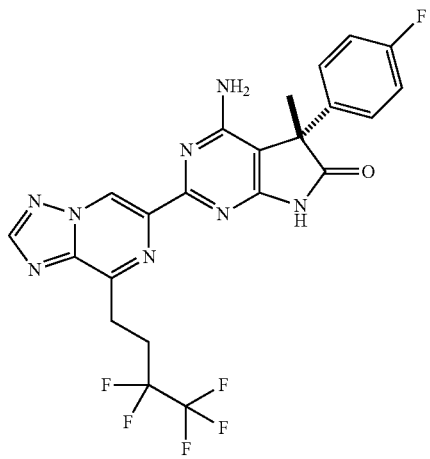 [SMILES: C[C@@]1(c2ccc(F)cc2)C(=O)Nc2nc(-c3cn4ncnc4c(CCC(F)(F)C(F)(F)F)n3)nc(N)c21]

Into a vial was placed I-A2 (50 mg, 0.16 mmol), I-1A (44 mg, 0.17 mmol), potassium bicarbonate (33 mg, 0.32 mmol) and t-BuOH (2 mL). The resulting mixture was warmed at 70° C. for 16 h. The reaction was cooled to RT and quenched by the addition of brine. The resulting solution was extracted with EtOAc (3×) and the organic layers were combined, dried over anhydr. $Na_2SO_4$, filtered and the filtrate was conc. in vacuo to dryness. The residue was purified by silica gel chromatography using MeOH:DCM (10%) to afford the title product. $^1$H NMR (300 MHz, DMSO-$d_6$): δ 11.26 (1H, brs), 9.44 (1H, s), 8.23 (1H, s), 7.30 (2H, dd, J=5.7, 9.0 Hz), 7.19 (2H, dd, J=9.0, 9.0 Hz), 6.66 (2H, brs), 3.55 (2H, t, J=7.8 Hz), 3.03-2.88 (2H, m), 1.80 (3H, s); m/z=523.4 (M+H).

Example 2A

4-Amino-5-cyclopropyl-2-(8-(4,4,4-trifluorobutyl)-[1,2,4]triazolo[1,5-a]pyrazin-6-yl)-5-(5-(trifluoromethyl)pyridin-2-yl)-5H-pyrrolo[2,3-d]pyrimidin-6(7H)-one

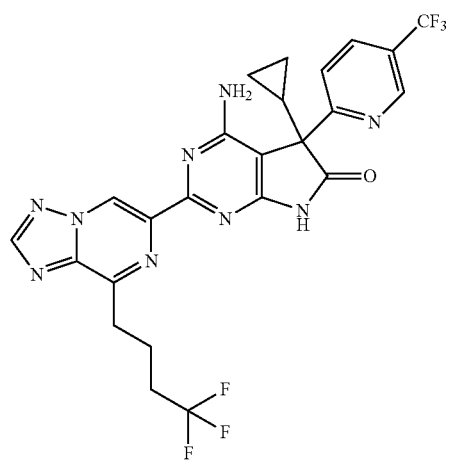 [SMILES: Nc1nc(-c2cn3ncnc3c(CCCC(F)(F)F)n2)nc2c1C(c1ccc(C(F)(F)F)cn1)(C1CC1)C(=O)N2]

Into a vial was placed I-A1 (50 mg, 0.18 mmol), I-28A (59 mg, 0.18 mmol), potassium bicarbonate (37 mg, 0.37 mmol), and t-BuOH (3 mL). The resulting mixture was warmed at 80° C. for 16 h. The reaction was cooled to RT and conc. to remove any volatiles. The residue was purified by silica gel chromatography using MeOH:DCM (1-3%) to afford the title product. $^1$H NMR (300 MHz, $CD_3OD$): δ 9.62 (1H, s), 8.92 (1H, s), 8.64 (1H, s), 8.22 (1H, dd, J=2.4, 8.4 Hz), 8.06 (1H, d, J=8.4 Hz), 3.42 (2H, t, J=7.8 Hz), 2.43-2.22 (4H, m), 2.03-1.98 (1H, m), 0.75-0.59 (4H, m); m z=564.3 (M+H).

Using essentially the same procedures described in Examples 1 & 2, the following compounds in Table 6 were prepared.

TABLE 6

| Ex | Structure | Name | MS (M + 1) | Chiral starting material |
|---|---|---|---|---|
| 3A | 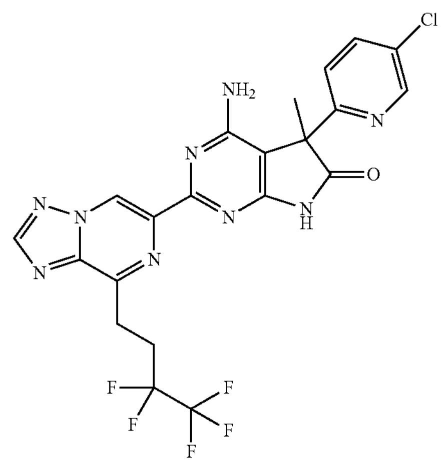 [SMILES: CC1(c2ccc(Cl)cn2)C(=O)Nc2nc(-c3cn4ncnc4c(CCC(F)(F)C(F)(F)F)n3)nc(N)c21] | 4-amino-5-(5-chloropyridin-2-yl)-5-methyl-2-(8-(3,3,4,4,4-pentafluorobutyl)-[1,2,4]triazolo[1,5-a]pyrazin-6-yl)-5H-pyrrolo[2,3-d]pyrimidin-6(7H)-one | 540.4 | I-9A |
| 4B | 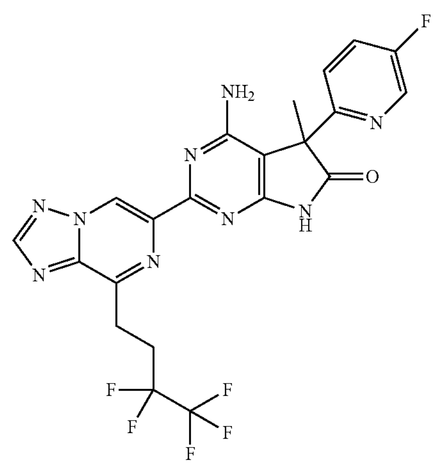 [SMILES: CC1(c2ccc(F)cn2)C(=O)Nc2nc(-c3cn4ncnc4c(CCC(F)(F)C(F)(F)F)n3)nc(N)c21] | 4-amino-5-(5-fluoropyridin-2-yl)-5-methyl-2-(8-(3,3,4,4,4-pentafluorobutyl)-[1,2,4]triazolo[1,5-a]pyrazin-6-yl)-5H-pyrrolo[2,3-d]pyrimidin-6(7H)-one | 524.2 | I-8B |
| 5B | 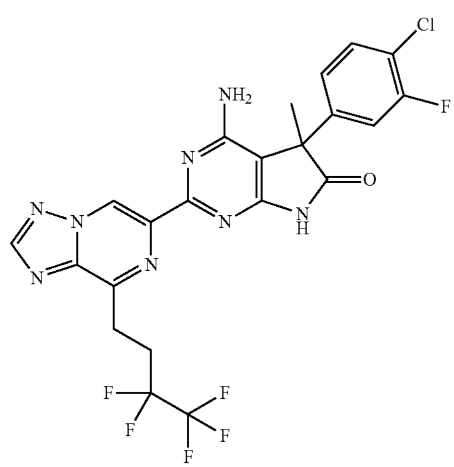 [SMILES: CC1(c2ccc(Cl)c(F)c2)C(=O)Nc2nc(-c3cn4ncnc4c(CCC(F)(F)C(F)(F)F)n3)nc(N)c21] | 4-amino-5-(4-chloro-3-fluorophenyl)-5-methyl-2-(8-(3,3,4,4,4-pentafluorobutyl)-[1,2,4]triazolo[1,5-a]pyrazin-6-yl)-5H-pyrrolo[2,3-d]pyrimidin-6(7H)-one | 557.3 | I-4B |

TABLE 6-continued

| Ex | Structure | Name | MS (M + 1) | Chiral starting material |
|---|---|---|---|---|
| 6A | 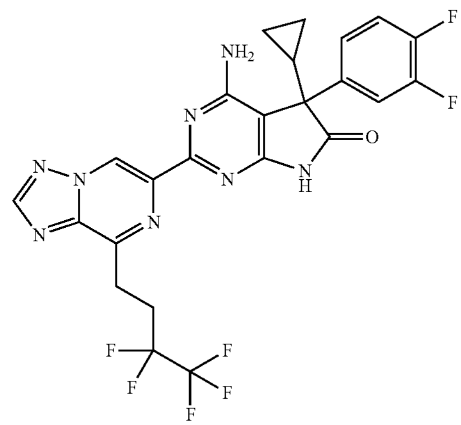 [SMILES: Nc1nc(-c2cn3ncnc3c(CCC(F)(F)C(F)(F)F)n2)nc2c1C(c1ccc(F)c(F)c1)(C1CC1)C(=O)N2] | 4-amino-5-cyclopropyl-5-(3,4-difluorophenyl)-2-(8-(3,3,4,4,4-pentafluorobutyl)-[1,2,4]triazolo[1,5-a]pyrazin-6-yl)-5H-pyrrolo[2,3-d]pyrimidin-6(7H)-one | 567.1 | I-32A |
| 7A | 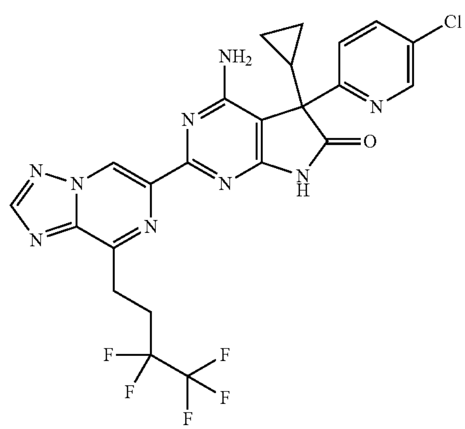 [SMILES: Nc1nc(-c2cn3ncnc3c(CCC(F)(F)C(F)(F)F)n2)nc2c1C(c1ccc(Cl)cn1)(C1CC1)C(=O)N2] | 4-amino-5-(5-chloropyridin-2-yl)-5-cyclopropyl-2-(8-(3,3,4,4,4-pentafluorobutyl)-[1,2,4]triazolo[1,5-a]pyrazin-6-yl)-5H-pyrrolo[2,3-d]pyrimidin-6(7H)-one | 566.3 | I-35A |
| 8B | 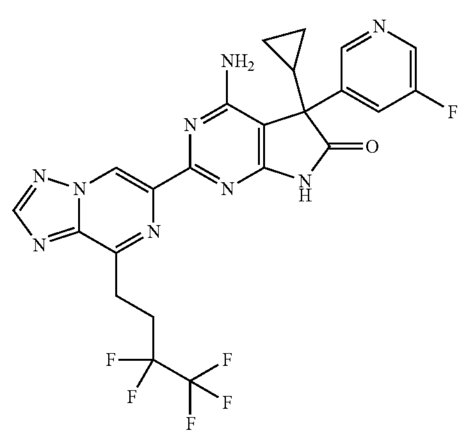 [SMILES: Nc1nc(-c2cn3ncnc3c(CCC(F)(F)C(F)(F)F)n2)nc2c1C(c1cncc(F)c1)(C1CC1)C(=O)N2] | 4-amino-5-cyclopropyl-5-(5-fluoropyridin-3-yl)-2-(8-(3,3,4,4,4-pentafluorobutyl)-[1,2,4]triazolo[1,5-a]pyrazin-6-yl)-5H-pyrrolo[2,3-d]pyrimidin-6(7H)-one | 550.1 | I-39B |

TABLE 6-continued

| Ex | Structure | Name | MS (M + 1) | Chiral starting material |
|---|---|---|---|---|
| 9A | 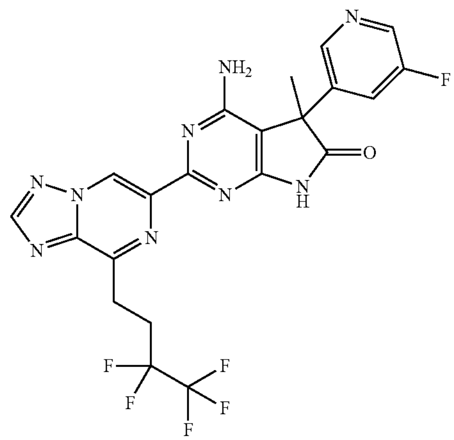 [SMILES: CC1(c2cncc(F)c2)C(=O)Nc2nc(-c3cn4ncnc4c(CCC(F)(F)C(F)(F)F)n3)nc(N)c21] | 4-amino-5-(5-fluoropyridin-3-yl)-5-methyl-2-(8-(3,3,4,4,4-pentafluorobutyl)-[1,2,4]triazolo[1,5-a]pyrazin-6-yl)-5H-pyrrolo[2,3-d]pyrimidin-6(7H)-one | 524.1 | I-24A |
| 10A | 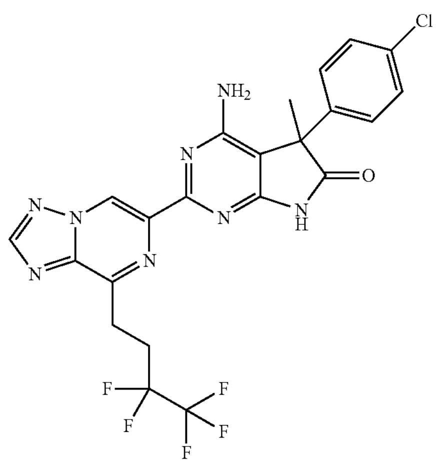 [SMILES: CC1(c2ccc(Cl)cc2)C(=O)Nc2nc(-c3cn4ncnc4c(CCC(F)(F)C(F)(F)F)n3)nc(N)c21] | 4-amino-5-(4-chlorophenyl)-5-methyl-2-(8-(3,3,4,4,4-pentafluorobutyl)-[1,2,4]triazolo[1,5-a]pyrazin-6-yl)-5H-pyrrolo[2,3-d]pyrimidin-6(7H)-one | 539.1 | I-2A |
| 11B | 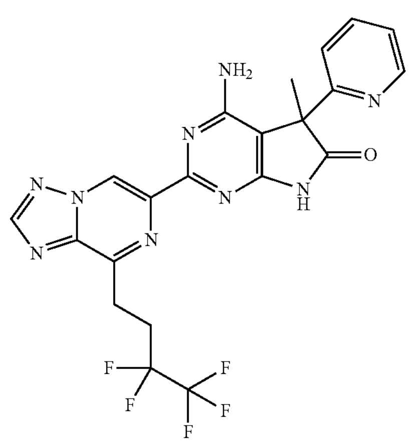 [SMILES: CC1(c2ccccn2)C(=O)Nc2nc(-c3cn4ncnc4c(CCC(F)(F)C(F)(F)F)n3)nc(N)c21] | 4-amino-5-methyl-2-(8-(3,3,4,4,4-pentafluorobutyl)-[1,2,4]triazolo[1,5-a]pyrazin-6-yl)-5-(pyridin-2-yl)-5H-pyrrolo[2,3-d]pyrimidin-6(7H)-one | 506.3 | I-22B |

TABLE 6-continued

| Ex | Structure | Name | MS (M + 1) | Chiral starting material |
|---|---|---|---|---|
| 12B | 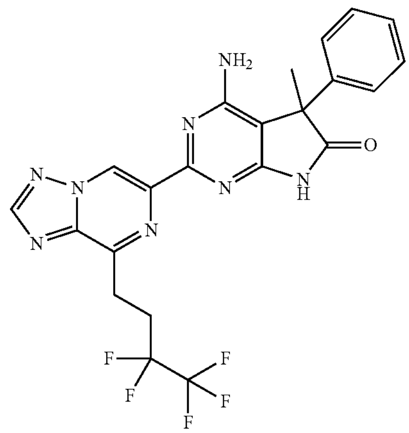 [SMILES: CC1(c2ccccc2)C(=O)Nc2nc(-c3cn4ncnc4c(CCC(F)(F)C(F)(F)F)n3)nc(N)c21] | 4-amino-5-methyl-2-(8-(3,3,4,4,4-pentafluorobutyl)-[1,2,4]triazolo[1,5-a]pyrazin-6-yl)-5-phenyl-5H-pyrrolo[2,3-d]pyrimidin-6(7H)-one | 505.0 | I-11B |
| 13B | 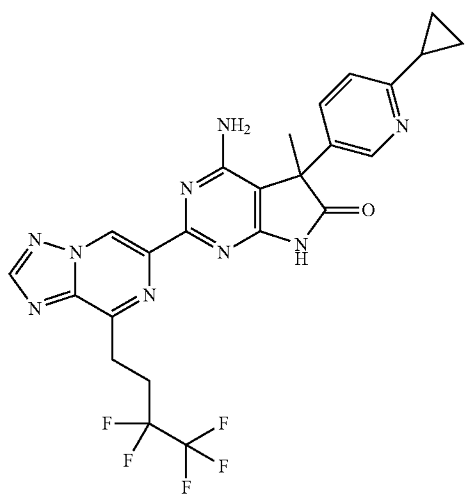 [SMILES: CC1(c2ccc(C3CC3)nc2)C(=O)Nc2nc(-c3cn4ncnc4c(CCC(F)(F)C(F)(F)F)n3)nc(N)c21] | 4-amino-5-(6-cyclopropylpyridin-3-yl)-5-methyl-2-(8-(3,3,4,4,4-pentafluorobutyl)-[1,2,4]triazolo[1,5-a]pyrazin-6-yl)-5H-pyrrolo[2,3-d]pyrimidin-6(7H)-one | 546.3 | I-21B |
| 14B | 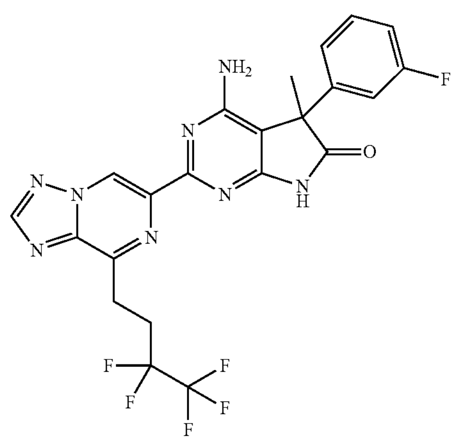 [SMILES: CC1(c2cccc(F)c2)C(=O)Nc2nc(-c3cn4ncnc4c(CCC(F)(F)C(F)(F)F)n3)nc(N)c21] | 4-amino-5-(3-fluorophenyl)-5-methyl-2-(8-(3,3,4,4,4-pentafluorobutyl)-[1,2,4]triazolo[1,5-a]pyrazin-6-yl)-5H-pyrrolo[2,3-d]pyrimidin-6(7H)-one | 523.2 | I-7B |

TABLE 6-continued

| Ex | Structure | Name | MS (M + 1) | Chiral starting material |
|---|---|---|---|---|
| 15A | 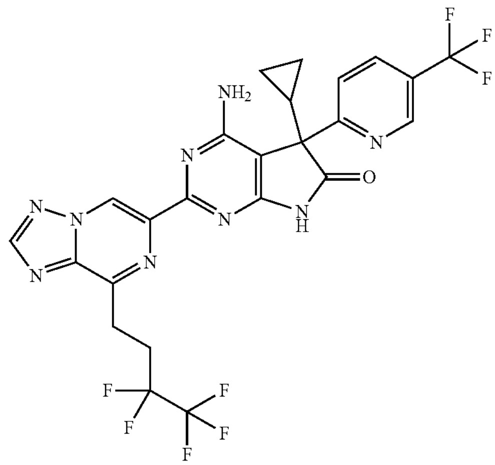 [SMILES: Nc1nc(-c2cn3ncnc3c(CCC(F)(F)C(F)(F)F)n2)nc2c1C(c1ccc(C(F)(F)F)cn1)(C1CC1)C(=O)N2] | 4-amino-5-cyclopropyl-2-(8-(3,3,4,4,4-pentafluorobutyl)-[1,2,4]triazolo[1,5-a]pyrazin-6-yl)-5-(5-(trifluoromethyl)pyridin-2-yl)-5H-pyrrolo[2,3-d]pyrimidin-6(7H)-one | 600.3 | I-28A |
| 16B | 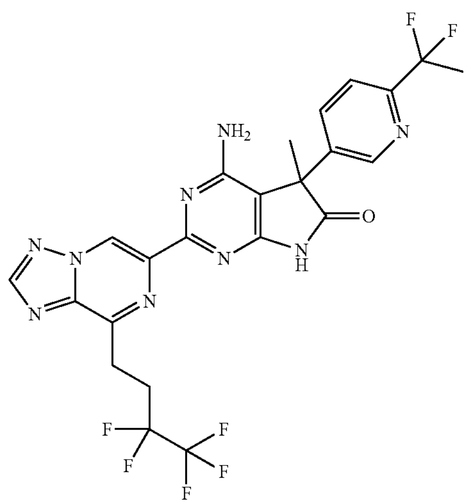 [SMILES: CC(F)(F)c1ccc(C2(C)C(=O)Nc3nc(-c4cn5ncnc5c(CCC(F)(F)C(F)(F)F)n4)nc(N)c32)cn1] | 4-amino-5-(6-(1,1-difluoroethyl)pyridin-3-yl)-5-methyl-2-(8-(3,3,4,4,4-pentafluorobutyl)-[1,2,4]triazolo[1,5-a]pyrazin-6-yl)-5H-pyrrolo[2,3-d]pyrimidin-6(7H)-one (slow eluting) | 570.3 | CHIRAL PAK IB (Rac-I-23) |
| 17B | 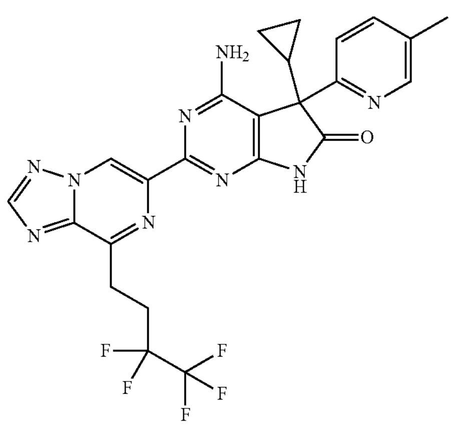 [SMILES: Cc1ccc(C2(C3CC3)C(=O)Nc3nc(-c4cn5ncnc5c(CCC(F)(F)C(F)(F)F)n4)nc(N)c32)nc1] | 4-amino-5-cyclopropyl-5-(5-methylpyridin-2-yl)-2-(8-(3,3,4,4,4-pentafluorobutyl)-[1,2,4]triazolo[1,5-a]pyrazin-6-yl)-5H-pyrrolo[2,3-d]pyrimidin-6(7H)-one (slow eluting) | 546.2 | CHIRAL PAK IC (Rac-I-37) |

TABLE 6-continued

| Ex | Structure | Name | MS (M + 1) | Chiral starting material |
|---|---|---|---|---|
| 18A | 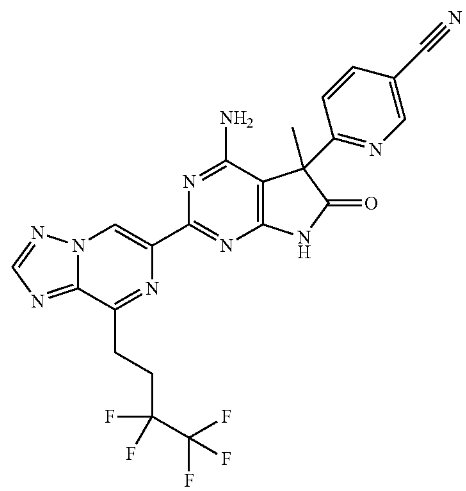 [SMILES: CC1(c2ccc(C#N)cn2)C(=O)Nc2nc(-c3cn4ncnc4c(CCC(F)(F)C(F)(F)F)n3)nc(N)c21] | 6-(4-amino-5-methyl-6-oxo-2-(8-(3,3,4,4,4-pentafluorobutyl)-[1,2,4]triazolo[1,5-a]pyrazin-6-yl)-6,7-dihydro-5H-pyrrolo[2,3-d)]pyrimidin-5-yl)nicotinonitrile | 531.3 | I-15A |
| 19B | 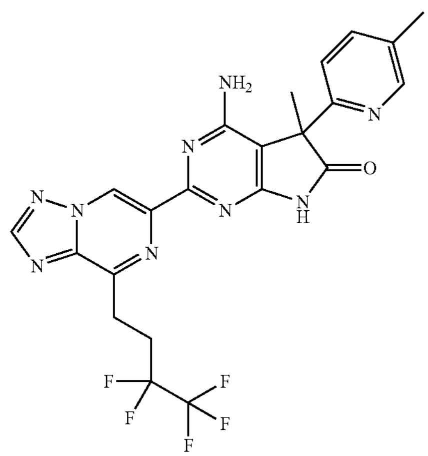 [SMILES: Cc1ccc(C2(C)C(=O)Nc3nc(-c4cn5ncnc5c(CCC(F)(F)C(F)(F)F)n4)nc(N)c32)nc1] | 4-amino-5-methyl-5-(5-methylpyridin-2-yl)-2-(8-(3,3,4,4,4-pentafluorobutyl)-[1,2,4]triazolo[1,5-a]pyrazin-6-yl)-5H-pyrrolo[2,3-d]pyrimidin-6(7H)-one | 520.2 | I-14B |
| 20A | 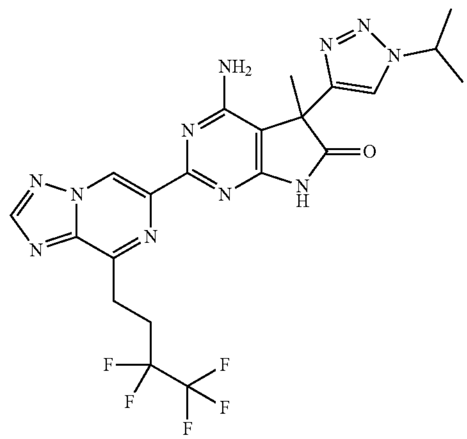 [SMILES: CC(C)n1cc(C2(C)C(=O)Nc3nc(-c4cn5ncnc5c(CCC(F)(F)C(F)(F)F)n4)nc(N)c32)nn1] | 4-amino-5-(1-isopropyl-1H-1,2,3-triazol-4-yl)-5-methyl-2-(8-(3,3,4,4,4-pentafluorobutyl)-[1,2,4]triazolo[1,5-a]pyrazin-6-yl)-5H-pyrrolo[2,3-d]pyrimidin-6(7H)-one | 538.1 | I-26A |

TABLE 6-continued

| Ex | Structure | Name | MS (M + 1) | Chiral starting material |
|---|---|---|---|---|
| 21B | 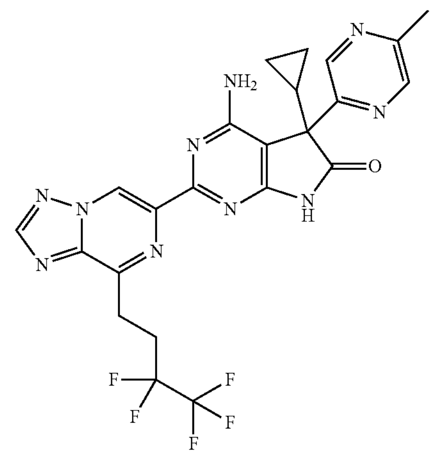 [SMILES: Cc1cnc(C2(C3CC3)C(=O)Nc3nc(-c4cn5ncnc5c(CCC(F)(F)C(F)(F)F)n4)nc(N)c32)cn1] | 4-amino-5-cyclopropyl-5-(5-methylpyrazin-2-yl)-2-(8-(3,3,4,4,4-pentafluorobutyl)-[1,2,4]triazolo[1,5-a]pyrazin-6-yl)-5H-pyrrolo[2,3-d]pyrimidin-6(7H)-one (slow eluting) | 547.3 | CHIRAL PAK IB (rac I-40) |
| 22B | 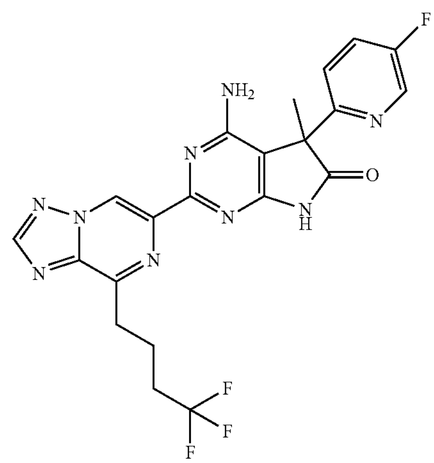 [SMILES: CC1(c2ccc(F)cn2)C(=O)Nc2nc(-c3cn4ncnc4c(CCCC(F)(F)F)n3)nc(N)c21] | 4-amino-5-(5-fluoropyridin-2-yl)-5-methyl-2-(8-(4,4,4-trifluorobutyl)-[1,2,4]triazolo[1,5-a]pyrazin-6-yl)-5H-pyrrolo[2,3-d]pyrimidin-6(7H)-one | 488.3 | I-8B |
| 23A | 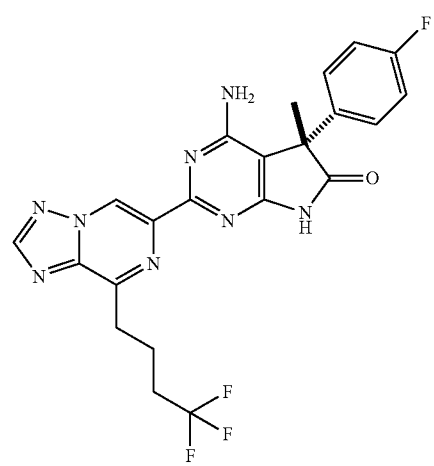 [SMILES: C[C@@]1(c2ccc(F)cc2)C(=O)Nc2nc(-c3cn4ncnc4c(CCCC(F)(F)F)n3)nc(N)c21] | (S)-4-amino-5-(4-fluorophenyl)-5-methyl-2-(8-(4,4,4-trifluorobutyl)-[1,2,4]triazolo[1,5-a]pyrazin-6-yl)-5,7-dihydro-6H-pyrrolo[2,3-d]pyrimidin-6-one | 487.1 | I-1A |

TABLE 6-continued

| Ex | Structure | Name | MS (M + 1) | Chiral starting material |
|---|---|---|---|---|
| 24B | 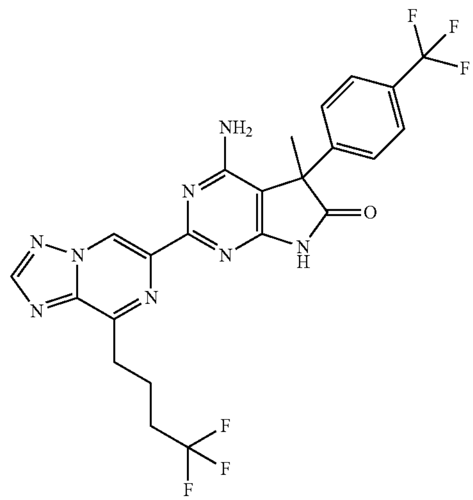 | 4-amino-5-methyl-2-(8-(4,4,4-trifluorobutyl)-[1,2,4]triazolo[1,5-a]pyrazin-6-yl)-5-(4-(trifluoromethyl)phenyl)-5H-pyrrolo[2,3-d]pyrimidin-6(7H)-one | 537.1 | I-3B |
| 25B | 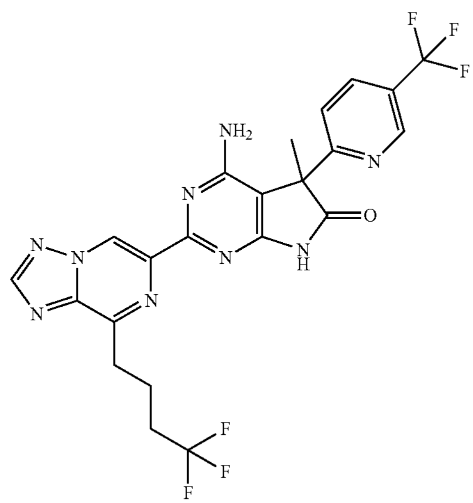 [SMILES: CC1(c2ccc(C(F)(F)F)cn2)C(=O)Nc2nc(-c3cn4ncnc4c(CCCC(F)(F)F)n3)nc(N)c21] | 4-amino-5-methyl-2-(8-(4,4,4-trifluorobutyl)-[1,2,4]triazolo[1,5-a]pyrazin-6-yl)-5-(5-(trifluoromethyl)pyridin-2-yl)-5H-pyrrolo[2,3-d]pyrimidin-6(7H)-one | 538.4 | I-13B |
| 26A | 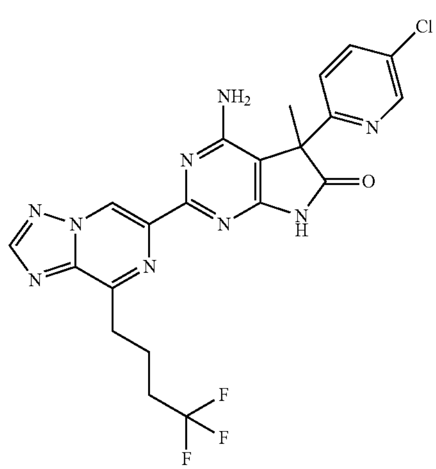 [SMILES: CC1(c2ccc(Cl)cn2)C(=O)Nc2nc(-c3cn4ncnc4c(CCCC(F)(F)F)n3)nc(N)c21] | 4-amino-5-(5-chloropyridin-2-yl)-5-methyl-2-(8-(4,4,4-trifluorobutyl)-[1,2,4]triazolo[1,5-a]pyrazin-6-yl)-5H-pyrrolo[2,3-d]pyrimidin-6(7H)-one | 504.1 | I-9A |

TABLE 6-continued

| Ex | Structure | Name | MS (M + 1) | Chiral starting material |
|---|---|---|---|---|
| 27A | 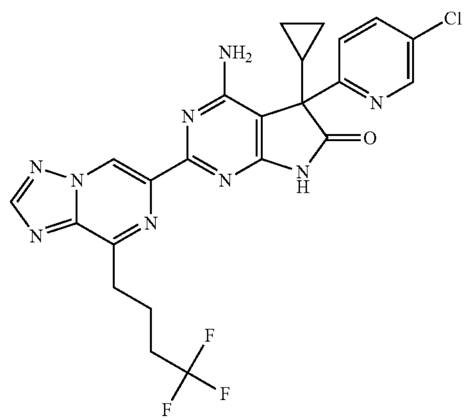 [SMILES: Nc1nc(-c2cn3ncnc3c(CCCC(F)(F)F)n2)nc2c1C(c1ccc(Cl)cn1)(C1CC1)C(=O)N2] | 4-amino-5-(5-chloropyridin-2-yl)-5-cyclopropyl-2-(8-(4,4,4-trifluorobutyl)-[1,2,4]triazolo[1,5-a]pyrazin-6-yl)-5H-pyrrolo[2,3-d]pyrimidin-6(7H)-one | 530.3 | I-35A |
| 28B | 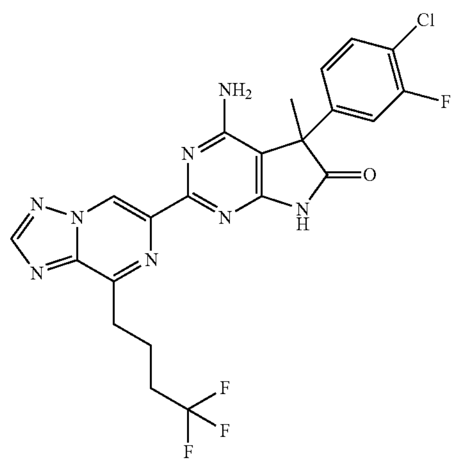 | 4-amino-5-(4-chloro-3-fluorophenyl)-5-methyl-2-(8-(4,4,4-trifluorobutyl)-[1,2,4]triazolo[1,5-a]pyrazin-6-yl)-5H-pyrrolo[2,3-d]pyrimidin-6(7H)-one | 521.3 | I-4B |
| 29A | 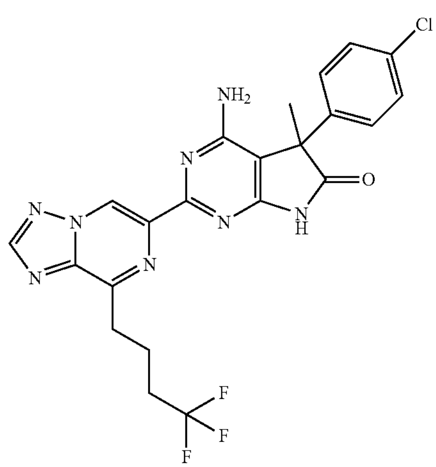 | 4-amino-5-(4-chlorophenyl)-5-methyl-2-(8-(4,4,4-trifluorobutyl)-[1,2,4]triazolo[1,5-a]pyrazin-6-yl)-5H-pyrrolo[2,3-d]pyrimidin-6(7H)-one | 503.2 | I-2A |

TABLE 6-continued

| Ex | Structure | Name | MS (M + 1) | Chiral starting material |
|---|---|---|---|---|
| 30B | 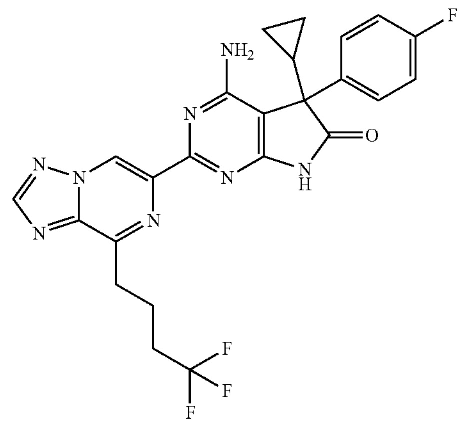 [SMILES: Nc1nc(-c2cn3ncnc3c(CCCC(F)(F)F)n2)nc2c1C(c1ccc(F)cc1)(C1CC1)C(=O)N2] | 4-amino-5-cyclopropyl-5-(4-fluorophenyl)-2-(8-(4,4,4-trifluorobutyl)-[1,2,4]triazolo[1,5-a]pyrazin-6-yl)-5H-pyrrolo[2,3-d]pyrimidin-6(7H)-one | 513.4 | I-29B |
| 31B | 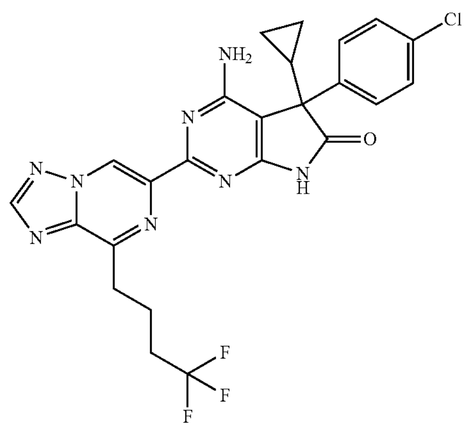 [SMILES: Nc1nc(-c2cn3ncnc3c(CCCC(F)(F)F)n2)nc2c1C(c1ccc(Cl)cc1)(C1CC1)C(=O)N2] | 4-amino-5-(4-chlorophenyl)-5-cyclopropyl-2-(8-(4,4,4-trifluorobutyl)-[1,2,4]triazolo[1,5-a]pyrazin-6-yl)-5H-pyrrolo[2,3-d]pyrimidin-6(7H)-one | 529.4 | I-30B |
| 32A | 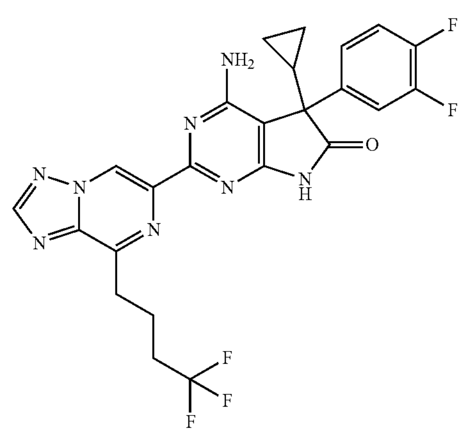 [SMILES: Nc1nc(-c2cn3ncnc3c(CCCC(F)(F)F)n2)nc2c1C(c1ccc(F)c(F)c1)(C1CC1)C(=O)N2] | 4-amino-5-cyclopropyl-5-(3,4-difluorophenyl)-2-(8-(4,4,4-trifluorobutyl)-[1,2,4]triazolo[1,5-a]pyrazin-6-yl)-5H-pyrrolo[2,3-d]pyrimidin-6(7H)-one | 531.3 | I-32A |

TABLE 6-continued

| Ex | Structure | Name | MS (M + 1) | Chiral starting material |
|---|---|---|---|---|
| 33A | 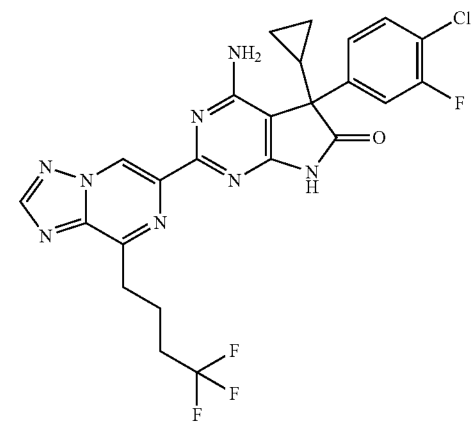 [SMILES: Nc1nc(-c2cn3ncnc3c(CCCC(F)(F)F)n2)nc2c1C(c1ccc(Cl)c(F)c1)(C1CC1)C(=O)N2] | 4-amino-5-(4-chloro-3-fluorophenyl)-5-cyclopropyl-2-(8-(4,4,4-trifluorobutyl)-[1,2,4]triazolo[1,5-a]pyrazin-6-yl)-5H-pyrrolo[2,3-d]pyrimidin-6(7H)-one | 547.3 | I-31A |
| 34A | 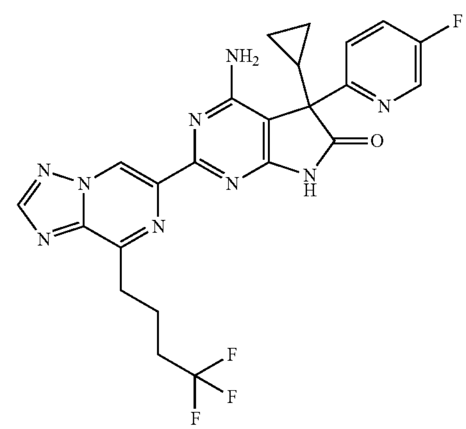 [SMILES: Nc1nc(-c2cn3ncnc3c(CCCC(F)(F)F)n2)nc2c1C(c1ccc(F)cn1)(C1CC1)C(=O)N2] | 4-amino-5-cyclopropyl-5-(5-fluoropyridin-2-yl)-2-(8-(4,4,4-trifluorobutyl)-[1,2,4]triazolo[1,5-a]pyrazin-6-yl)-5H-pyrrolo[2,3-d]pyrimidin-6(7H)-one | 514.1 | I-34A |
| 35A | 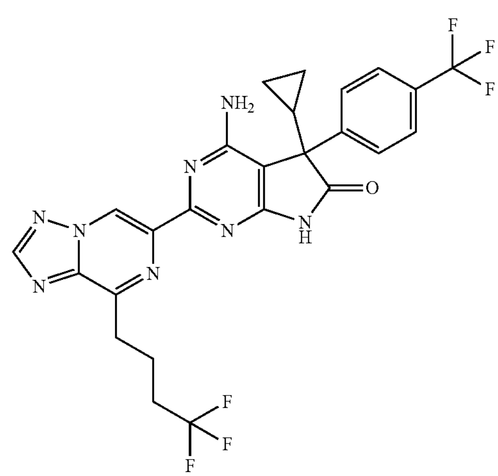 [SMILES: Nc1nc(-c2cn3ncnc3c(CCCC(F)(F)F)n2)nc2c1C(c1ccc(C(F)(F)F)cc1)(C1CC1)C(=O)N2] | 4-amino-5-cyclopropyl-2-(8-(4,4,4-trifluorobutyl)-[1,2,4]triazolo[1,5-a]pyrazin-6-yl)-5-(4-(trifluoromethyl)phenyl)-5H-pyrrolo[2,3-d]pyrimidin-6(7H)-one | 563.0 | I-33A |

TABLE 6-continued

| Ex | Structure | Name | MS (M + 1) | Chiral starting material |
|---|---|---|---|---|
| 36B | 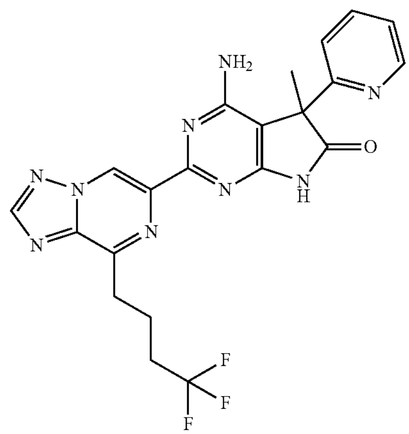 | 4-amino-5-methyl-5-(pyridin-2-yl)-2-(8-(4,4,4-trifluorobutyl)-[1,2,4]triazolo[1,5-a]pyrazin-6-yl)-5H-pyrrolo[2,3-d]pyrimidin-6(7H)-one | 470.2 | I-22B |
| 37B | 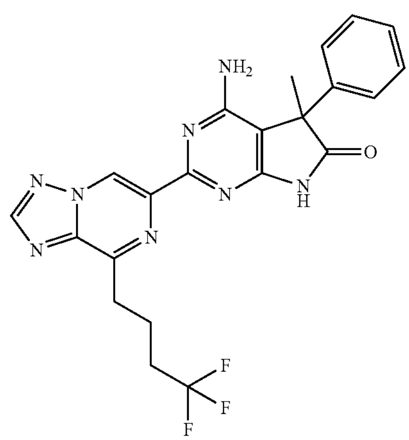 | 4-amino-5-methyl-5-phenyl-2-(8-(4,4,4-trifluorobutyl)-[1,2,4]triazolo[1,5-a]pyrazin-6-yl)-5H-pyrrolo[2,3-d]pyrimidin-6(7H)-one | 469.3 | I-11B |
| 38B | 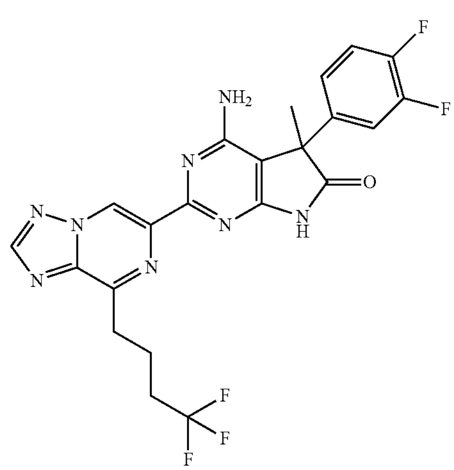 | 4-amino-5-(3,4-difluorophenyl)-5-methyl-2-(8-(4,4,4-trifluorobutyl)-[1,2,4]triazolo[1,5-a]pyrazin-6-yl)-5H-pyrrolo[2,3-d]pyrimidin-6(7H)-one | 505.1 | I-5B |

TABLE 6-continued

| Ex | Structure | Name | MS (M + 1) | Chiral starting material |
|---|---|---|---|---|
| 39A | 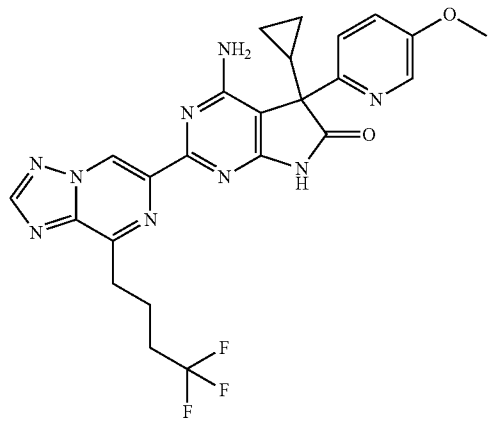 [SMILES: COc1ccc(C2(C3CC3)C(=O)Nc3nc(-c4cn5ncnc5c(CCCC(F)(F)F)n4)nc(N)c32)nc1] | 4-amino-5-cyclopropyl-5-(5-methoxypyridin-2-yl)-2-(8-(4,4,4-trifluorobutyl)-[1,2,4]triazolo[1,5-a]pyrazin-6-yl)-5H-pyrrolo[2,3-d]pyrimidin-6(7H)-one | 526.2 | I-36A |
| 40A | 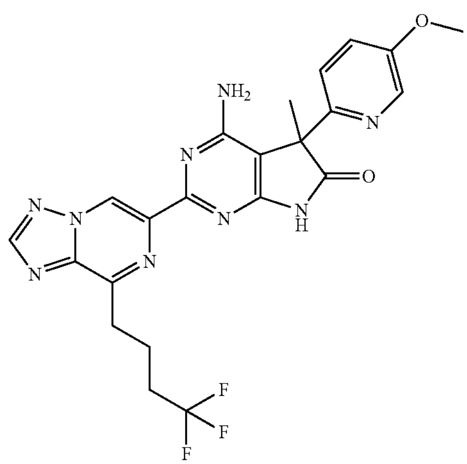 [SMILES: COc1ccc(C2(C)C(=O)Nc3nc(-c4cn5ncnc5c(CCCC(F)(F)F)n4)nc(N)c32)nc1] | 4-amino-5-(5-methoxypyridin-2-yl)-5-methyl-2-(8-(4,4,4-trifluorobutyl)-[1,2,4]triazolo[1,5-a]pyrazin-6-yl)-5H-pyrrolo[2,3-d]pyrimidin-6(7H)-one | 500.3 | I-10A |
| 41A | 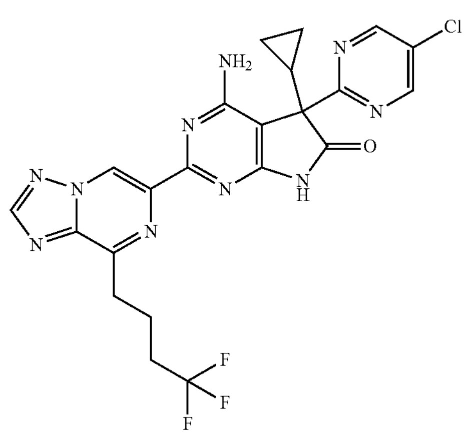 [SMILES: Nc1nc(-c2cn3ncnc3c(CCCC(F)(F)F)n2)nc2c1C(c1ncc(Cl)cn1)(C1CC1)C(=O)N2] | 4-amino-5-(5-chloropyrimidin-2-yl)-5-cyclopropyl-2-(8-(4,4,4-trifluorobutyl)-[1,2,4]triazolo[1,5-a]pyrazin-6-yl)-5H-pyrrolo[2,3-d]pyrimidin-6(7H)-one | 531.4 | I-43A |

TABLE 6-continued

| Ex | Structure | Name | MS (M + 1) | Chiral starting material |
|---|---|---|---|---|
| 42B | 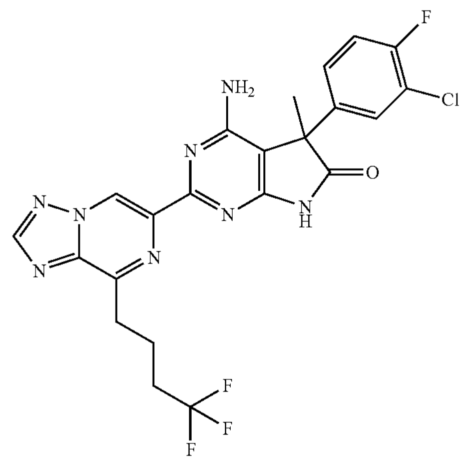 | 4-amino-5-(3-chloro-4-fluorophenyl)-5-methyl-2-(8-(4,4,4-trifluorobutyl)-[1,2,4]triazolo[1,5-a]pyrazin-6-yl)-5H-pyrrolo[2,3-d]pyrimidin-6(7H)-one | 521.2 | I-6B |
| 43B | 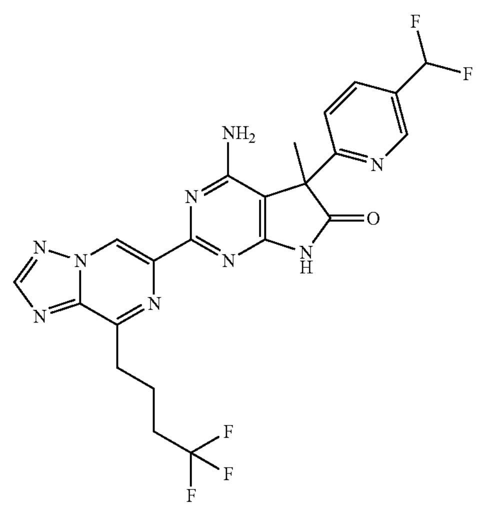 [SMILES: CC1(c2ccc(C(F)F)cn2)C(=O)Nc2nc(-c3cn4ncnc4c(CCCC(F)(F)F)n3)nc(N)c21] | 4-amino-5-(5-(difluoromethyl)pyridin-2-yl)-5-methyl-2-(8-(4,4,4-trifluorobutyl)-[1,2,4]triazolo[1,5-a]pyrazin-6-yl)-5H-pyrrolo[2,3-d]pyrimidin-6(7H)-one | 520.4 | I-20B |
| 44B | 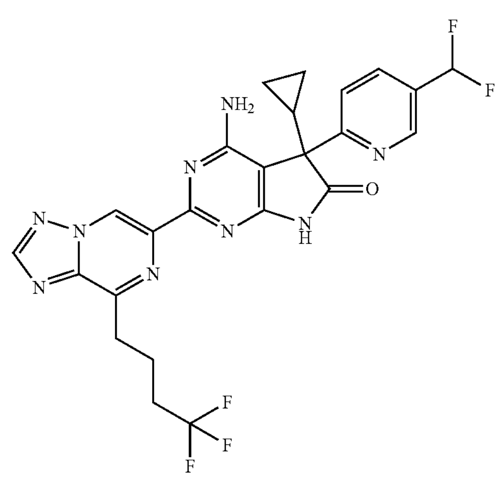 [SMILES: Nc1nc(-c2cn3ncnc3c(CCCC(F)(F)F)n2)nc2c1C(c1ccc(C(F)F)cn1)(C1CC1)C(=O)N2] | 4-amino-5-cyclopropyl-5-(5-(difluoromethyl)pyridin-2-yl)-2-(8-(4,4,4-trifluorobutyl)-[1,2,4]triazolo[1,5-a]pyrazin-6-yl)-5H-pyrrolo[2,3-d]pyrimidin-6(7H)-one (slow eluting) | 546.1 | CHIRAL PAK IC (Rac-I-38) |

TABLE 6-continued

| Ex | Structure | Name | MS (M + 1) | Chiral starting material |
|---|---|---|---|---|
| 45B | 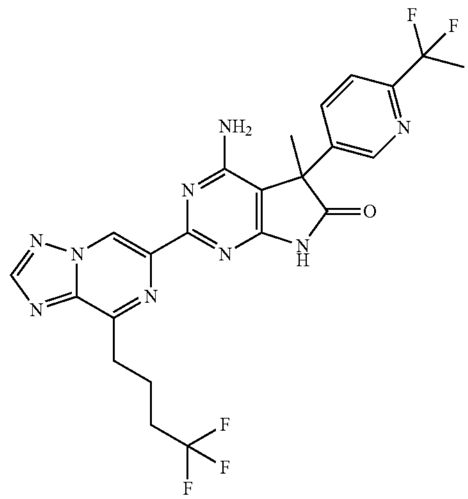 [SMILES: CC(F)(F)c1ccc(C2(C)C(=O)Nc3nc(-c4cn5ncnc5c(CCCC(F)(F)F)n4)nc(N)c32)cn1] | 4-amino-5-(6-(1,1-difluoroethyl)pyridin-3-yl)-5-methyl-2-(8-(4,4,4-trifluorobutyl)-[1,2,4]triazolo[1,5-a]pyrazin-6-yl)-5H-pyrrolo[2,3-d]pyrimidin-6(7H)-one (slow eluting) | 534.2 | CHIRAL PAK IB (Rac-I-23) |
| 46B | 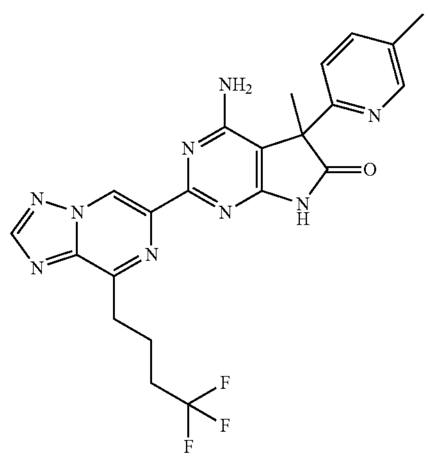 | 4-amino-5-methyl-5-(5-methylpyridin-2-yl)-2-(8-(4,4,4-trifluorobutyl)-[1,2,4]triazolo[1,5-a]pyrazin-6-yl)-5H-pyrrolo[2,3-d]pyrimidin-6(7H)-one | 484.1 | I-14B |
| 47B | 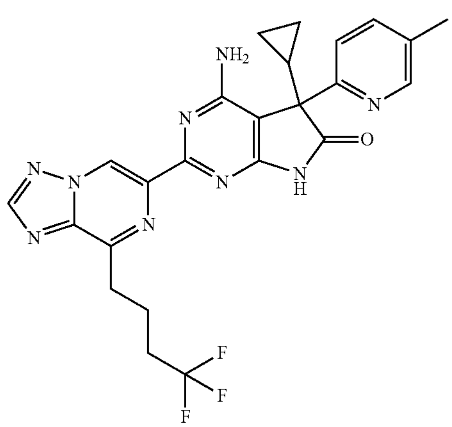 [SMILES: Cc1ccc(C2(C3CC3)C(=O)Nc3nc(-c4cn5ncnc5c(CCCC(F)(F)F)n4)nc(N)c32)nc1] | 4-amino-5-cyclopropyl-5-(5-methylpyridin-2-yl)-2-(8-(4,4,4-trifluorobutyl)-[1,2,4]triazolo[1,5-a]pyrazin-6-yl)-5H-pyrrolo[2,3-d]pyrimidin-6(7H)-one (slow eluting) | 510.4 | CHIRAL PAK IC (Rac-I-37) |

TABLE 6-continued

| Ex | Structure | Name | MS (M + 1) | Chiral starting material |
|---|---|---|---|---|
| 48A | 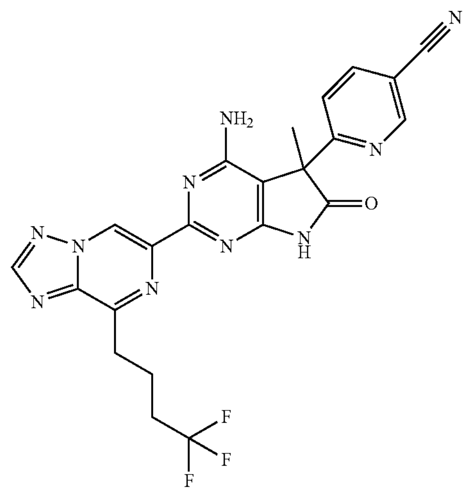 [SMILES: CC1(c2ccc(C#N)cn2)C(=O)Nc2nc(-c3cn4ncnc4c(CCCC(F)(F)F)n3)nc(N)c21] | 6-(4-amino-5-methyl-6-oxo-2-(8-(4,4,4-trifluorobutyl)-[1,2,4]triazolo[1,5-a]pyrazin-6-yl)-6,7-dihydro-5H-pyrrolo[2,3-d]pyrimidin-5-yl)nicotinonitrile | 495.3 | I-15A |
| 49B | 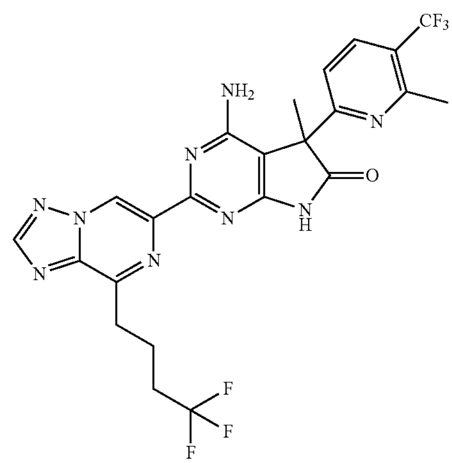 [SMILES: Cc1nc(C2(C)C(=O)Nc3nc(-c4cn5ncnc5c(CCCC(F)(F)F)n4)nc(N)c32)ccc1C(F)(F)F] | 4-amino-5-methyl-5-(6-methyl-5-(trifluoromethyl)pyridin-2-yl)-2-(8-(4,4,4-trifluorobutyl)-[1,2,4]triazolo[1,5-a]pyrazin-6-yl)-5H-pyrrolo[2,3-d]pyrimidin-6(7H)-one (slow eluting) | 552.3 | CHIRAL PAK IA (Rac-I-25) |
| 50B | 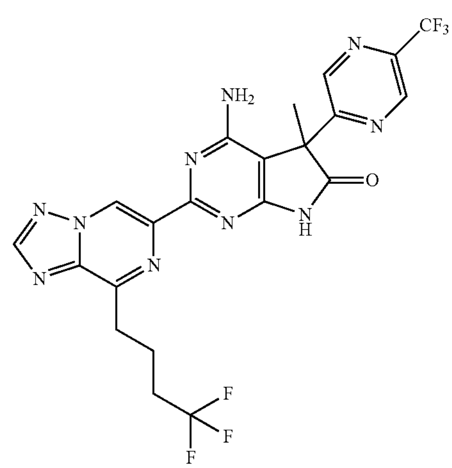 [SMILES: CC1(c2cnc(C(F)(F)F)cn2)C(=O)Nc2nc(-c3cn4ncnc4c(CCCC(F)(F)F)n3)nc(N)c21] | 4-amino-5-methyl-2-(8-(4,4,4-trifluorobutyl)-[1,2,4]triazolo[1,5-a]pyrazin-6-yl)-5-(5-(trifluoromethyl)pyrazin-2-yl)-5H-pyrrolo[2,3-d]pyrimidin-6(7H)-one | 539.2 | I-17B |

TABLE 6-continued

| Ex | Structure | Name | MS (M + 1) | Chiral starting material |
|---|---|---|---|---|
| 51B | 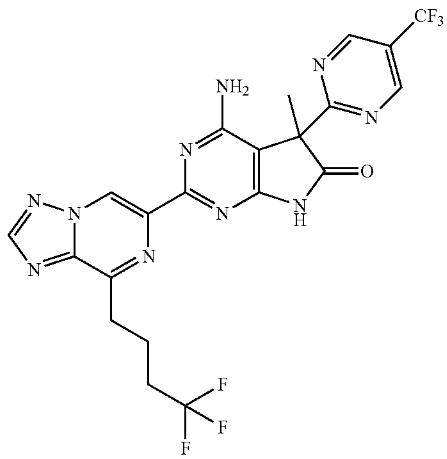 [SMILES: CC1(c2ncc(C(F)(F)F)cn2)C(=O)Nc2nc(-c3cn4ncnc4c(CCCC(F)(F)F)n3)nc(N)c21] | 4-amino-5-methyl-2-(8-(4,4,4-trifluorobutyl)-[1,2,4]triazolo[1,5-a]pyrazin-6-yl)-5-(5-(trifluoromethyl)pyrimidin-2-yl)-5H-pyrrolo[2,3-d]pyrimidin-6(7H)-one (slow eluting) | 539.2 | LUX CELLULOSE-4 (Rac I-18) |
| 52A | 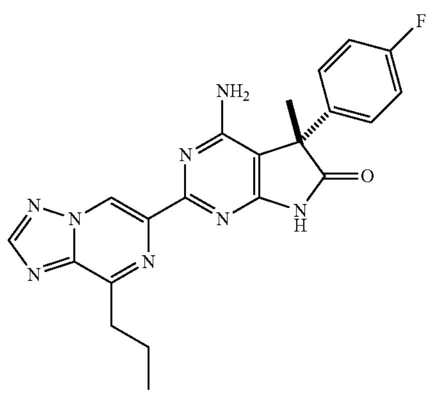 | (S)-4-amino-5-(4-fluorophenyl)-5-methyl-2-(8-propyl-[1,2,4]triazolo[1,5-a]pyrazin-6-yl)-5,7-dihydro-6H-pyrrolo[2,3-d]pyrimidin-6-one | 419.3 | I-1A |
| 53A | 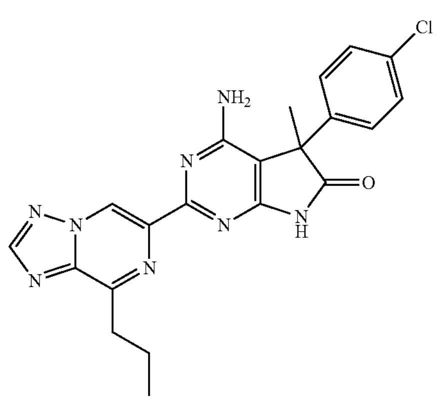 | 4-amino-5-(4-chlorophenyl)-5-methyl-2-(8-propyl-[1,2,4]triazolo[1,5-a]pyrazin-6-yl)-5H-pyrrolo[2,3-d]pyrimidin-6(7H)-one | 435.2 | I-2A |

TABLE 6-continued

| Ex | Structure | Name | MS (M + 1) | Chiral starting material |
|---|---|---|---|---|
| 54B | 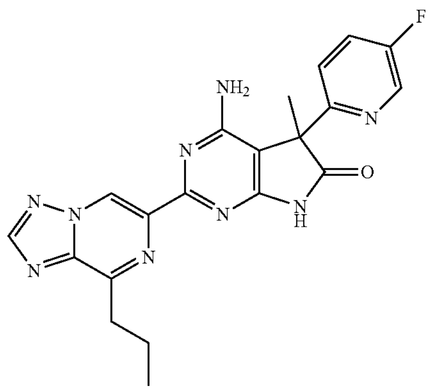 [SMILES: CCCc1nc(-c2nc(N)c3c(n2)NC(=O)C3(C)c2ccc(F)cn2)cn2ncnc12] | 4-amino-5-(5-fluoropyridin-2-yl)-5-methyl-2-(8-propyl-[1,2,4]triazolo[1,5-a]pyrazin-6-yl)-5H-pyrrolo[2,3-d]pyrimidin-6(7H)-one | 420.2 | I-8B |
| 55B | 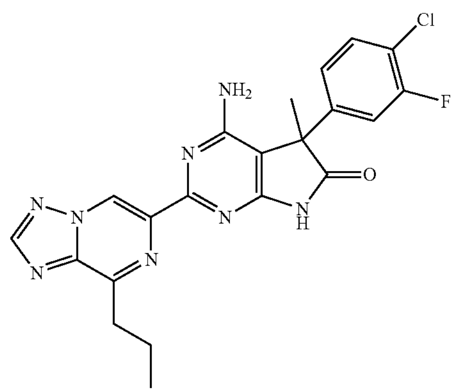 [SMILES: CCCc1nc(-c2nc(N)c3c(n2)NC(=O)C3(C)c2ccc(Cl)c(F)c2)cn2ncnc12] | 5-(5-fluoropyridin-2-yl)-4-hydroxy-5-methyl-2-(8-propyl-[1,2,4]triazolo[1,5-a]pyrazin-6-yl)-5H-pyrrolo[2,3-d]pyrimidin-6(7H)-one | 453.3 | I-4B |
| 56A | 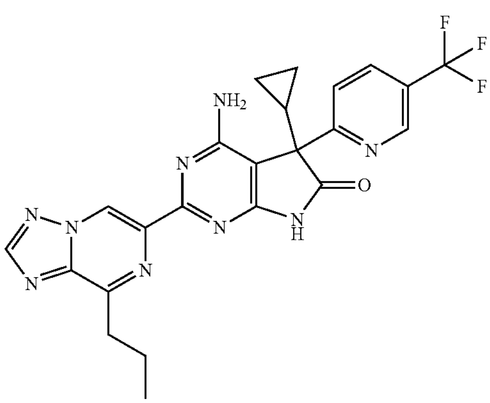 [SMILES: CCCc1nc(-c2nc(N)c3c(n2)NC(=O)C3(c2ccc(C(F)(F)F)cn2)C2CC2)cn2ncnc12] | 4-amino-5-cyclopropyl-2-(8-propyl-[1,2,4]triazolo[1,5-a]pyrazin-6-yl)-5-(5-(trifluoromethyl)pyridin-2-yl)-5H-pyrrolo[2,3-d]pyrimidin-6(7H)-one | 496.3 | I-28A |
| 57A | 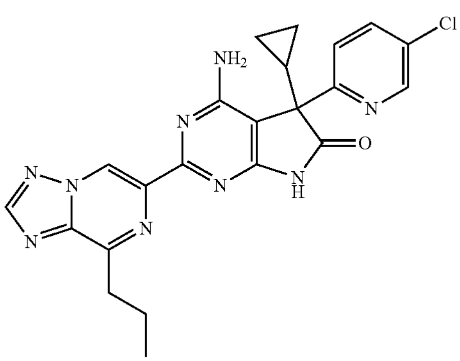 [SMILES: CCCc1nc(-c2nc(N)c3c(n2)NC(=O)C3(c2ccc(Cl)cn2)C2CC2)cn2ncnc12] | 4-amino-5-(5-chloropyridin-2-yl)-5-cyclopropyl-2-(8-propyl-[1,2,4]triazolo[1,5-a]pyrazin-6-yl)-5H-pyrrolo[2,3-d]pyrimidin-6(7H)-one | 462.3 | I-35A |

TABLE 6-continued

| Ex | Structure | Name | MS (M + 1) | Chiral starting material |
|---|---|---|---|---|
| 58A | 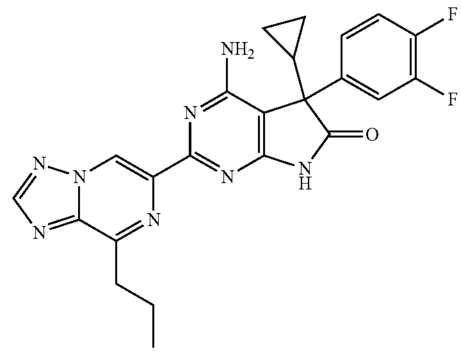 [SMILES: CCCc1nc(-c2nc(N)c3c(n2)NC(=O)C3(c2ccc(F)c(F)c2)C2CC2)cn2ncnc12] | 4-amino-5-cyclopropyl-5-(3,4-difluorophenyl)-2-(8-propyl-[1,2,4]triazolo[1,5-a]pyrazin-6-yl)-5H-pyrrolo[2,3-d]pyrimidin-6(7H)-one | 463.2 | I-32A |
| 59A | 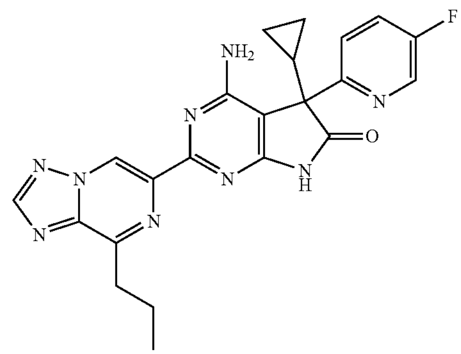 [SMILES: CCCc1nc(-c2nc(N)c3c(n2)NC(=O)C3(c2ccc(F)cn2)C2CC2)cn2ncnc12] | 4-amino-5-cyclopropyl-5-(5-fluoropyridin-2-yl)-2-(8-propyl-[1,2,4]triazolo[1,5-a]pyrazin-6-yl)-5H-pyrrolo[2,3-d]pyrimidin-6(7H)-one | 446.1 | I-34A |
| 60A | 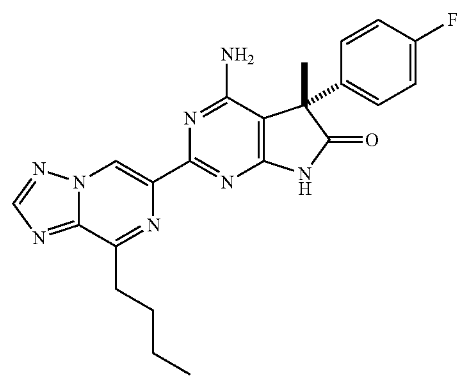 [SMILES: CCCCc1nc(-c2nc(N)c3c(n2)NC(=O)[C@@]3(C)c2ccc(F)cc2)cn2ncnc12] | (S)-4-amino-2-(8-butyl-[1,2,4]triazolo[1,5-a]pyrazin-6-yl)-5-(4-fluorophenyl)-5-methyl-5,7-dihydro-6H-pyrrolo[2,3-d]pyrimidin-6-one | 433.3 | I-1A |
| 61B | 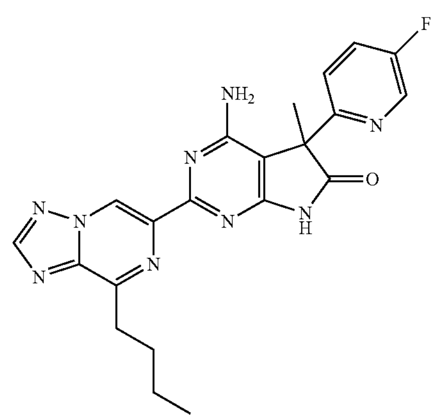 | 4-amino-2-(8-butyl-[1,2,4]triazolo[1,5-a]pyrazin-6-yl)-5-(5-fluoropyridin-2-yl)-5-methyl-5H-pyrrolo[2,3-d]pyrimidin-6(7H)-one | 434.2 | I-8B |

TABLE 6-continued

| Ex | Structure | Name | MS (M + 1) | Chiral starting material |
|---|---|---|---|---|
| 62B | 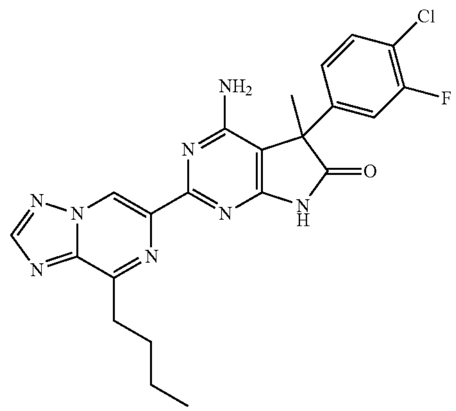 | 4-amino-2-(8-butyl-[1,2,4]triazolo[1,5-a]pyrazin-6-yl)-5-(4-chloro-3-fluorophenyl)-5-methyl-5H-pyrrolo[2,3-d]pyrimidin-6(7H)-one | 467.2 | I-4B |
| 63A | 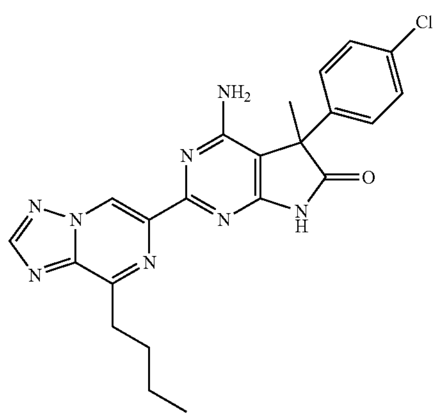 | 4-amino-2-(8-butyl-[1,2,4]triazolo[1,5-a]pyrazin-6-yl)-5-(4-chlorophenyl)-5-methyl-5H-pyrrolo[2,3-d]pyrimidin-6(7H)-one | 449.1 | I-2A |
| 64B | 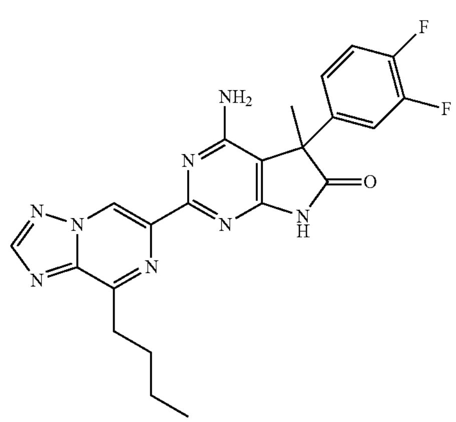 | 4-amino-2-(8-butyl-[1,2,4]triazolo[1,5-a]pyrazin-6-yl)-5-(3,4-difluorophenyl)-5-methyl-5H-pyrrolo[2,3-d]pyrimidin-6(7H)-one | 451.1 | I-5B |

TABLE 6-continued

| Ex | Structure | Name | MS (M + 1) | Chiral starting material |
|---|---|---|---|---|
| 65A | 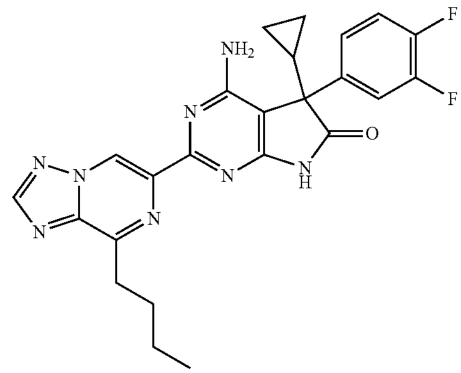 [SMILES: CCCCc1nc(-c2nc(N)c3c(n2)NC(=O)C3(c2ccc(F)c(F)c2)C2CC2)cn2ncnc12] | 4-amino-2-(8-butyl-[1,2,4]triazolo[1,5-a]pyrazin-6-yl)-5-cyclopropyl-5-(3,4-difluorophenyl)-5H-pyrrolo[2,3-d]pyrimidin-6(7H)-one | 477.4 | I-32A |
| 66A | 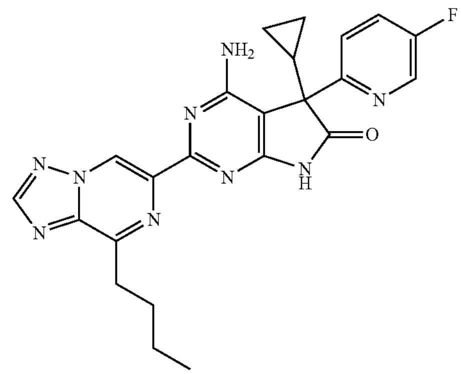 [SMILES: CCCCc1nc(-c2nc(N)c3c(n2)NC(=O)C3(c2ccc(F)cn2)C2CC2)cn2ncnc12] | 4-amino-2-(8-butyl-[1,2,4]triazolo[1,5-a]pyrazin-6-yl)-5-cyclopropyl-5-(5-fluoropyridin-2-yl)-5H-pyrrolo[2,3-d]pyrimidin-6(7H)-one | 460.3 | I-34A |
| 67B | 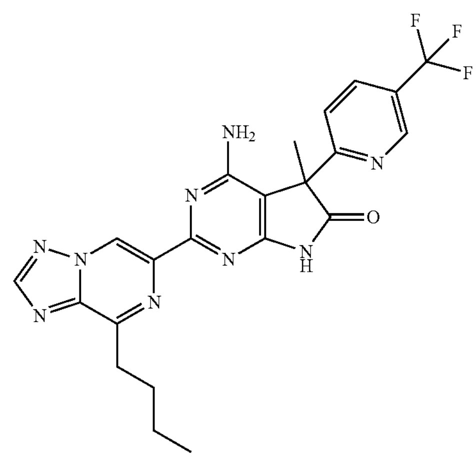 [SMILES: CCCCc1nc(-c2nc(N)c3c(n2)NC(=O)C3(C)c2ccc(C(F)(F)F)cn2)cn2ncnc12] | 4-amino-2-(8-butyl-[1,2,4]triazolo[1,5-a]pyrazin-6-yl)-5-methyl-5-(5-(trifluoromethyl)pyridin-2-yl)-5H-pyrrolo[2,3-d]pyrimidin-6(7H)-one | 484.4 | I-13B |
| 68A | 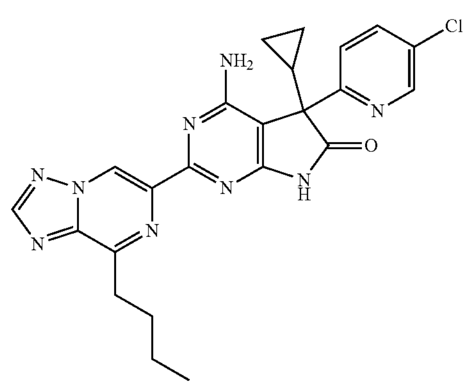 [SMILES: CCCCc1nc(-c2nc(N)c3c(n2)NC(=O)C3(c2ccc(Cl)cn2)C2CC2)cn2ncnc12] | 4-amino-2-(8-butyl-[1,2,4]triazolo[1,5-a]pyrazin-6-yl)-5-(5-chloropyridin-2-yl)-5-cyclopropyl-5H-pyrrolo[2,3-d]pyrimidin-6(7H)-one | 476.3 | I-35A |

TABLE 6-continued

| Ex | Structure | Name | MS (M + 1) | Chiral starting material |
|---|---|---|---|---|
| 69A | 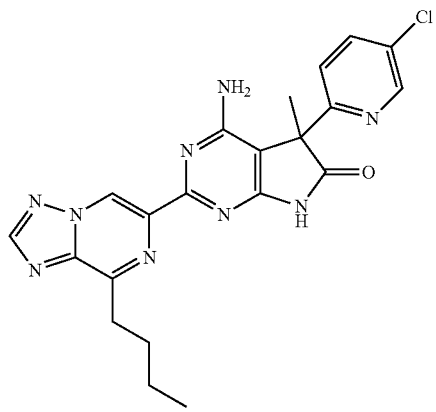 | 4-amino-2-(8-butyl-[1,2,4]triazolo[1,5-a]pyrazin-6-yl)-5-(5-chloropyridin-2-yl)-5-methyl-5H-pyrrolo[2,3-d]pyrimidin-6(7H)-one | 450.2 | I-9A |
| 70A | 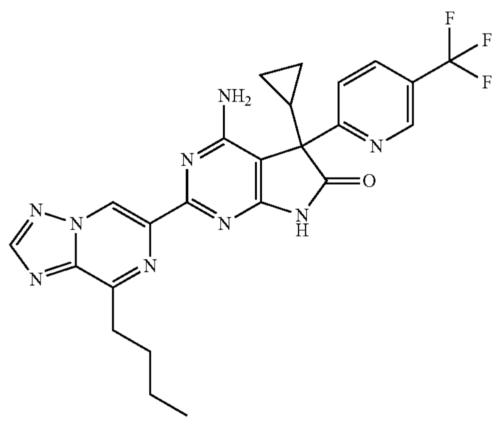 [SMILES: CCCCc1nc(-c2nc(N)c3c(n2)NC(=O)C3(c2ccc(C(F)(F)F)cn2)C2CC2)cn2ncnc12] | 4-amino-2-(8-butyl-[1,2,4]triazolo[1,5-a]pyrazin-6-yl)-5-cyclopropyl-5-(5-(trifluoromethyl)pyridin-2-yl)-5H-pyrrolo[2,3-d]pyrimidin-6(7H)-one | 510.4 | I-28A |
| 71B | 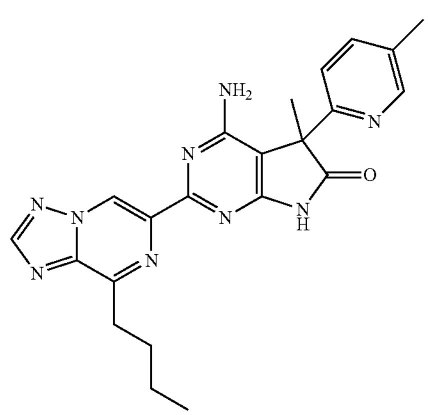 | 4-amino-2-(8-butyl-[1,2,4]triazolo[1,5-a]pyrazin-6-yl)-5-methyl-5-(5-methylpyridin-2-yl)-5H-pyrrolo[2,3-d]pyrimidin-6(7H)-one | 430.3 | I-14B |

TABLE 6-continued

| Ex | Structure | Name | MS (M + 1) | Chiral starting material |
|---|---|---|---|---|
| 72B | 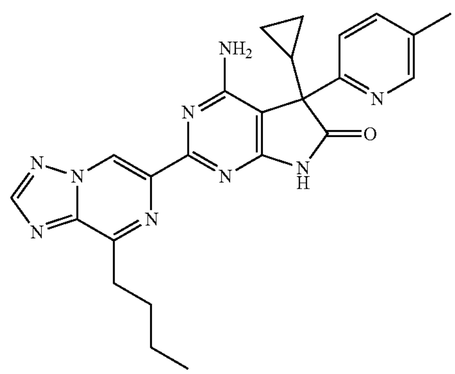 [SMILES: CCCCc1nc(-c2nc(N)c3c(n2)NC(=O)C3(c2ccc(C)cn2)C2CC2)cn2ncnc12] | 4-amino-2-(8-butyl-[1,2,4]triazolo[1,5-a]pyrazin-6-yl)-5-cyclopropyl-5-(5-methylpyridin-2-yl)-5H-pyrrolo[2,3-d]pyrimidin-6(7H)-one (slow eluting) | 456.4 | CHIRALPAK IC (Rac-I-37) |
| 73A | 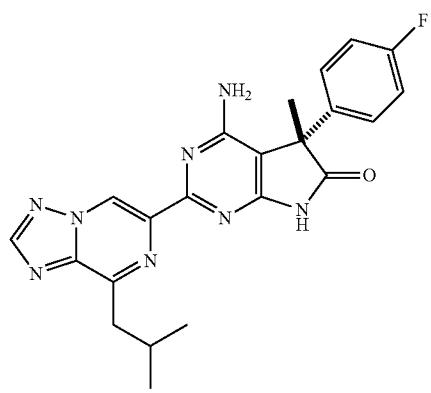 | (S)-4-amino-5-(4-fluorophenyl)-2-(8-isobutyl-[1,2,4]triazolo[1,5-a]pyrazin-6-yl)-5-methyl-5,7-dihydro-6H-pyrrolo[2,3-d]pyrimidin-6-one | 433.3 | I-1A |
| 74A | 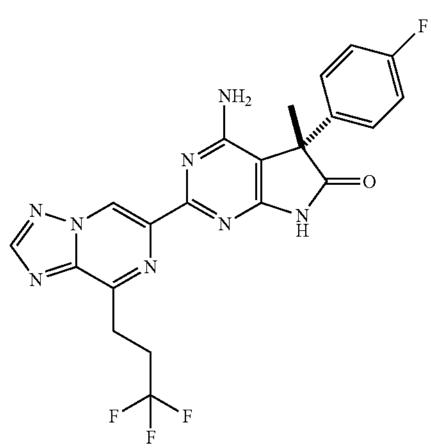 | (S)-4-amino-5-(4-fluorophenyl)-5-methyl-2-(8-(3,3,3-trifluoropropyl)-[1,2,4]triazolo[1,5-a]pyrazin-6-yl)-5,7-dihydro-6H-pyrrolo[2,3-d]pyrimidin-6-one | 473.3 | I-1A |

TABLE 6-continued

| Ex | Structure | Name | MS (M + 1) | Chiral starting material |
|---|---|---|---|---|
| 75B | 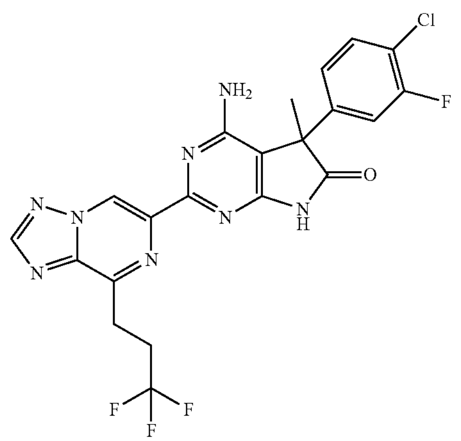 | 4-amino-5-(4-chloro-3-fluorophenyl)-5-methyl-2-(8-(3,3,3-trifluoropropyl)-[1,2,4]triazolo[1,5-a]pyrazin-6-yl)-5H-pyrrolo[2,3-d]pyrimidin-6(7H)-one | 507.2 | I-4B |
| 76A | 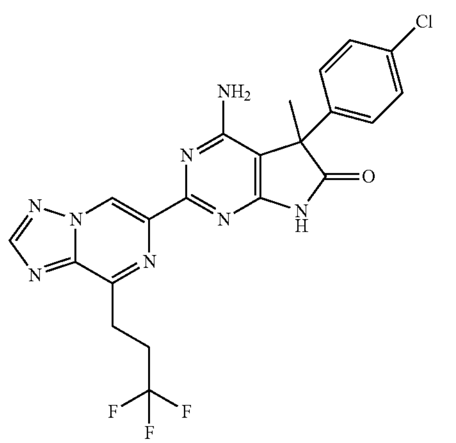 | 4-amino-5-(4-chlorophenyl)-5-methyl-2-(8-(3,3,3-trifluoropropyl)-[1,2,4]triazolo[1,5-a]pyrazin-6-yl)-5H-pyrrolo[2,3-d]pyrimidin-6(7H)-one | 489.1 | I-2A |
| 77B | 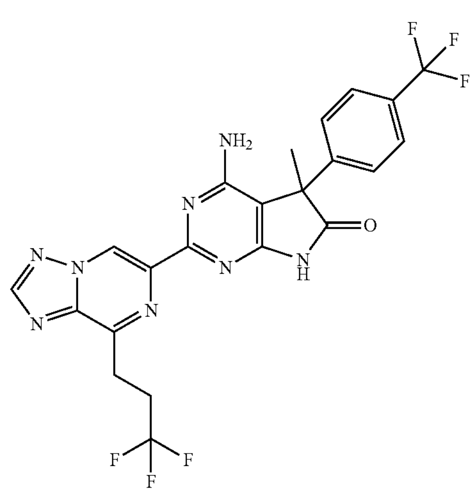 [SMILES: CC1(c2ccc(C(F)(F)F)cc2)C(=O)Nc2nc(-c3cn4ncnc4c(CCC(F)(F)F)n3)nc(N)c21] | 4-amino-5-methyl-5-(4-(trifluoromethyl)phenyl)-2-(8-(3,3,3-trifluoropropyl)-[1,2,4]triazolo[1,5-a]pyrazin-6-yl)-5H-pyrrolo[2,3-d]pyrimidin-6(7H)-one | 523.2 | I-3B |

TABLE 6-continued

| Ex | Structure | Name | MS (M + 1) | Chiral starting material |
|---|---|---|---|---|
| 78B | 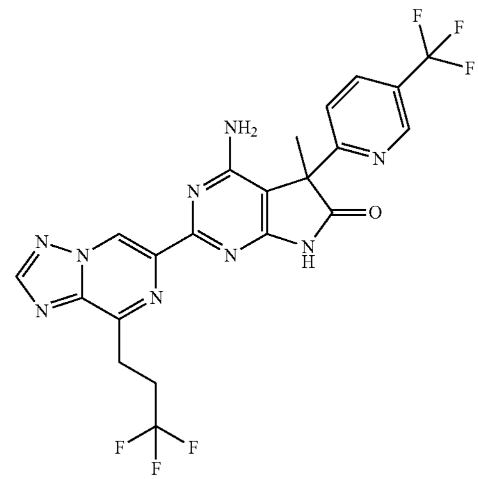 [SMILES: CC1(c2ccc(C(F)(F)F)cn2)C(=O)Nc2nc(-c3cn4ncnc4c(CCC(F)(F)F)n3)nc(N)c21] | 4-amino-5-methyl-5-(5-(trifluoromethyl)pyridin-2-yl)-2-(8-(3,3,3-trifluoropropyl)-[1,2,4]triazolo[1,5-a]pyrazin-6-yl)-5H-pyrrolo[2,3-d]pyrimidin-6(7H)-one | 524.1 | I-13B |
| 79A | 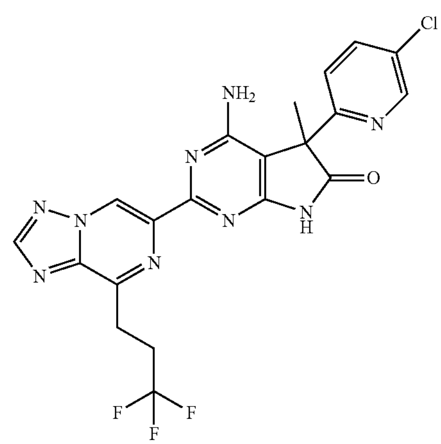 [SMILES: CC1(c2ccc(Cl)cn2)C(=O)Nc2nc(-c3cn4ncnc4c(CCC(F)(F)F)n3)nc(N)c21] | 4-amino-5-(5-chloropyridin-2-yl)-5-methyl-2-(8-(3,3,3-trifluoropropyl)-[1,2,4]triazolo[1,5-a]pyrazin-6-yl)-5H-pyrrolo[2,3-d]pyrimidin-6(7H)-one | 490.3 | I-9A |
| 80A | 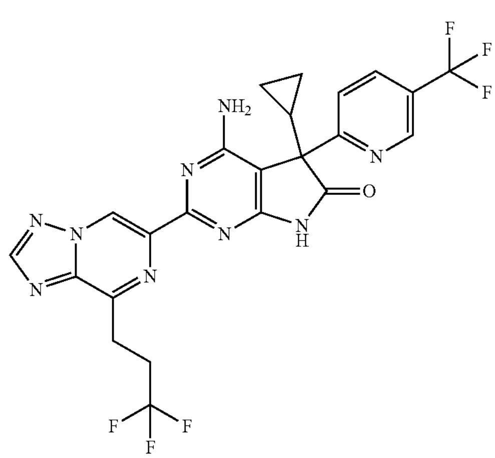 [SMILES: Nc1nc(-c2cn3ncnc3c(CCC(F)(F)F)n2)nc2c1C(c1ccc(C(F)(F)F)cn1)(C1CC1)C(=O)N2] | 4-amino-5-cyclopropyl-5-(5-(trifluoromethyl)pyridin-2-yl)-2-(8-(3,3,3-trifluoropropyl)-[1,2,4]triazolo[1,5-a]pyrazin-6-yl)-5H-pyrrolo[2,3-d]pyrimidin-6(7H)-one | 550.3 | I-28A |

TABLE 6-continued

| Ex | Structure | Name | MS (M + 1) | Chiral starting material |
|---|---|---|---|---|
| 81B | 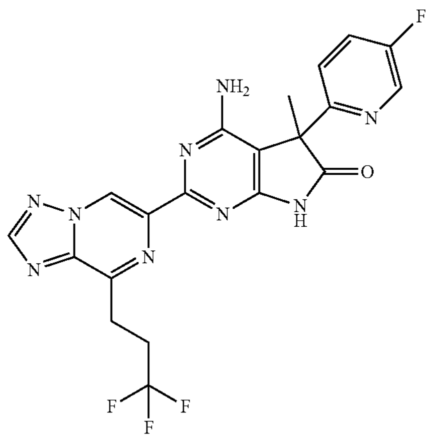 [SMILES: CC1(c2ccc(F)cn2)C(=O)Nc2nc(-c3cn4ncnc4c(CCC(F)(F)F)n3)nc(N)c21] | 4-amino-5-(5-fluoropyridin-2-yl)-5-methyl-2-(8-(3,3,3-trifluoropropyl)-[1,2,4]triazolo[1,5-a]pyrazin-6-yl)-5H-pyrrolo[2,3-d]pyrimidin-6(7H)-one | 474.3 | I-8B |
| 82A | 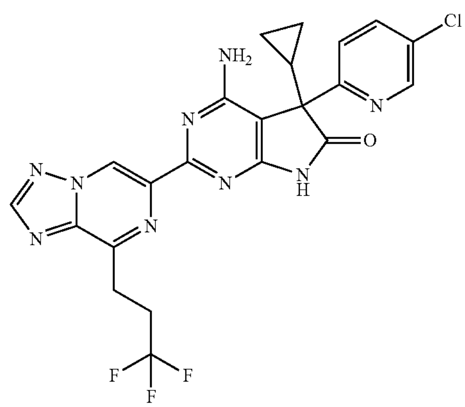 [SMILES: Nc1nc(-c2cn3ncnc3c(CCC(F)(F)F)n2)nc2c1C(c1ccc(Cl)cn1)(C1CC1)C(=O)N2] | 4-amino-5-(5-chloropyridin-2-yl)-5-cyclopropyl-2-(8-(3,3,3-trifluoropropyl)-[1,2,4]triazolo[1,5-a]pyrazin-6-yl)-5H-pyrrolo[2,3-d]pyrimidin-6(7H)-one | 516.3 | I-35A |
| 83A | 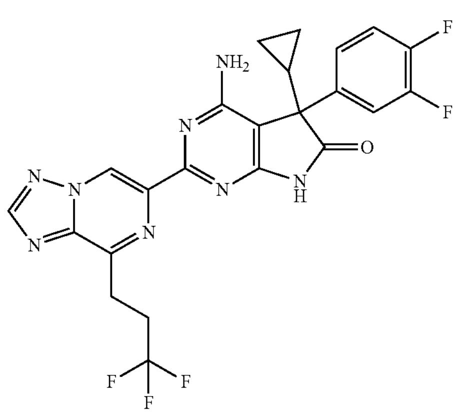 [SMILES: Nc1nc(-c2cn3ncnc3c(CCC(F)(F)F)n2)nc2c1C(c1ccc(F)c(F)c1)(C1CC1)C(=O)N2] | 4-amino-5-cyclopropyl-5-(3,4-difluorophenyl)-2-(8-(3,3,3-trifluoropropyl)-[1,2,4]triazolo[1,5-a]pyrazin-6-yl)-5H-pyrrolo[2,3-d]pyrimidin-6(7H)-one | 517.0 | I-32A |

TABLE 6-continued

| Ex | Structure | Name | MS (M + 1) | Chiral starting material |
|---|---|---|---|---|
| 84B | 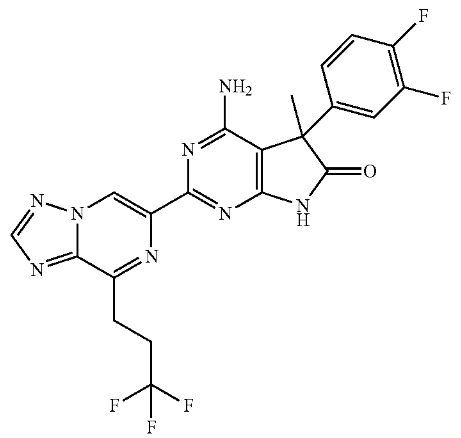 [SMILES: CC1(c2ccc(F)c(F)c2)C(=O)Nc2nc(-c3cn4ncnc4c(CCC(F)(F)F)n3)nc(N)c21] | 4-amino-5-(3,4-difluorophenyl)-5-methyl-2-(8-(3,3,3-trifluoropropyl)-[1,2,4]triazolo[1,5-a]pyrazin-6-yl)-5H-pyrrolo[2,3-d]pyrimidin-6(7H)-one | 491.0 | I-5B |
| 85B | 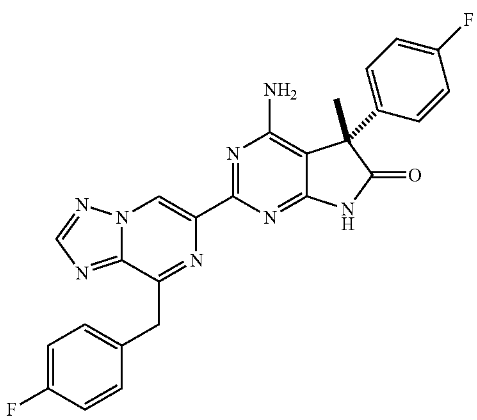 [SMILES: C[C@@]1(c2ccc(F)cc2)C(=O)Nc2nc(-c3cn4ncnc4c(Cc4ccc(F)cc4)n3)nc(N)c21] | (S)-4-amino-2-(8-(4-fluorobenzyl)-[1,2,4]triazolo[1,5-a]pyrazin-6-yl)-5-(4-fluorophenyl)-5-methyl-5H-pyrrolo[2,3-d]pyrimidin-6(7H)-one | 485.0 | I-16B |
| 86B | 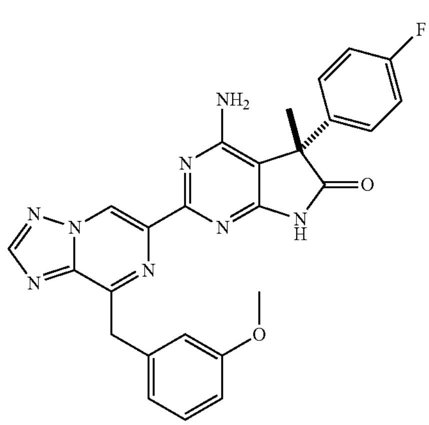 [SMILES: COc1cccc(Cc2nc(-c3nc(N)c4c(n3)NC(=O)[C@@]4(C)c3ccc(F)cc3)cn3ncnc23)c1] | (S)-4-amino-5-(4-fluorophenyl)-2-(8-(3-methoxybenzyl)-[1,2,4]triazolo[1,5-a]pyrazin-6-yl)-5-methyl-5H-pyrrolo[2,3-d]pyrimidin-6(7H)-one | 497.1 | I-16B |

TABLE 6-continued

| Ex | Structure | Name | MS (M + 1) | Chiral starting material |
|---|---|---|---|---|
| 87B | 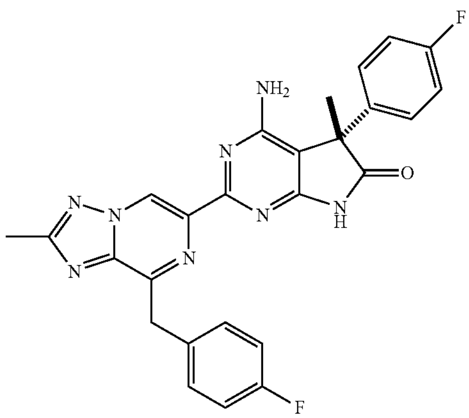 [SMILES: Cc1nc2c(Cc3ccc(F)cc3)nc(-c3nc(N)c4c(n3)NC(=O)[C@@]4(C)c3ccc(F)cc3)cn2n1] | (S)-4-amino-2-(8-(4-fluorobenzyl)-2-methyl-[1,2,4]triazolo[1,5-a]pyrazin-6-yl)-5-(4-fluorophenyl)-5-methyl-5H-pyrrolo[2,3-d]pyrimidin-6(7H)-one | 499.1 | I-16B |
| 88B | 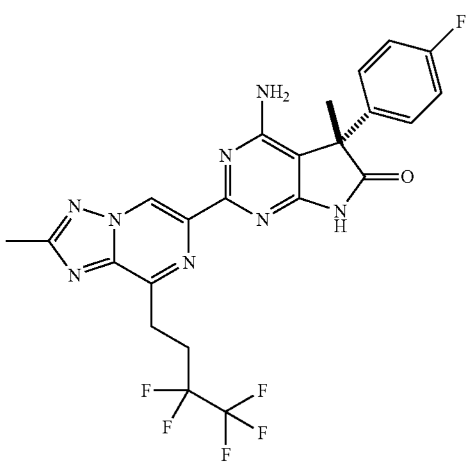 [SMILES: Cc1nc2c(CCC(F)(F)C(F)(F)F)nc(-c3nc(N)c4c(n3)NC(=O)[C@@]4(C)c3ccc(F)cc3)cn2n1] | (S)-4-amino-5-(4-fluorophenyl)-5-methyl-2-(2-methyl-8-(3,3,4,4,4-pentafluorobutyl)-[1,2,4]triazolo[1,5-a]pyrazin-6-yl)-5H-pyrrolo[2,3-d]pyrimidin-6(7H)-one | 537.1 | I-16B |
| 89B | 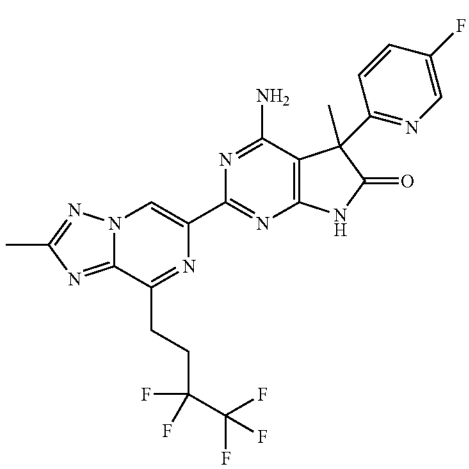 [SMILES: Cc1nc2c(CCC(F)(F)C(F)(F)F)nc(-c3nc(N)c4c(n3)NC(=O)C4(C)c3ccc(F)cn3)cn2n1] | 4-amino-5-(5-fluoropyridin-2-yl)-5-methyl-2-(2-methyl-8-(3,3,4,4,4-pentafluorobutyl)-[1,2,4]triazolo[1,5-a]pyrazin-6-yl)-5H-pyrrolo[2,3-d]pyrimidin-6(7H)-one | 538.1 | I-8B |

TABLE 6-continued

| Ex | Structure | Name | MS (M + 1) | Chiral starting material |
|---|---|---|---|---|
| 90B | 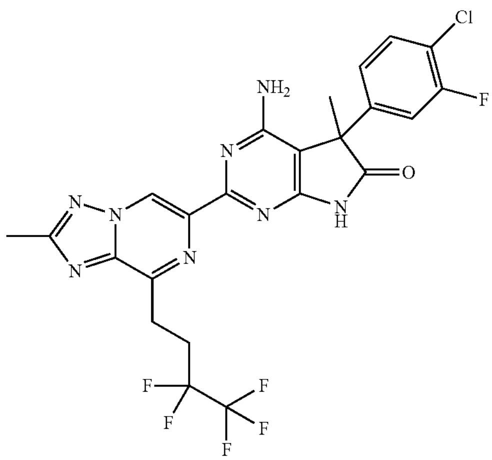 [SMILES: Cc1nc2c(CCC(F)(F)C(F)(F)F)nc(-c3nc(N)c4c(n3)NC(=O)C4(C)c3ccc(Cl)c(F)c3)cn2n1] | 4-amino-5-(4-chloro-3-fluorophenyl)-5-methyl-2-(2-methyl-8-(3,3,4,4,4-pentafluorobutyl)-[1,2,4]triazolo[1,5-a]pyrazin-6-yl)-5H-pyrrolo[2,3-d]pyrimidin-6(7H)-one | 571.3 | I-4B |
| 91A | 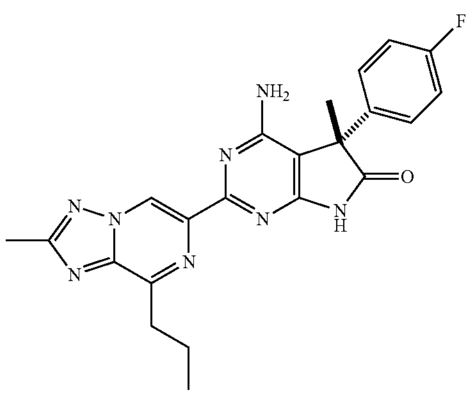 [SMILES: CCCc1nc(-c2nc(N)c3c(n2)NC(=O)[C@@]3(C)c2ccc(F)cc2)cn2nc(C)nc12] | (S)-4-amino-5-(4-fluorophenyl)-5-methyl-2-(2-methyl-8-propyl-[1,2,4]triazolo[1,5-a]pyrazin-6-yl)-5,7-dihydro-6H-pyrrolo[2,3-d]pyrimidin-6-one | 433.3 | I-1A |
| 92B | 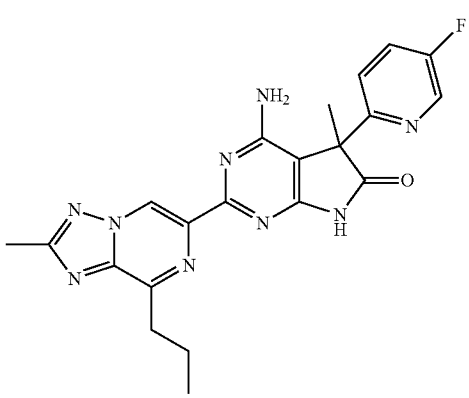 [SMILES: CCCc1nc(-c2nc(N)c3c(n2)NC(=O)C3(C)c2ccc(F)cn2)cn2nc(C)nc12] | 4-amino-5-(5-fluoropyridin-2-yl)-5-methyl-2-(2-methyl-8-propyl-[1,2,4]triazolo[1,5-a]pyrazin-6-yl)-5H-pyrrolo[2,3-d]pyrimidin-6(7H)-one | 434.3 | I-8B |

TABLE 6-continued

| Ex | Structure | Name | MS (M + 1) | Chiral starting material |
|---|---|---|---|---|
| 93A | 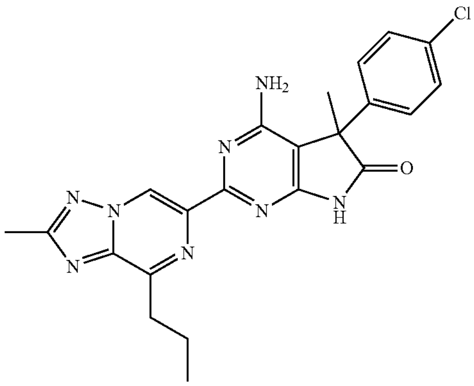 | 4-amino-5-(4-chlorophenyl)-5-methyl-2-(2-methyl-8-propyl-[1,2,4]triazolo[1,5-a]pyrazin-6-yl)-5H-pyrrolo[2,3-d]pyrimidin-6(7H)-one | 449.2 | I-2A |
| 94A | 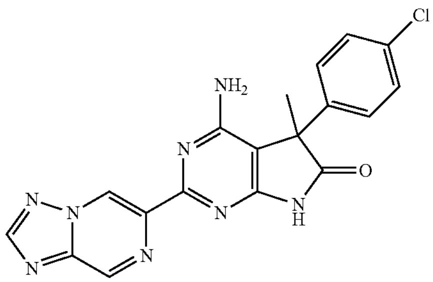 [SMILES: CC1(c2ccc(Cl)cc2)C(=O)Nc2nc(-c3cn4ncnc4cn3)nc(N)c21] | 2-([1,2,4]triazolo[1,5-a]pyrazin-6-yl)-4-amino-5-(4-chlorophenyl)-5-methyl-5H-pyrrolo[2,3-d]pyrimidin-6(7H)-one | 393.0 | I-2A |

Example 95B

4-Amino-5-(1-cyclopropyl-1H-1,2,3-triazol-4-yl)-5-methyl-2-(8-(3,3,4,4,4-pentafluorobutyl)-[1,2,4]triazolo[1,5-a]pyrazin-6-yl)-5H-pyrrolo[2,3-d]pyrimidin-6(7H)-one

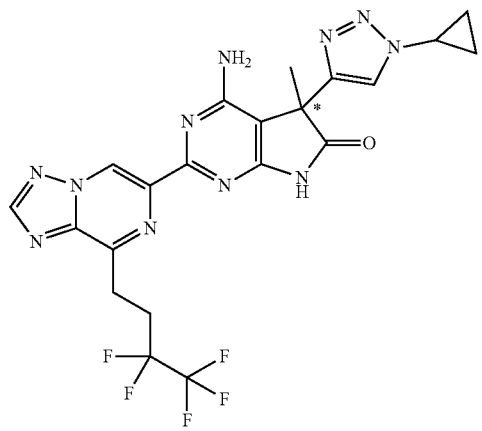 [SMILES: CC1(c2cn(C3CC3)nn2)C(=O)Nc2nc(-c3cn4ncnc4c(CCC(F)(F)C(F)(F)F)n3)nc(N)c21]

Step A—4-Amino-5-ethynyl-5-methyl-2-(8-(3,3,4,4,4-pentafluorobutyl)-[1,2,4]triazolo[1,5-a]pyrazin-6-yl)-5H-pyrrolo[2,3-d]pyrimidin-6(7H)-one Into a vial was placed I-A2 (100 mg, 0.324 mmol), I-19B (67.9 mg, 0.357 mmol), potassium bicarbonate (39.0 mg, 0.389 mmol) and t-BuOH (5 mL). The resulting mixture was warmed at 70° C. for 16 h. The reaction was cooled to RT and quenched by the addition of brine. The resulting solution was extracted with EtOAc (3×) and the organic layers were combined, dried over anhydr. $Na_2SO_4$, filtered and the filtrate was conc. in vacuo to dryness. The residue was purified by silica gel chromatography using MeOH:DCM (10%) to afford the title product.

Step B—4-amino-5-(1-cyclopropyl-1H-1,2,3-triazol-4-yl)-5-methyl-2-(8-(3,3,4,4,4-pentafluorobutyl)-[1,2,4]triazolo[1,5-a]pyrazin-6-yl)-5H-pyrrolo[2,3-d]pyrimidin-6(7H)-one To a flask containing potassium carbonate (306 mg, 2.21 mmol), copper(II) sulfate (21 mg, 0.13 mmol), cyclopropanamine (63 mg, 1.11 mmol) and MeOH (7.4 mL) at RT was added 1H-imidazole-1-sulfonyl azide hydrochloride (278 mg, 1.33 mmol) in water (3.7 mL). The resulting mixture was stirred for 16 h at 70° C. This was followed by the addition of sodium (R)-2-((S)-1,2-dihydroxyethyl)-4-hydroxy-5-oxo-2,5-dihydrofuran-3-olate (70 mg, 0.35 mmol) and the intermediate from Step A (100 mg, 0.22 mmol). The resulting mixture was stirred for 16 h at 70° C. The reaction was then cooled to RT and quenched by the addition of ammonia (100 mL). The resulting solution was extracted with EtOAc (3×) and the organic layers combined, washed with ammonia then brine, dried over anhydr. $Na_2SO_4$, and filtered. The residue was purified by silica gel chromatography with EtOAc:petroleum ether (5-20%). The crude product was purified by Prep-HPLC, water:acetonitrile (with 0.05% ammonia) to afford the title compound. $^1$H NMR ($CD_3OD$, 300 MHz): δ 9.61 (s, 1H), 8.61 (s, 1H), 7.95 (s, 1H), 3.92-3.85 (m, 1H), 3.65-3.59 (m, 2H), 3.04-2.86 (m, 2H), 1.81 (s, 3H), 1.25-1.19 (m, 4H); m/z=536.3 [M+1]+.

Example 96B 4-amino-5-cyclopropyl-5-(1-cyclopropyl-1H-1,2,3-triazol-4-yl)-2-(8-(3,3,4,4,4-pentafluorobutyl)-[1,2,4]triazolo[1,5-a]pyrazin-6-yl)-5H-pyrrolo[2,3-d]pyrimidin-6(7H)-one

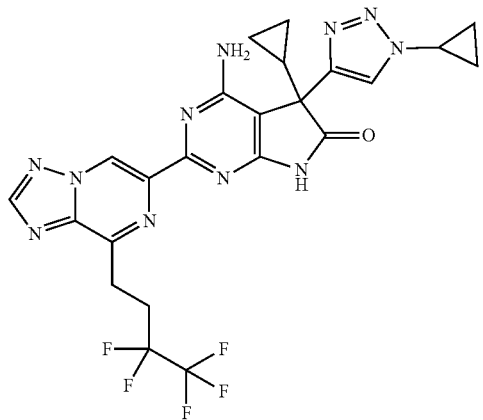 [SMILES: Nc1nc(-c2cn3ncnc3c(CCC(F)(F)C(F)(F)F)n2)nc2c1C(c1cn(C3CC3)nn1)(C1CC1)C(=O)N2]

Using essentially the same procedures described in Example 95, Example 96 was prepared, using intermediate I-A2 and I-27B as starting material. m/z=562.2 [M+1]$^+$.

Example 97A and 97B

4-Amino-5-methyl-5-(5-methyl-1,3,4-oxadiazol-2-yl)-2-(8-(3,3,4,4,4-pentafluorobutyl)-[1,2,4]triazolo[1,5-a]pyrazin-6-yl)-5H-pyrrolo[2,3-d]pyrimidin-6(7H)-one

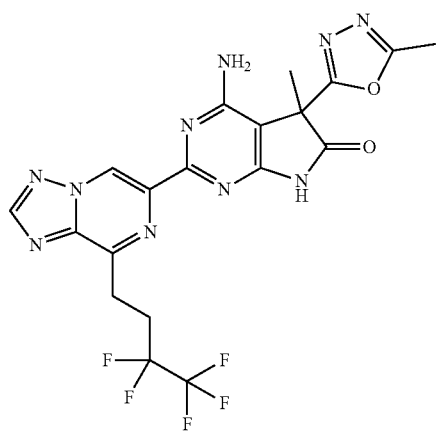 [SMILES: Cc1nnc(C2(C)C(=O)Nc3nc(-c4cn5ncnc5c(CCC(F)(F)C(F)(F)F)n4)nc(N)c32)o1]

Step A—Ethyl 4-amino-5-methyl-6-oxo-2-(8-(3,3,4,4,4-pentafluorobutyl)-[1,2,4]triazolo[1,5-a]pyrazin-6-yl)-6,7-dihydro-5H-pyrrolo[2,3-d]pyrimidine-5-carboxylate Into a vial was placed I-42 (312 mg, 1.31 mmol), I-A2 (336 mg, 1.09 mmol), potassium bicarbonate (218 mg, 2.18 mmol) and t-BuOH (5 mL). The resulting mixture was warmed at 70° C. for 16 h. The reaction was cooled to RT and quenched by the addition of brine. The resulting solution was extracted with EtOAc (3×) and the organic layers were combined, dried over anhydr. Na$_2$SO$_4$, filtered and the filtrate was conc. in vacuo to dryness. The residue was purified by silica gel chromatography using MeOH:DCM (10%) to afford the title compound.

Step B—4-Amino-5-methyl-6-oxo-2-(8-(3,3,4,4,4-pentafluorobutyl)-[1,2,4]triazolo[1,5-a]pyrazin-6-yl)-6,7-dihydro-5H-pyrrolo[2,3-d]pyrimidine-5-carbohydrazide Into a flask was placed the intermediate from Step A (456 mg, 0.91 mmol), MeOH (8 mL) and hydrazine hydrate (228 mg, 4.56 mmol). The resulting mixture was warmed at 65° C. for 4 h. The reaction was cooled to RT and conc. to remove any volatiles. The residue was purified by silica gel chromatography using MeOH:DCM (10%) to afford the title compound.

Step C—N'-Acetyl-4-amino-5-methyl-6-oxo-2-(8-(3,3,4,4,4-pentafluorobutyl)-[1,2,4]triazolo[1,5-a]pyrazin-6-yl)-6,7-dihydro-5H-pyrrolo[2,3-d]pyrimidine-5-carbohydrazide Into a vial was placed AcOH (18 µL, 0.32 mmol), DMF (6 mL), HATU (123 mg, 0.32 mmol) and Et$_3$N (0.086 mL, 0.62 mmol). After 20 min, the intermediate from Step B (150 mg, 0.31 mmol) was added. The resulting mixture was stirred at RT for 16 h. The reaction was quenched by the addition of brine, and the resulting solution was extracted with EtOAc (3×). The organic layers were combined, dried over anhydr. Na$_2$SO$_4$, filtered and the filtrate was conc. in vacuo to dryness. The residue was purified by silica gel chromatography using MeOH:DCM (10%) to afford the title compound.

Step D—4-Amino-5-methyl-5-(5-methyl-1,3,4-oxadiazol-2-yl)-2-(8-(3,3,4,4,4-pentafluorobutyl)-[1,2,4]triazolo[1,5-a]pyrazin-6-yl)-5H-pyrrolo[2,3-d]pyrimidin-6(7H)-one Into a flask was placed the intermediate from Step C (150 mg, 0.28 mmol) and polyphosphoric acid (2 mL). The resulting mixture was warmed at 80° C. for 16 h. The reaction was quenched by the addition of ice water. The pH of the resulting mixture was adjusted to pH 8 with sat. aq. NaHCO$_3$. The resulting solution was extracted with EtOAc (3×) and the organic layers were combined, dried over anhydr. Na$_2$SO$_4$, filtered and the filtrate was conc. in vacuo to dryness. The residue was purified by silica gel chromatography using MeOH:DCM (10%) to afford the title compound as a racemate. The racemic material was resolved using chiral SFC (IA column) to afford isomers Ex-97A (faster eluting) and Ex-97B (slower eluting) of the title compound. $^1$H NMR (400 MHz, CD$_3$OD): δ 9.68 (1H, s), 8.67 (1H, s), 3.70-3.65 (2H, m), 3.07-2.93 (2H, m), 2.57 (3H, s), 1.98 (3H, s); m/z=511.1 (M+H).

Using essentially the same procedures described in Example 97, the following compounds in Table 7 were prepared.

TABLE 7

| Ex. | Structure | Name | MS (M + 1) | Chiral separation conditions |
|---|---|---|---|---|
| 98B | 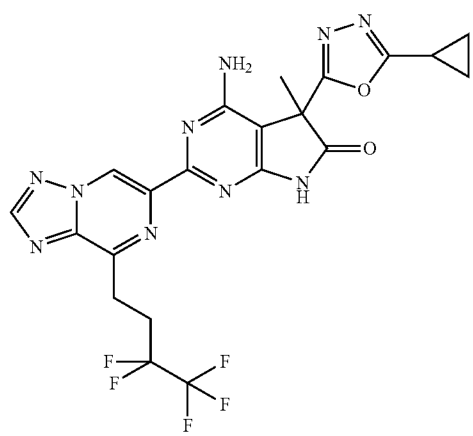 [SMILES: CC1(c2nnc(C3CC3)o2)C(=O)Nc2nc(-c3cn4ncnc4c(CCC(F)(F)C(F)(F)F)n3)nc(N)c21] | 4-amino-5-(5-cyclopropyl-1,3,4-oxadiazol-2-yl)-5-methyl-2-(8-(3,3,4,4,4-pentafluorobutyl)-[1,2,4]triazolo[1,5-a]pyrazin-6-yl)-5H-pyrrolo[2,3-d]pyrimidin-6(7H)-one (slow eluting) | 537.5 | CHIRALPAK IB |
| 99A | 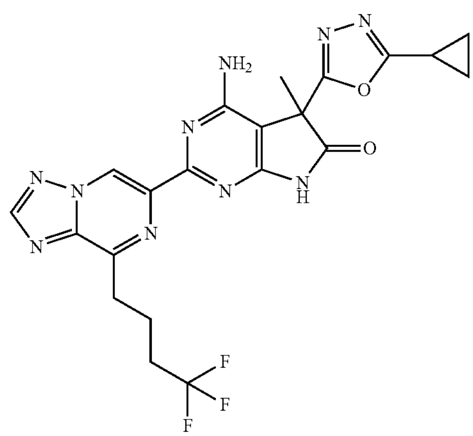 [SMILES: CC1(c2nnc(C3CC3)o2)C(=O)Nc2nc(-c3cn4ncnc4c(CCCC(F)(F)F)n3)nc(N)c21] | 4-amino-5-(5-cyclopropyl-1,3,4-oxadiazol-2-yl)-5-methyl-2-(8-(4,4,4-trifluorobutyl)-[1,2,4]triazolo[1,5-a]pyrazin-6-yl)-5H-pyrrolo[2,3-d]pyrimidin-6(7H)-one (fast eluting) | 501.1 | CHIRALPAK IB |
| 100A | 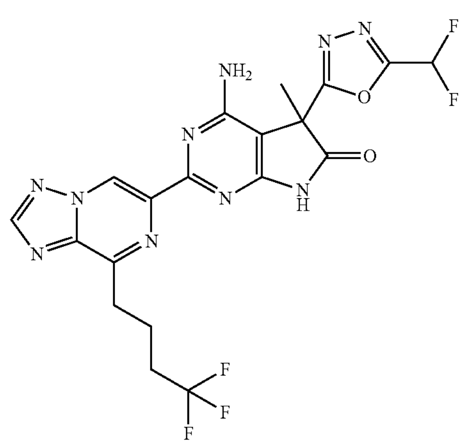 [SMILES: CC1(c2nnc(C(F)F)o2)C(=O)Nc2nc(-c3cn4ncnc4c(CCCC(F)(F)F)n3)nc(N)c21] | 4-amino-5-(5-(difluoromethyl)-1,3,4-oxadiazol-2-yl)-5-methyl-2-(8-(4,4,4-trifluorobutyl)-[1,2,4]triazolo[1,5-a]pyrazin-6-yl)-5H-pyrrolo[2,3-d]pyrimidin-6(7H)-one | 511.3 | CHIRALPAK IA |

TABLE 7-continued

| Ex. | Structure | Name | MS (M + 1) | Chiral separation conditions |
|---|---|---|---|---|
| 101A | 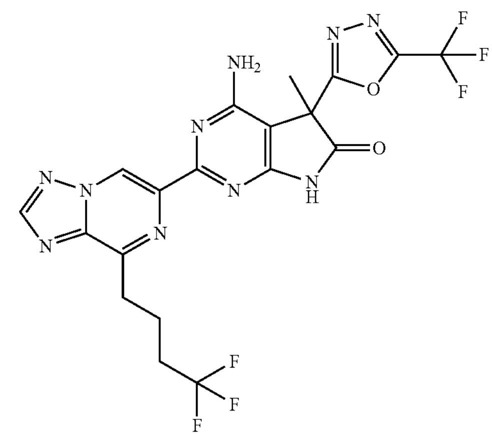 [SMILES: CC1(c2nnc(C(F)(F)F)o2)C(=O)Nc2nc(-c3cn4ncnc4c(CCCC(F)(F)F)n3)nc(N)c21] | 4-amino-5-methyl-2-(8-(4,4,4-trifluorobutyl)-[1,2,4]triazolo[1,5-a]pyrazin-6-yl)-5-(5-(trifluoromethyl)-1,3,4-oxadiazol-2-yl)-5H-pyrrolo[2,3-d]pyrimidin-6(7H)-one (fast eluting) | 529.3 | CHIRALPAK IA |
| 102A | 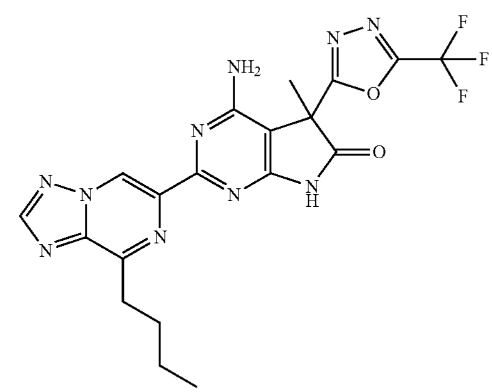 [SMILES: CCCCc1nc(-c2nc(N)c3c(n2)NC(=O)C3(C)c2nnc(C(F)(F)F)o2)cn2ncnc12] | 4-amino-2-(8-butyl-[1,2,4]triazolo[1,5-a]pyrazin-6-yl)-5-methyl-5-(5-(trifluoromethyl)-1,3,4-oxadiazol-2-yl)-5H-pyrrolo[2,3-d]pyrimidin-6(7H)-one (fast eluting) | 475.2 | CHIRALPAK IA |
| 103A | 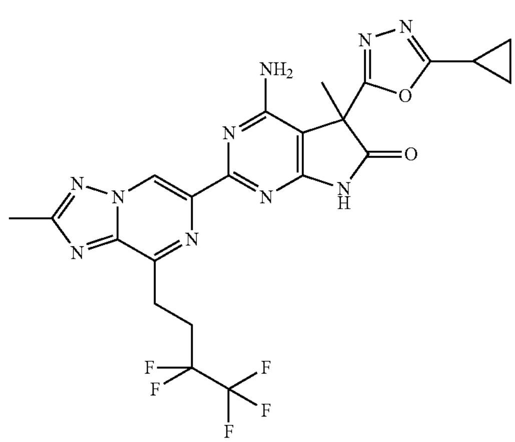 [SMILES: Cc1nc2c(CCC(F)(F)C(F)(F)F)nc(-c3nc(N)c4c(n3)NC(=O)C4(C)c3nnc(C4CC4)o3)cn2n1] | 4-amino-5-(5-cyclopropyl-1,3,4-oxadiazol-2-yl)-5-methyl-2-(2-methyl-8-(3,3,4,4,4-pentafluorobutyl)-[1,2,4]triazolo[1,5-a]pyrazin-6-yl)-5H-pyrrolo[2,3-d]pyrimidin-6(7H)-one (fast eluting) | 551.0 | CHIRALPAK IA |

TABLE 7-continued

| Ex. | Structure | Name | MS (M + 1) | Chiral separation conditions |
|---|---|---|---|---|
| 104A | 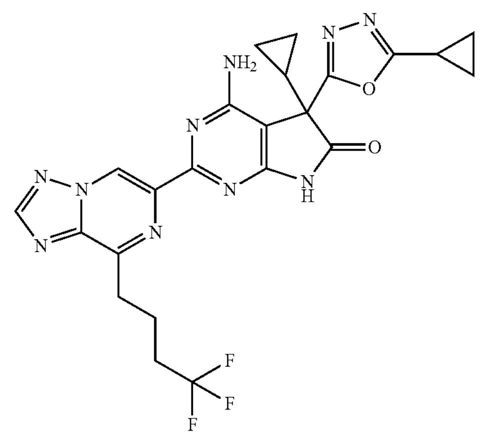 [SMILES: Nc1nc(-c2cn3ncnc3c(CCCC(F)(F)F)n2)nc2c1C(c1nnc(C3CC3)o1)(C1CC1)C(=O)N2] | 4-amino-5-cyclopropyl-5-(5-cyclopropyl-1,3,4-oxadiazol-2-yl)-2-(8-(4,4,4-trifluorobutyl)-[1,2,4]triazolo[1,5-a]pyrazin-6-yl)-5H-pyrrolo[2,3-d]pyrimidin-6(7H)-one (fast eluting) | 527.4 | CHIRALPAK IA |
| 105A | 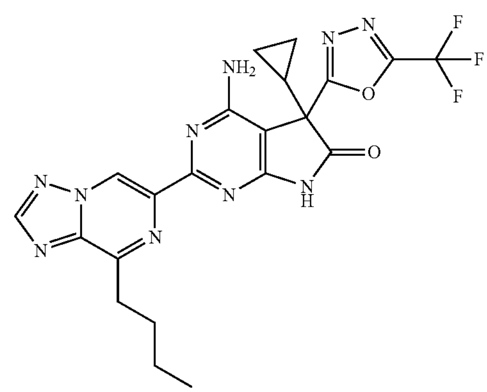 [SMILES: CCCCc1nc(-c2nc(N)c3c(n2)NC(=O)C3(c2nnc(C(F)(F)F)o2)C2CC2)cn2ncnc12] | 4-amino-2-(8-butyl-[1,2,4]triazolo[1,5-a]pyrazin-6-yl)-5-cyclopropyl-5-(5-(trifluoromethyl)-1,3,4-oxadiazol-2-yl)-5H-pyrrolo[2,3-d]pyrimidin-6(7H)-one (fast eluting) | 501.2 | CHIRALPAK IA |
| 106A | 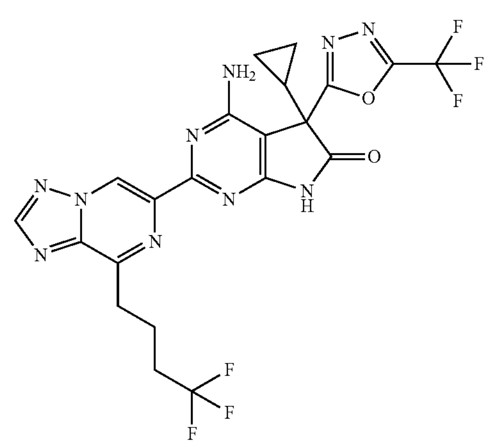 [SMILES: Nc1nc(-c2cn3ncnc3c(CCCC(F)(F)F)n2)nc2c1C(c1nnc(C(F)(F)F)o1)(C1CC1)C(=O)N2] | 4-amino-5-cyclopropyl-2-(8-(4,4,4-trifluorobutyl)-[1,2,4]triazolo[1,5-a]pyrazin-6-yl)-5-(5-(trifluoromethyl)-1,3,4-oxadiazol-2-yl)-5H-pyrrolo[2,3-d]pyrimidin-6(7H)-one (fast eluting) | 555.1 | CHIRALPAK IA |

TABLE 7-continued

| Ex. | Structure | Name | MS (M + 1) | Chiral separation conditions |
|---|---|---|---|---|
| 107A | 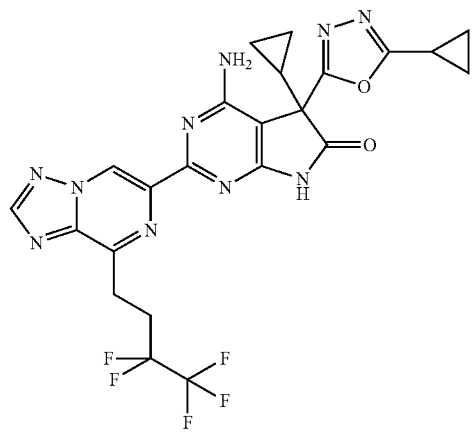 [SMILES: Nc1nc(-c2cn3ncnc3c(CCC(F)(F)C(F)(F)F)n2)nc2c1C(c1nnc(C3CC3)o1)(C1CC1)C(=O)N2] | 4-amion-5-cyclopropyl-5-(5-cyclopropyl-1,3,4-oxadiazol-2-yl)-2-(8-(3,3,4,4,4-pentafluorobutyl)-[1,2,4]triazolo[1,5-a]pyrazin-6-yl)-5H-pyrrolo[2,3-d]pyrimidin-6(7H)-one (fast eluting) | 563.3 | CHIRALPAK IA |
| 108A | 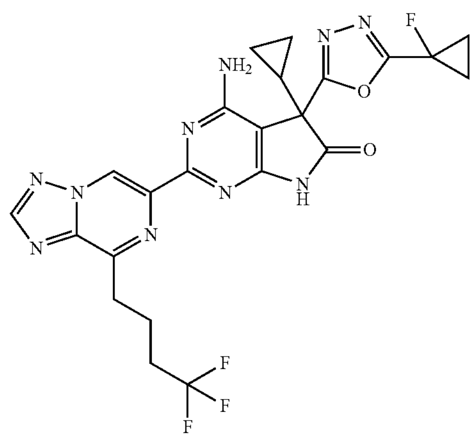 [SMILES: Nc1nc(-c2cn3ncnc3c(CCCC(F)(F)F)n2)nc2c1C(c1nnc(C3(F)CC3)o1)(C1CC1)C(=O)N2] | 4-amino-5-cyclopropyl-5-(5-(1-fluorocyclopropyl)-1,3,4-oxadiazol-2-yl)-2-(8-(4,4,4-trifluorobutyl)-[1,2,4]triazolo[1,5-a]pyrazin-6-yl)-5H-pyrrolo[2,3-d]pyrimidin-6(7H)-one (fast eluting) | 545.2 | CHIRALPAK IB |
| 109A | 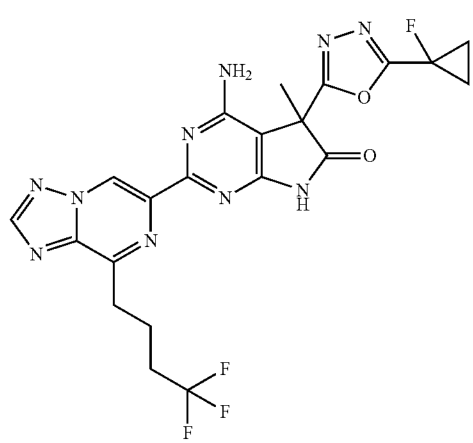 [SMILES: CC1(c2nnc(C3(F)CC3)o2)C(=O)Nc2nc(-c3cn4ncnc4c(CCCC(F)(F)F)n3)nc(N)c21] | 4-amino-5-(5-(1-fluorocyclopropyl)-1,3,4-oxadiazol-2-yl)-5-methyl-2-(8-(4,4,4-trifluorobutyl)-[1,2,4]triazolo[1,5-a]pyrazin-6-yl)-5H-pyrrolo[2,3-d]pyrimidin-6(7H)-one (fast eluting) | 519.2 | CHIRALPAK IB |

Example 110A

4-Amino-5-(5-hydroxypyridin-2-yl)-5-methyl-2-(8-(3,3,4,4,4-pentafluorobutyl)-[1,2,4]triazolo[1,5-a]pyrazin-6-yl)-5,7-dihydro-6H-pyrrolo[2,3-d]pyrimidin-6-one

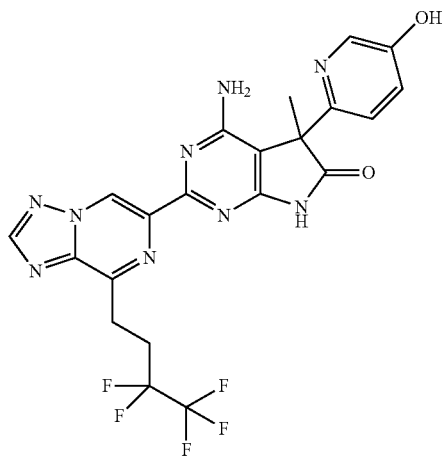 [SMILES: CC1(c2ccc(O)cn2)C(=O)Nc2nc(-c3cn4ncnc4c(CCC(F)(F)C(F)(F)F)n3)nc(N)c21]

Step A—4-Amino-5-(5-methoxypyridin-2-yl)-5-methyl-2-(8-(3,3,4,4,4-pentafluorobutyl)-[1,2,4]triazolo[1,5-a]pyrazin-6-yl)-5,7-dihydro-6H-pyrrolo[2,3-d]pyrimidin-6-one Into a vial was placed I-A2 (100 mg, 0.324 mmol), I-10A (98 mg, 0.357 mmol), potassium bicarbonate (39.0 mg, 0.389 mmol) and t-BuOH (8 mL). The resulting mixture was warmed at 70° C. for 16 h. The reaction was cooled to RT and quenched by the addition of brine. The resulting solution was extracted with EtOAc (3×) and the organic layers were combined, dried over anhydr. Na$_2$SO$_4$, filtered and the filtrate was conc. in vacuo to dryness. The residue was purified by silica gel chromatography using MeOH:DCM (10%) to afford the title product.

Step B—4-Amino-5-(5-hydroxypyridin-2-yl)-5-methyl-2-(8-(3,3,4,4,4-pentafluorobutyl)-[1,2,4]triazolo[1,5-a]pyrazin-6-yl)-5,7-dihydro-6H-pyrrolo[2,3-d]pyrimidin-6-one Into a vial, under an inert atmosphere of nitrogen, was placed intermediate from step A (90 mg, 0.16 mmol) and DCM (9 mL) and the reaction mixture was cooled to 0° C. To the mixture was added tribromoborane (0.9 mL, 9.52 mmol) dropwise at 0° C. The reaction was then stirred 16 h at rt. The reaction mixture was cooled to 0° C., then quenched by the addition of sat. aq. NaHCO$_3$. The mixture was extracted with EtOAc (3×). The organic layer was washed with brine, dried over anhydr. Na$_2$SO$_4$, and filtered. The filtrate was conc. in vacuo to dryness. The residue was purified by silica gel column chromatography with MeOH:DCM (1-6%) to afford the title compound. $^1$H NMR (300 MHz, CD$_3$OD) δ 9.63 (s, 1H), 8.63 (s, 1H), 8.15 (d, J=2.4 Hz, 1H), 7.32 (d, J=8.7 Hz, 1H), 7.20 (dd, J=2.4, 8.7 Hz, 1H), 3.68-3.62 (m, 2H), 3.07-2.89 (m, 2H), 1.86 (s, 3H); m/z 522.1 [M+1]$^+$.

Using essentially the same procedures described in Example 110A, the following compounds in Table 8 were prepared.

TABLE 8

| Ex. | Structure | Name | MS (M + 1) | Chiral starting material |
|---|---|---|---|---|
| 111A | 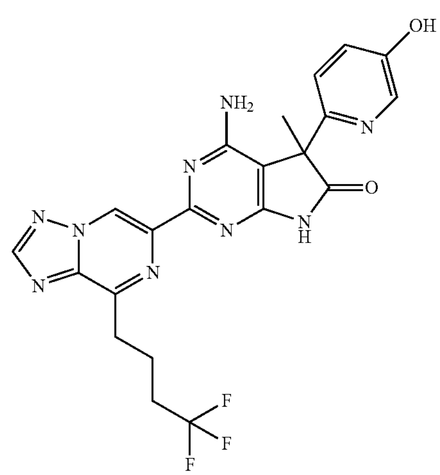 [SMILES: CC1(c2ccc(O)cn2)C(=O)Nc2nc(-c3cn4ncnc4c(CCCC(F)(F)F)n3)nc(N)c21] | 4-amino-5-(5-hydroxypyridin-2-yl)-5-methyl-2-(8-(4,4,4-trifluorobutyl)-[1,2,4]triazolo[1,5-a]pyrazin-6-yl)-5H-pyrrolo[2,3-d]pyrimidin-6(7H)-one | 486.4 | Ex-40A |

TABLE 8-continued

| Ex. | Structure | Name | MS (M + 1) | Chiral starting material |
|---|---|---|---|---|
| 112A | 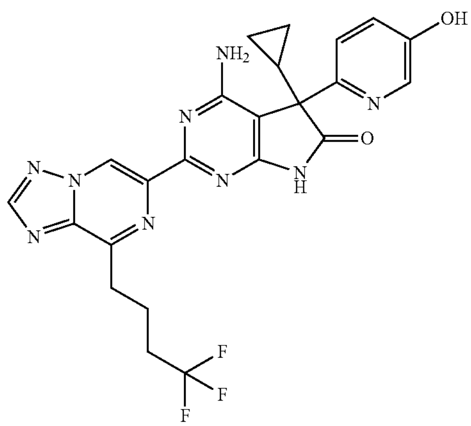 [SMILES: Nc1nc(-c2cn3ncnc3c(CCCC(F)(F)F)n2)nc2c1C(c1ccc(O)cn1)(C1CC1)C(=O)N2] | 4-amino-5-cyclopropyl-5-(5-hydroxypyridin-2-yl)-2-(8-(4,4,4-trifluorobutyl)-[1,2,4]triazolo[1,5-a]pyrazin-6-yl)-5H-pyrrolo[2,3-d]pyrimidin-6(7H)-one | 512.2 | Ex-39A |
| 113B | 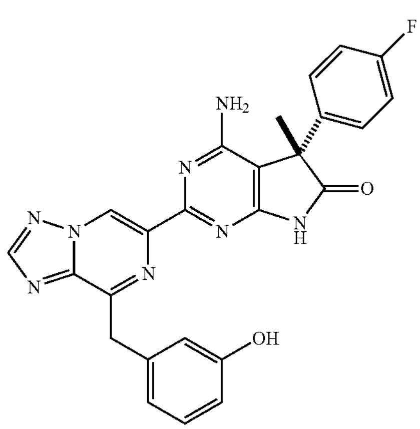 [SMILES: C[C@@]1(c2ccc(F)cc2)C(=O)Nc2nc(-c3cn4ncnc4c(Cc4cccc(O)c4)n3)nc(N)c21] | (S)-4-amino-5-(4-fluorophenyl)-2-(8-(3-hydroxybenzyl)-[1,2,4]triazolo[1,5-a]pyrazin-6-yl)-5-methyl-5H-pyrrolo[2,3-d]pyrimidin-6(7H)-one | 483.1 | Ex-86B |

Example 114A 4-amino-5-cyclopropyl-2-(8-(3,3,4,4,4-pentafluorobutyl)-[1,2,4]triazolo[1,5-a]pyrazin-6-yl)-5-(pyridin-2-yl)-5,7-dihydro-6H-pyrrolo[2,3-d]pyrimidin-6-one

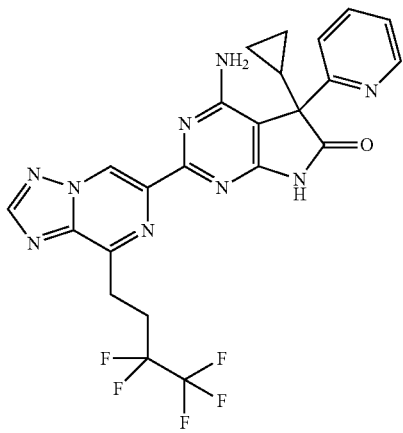 [SMILES: Nc1nc(-c2cn3ncnc3c(CCC(F)(F)C(F)(F)F)n2)nc2c1C(c1ccccn1)(C1CC1)C(=O)N2]

Into a 40-mL vial were placed 4-amino-5-(5-chloropyridin-2-yl)-5-cyclopropyl-2-(8-(3,3,4,4,4-pentafluorobutyl)-[1,2,4]triazolo[1,5-a]pyrazin-6-yl)-5H-pyrrolo[2,3-d]pyrimidin-6(7H)-one (130 mg, 0.23 mmol), Pd/C (130 mg, 10%), ammonium formate (56 mg, 0.88 mmol) and MeOH (13 mL). The resulting solution was stirred 1 h at 60° C. then cooled to RT and filtered. The filtrate was conc. in vacuo to dryness. The residue was purified by silica gel column chromatography with MeOH:DCM (10%) to afford the title compound. $^1$H NMR (400 MHz, CD$_3$OD) δ 9.65 (s, 1H), 8.65 (s, 1H), 8.62-8.56 (m, 1H), 7.93-7.82 (m, 2H), 7.40-7.37 (m, 1H), 3.66 (t, J=8.0 Hz, 2H), 3.05-2.92 (m, 2H), 2.01-1.94 (m, 1H), 0.73-052 (m, 4H); m/z 532.1 [M+1]$^+$.

Using essentially the same procedures described in Example 114A, the following compounds in Table 9 were prepared.

TABLE 9

| Ex. | Structure | Name | MS (M + 1) | Chiral starting material |
|---|---|---|---|---|
| 115A | 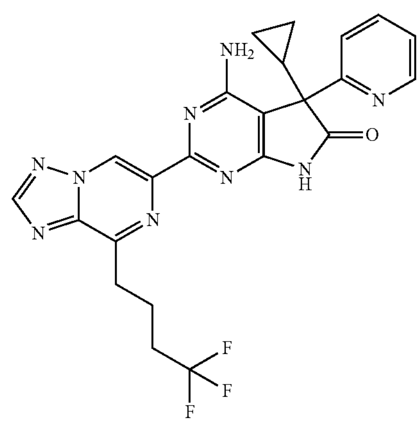 [SMILES: Nc1nc(-c2cn3ncnc3c(CCCC(F)(F)F)n2)nc2c1C(c1ccccn1)(C1CC1)C(=O)N2] | 4-amino-5-cyclopropyl-5-(pyridin-2-yl)-2-(8-(4,4,4-trifluorobutyl)-[1,2,4]triazolo[1,5-a]pyrazin-6-yl)-5H-pyrrolo[2,3-d]pyrimidin-6(7H)-one | 496.0 | Ex-27A |
| 116A | 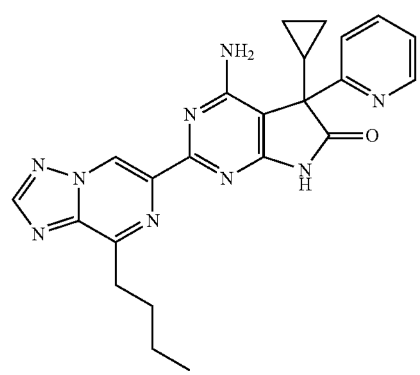 [SMILES: CCCCc1nc(-c2nc(N)c3c(n2)NC(=O)C3(c2ccccn2)C2CC2)cn2ncnc12] | 4-amino-2-(8-butyl-[1,2,4]triazolo[1,5-a]pyrazin-6-yl)-5-cyclopropyl-5-(pyridin-2-yl)-5H-pyrrolo[2,3-d]pyrimidin-6(7H)-one | 442.3 | EX-68A |

Example 117A 6-(4-Amino-5-cyclopropyl-6-oxo-2-(8-(4,4,4-trifluorobutyl)-[1,2,4]triazolo[1,5-a]pyrazin-6-yl)-6,7-dihydro-5H-pyrrolo[2,3-d]pyrimidin-5-yl)nicotinonitrile

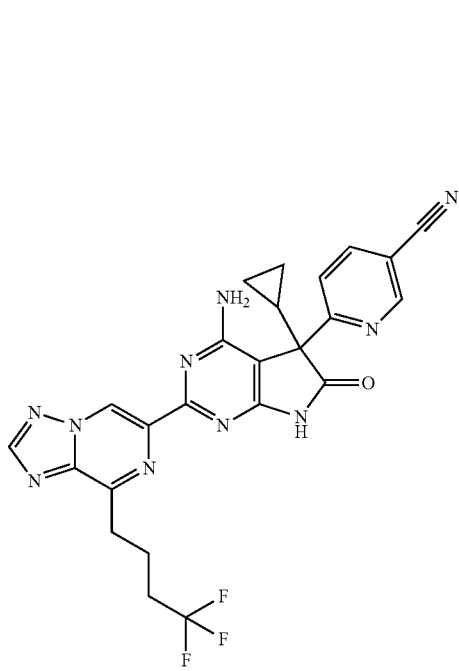 [SMILES: N#Cc1ccc(C2(C3CC3)C(=O)Nc3nc(-c4cn5ncnc5c(CCCC(F)(F)F)n4)nc(N)c32)nc1]

Into a microwave vial, under an inert atmosphere of nitrogen, was placed 4-amino-5-(5-chloropyridin-2-yl)-5-cyclopropyl-2-(8-(4,4,4-trifluorobutyl)-[1,2,4]triazolo[1,5-a]pyrazin-6-yl)-5H-pyrrolo[2,3-d]pyrimidin-6(7H)-one (120 mg, 0.23 mmol), water (50 μL), zinc cyanide (85 mg, 0.72 mmol), tris(dibenzylideneacetone)dipalladium(0)-chloroform (85 mg, 0.093 mmol), dicyclohexyl(2',6'-dimethoxybiphenyl-2-yl)phosphine (85 mg, 0.21 mmol) and DMF (5 mL). The reaction mixture was then heated to 150° C. for 40 min in a microwave reactor. The reaction mixture was cooled to RT, quenched by the addition of brine. The mixture was extracted with EtOAc (3×). The organic layer was washed with brine, dried over anhydr. Na$_2$SO$_4$, and filtered. The filtrate was conc. in vacuo to dryness. The residue was purified by silica gel column chromatography with EtOAc:petroleum ether (30-100%). The reaction mixture was filtered and purified by reverse phase HPLC acetonitrile:water (with 0.05% ammonium bicarbonate modifier) to afford the title compound. $^1$H NMR (300 MHz, CD$_3$OD) δ 9.58 (s, 1H), 8.88 (dd, J=0.9, 2.1 Hz, 1H), 8.60 (s, 1H), 8.22 (dd, J=2.1, 8.4 Hz, 1H), 7.98 (dd, J=0.9, 8.4 Hz, 1H), 3.38 (t, J=7.5 Hz, 2H), 2.37-2.16 (m, 4H), 1.98-1.89 (m, 1H), 0.71-0.51 (m, 4H); m/z=521.2 [M+1]$^+$.

Example 118A 6-(4-Amino-5-cyclopropyl-6-oxo-2-(8-(3,3,4,4,4-pentafluorobutyl)-[1,2,4]triazolo[1,5-a]pyrazin-6-yl)-6,7-dihydro-5H-pyrrolo[2,3-d]pyrimidin-5-yl)nicotinonitrile

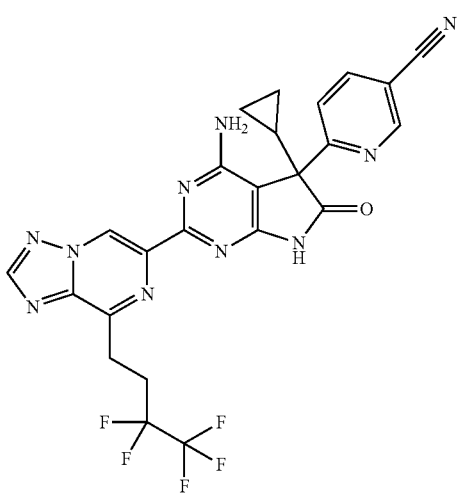 [SMILES: N#Cc1ccc(C2(C3CC3)C(=O)Nc3nc(-c4cn5ncnc5c(CCC(F)(F)C(F)(F)F)n4)nc(N)c32)nc1]

Using essentially the same procedures described in Example 117A, Example 118A was prepared, using 4-amino-5-(5-chloropyridin-2-yl)-5-cyclopropyl-2-(8-(3,3,4,4,4-pentafluorobutyl)-[1,2,4]triazolo[1,5-a]pyrazin-6-yl)-5H-pyrrolo[2,3-d]pyrimidin-6(7H)-one as starting material. m/z=557.4 [M+1]$^+$.

Example 119A (S)-5-(4-fluorophenyl)-4-hydroxy-5-methyl-2-(8-(3,3,4,4,4-pentafluorobutyl)-[1,2,4]triazolo[1,5-a]pyrazin-6-yl)-5,7-dihydro-6H-pyrrolo[2,3-d]pyrimidin-6-one

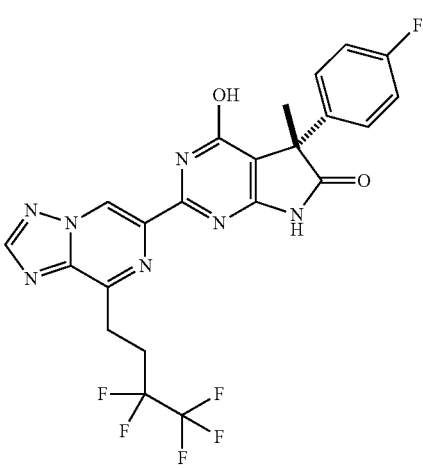 [SMILES: C[C@@]1(c2ccc(F)cc2)C(=O)Nc2nc(-c3cn4ncnc4c(CCC(F)(F)C(F)(F)F)n3)nc(O)c21]

Into a vial, under an inert atmosphere of nitrogen, was placed Example 1A (100 mg, 0.19 mmol), tert-butyl nitrite (138 mg, 1.34 mmol), DMF (10 mL) and water (50 μL). The resulting mixture was stirred for 30 min at 80° C., then cooled to RT and quenched by the addition of water. The mixture was extracted with EtOAc (3×). The organic layer was washed with brine, dried over anhydr. $Na_2SO_4$, and filtered. The filtrate was conc. in vacuo to dryness. The residue was purified by silica gel column chromatography with DCM:MeOH (10%) to afford the title compound. $^1$H NMR (500, DMSO-$d_6$): δ 12.73 (s, 1H). 11.37 (s, 1H), 9.51 (s, 1H), 8.93 (s, 1H), 7.46-7.43 (m, 2H), 7.20-7.16 (m, 2H), 3.57 (t, J=8.0 Hz, 2H), 3.25-3.05 (m, 2H,), 1.75 (s, 3H), m/z=524.0 [M+1]$^+$.

Using essentially the same procedures described in Example 119A, the following compounds in Table 10 were prepared. The conditions employed may utilize slight variations of reagents such as tert-butyl nitrite, isopentyl nitrite, or a combination of sodium nitrite and an acid such as sulfuric acid in 1,2-DCE, DMA, DMF, MeCN, THF, or combinations of solvents thereof at elevated temperatures of 40-80° C.

TABLE 10

| Ex. | Structure | Name | MS (M + 1) | Chiral starting material |
|---|---|---|---|---|
| 120A | 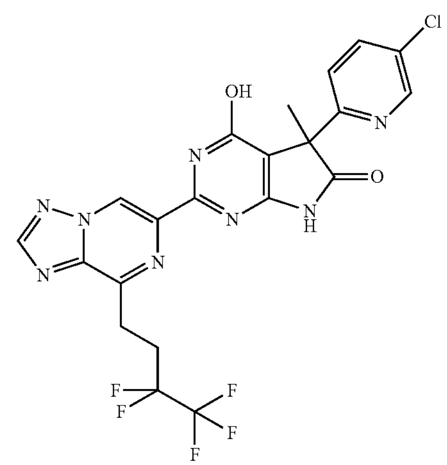 [SMILES: CC1(c2ccc(Cl)cn2)C(=O)Nc2nc(-c3cn4ncnc4c(CCC(F)(F)C(F)(F)F)n3)nc(O)c21] | 5-(5-chloropyridin-2-yl)-4-hydroxy-5-methyl-2-(8-(3,3,4,4,4-pentafluorobutyl)-[1,2,4]triazolo[1,5-a]pyrazin-6-yl)-5H-pyrrolo[2,3-d]pyrimidin-6(7H)-one | 541.1 | Ex-3A |
| 121B | 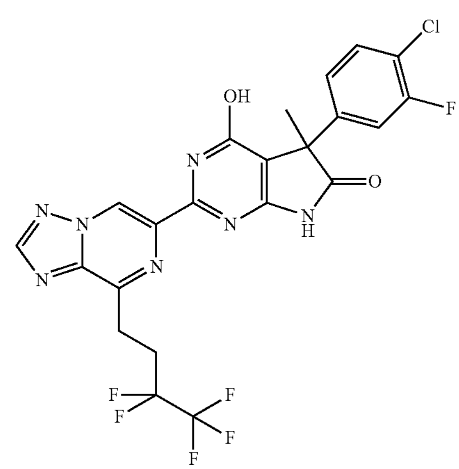 | 5-(4-chloro-3-fluorophenyl)-4-hydroxy-5-methyl-2-(8-(3,3,4,4,4-pentafluorobutyl)-[1,2,4]triazolo[1,5-a]pyrazin-6-yl)-5H-pyrrolo[2,3-d]pyrimidin-6(7H)-one | 558.3 | Ex-5B |

TABLE 10-continued

| Ex. | Structure | Name | MS (M + 1) | Chiral starting material |
|---|---|---|---|---|
| 122B | 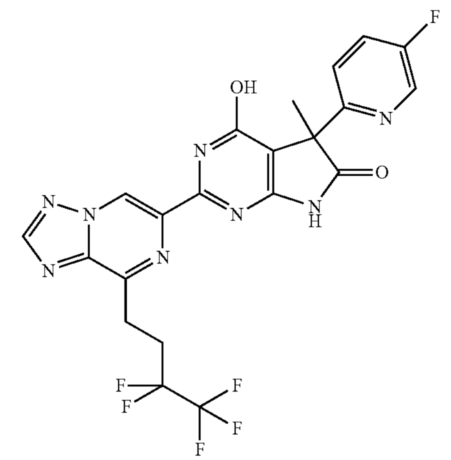 [SMILES: CC1(c2ccc(F)cn2)C(=O)Nc2nc(-c3cn4ncnc4c(CCC(F)(F)C(F)(F)F)n3)nc(O)c21] | 5-(5-fluoropyridin-2-yl)-4-hydroxy-5-methyl-2-(8-(3,3,4,4,4-pentafluorobutyl)-[1,2,4]triazolo[1,5-a]pyrazin-6-yl)-5H-pyrrolo[2,3-d]pyrimidin-6(7H)-one | 525.1 | Ex-4B |
| 123A | 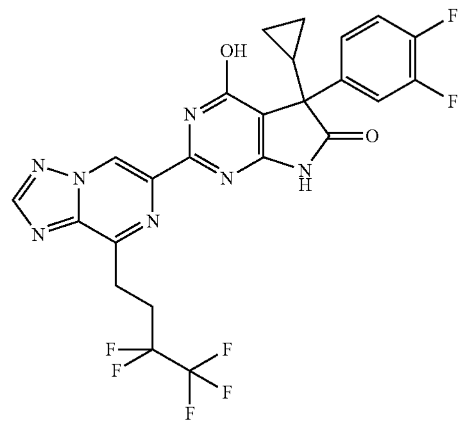 [SMILES: O=C1Nc2nc(-c3cn4ncnc4c(CCC(F)(F)C(F)(F)F)n3)nc(O)c2C1(c1ccc(F)c(F)c1)C1CC1] | 5-cyclopropyl-5-(3,4-difluorophenyl)-4-hydroxy-2-(8-(3,3,4,4,4-pentafluorobutyl)-[1,2,4]triazolo[1,5-a]pyrazin-6-yl)-5H-pyrrolo[2,3-b]pyrimidin-6(7H)-one | 568.1 | Ex-6A |
| 124B | 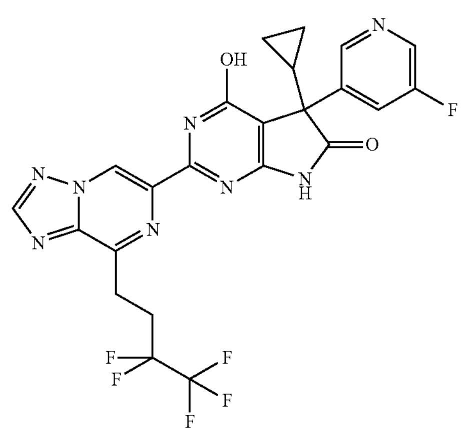 [SMILES: O=C1Nc2nc(-c3cn4ncnc4c(CCC(F)(F)C(F)(F)F)n3)nc(O)c2C1(c1cncc(F)c1)C1CC1] | 5-cyclopropyl-5-(5-fluoropyridin-3-yl)-4-hydroxy-2-(8-(3,3,4,4,4-pentafluorobutyl)-[1,2,4]triazolo[1,5-a]pyrazin-6-yl)-5H-pyrrolo[2,3-d]pyrimidin-6(7H)-one | 551.2 | Ex-8B |

TABLE 10-continued

| Ex. | Structure | Name | MS (M + 1) | Chiral starting material |
|---|---|---|---|---|
| 125A | 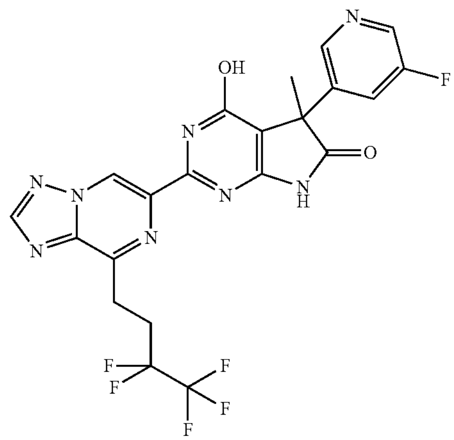 [SMILES: CC1(c2cncc(F)c2)C(=O)Nc2nc(-c3cn4ncnc4c(CCC(F)(F)C(F)(F)F)n3)nc(O)c21] | 5-(5-fluoropyridin-3-yl)-4-hydroxy-5-methyl-2-(8-(3,3,4,4,4-pentafluorobutyl)-[1,2,4]triazolo[1,5-a]pyrazin-6-yl)-5H-pyrrolo[2,3-d]pyrimidin-6(7H)-one | 525.1 | Ex-9A |
| 126A | 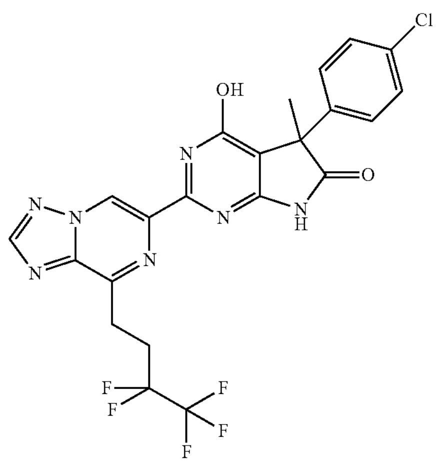 [SMILES: CC1(c2ccc(Cl)cc2)C(=O)Nc2nc(-c3cn4ncnc4c(CCC(F)(F)C(F)(F)F)n3)nc(O)c21] | 5-(4-chlorophenyl)-4-hydroxy-5-methyl-2-(8-(3,3,4,4,4-pentafluorobutyl)-[1,2,4]triazolo[1,5-a]pyrazin-6-yl)-5H-pyrrolo[2,3-d]pyrimidin-6(7H)-one | 540.0 | Ex-10A |
| 127B | 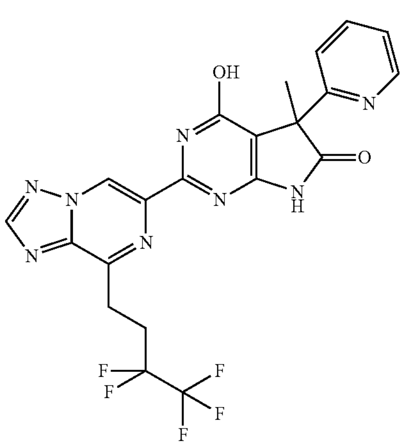 [SMILES: CC1(c2ccccn2)C(=O)Nc2nc(-c3cn4ncnc4c(CCC(F)(F)C(F)(F)F)n3)nc(O)c21] | 4-hydroxy-5-methyl-2-(8-(3,3,4,4,4-pentafluorobutyl)-[1,2,4]triazolo[1,5-a]pyrazin-6-yl)-5-(pyridin-2-yl)-5H-pyrrolo[2,3-d]pyrimidin-6(7H)-one | 507.3 | Ex-11B |

TABLE 10-continued

| Ex. | Structure | Name | MS (M + 1) | Chiral starting material |
|---|---|---|---|---|
| 128B | 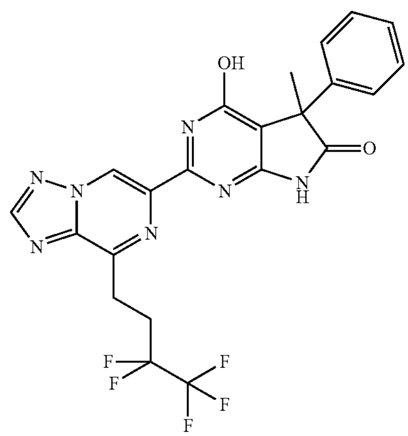 [SMILES: CC1(c2ccccc2)C(=O)Nc2nc(-c3cn4ncnc4c(CCC(F)(F)C(F)(F)F)n3)nc(O)c21] | 4-hydroxy-5-methyl-2-(8-(3,3,4,4,4-pentafluorobutyl)-[1,2,4]triazolo[1,5-a]pyrazin-6-yl)-5-phenyl-5H-pyrrolo[2,3-d]pyrimidin-6(7H)-one | 506.0 | Ex-12B |
| 129B | 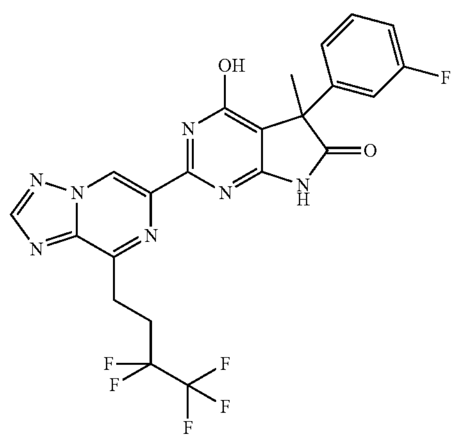 [SMILES: CC1(c2cccc(F)c2)C(=O)Nc2nc(-c3cn4ncnc4c(CCC(F)(F)C(F)(F)F)n3)nc(O)c21] | 5-(3-fluorophenyl)-4-hydroxy-5-methyl-2-(8-(3,3,4,4,4-pentafluorobutyl)-[1,2,4]triazolo[1,5-a]pyrazin-6-yl)-5,7-dihydro-6H-pyrrolo[2,3-d]pyrimidin-6-one | 524.3 | Ex-14B |
| 130B | 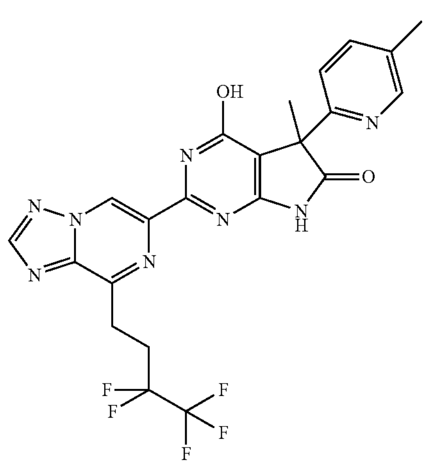 [SMILES: Cc1ccc(C2(C)C(=O)Nc3nc(-c4cn5ncnc5c(CCC(F)(F)C(F)(F)F)n4)nc(O)c32)nc1] | 4-hydroxy-5-methyl-5-(5-methylpyridin-2-yl)-2-(8-(3,3,4,4,4-pentafluorobutyl)-[1,2,4]triazolo[1,5-a]pyrazin-6-yl)-5H-pyrrolo[2,3-d]pyrimidin-6(7H)-one | 521.1 | Ex-19B |

TABLE 10-continued

| Ex. | Structure | Name | MS (M + 1) | Chiral starting material |
|---|---|---|---|---|
| 131A | 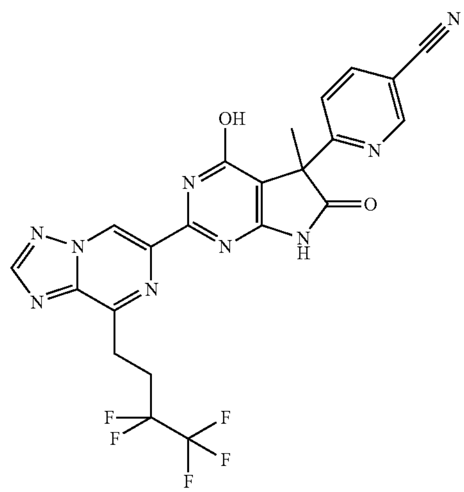 [SMILES: CC1(c2ccc(C#N)cn2)C(=O)Nc2nc(-c3cn4ncnc4c(CCC(F)(F)C(F)(F)F)n3)nc(O)c21] | 6-(4-hydroxy-5-methyl-6-oxo-2-(8-(3,3,4,4,4-pentafluorobutyl)-[1,2,4]triazolo[1,5-a]pyrazin-6-yl)-6,7-dihydro-5H-pyrrolo[2,3-d]pyrimidin-5-yl)nicotinonitrile | 532.3 | Ex-18A |
| 132B | 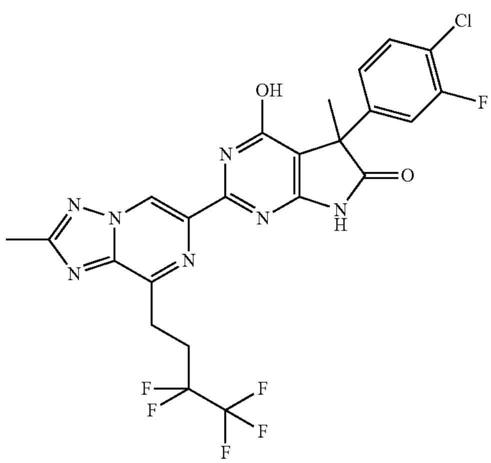 [SMILES: Cc1nc2c(CCC(F)(F)C(F)(F)F)nc(-c3nc(O)c4c(n3)NC(=O)C4(C)c3ccc(Cl)c(F)c3)cn2n1] | 5-(4-chloro-3-fluorophenyl)-4-hydroxy-5-methyl-2-(2-methyl-8-(3,3,4,4,4-pentafluorobutyl)-[1,2,4]triazolo[1,5-a]pyrazin-6-yl)-5H-pyrrolo[2,3-d]pyrimidin-6(7H)-one | 572.0 | Ex-90B |
| 133B | 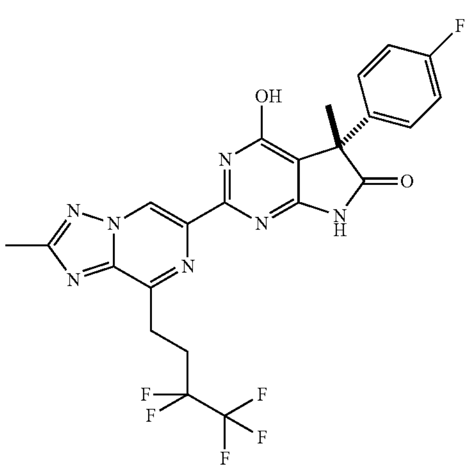 [SMILES: Cc1nc2c(CCC(F)(F)C(F)(F)F)nc(-c3nc(O)c4c(n3)NC(=O)[C@@]4(C)c3ccc(F)cc3)cn2n1] | (S)-5-(4-fluorophenyl)-4-hydroxy-5-methyl-2-(2-methyl-8-(3,3,4,4,4-pentafluorobutyl)-[1,2,4]triazolo[1,5-a]pyrazin-6-yl)-5H-pyrrolo[2,3-d]pyrimidin-6(7H)-one | 538.0 | Ex-88B |

TABLE 10-continued

| Ex. | Structure | Name | MS (M + 1) | Chiral starting material |
|---|---|---|---|---|
| 134A | 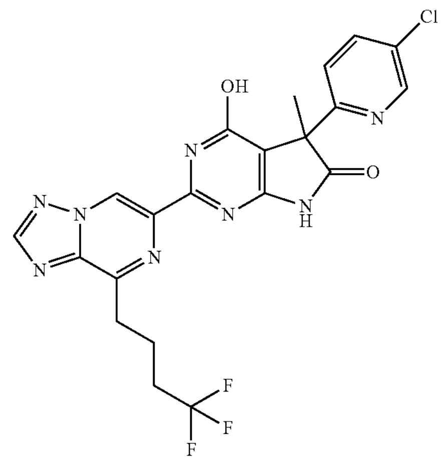 [SMILES: CC1(c2ccc(Cl)cn2)C(=O)Nc2nc(-c3cn4ncnc4c(CCCC(F)(F)F)n3)nc(O)c21] | 5-(5-chloropyridin-2-yl)-4-hydroxy-5-methyl-2-(8-(4,4,4-trifluorobutyl)-[1,2,4]triazolo[1,5-a]pyrazin-6-yl)-5H-pyrrolo[2,3-d]pyrimidin-6(7H)-one | 505.3 | Ex-26A |
| 135A | 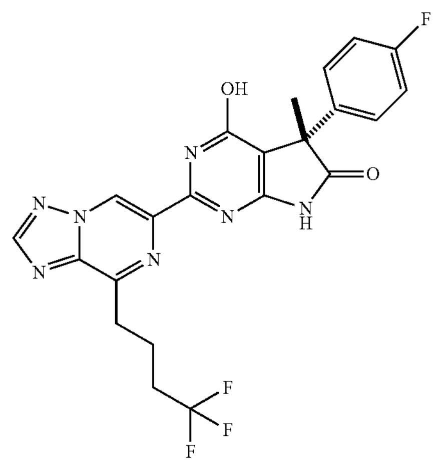 [SMILES: C[C@@]1(c2ccc(F)cc2)C(=O)Nc2nc(-c3cn4ncnc4c(CCCC(F)(F)F)n3)nc(O)c21] | 5-(4-fluorophenyl)-4-hydroxy-5-methyl-2-(8-(4,4,4-trifluorobutyl)-[1,2,4]triazolo[1,5-a]pyrazin-6-yl)-5,7-dihydro-6H-pyrrolo[2,3-d]pyrimidin-6-one | 488.3 | Ex-23A |
| 136B | 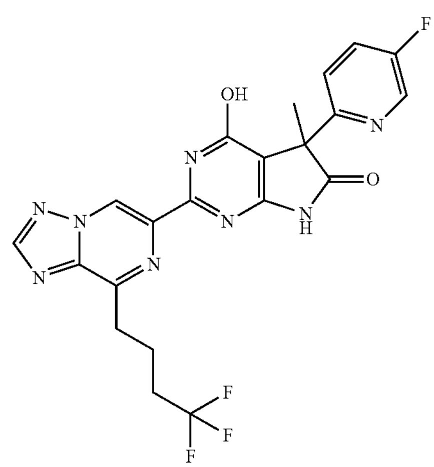 [SMILES: CC1(c2ccc(F)cn2)C(=O)Nc2nc(-c3cn4ncnc4c(CCCC(F)(F)F)n3)nc(O)c21] | 5-(5-fluoropyridin-2-yl)-4-hydroxy-5-methyl-2-(8-(4,4,4-trifluorobutyl)-[1,2,4]triazolo[1,5-a]pyrazin-6-yl)-5H-pyrrolo[2,3-d]pyrimidin-6(7H)-one | 489.1 | Ex-22B |

TABLE 10-continued

| Ex. | Structure | Name | MS (M + 1) | Chiral starting material |
|---|---|---|---|---|
| 137B | 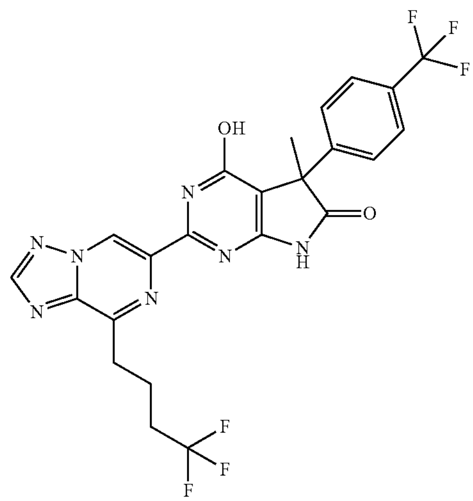 [SMILES: CC1(c2ccc(C(F)(F)F)cc2)C(=O)Nc2nc(-c3cn4ncnc4c(CCCC(F)(F)F)n3)nc(O)c21] | 4-hydroxy-5-methyl-2-(8-(4,4,4-trifluorobutyl)-[1,2,4]triazolo[1,5-a]pyrazin-6-yl)-5-(4-(trifluoromethyl)phenyl)-5H-pyrrolo[2,3-d]pyrimidin-6(7H)-one | 538.3 | Ex-24B |
| 138B | 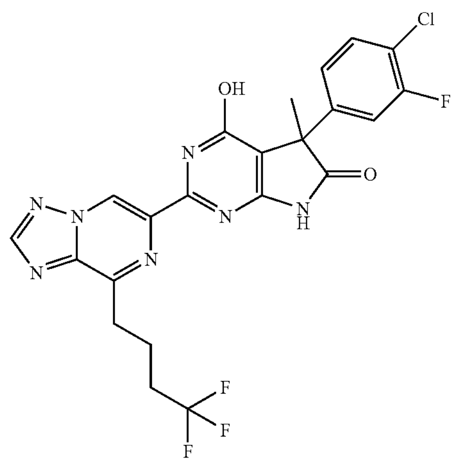 [SMILES: CC1(c2ccc(Cl)c(F)c2)C(=O)Nc2nc(-c3cn4ncnc4c(CCCC(F)(F)F)n3)nc(O)c21] | 5-(4-chloro-3-fluorophenyl)-4-hydroxy-5-methyl-2-(8-(4,4,4-trifluorobutyl)-[1,2,4]triazolo[1,5-a]pyrazin-6-yl)-5H-pyrrolo[2,3-d]pyrimidin-6(7H)-one | 522.2 | Ex-28B |
| 139B | 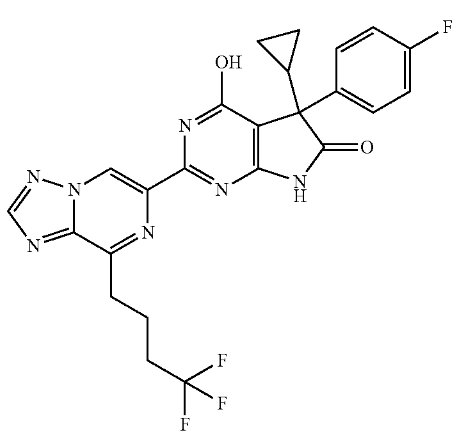 [SMILES: O=C1Nc2nc(-c3cn4ncnc4c(CCCC(F)(F)F)n3)nc(O)c2C1(c1ccc(F)cc1)C1CC1] | 5-cyclopropyl-5-(4-fluorophenyl)-4-hydroxy-2-(8-(4,4,4-trifluorobutyl)-[1,2,4]triazolo[1,5-a]pyrazin-6-yl)-5H-pyrrolo[2,3-d]pyrimidin-6(7H)-one | 514.1 | Ex-30B |

TABLE 10-continued

| Ex. | Structure | Name | MS (M + 1) | Chiral starting material |
|---|---|---|---|---|
| 140B | 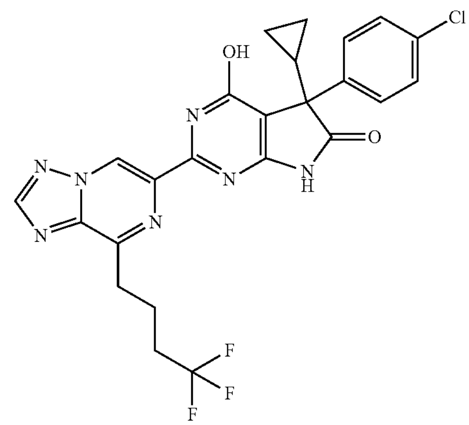 | 5-(4-chlorophenyl)-5-cyclopropyl-4-hydroxy-2-(8-(4,4,4-trifluorobutyl)-[1,2,4]triazolo[1,5-a]pyrazin-6-yl)-5H-pyrrolo[2,3-d]pyrimidin-6(7H)-one | 530.5 | Ex-31B |
| 141A | 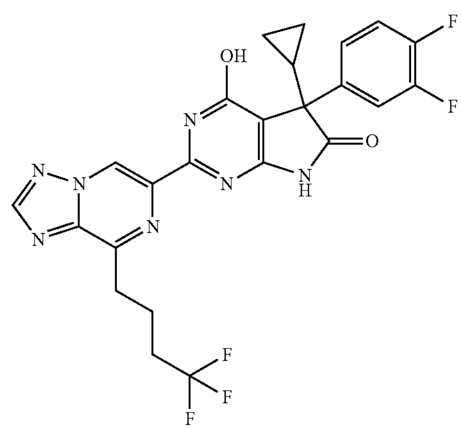 [SMILES: O=C1Nc2nc(-c3cn4ncnc4c(CCCC(F)(F)F)n3)nc(O)c2C1(c1ccc(F)c(F)c1)C1CC1] | 5-cyclopropyl-5-(3,4-difluorophenyl)-4-hydroxy-2-(8-(4,4,4-trifluorobutyl)-[1,2,4]triazolo[1,5-a]pyrazin-6-yl)-5H-pyrrolo[2,3-d]pyrimidin-6(7H)-one | 532.0 | Ex-32A |
| 142A | 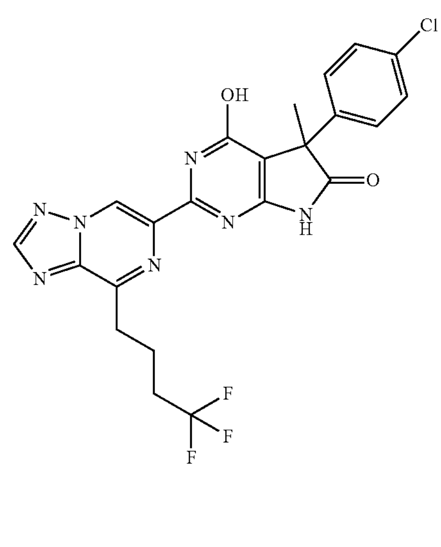 [SMILES: CC1(c2ccc(Cl)cc2)C(=O)Nc2nc(-c3cn4ncnc4c(CCCC(F)(F)F)n3)nc(O)c21] | 5-(4-chlorophenyl)-4-hydroxy-5-methyl-2-(8-(4,4,4-trifluorobutyl)-[1,2,4]triazolo[1,5-a]pyrazin-6-yl)-5H-pyrrolo[2,3-d]pyrimidin-6(7H)-one | 504.0 | Ex-29A |

TABLE 10-continued

| Ex. | Structure | Name | MS (M + 1) | Chiral starting material |
|---|---|---|---|---|
| 143B | 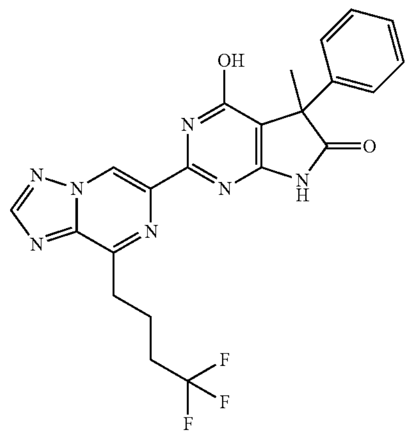 [SMILES: CC1(c2ccccc2)C(=O)Nc2nc(-c3cn4ncnc4c(CCCC(F)(F)F)n3)nc(O)c21] | 4-hydroxy-5-methyl-5-phenyl-2-(8-(4,4,4-trifluorobutyl)-[1,2,4]triazolo[1,5-a]pyrazin-6-yl)-5H-pyrrolo[2,3-d]pyrimidin-6(7H)-one | 470.3 | Ex-37B |
| 144A | 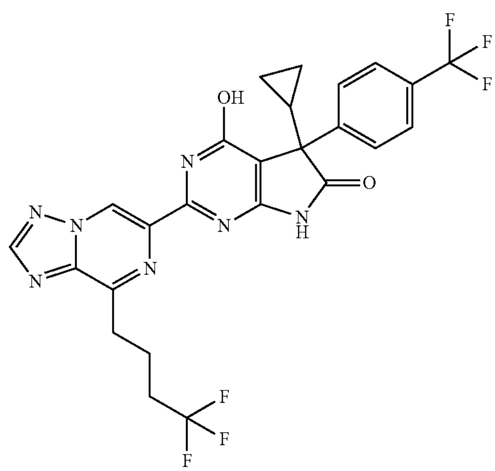 [SMILES: O=C1Nc2nc(-c3cn4ncnc4c(CCCC(F)(F)F)n3)nc(O)c2C1(c1ccc(C(F)(F)F)cc1)C1CC1] | 5-cyclopropyl-4-hydroxy-2-(8-(4,4,4-trifluorobutyl)-[1,2,4]triazolo[1,5-a]pyrazin-6-yl)-5-(4-(trifluoromethyl)phenyl)-5H-pyrrolo[2,3-d]pyrimidin-6(7H)-one | 564.0 | Ex-35A |
| 145B | 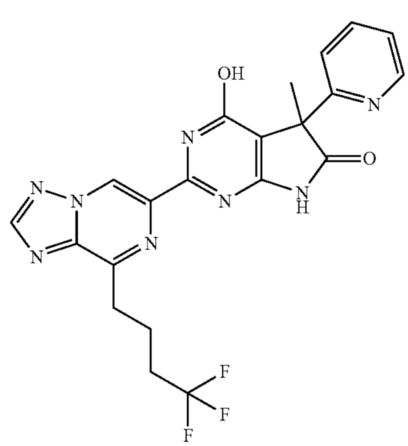 [SMILES: CC1(c2ccccn2)C(=O)Nc2nc(-c3cn4ncnc4c(CCCC(F)(F)F)n3)nc(O)c21] | 4-hydroxy-5-methyl-5-(pyridin-2-yl)-2-(8-(4,4,4-trifluorobutyl)-[1,2,4]triazolo[1,5-a]pyrazin-6-yl)-5H-pyrrolo[2,3-d]pyrimidin-6(7H)-one | 471.1 | Ex-36B |

TABLE 10-continued

| Ex. | Structure | Name | MS (M + 1) | Chiral starting material |
|---|---|---|---|---|
| 146B | 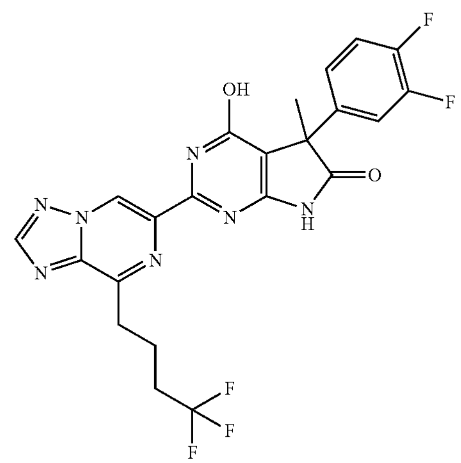 [SMILES: CC1(c2ccc(F)c(F)c2)C(=O)Nc2nc(-c3cn4ncnc4c(CCCC(F)(F)F)n3)nc(O)c21] | 5-(3,4-difluorophenyl)-4-hydroxy-5-methyl-2-(8-(4,4,4-trifluorobutyl)-[1,2,4]triazolo[1,5-a]pyrazin-6-yl)-5H-pyrrolo[2,3-d]pyrimidin-6(7H)-one | 506.1 | Ex-38B |
| 147B | 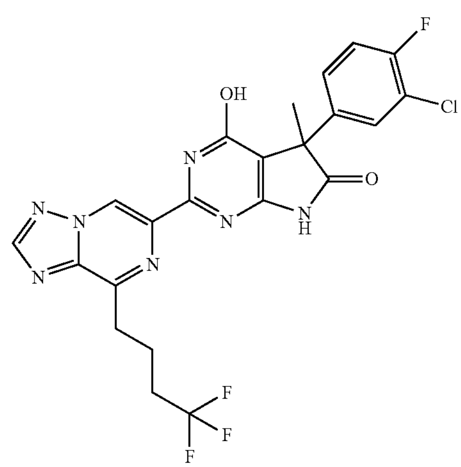 [SMILES: CC1(c2ccc(F)c(Cl)c2)C(=O)Nc2nc(-c3cn4ncnc4c(CCCC(F)(F)F)n3)nc(O)c21] | 5-(3-chloro-4-fluorophenyl)-4-hydroxy-5-methyl-2-(8-(4,4,4-trifluorobutyl)-[1,2,4]triazolo[1,5-a]pyrazin-6-yl)-5,7-dihydro-6H-pyrrolo[2,3-d]pyrimidin-6-one | 522.3 | Ex-42B |
| 148A | 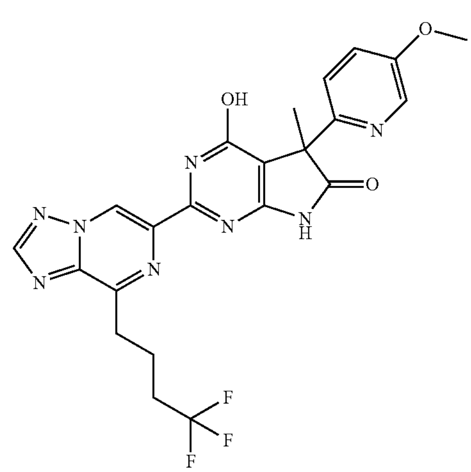 | 4-hydroxy-5-(5-methoxypyridin-2-yl)-5-methyl-2-(8-(4,4,4-trifluorobutyl)-[1,2,4]triazolo[1,5-a]pyrazin-6-yl)-5H-pyrrolo[2,3-d]pyrimidin-6(7H)-one | 501.3 | Ex-40A |

TABLE 10-continued

| Ex. | Structure | Name | MS (M + 1) | Chiral starting material |
|---|---|---|---|---|
| 149B | 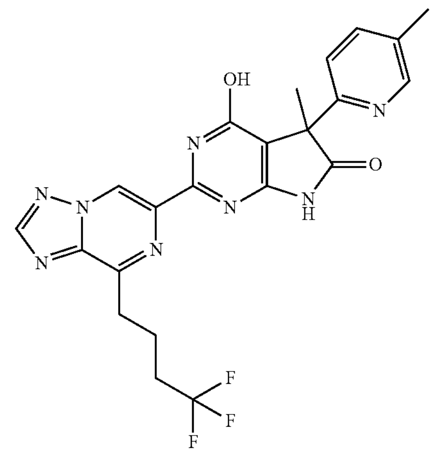 [SMILES: Cc1ccc(C2(C)C(=O)Nc3nc(-c4cn5ncnc5c(CCCC(F)(F)F)n4)nc(O)c32)nc1] | 4-hydroxy-5-methyl-5-(5-methylpyridin-2-yl)-2-(8-(4,4,4-trifluorobutyl)-[1,2,4]triazolo[1,5-a]pyrazin-6-yl)-5H-pyrrolo[2,3-d]pyrimidin-6(7H)-one | 485.1 | Ex-46B |
| 150A | 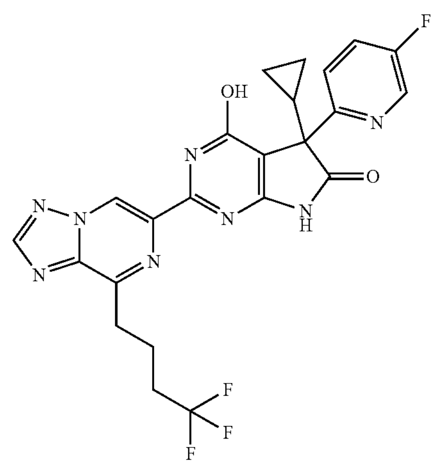 [SMILES: O=C1Nc2nc(-c3cn4ncnc4c(CCCC(F)(F)F)n3)nc(O)c2C1(c1ccc(F)cn1)C1CC1] | 5-cyclopropyl-5-(5-fluoropyridin-2-yl)-4-hydroxy-2-(8-(4,4,4-trifluorobutyl)-[1,2,4]triazolo[1,5-a]pyrazin-6-yl)-5,7-dihydro-6H-pyrrolo[2,3-d]pyrimidin-6-one | 515.1 | Ex-34A |
| 151A | 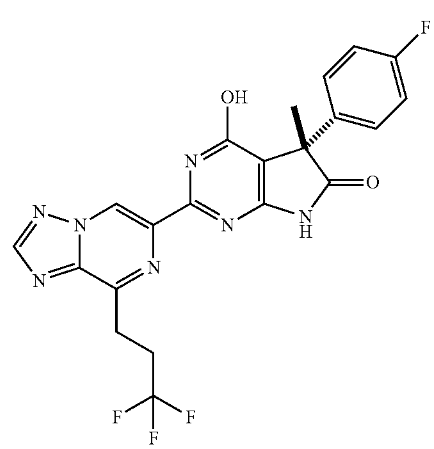 [SMILES: C[C@@]1(c2ccc(F)cc2)C(=O)Nc2nc(-c3cn4ncnc4c(CCC(F)(F)F)n3)nc(O)c21] | (S)-5-(4-fluroophenyl)-4-hydroxy-5-methyl-2-(8-(3,3,3-trifluoropropyl)-[1,2,4]triazolo[1,5-a]pyrazin-6-yl)-5,7-dihydro-6H-pyrrolo[2,3-d]pyrimidin-6-one | 474.1 | Ex-74A |

TABLE 10-continued

| Ex. | Structure | Name | MS (M + 1) | Chiral starting material |
|---|---|---|---|---|
| 152A | 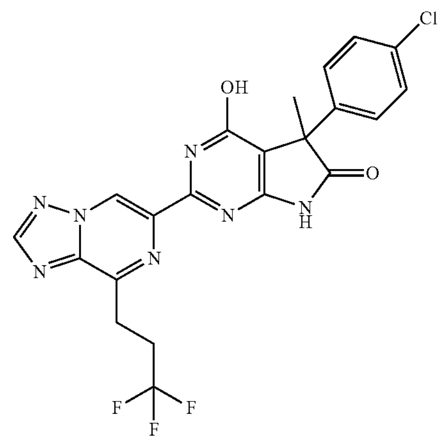 [SMILES: CC1(c2ccc(Cl)cc2)C(=O)Nc2nc(-c3cn4ncnc4c(CCC(F)(F)F)n3)nc(O)c21] | 5-(4-chlorophenyl)-4-hydroxy-5-methyl-2-(8-(3,3,3-trifluoropropyl)-[1,2,4]triazolo[1,5-a]pyrazin-6-yl)-5H-pyrrolo[2,3-d]pyrimidin-6(7H)-one | 490.2 | Ex-76A |
| 153B | 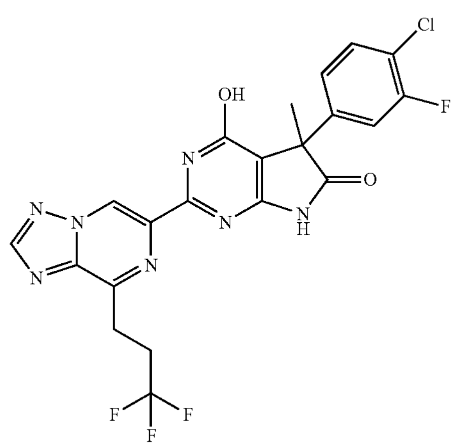 [SMILES: CC1(c2ccc(Cl)c(F)c2)C(=O)Nc2nc(-c3cn4ncnc4c(CCC(F)(F)F)n3)nc(O)c21] | 5-(4-chloro-3-fluorophenyl)-4-hydroxy-5-methyl-2-(8-(3,3,3-trifluoropropyl)-[1,2,4]triazolo[1,5-a]pyrazin-6-yl)-5H-pyrrolo[2,3-d]pyrimidin-6(7H)-one | 508.0 | Ex-75B |
| 154A | 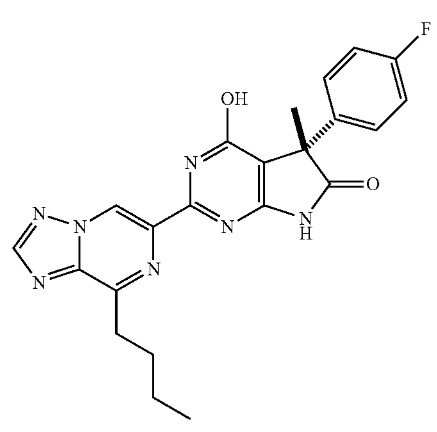 [SMILES: CCCCc1nc(-c2nc(O)c3c(n2)NC(=O)[C@@]3(C)c2ccc(F)cc2)cn2ncnc12] | (S)-2-(8-butyl-[1,2,4]triazolo[1,5-a]pyrazin-6-yl)-5-(4-fluorophenyl)-4-hydroxy-5-methyl-5,7-dihydro-6H-pyrrolo[2,3-d]pyrimidin-6-one | 434.2 | Ex-60A |

TABLE 10-continued

| Ex. | Structure | Name | MS (M + 1) | Chiral starting material |
|---|---|---|---|---|
| 155B | 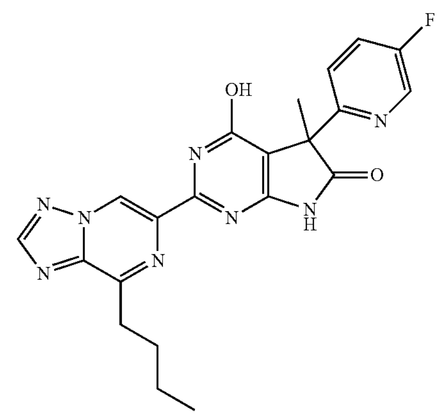 [SMILES: CCCCc1nc(-c2nc(O)c3c(n2)NC(=O)C3(C)c2ccc(F)cn2)cn2ncnc12] | 2-(8-butyl-[1,2,4]triazolo[1,5-a]pyrazin-6-yl)-5-(5-fluoropyridin-2-yl)-4-hydroxy-5-methyl-5H-pyrrolo[2,3-d]pyrimidin-6(7H)-one | 435.1 | Ex-61B |
| 156B | 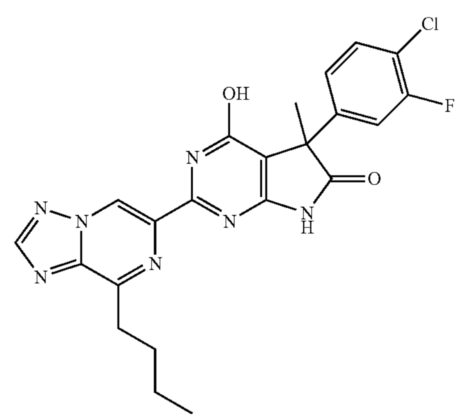 | 2-(8-butyl-[1,2,4]triazolo[1,5-a]pyrazin-6-yl)-5-(4-chloro-3-fluorophenyl)-4-hydroxy-5-methyl-5H-pyrrolo[2,3-d]pyrimidin-6(7H)-one | 468.2 | Ex-62B |
| 157A | 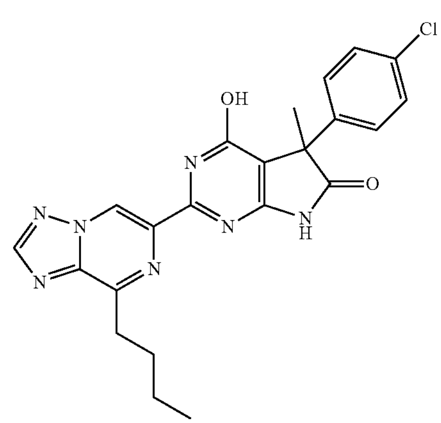 [SMILES: CCCCc1nc(-c2nc(O)c3c(n2)NC(=O)C3(C)c2ccc(Cl)cc2)cn2ncnc12] | 2-(8-butyl-[1,2,4]triazolo[1,5-a]pyrazin-6-yl)-5-(4-chlorophenyl)-4-hydroxy-5-methyl-5H-pyrrolo[2,3-d]pyrimidin-6(7H)-one | 450.2 | Ex-63A |

TABLE 10-continued

| Ex. | Structure | Name | MS (M + 1) | Chiral starting material |
|---|---|---|---|---|
| 158B | 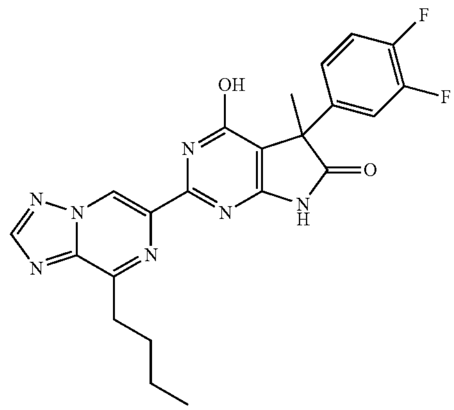 [SMILES: CCCCc1nc(-c2nc(O)c3c(n2)NC(=O)C3(C)c2ccc(F)c(F)c2)cn2ncnc12] | 2-(8-butyl-[1,2,4]triazolo[1,5-a]pyrazin-6-yl)-5-(3,4-difluorophenyl)-4-hydroxy-5-methyl-5H-pyrrolo[2,3-d]pyrimidin-6(7H)-one | 452.1 | Ex-64B |
| 159B | 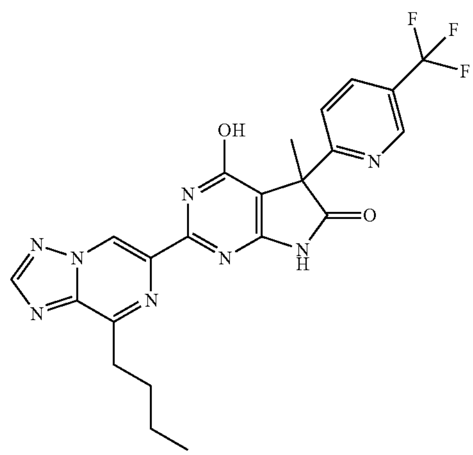 [SMILES: CCCCc1nc(-c2nc(O)c3c(n2)NC(=O)C3(C)c2ccc(C(F)(F)F)cn2)cn2ncnc12] | 2-(8-butyl-[1,2,4]triazolo[1,5-a]pyrazin-6-yl)-4-hydroxy-5-methyl-5-(5-(trifluoromethyl)pyridin-2-yl)-5H-pyrrolo[2,3-d]pyrimidin-6(7H)-one | 485.1 | Ex-67B |
| 160A | 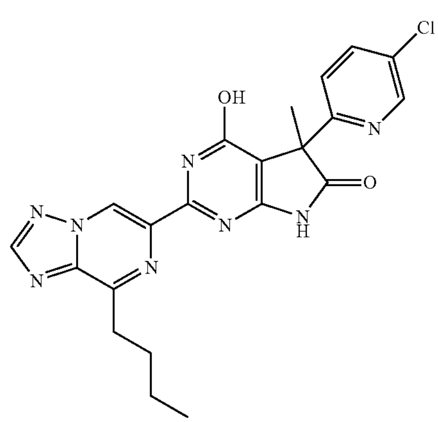 [SMILES: CCCCc1nc(-c2nc(O)c3c(n2)NC(=O)C3(C)c2ccc(Cl)cn2)cn2ncnc12] | 2-(8-butyl-[1,2,4]triazolo[1,5-a]pyrazin-6-yl)-5-(5-chloropyridin-2-yl)-4-hydroxy-5-methyl-5H-pyrrolo[2,3-d]pyrimidin-6(7H)-one | 451.2 | Ex-69A |

TABLE 10-continued

| Ex. | Structure | Name | MS (M + 1) | Chiral starting material |
|---|---|---|---|---|
| 161B | 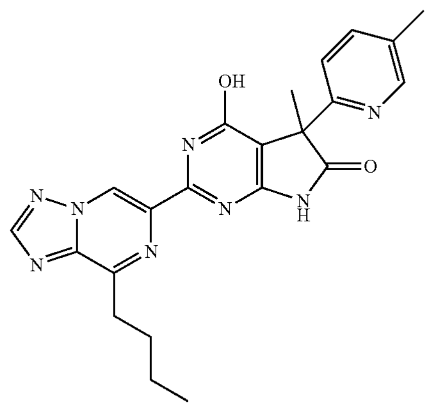 [SMILES: CCCCc1nc(-c2nc(O)c3c(n2)NC(=O)C3(C)c2ccc(C)cn2)cn2ncnc12] | 2-(8-butyl-[1,2,4]triazolo[1,5-a]pyrazin-6-yl)-4-hydroxy-5-methyl-5-(5-methylpyridin-2-yl)-5H-pyrrolo[2,3-d]pyrimidin-6(7H)-one | 431.2 | Ex-71B |
| 162B | 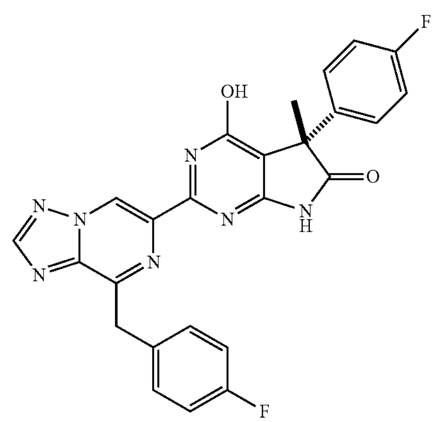 [SMILES: C[C@@]1(c2ccc(F)cc2)C(=O)Nc2nc(-c3cn4ncnc4c(Cc4ccc(F)cc4)n3)nc(O)c21] | (S)-2-(8-(4-fluorobenzyl)-[1,2,4]triazolo[1,5-a]pyrazin-6-yl)-5-(4-fluorophenyl)-4-hydroxy-5-methyl-5H-pyrrolo[2,3-d]pyrimidin-6(7H)-one | 486.1 | Ex-85B |
| 163A | 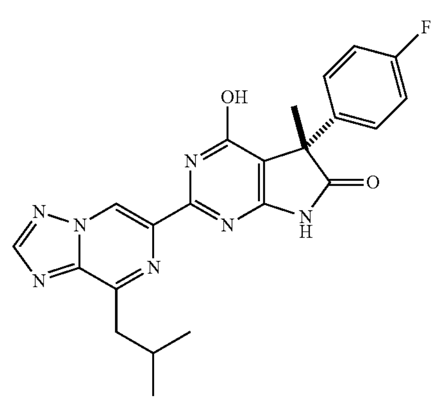 [SMILES: CC(C)Cc1nc(-c2nc(O)c3c(n2)NC(=O)[C@@]3(C)c2ccc(F)cc2)cn2ncnc12] | (S)-5-(4-fluorophenyl)-4-hydroxy-2-(8-isobutyl-[1,2,4]triazolo[1,5-a]pyrazin-6-yl)-5-methyl-5,7-dihydro-6H-pyrrolo[2,3-d]pyrimidin-6-one | 434.2 | Ex-73A |

TABLE 10-continued

| Ex. | Structure | Name | MS (M + 1) | Chiral starting material |
|---|---|---|---|---|
| 164A | 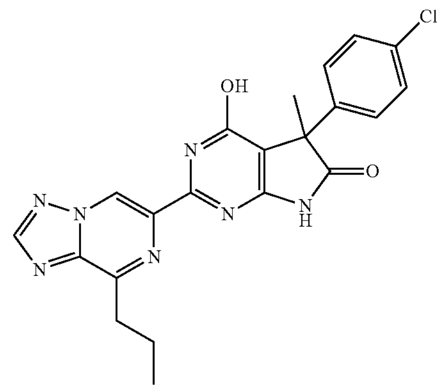 [SMILES: CCCc1nc(-c2nc(O)c3c(n2)NC(=O)C3(C)c2ccc(Cl)cc2)cn2ncnc12] | 5-(4-chlorophenyl)-4-hydroxy-5-methyl-2-(8-propyl-[1,2,4]triazolo[1,5-a]pyrazin-6-yl)-5H-pyrrolo[2,3-d]pyrimidin-6(7H)-one | 436.1 | Ex-53A |
| 165A | 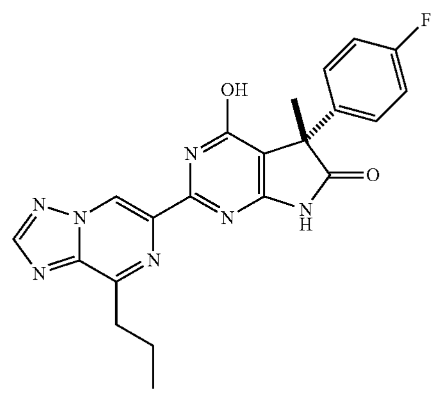 [SMILES: CCCc1nc(-c2nc(O)c3c(n2)NC(=O)[C@@]3(C)c2ccc(F)cc2)cn2ncnc12] | (S)-5-(4-fluorophenyl)-4-hydroxy-5-methyl-2-(8-propyl-[1,2,4]triazolo[1,5-a]pyrazin-6-yl)-5,7-dihydro-6H-pyrrolo[2,3-d]pyrimidin-6-one | 420.1 | Ex-52A |
| 166B | 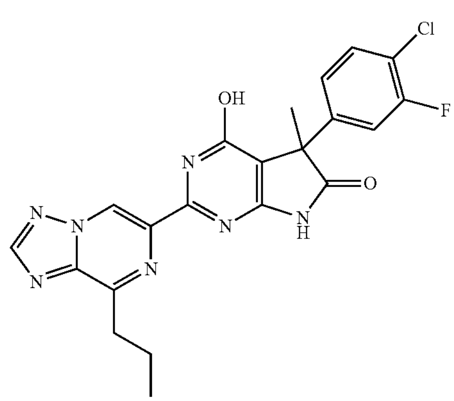 [SMILES: CCCc1nc(-c2nc(O)c3c(n2)NC(=O)C3(C)c2ccc(Cl)c(F)c2)cn2ncnc12] | 5-(4-chloro-3-fluorophenyl)-4-hydroxy-5-methyl-2-(8-propyl-[1,2,4]triazolo[1,5-a]pyrazin-6-yl)-5H-pyrrolo[2,3-d]pyrimidin-6(7H)-one | 454.1 | Ex-55B |

TABLE 10-continued

| Ex. | Structure | Name | MS (M + 1) | Chiral starting material |
|---|---|---|---|---|
| 167A | 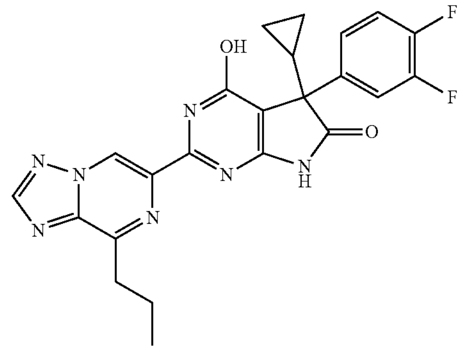 [SMILES: CCCc1nc(-c2nc(O)c3c(n2)NC(=O)C3(c2ccc(F)c(F)c2)C2CC2)cn2ncnc12] | 5-cyclopropyl-5-(3,4-difluorophenyl)-4-hydroxy-2-(8-propyl-[1,2,4]triazolo[1,5-a]pyrazin-6-yl)-5H-pyrrolo[2,3-d]pyrimidin-6(7H)-one | 464.1 | Ex-58A |
| 168A | 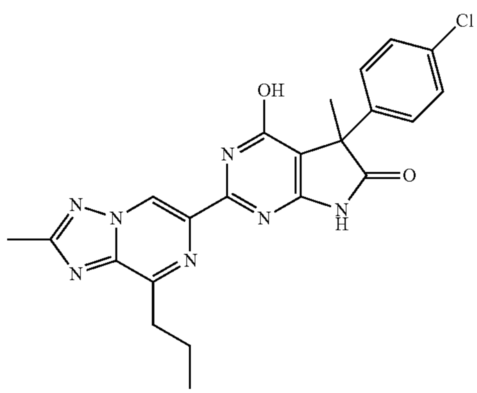 [SMILES: CCCc1nc(-c2nc(O)c3c(n2)NC(=O)C3(C)c2ccc(Cl)cc2)cn2nc(C)nc12] | 5-(4-chlorophenyl)-4-hydroxy-5-methyl-2-(2-methyl-8-propyl-[1,2,4]triazolo[1,5-a]pyrazin-6-yl)-5H-pyrrolo[2,3-d]pyrimidin-6(7H)-one | 450.2 | Ex-93A |

Example 169B 5-(3,4-Difluorophenyl)-4-hydroxy-5-methyl-2-(8-(3,3,4,4,4-pentafluorobutyl)-[1,2,4]triazolo[1,5-a]pyrazin-6-yl)-5,7-dihydro-6H-pyrrolo[2,3-d]pyrimidin-6-one

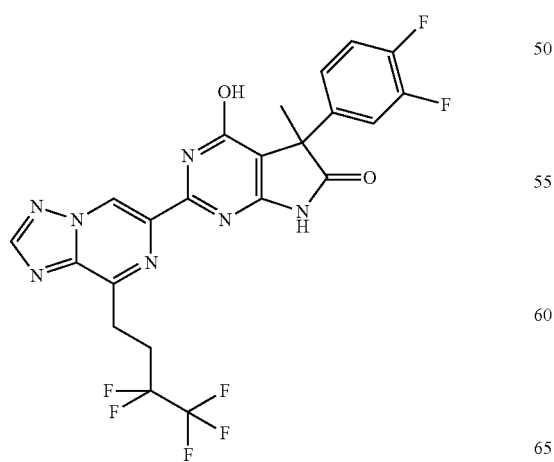

Step A—4-Amino-5-(3,4-difluorophenyl)-5-methyl-2-(8-(3,3,4,4,4-pentafluorobutyl)-[1,2,4]triazolo[1,5-a]pyrazin-6-yl)-5,7-dihydro-6H-pyrrolo[2,3-d]pyrimidin-6-one The title compound was prepared using essentially the same procedures described in Example 1A, using intermediate I-A2 and I-5B as starting material. m/z 541 [M+1]⁺.

Step B—5-(3,4-difluorophenyl)-4-hydroxy-5-methyl-2-(8-(3,3,4,4,4-pentafluorobutyl)-[1,2,4]triazolo[1,5-a]pyrazin-6-yl)-5,7-dihydro-6H-pyrrolo[2,3-d]pyrimidin-6-one The title compound was prepared using essentially the same procedures described in Example 119A, using intermediate from step A as starting material. m/z 542.0 [M+1]⁺.

Example 170A 5-(2-Fluorophenyl)-4-hydroxy-5-methyl-2-(8-(3,3,4,4,4-pentafluorobutyl)-[1,2,4]triazolo[1,5-a]pyrazin-6-yl)-5,7-dihydro-6H-pyrrolo[2,3-d]pyrimidin-6-one

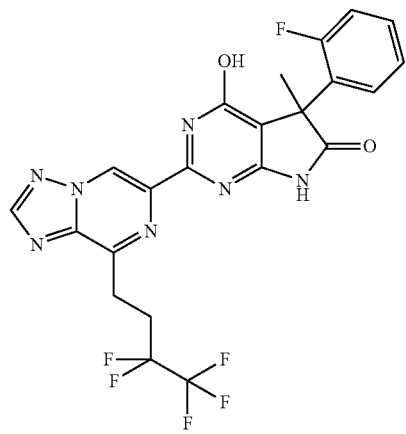 [SMILES: CC1(c2ccccc2F)C(=O)Nc2nc(-c3cn4ncnc4c(CCC(F)(F)C(F)(F)F)n3)nc(O)c21]

Step A—4-Amino-5-(2-fluorophenyl)-5-methyl-2-(8-(3,3,4,4,4-pentafluorobutyl)-[1,2,4]triazolo[1,5-a]pyrazin-6-yl)-5,7-dihydro-6H-pyrrolo[2,3-d]pyrimidin-6-one The title compound was prepared using essentially the same procedures described in Example 1A, using intermediate I-A2 and I-12B as starting material. m/z 523.1 [M+1]⁺.

Step B—5-(2-Fluorophenyl)-4-hydroxy-5-methyl-2-(8-(3,3,4,4,4-pentafluorobutyl)-[1,2,4]triazolo[1,5-a]pyrazin-6-yl)-5,7-dihydro-6H-pyrrolo[2,3-d]pyrimidin-6-one The title compound was prepared using essentially the same procedures described in Example 119A, using intermediate from step A as starting material. m/z=524.2 [M+1]⁺.

Example 171A 2-(8-Butyl-[1,2,4]triazolo[1,5-a]pyrazin-6-yl)-5-(3-fluorophenyl)-4-hydroxy-5-methyl-5,7-dihydro-6H-pyrrolo[2,3-d]pyrimidin-6-one

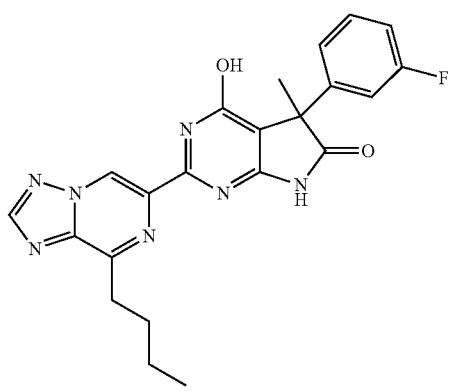 [SMILES: CCCCc1nc(-c2nc(O)c3c(n2)NC(=O)C3(C)c2cccc(F)c2)cn2ncnc12]

Step A—4-amino-2-(8-butyl-[1,2,4]triazolo[1,5-a]pyrazin-6-yl)-5-(3-fluorophenyl)-5-methyl-5,7-dihydro-6H-pyrrolo[2,3-d]pyrimidin-6-one The title compound was prepared using essentially the same procedures described in Example 1A, using intermediate I-A5 and I-7B as starting material. m/z=433.3 [M+1]⁺.

Step B—2-(8-butyl-[1,2,4]triazolo[1,5-a]pyrazin-6-yl)-5-(3-fluorophenyl)-4-hydroxy-5-methyl-5,7-dihydro-6H-pyrrolo[2,3-d]pyrimidin-6-one The title compound was prepared using essentially the same procedures described in Example 119A, using intermediate from step A as starting material. m/z=434.1 [M+1]⁺.

Example 172A (S)-5-(4-fluorophenyl)-5-methyl-2-(8-(3,3,4,4,4-pentafluorobutyl)-[1,2,4]triazolo[1,5-a]pyrazin-6-yl)-5,7-dihydro-6H-pyrrolo[2,3-d]pyrimidin-6-one

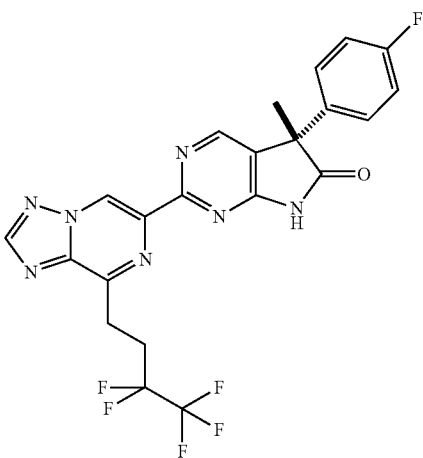 [SMILES: C[C@@]1(c2ccc(F)cc2)C(=O)Nc2nc(-c3cn4ncnc4c(CCC(F)(F)C(F)(F)F)n3)ncc21]

Into a vial, under an inert atmosphere of nitrogen, was placed Example 1A (100 mg, 0.191 mmol), tert-butyl nitrite (138 mg, 1.340 mmol) and anhydr. DMF (10 mL) The resulting mixture was stirred for 30 min at 80° C., then cooled to RT and quenched by the addition of water. The mixture was extracted with EtOAc (3×). The organic layer was washed with brine, dried over anhydr. Na$_2$SO$_4$, and filtered. The filtrate was conc. in vacuo to dryness. The residue was purified by silica gel column chromatography with DCM:MeOH (10%) to afford Example 119A and the title compound. $^1$H NMR (300, MeOD): δ 9.75 (s, 1H), 8.68 (s, 1H), 8.57 (s, 1H), 7.49-7.44 (m, 2H), 7.16-7.10 (m, 2H), 3.70-3.65 (m, 2H), 3.11-3.93 (m, 2H,), 1.91 (s, 3H), m/z=508.2 [M+1]$^+$.

Using essentially the same procedures described in Example 172A, the following compounds in Table 11 were prepared.

TABLE 11

| Ex. | Structure | Name | MS (M + 1) | Chiral starting material |
|---|---|---|---|---|
| 173A | 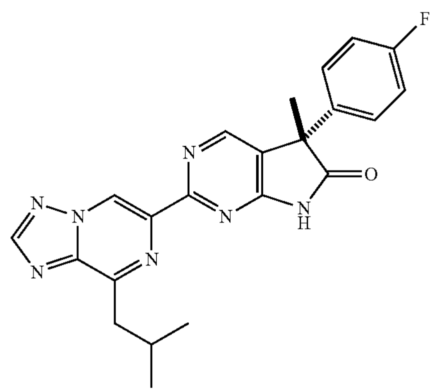 [SMILES: CC(C)Cc1nc(-c2ncc3c(n2)NC(=O)[C@@]3(C)c2ccc(F)cc2)cn2ncnc12] | (S)-5-(4-fluorophenyl)-2-(8-isobutyl-[1,2,4]triazolo[1,5-a]pyrazin-6-yl)-5-methyl-5,7-dihydro-6H-pyrrolo[2,3-d]pyrimidin-6-one | 418.2 | Ex-73A |
| 174A | 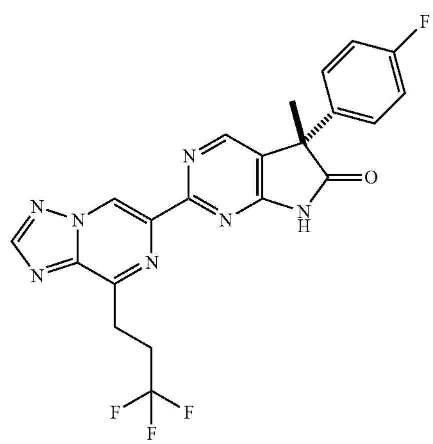 [SMILES: C[C@@]1(c2ccc(F)cc2)C(=O)Nc2nc(-c3cn4ncnc4c(CCC(F)(F)F)n3)ncc21] | (S)-5-(4-fluorophenyl)-5-methyl-2-(8-(3,3,3-trifluoropropyl)-[1,2,4]triazolo[1,5-a]pyrazin-6-yl)-5,7-dihydro-6H-pyrrolo[2,3-d]pyrimidin-6-one | 458.1 | Ex-74A |
| 175A | 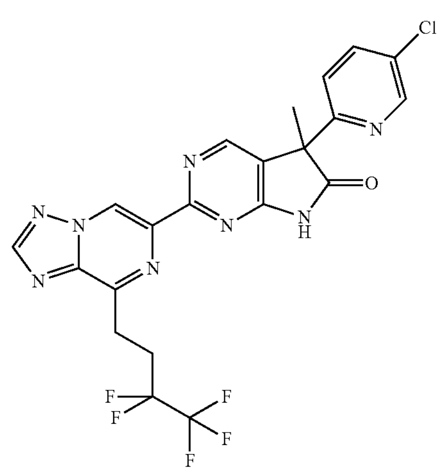 [SMILES: CC1(c2ccc(Cl)cn2)C(=O)Nc2nc(-c3cn4ncnc4c(CCC(F)(F)C(F)(F)F)n3)ncc21] | 5-(5-chloropyridin-2-yl)-5-methyl-2-(8-(3,3,4,4,4-pentafluorobutyl)-[1,2,4]triazolo[1,5-a]pyrazin-6-yl)-5H-pyrrolo[2,3-d]pyrimidin-6(7H)-one | 525.1 | Ex-3A |

TABLE 11-continued

| Ex. | Structure | Name | MS (M + 1) | Chiral starting material |
|---|---|---|---|---|
| 176B | 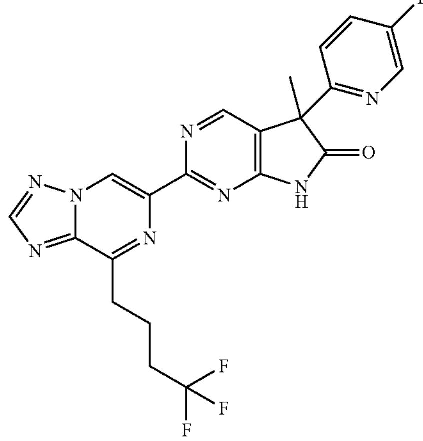 | 5-(5-fluoropyridin-2-yl)-5-methyl-2-(8-(4,4,4-trifluorobutyl)-[1,2,4]triazolo[1,5-a]pyrazin-6-yl)-5H-pyrrolo[2,3-d]pyrimidin-6(7H)-one | 473.1 | Ex-22B |

Example 177A 5-(4-Fluorophenyl)-5-methyl-6-oxo-2-(8-(3,3,4,4,4-pentafluorobutyl)-[1,2,4]triazolo[1,5-a]pyrazin-6-yl)-6,7-dihydro-5H-pyrrolo[2,3-d]pyrimidine-4-carboxamide

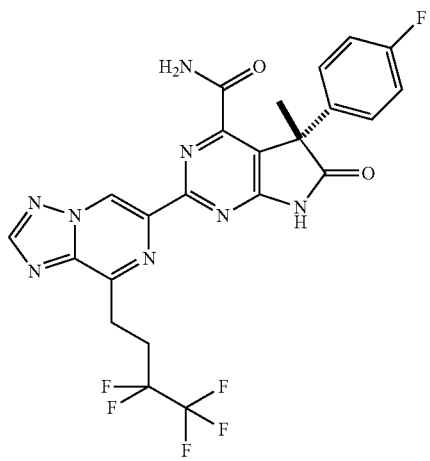 [SMILES: C[C@@]1(c2ccc(F)cc2)C(=O)Nc2nc(-c3cn4ncnc4c(CCC(F)(F)C(F)(F)F)n3)nc(C(N)=O)c21]

Step A—4-Bromo-5-(4-fluorophenyl)-5-methyl-2-(8-(3,3,4,4,4-pentafluorobutyl)-[1,2,4]triazolo[1,5-a]pyrazin-6-yl)-5,7-dihydro-6H-pyrrolo[2,3-d]pyrimidin-6-one Into a vial, under an inert atmosphere of $N_2$, was placed 4-Amino-5-(4-fluorophenyl)-5-methyl-2-(8-(3,3,4,4,4-pentafluorobutyl)-[1,2,4]triazolo[1,5-a]pyrazin-6-yl)-5H-pyrrolo[2,3-d]pyrimidin-6(7H)-one (410 mg, 0.79 mmol), tert-butyl nitrite (324 mg, 3.14 mmol), copper(II) bromide (1227 mg, 5.49 mmol) and DCE (8 mL). The resulting mixture was stirred at 65° C. for 1 h then cooled to RT, diluted with EtOAc. The organic layer was washed with a 9:1 mixture of sat. $NH_4Cl:NH_4OH$, dried over anhydr. $Na_2SO_4$, and filtered. The filtrate was conc. in vacuo to dryness. The residue was purified by silica gel column chromatography with EtOAc:petroleum ether (0-60%) to afford the title compound.

Step B—5-(4-Fluorophenyl)-5-methyl-6-oxo-2-(8-(3,3,4,4,4-pentafluorobutyl)-[1,2,4]triazolo[1,5-a]pyrazin-6-yl)-6,7-dihydro-5H-pyrrolo[2,3-d]pyrimidine-4-carbonitrile Into a vial, under an inert atmosphere of $N_2$, was placed intermediate from step A (160 mg, 0.27 mmol), copper(I) cyanide (86 mg, 0.96 mmol) and DMF (4 mL). The resulting mixture was stirred for 3 h at 150° C. then cooled to RT, diluted with EtOAc. The organic layer was washed with a 9:1 mixture of sat. $NH_4Cl:NH_4OH$, dried over anhydr. $Na_2SO_4$, and filtered. The filtrate was conc. in vacuo to dryness. The residue was purified by silica gel column chromatography with EtOAc:petroleum ether (0-0%) to afford the title compound.

Step C—5-(4-Fluorophenyl)-5-methyl-6-oxo-2-(8-(3,3,4,4,4-pentafluorobutyl)-[1,2,4]triazolo[1,5-a]pyrazin-6-yl)-6,7-dihydro-5H-pyrrolo[2,3-d]pyrimidine-4-carboxamide Into a vial was placed intermediate from step B (35 mg, 0.066 mmol) and HCl (4 mL, 12 N). The resulting mixture was stirred for 1 h at 40° C. then cooled to 0° C. and quenched by the addition of water and EtOAc. The pH value was adjusted to pH 8 with sat. $NaHCO_3$. The mixture was extracted with EtOAc (3×). The organic layer was washed with brine, dried over anhydr. $Na_2SO_4$, and filtered. The filtrate was conc. in vacuo to dryness. The residue was purified by silica gel column chromatography with EtOAc:petroleum ether (0-80%) to afford the title compound. $^1$H NMR (300 MHz, $CD_3OD$) δ 9.99 (s, 1H), 8.67 (s, 1H), 7.23-7.18 (m, 2H), 6.98 (dd, J=8.7, 8.7 Hz, 2H), 3.69-3.64 (m, 2H), 3.05-2.87 (m, 2H), 2.04 (s, 3H); m/z=551.0 [M+1]$^+$.

Using essentially the same procedures described in Example 177A, the following compounds in Table 12 were prepared.

TABLE 12
| Ex. | Structure | Name | MS (M + 1) | Chiral starting material |
|---|---|---|---|---|
| 178A | 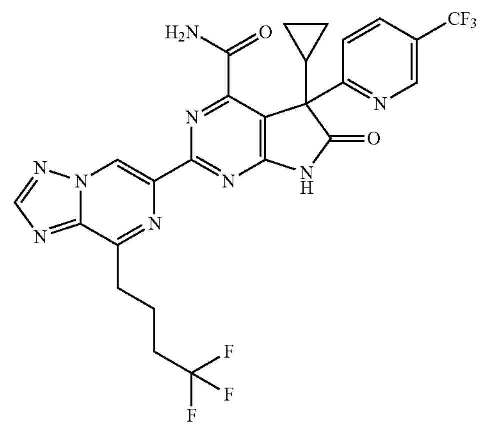 [SMILES: NC(=O)c1nc(-c2cn3ncnc3c(CCCC(F)(F)F)n2)nc2c1C(c1ccc(C(F)(F)F)cn1)(C1CC1)C(=O)N2] | 5-cyclopropyl-6-oxo-2-(8-(3,3,4,4,4-pentafluorobutyl)-[1,2,4]triazolo[1,5-a]pyrazin-6-yl)-5-(5-(trifluoromethyl)pyridin-2-yl)-6,7-dihydro-5H-pyrrolo[2,3-d]pyrimidine-4-carboxamide | 592.1 | Ex-2A |
| 179B | 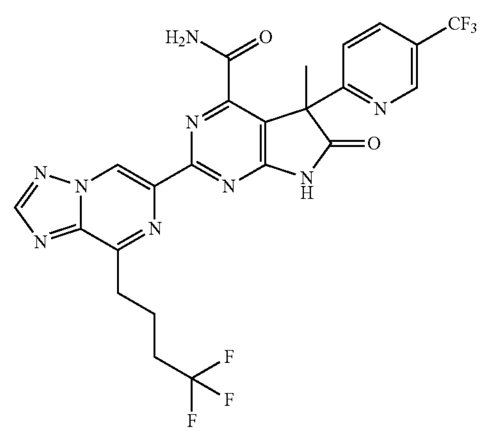 [SMILES: CC1(c2ccc(C(F)(F)F)cn2)C(=O)Nc2nc(-c3cn4ncnc4c(CCCC(F)(F)F)n3)nc(C(N)=O)c21] | 5-methyl-6-oxo-2-(8-(4,4,4-trifluorobutyl)-[1,2,4]triazolo[1,5-a]pyrazin-6-yl)-5-(5-(trifluoromethyl)pyridin-2-yl)-6,7-dihydro-5H-pyrrolo[2,3-d]pyrimidine-4-carboxamide | 566.1 | Ex-25B |
Example 180A
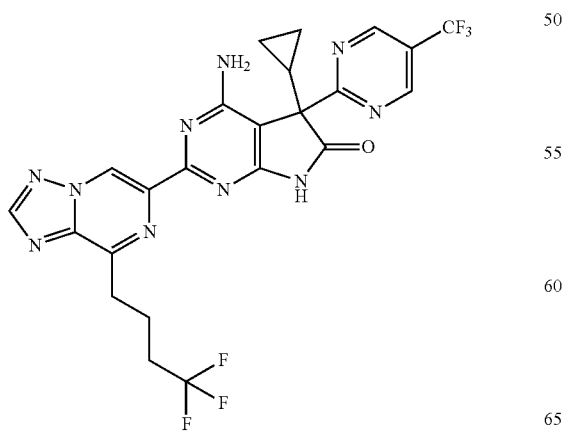

4-amino-5-cyclopropyl-2-(8-(4,4,4-trifluorobutyl)-[1,2,4]triazolo[1,5-a]pyrazin-6-yl)-5-(5-(trifluoromethyl)pyrimidin-2-yl)-5,7-dihydro-6H-pyrrolo[2,3-d]pyrimidin-6-one The title compound was prepared using essentially the same procedures described in Example 1A, using intermediate I-A1 and 1-44 as starting material. The racemic material was resolved using chiral SFC (IB column) to afford isomers Ex-180A (faster eluting) and Ex-180B (slower eluting) of the title compound m/z=531.4[M+1]$^+$ Example 181A

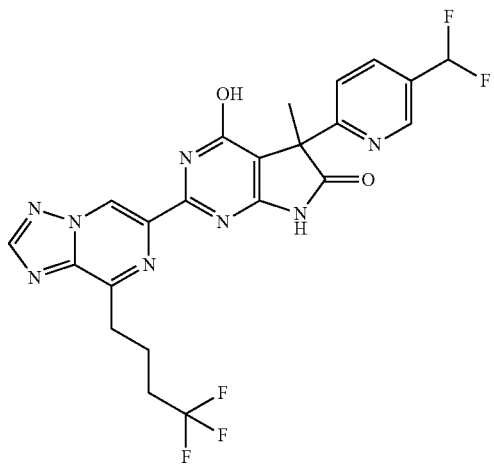 [SMILES: CC1(c2ccc(C(F)F)cn2)C(=O)Nc2nc(-c3cn4ncnc4c(CCCC(F)(F)F)n3)nc(O)c21]

4-hydroxy-5-(5-(difluoromethyl)pyridin-2-yl)-5-methyl-2-(8-(4,4,4-trifluorobutyl)-[1,2,4]triazolo[1,5-a]pyrazin-6-yl)-5H-pyrrolo[2,3-d]pyrimidin-6(7H)-one The title compound was prepared using essentially the same procedures described in Example 119A, using Ex-43B as starting material. m/z=521.2 [M+1]$^+$.

Pharmacokinetic Profile in Rats

The triazolo-pyrazinyl compounds of Formula I have longer PK T$_{1/2}$ (hr) in rats than the corresponding imidazo-pyrazinyl analogs

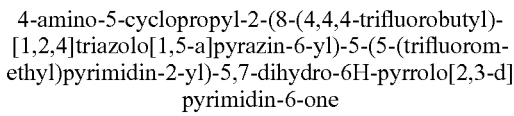

Imidazo-pyrazinyl          vs          triazolo-pyrazinyl

Certain imidazo-pyrazinyl analogs are disclosed in International Application No. PCT/US2015/33084, filed May 29, 2015.

Table 13 provides the pharmacokinetic profiles for rats for a representative set of compounds. The results were obtained using the following the procedure:

IV Cassette PK Assay:

Adult male Wistar-Han rats were fasted overnight and administered a cassette IV dose of mixture of several compounds via a previously implanted catheter in the femoral vein. Animals were allowed access to food 4 h post dose. Blood samples were collected into EDTA-containing tubes at the following time points: 0.03, 0.13, 0.25, 0.5, 1, 2, 4, 8 h post-dose. Blood samples were stored on ice until plasma was harvested by centrifugation. Plasma was transferred to a 96-well plate and stored at −20° C. until analysis. Concentrations of each compound in rat plasma were determined by LC-MS/MS following protein precipitation.

TABLE 13

| | Compound of Formula I | Imidazo-Pyrazinyl Analogs | |
|---|---|---|---|
| Ex. | Cassette PK T$_{1/2}$ (hr) | Imidazo-Pyrazinyl Analog | Cassette PK T$_{1/2\ (hr)}$ |
| 1A | 3.35 | 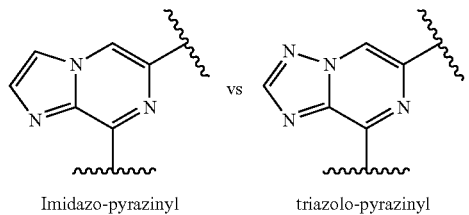 [SMILES: *c1cn2ccnc2c(*)n1 ; *c1cn2ncnc2c(*)n1] | 1.04 |

TABLE 13-continued

| | Compound of Formula I | Imidazo-Pyrazinyl Analogs | |
|---|---|---|---|
| Ex. | Cassette PK $T_{1/2}$ (hr) | Imidazo-Pyrazinyl Analog | Cassette PK $T_{1/2\ (hr)}$ |
| 4B | 2.97 | | 1.41 |
| 44B | 3.94 | | 2.12 |

Cell-Based sGC Functional Assay (CASA Assay)

Rationale sGC is a heme-containing enzyme that converts GTP to secondary messenger cGMP. Increases in cGMP levels affect several physiological processes including vasorelaxation through multiple downstream pathways. The rate by which sGC catalyzes cGMP formation is greatly increased by NO and by recently discovered NO-independent activators and stimulators. Heme-dependent activators (HDAs) preferentially activate sGC containing a ferrous heme group. To determine the effect of sGC activators on enzyme activity, the CASA assay was developed to monitor the generation of cGMP in a cell line that stably expresses the heterodimeric sGC protein.

Methods

A CHO-K1 cell line stably expressing the sGC α1/β1 heterodimer was generated using a standard transfection protocol. CHO-K1 cells were transfected with plasmids pIREShyghsGCα1 and pIRESneo-hsGCβ1 simultaneously using FUGENE reagent. Clones that stably express both subunits were selected with hygromycin and neomycin for ~2 weeks. Clone #7 was chosen for the assay and was designated CHO-K1/sGC. CHO-K1/sGC cells were maintained in F-K12 medium containing 10% heat-inactivated Fetal Bovine Serum (FBS), 100 µg/mL penicillin/streptomycin, 0.5 mg/mL hygromycin and 0.25 mg/mL G418. The cells were then cryopreserved in LN2. On the day of the assay, cells thawed and resuspended in EBSS Assay Buffer (Sigma, E3024) supplemented with 5 mM $MgCl_2$, 10 mM HEPES (4-(2-hydroxyethyl)piperazine-1-ethanesulfonic acid) and 0.05% BSA (bovine serum albumin) (EAB) and cell density was then adjusted to 4×105/mL with EAB. IBMX (3-isobutyl-1-methylxanthin, 0.5 mM) was added to inhibit degradation of cGMP. Compounds were diluted from DMSO stock solutions and added to the assay at a final DMSO concentration of 2.5%. Cells were incubated with compounds in the presence and absence of 1 µM of Diethylenetriamine/nitric oxide adduct (DETA-NO; Sigma, 17018) for 1 hr at 37° C. At the end of the incubation period, the reaction was terminated and the cells were lysed with the detection reagents from Cisbio Kits. The level of intracellular cGMP was determined using an HTRF-based assay kit (CisBio, 62GM2PEC), which detects the displacement of a fluorescence labeled cGMP from its specific antibody. The cGMP produced by test compounds was directly compared to the maximum cGMP production (this value was set to equal 100% activation.) of the published sGC-HDA Compound A:

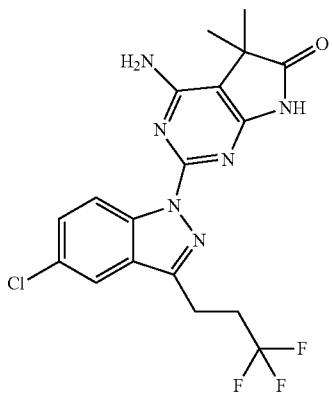

Compound A (Example 1 in WO 2010/065275, published Jun. 10, 2010). The test compounds' activities were then expressed as a percentage of Compound A, the standard in every experiment. This percent activation was calculated either in the presence or absence of DETA-NO which was then plotted. IP and maximum fold induction was derived using ADA analysis software for 4P fit.

The compounds in the Examples of the instant invention had inflection points (IP) less than or equal to 10 µM and more particularly less than or equal to about 1 µM. Most preferred compounds had an IP of less than or equal to about 500 nM. Data for the compounds of the Examples is provided in Table 14.

TABLE 14

| Ex. | IP (nM) | % Act. |
|---|---|---|
| 1A | 186.5 | 196 |
| 2A | 127.8 | 111 |
| 3A | 40.4 | 161 |
| 4B | 117.5 | 157 |
| 5B | 20.9 | 147 |
| 6A | 27.0 | 140 |
| 7A | 41.4 | 185 |
| 8B | 294.5 | 177 |
| 9A | 63.0 | 119 |
| 10A | 15.8 | 137 |
| 11B | 25.2 | 208 |
| 12B | 11.1 | 122 |
| 13B | 80.6 | 109 |
| 14B | 5.5 | 90 |
| 15A | 315.7 | 139 |
| 16B | 13.1 | 77 |
| 17B | 36.1 | 119 |
| 18A | 38.6 | 75 |
| 19B | 14.7 | 71 |
| 20A | 176.1 | 131 |
| 21B | 43.1 | 99 |
| 22B | 38.3 | 130 |
| 23A | 29.6 | 163 |
| 24B | 27.1 | 133 |
| 25B | 27.0 | 131 |

TABLE 14-continued

| Ex. | IP (nM) | % Act. |
|---|---|---|
| 26A | 27.8 | 162 |
| 27A | 277.6 | 178 |
| 28B | 20.0 | 171 |
| 29A | 11.4 | 101 |
| 30B | 36.7 | 117 |
| 31B | 13.0 | 104 |
| 32A | 77.4 | 144 |
| 33A | 5.6 | 107 |
| 34A | 427.9 | 235 |
| 35A | 416.3 | 164 |
| 36B | 56.5 | 82 |
| 37B | 11.5 | 112 |
| 38A | 11.0 | 120 |
| 39A | 20.1 | 96 |
| 40A | 98.9 | 130 |
| 41A | 27.8 | 151 |
| 42B | 8.7 | 82 |
| 43B | 45.6 | 69 |
| 44B | 110.9 | 120 |
| 45B | 44.2 | 156 |
| 46B | 10.1 | 67 |
| 47B | 143.7 | 114 |
| 48A | 77.9 | 85 |
| 49B | 595.1 | 127 |
| 50B | 150.2 | 191 |
| 51B | 15.1 | 144 |
| 52A | 63.2 | 96 |
| 53A | 26.9 | 122 |
| 54B | 318.2 | 210 |
| 55B | 45.6 | 99 |
| 56A | 384.0 | 81 |
| 57A | 576.8 | 119 |
| 58A | 242.0 | 169 |
| 59A | 263.0 | 119 |
| 60A | 22.6 | 121 |
| 61B | 9.7 | 177 |
| 62B | 51.0 | 267 |
| 63A | 21.9 | 187 |
| 64B | 5.1 | 90 |
| 65A | 2.6 | 104 |
| 66A | 34.2 | 162 |
| 67B | 25.5 | 119 |
| 68A | 18.7 | 113 |
| 69A | 13.7 | 158 |
| 70A | 41.8 | 133 |
| 71B | 5.5 | 118 |
| 72B | 28.5 | 82 |
| 73A | 44.1 | 101 |
| 74A | 55.6 | 110 |
| 75B | 20.0 | 136 |
| 76A | 153.6 | 120 |
| 77B | 332.8 | 112 |
| 78B | 550.4 | 83 |
| 79A | 324.6 | 152 |
| 80A | 2488.0 | 115 |
| 81B | 698.4 | 115 |
| 82A | 555.4 | 125 |
| 83A | 269.7 | 100 |
| 84B | 55.7 | 101 |
| 85B | 10.6 | 106 |
| 86B | 26.4 | 126 |
| 87B | 80.2 | 138 |
| 88B | 65.0 | 137 |
| 89B | 260.2 | 109 |
| 90B | 36.6 | 135 |
| 91A | 668.1 | 105 |
| 92B | 4828.0 | 167 |
| 93A | 439.0 | 159 |
| 94A | 79.4 | 138 |
| 95B | 256.7 | 74 |
| 96B | 134.3 | 108 |
| 97B | 219.5 | 106 |
| 98B | 86.1 | 164 |
| 99A | 47.5 | 113 |
| 100A | 127.4 | 184 |
| 101A | 120.6 | 154 |
| 102A | 29.1 | 132 |
| 103A | 218.6 | 104 |

TABLE 14-continued

| Ex. | IP (nM) | % Act. |
|---|---|---|
| 104A | 257.9 | 117 |
| 105A | 26.7 | 176 |
| 106A | 15.5 | 95 |
| 107A | 74.7 | 76 |
| 108A | 14.7 | 107 |
| 109A | 7.3 | 92 |
| 110A | 138.9 | 70 |
| 111A | 369.5 | 75 |
| 112A | 212.5 | 91 |
| 113B | 762.9 | 171 |
| 114A | 143.6 | 122 |
| 115A | 232.7 | 118 |
| 116A | 19.7 | 85 |
| 117A | 49.2 | 140 |
| 118A | 84.1 | 72 |
| 119A | 133.7 | 124 |
| 120A | 155.3 | 107 |
| 121B | 130.4 | 222 |
| 122B | 140.6 | 100 |
| 123A | 203.6 | 78 |
| 124B | 1051.0 | 88 |
| 125A | 575.1 | 87 |
| 126A | 131.9 | 102 |
| 127B | 1255.0 | 129 |
| 128B | 127.9 | 106 |
| 129B | 51.7 | 66 |
| 130B | 503.1 | 109 |
| 131A | 1471.0 | 99 |
| 132B | 441.9 | 119 |
| 133B | 856.2 | 87 |
| 134A | 856.8 | 134 |
| 135A | 182.9 | 108 |
| 136B | 513.9 | 69 |
| 137B | 596.7 | 102 |
| 138B | 343.9 | 164 |
| 139B | 672.8 | 169 |
| 140B | 277.3 | 150 |
| 141A | 183.5 | 133 |
| 142A | 207.2 | 137 |
| 143A | 301.0 | 114 |
| 144A | 1296.0 | 87 |
| 145B | 1218.0 | 64 |
| 146B | 45.5 | 154 |
| 147B | 213.5 | 94 |
| 148A | 1092.0 | 96 |
| 149B | 990.3 | 63 |
| 150A | 1222.0 | 74 |
| 151A | 1489.0 | 120 |
| 152A | 132.6 | 70 |
| 153B | 310.1 | 104 |
| 154A | 27.2 | 100 |
| 155B | 163.0 | 159 |
| 156B | 23.3 | 102 |
| 157A | 72.7 | 161 |
| 158B | 102.0 | 232 |
| 159B | 208.6 | 73 |
| 160A | 50.2 | 96 |
| 161B | 303.0 | 95 |
| 162B | 96.7 | 100 |
| 163A | 1635.0 | 109 |
| 164A | 780.0 | 253 |
| 165A | 1518.0 | 114 |
| 166B | 711.4 | 117 |
| 167A | 1088.0 | 70 |
| 168A | 1454.0 | 77 |
| 169B | 110.9 | 116 |
| 170A | 9.5 | 125 |
| 171A | 136.9 | 90 |
| 172A | 212.5 | 122 |
| 173A | 574.0 | 176 |
| 174A | 1346.0 | 133 |
| 175A | 384.1 | 115 |
| 176B | 526.0 | 166 |
| 177A | 127.7 | 168 |
| 178A | 199.0 | 108 |
| 179B | 90.2 | 101 |
| 180B | 487.5 | 97 |
| 181B | 749.0 | 55 |

Acute Efficacy in Spontaneously Hypertensive Rats (SHR)

Spontaneously hypertensive rats (SHR, male, Charles River) were implanted with DSI TA11PA-C40 telemetry device (Data Sciences, Inc., St. Paul, Minn.) under isoflurane or ketamine/metomidine anesthesia. The telemetry unit catheter was inserted into the descending aorta via the femoral artery and the telemetry device was implanted subcutaneously in the left flank area. Animals were allowed to recover from surgery for 14 days before the start of any studies. Blood pressure, heart rate, and activity signals from conscious, freely moving rats were recorded continuously for 30 seconds every 10 minutes. On the day prior to administration of compound, a single oral dose of vehicle (10% transcutol/20% Cremophor/70% water) was administered to all animals to establish baseline control data. The blood pressure lowering efficacy of compound (PO) or vehicle was evaluated following a single oral gavage. Data were collected as hourly averages, and changes in blood pressure were calculated by subtracting control baseline data on an hourly basis. Animals were maintained on normal diet with a 12 hour light-dark cycle.

Maximum peak decreases of systolic blood pressure (SBP) in SHR at a particular P.O. dose (mpk milligrams per kilogram) for the following representative compounds are provided. Category A=SBP in SHRs <20 mmHg; Category B=SBP in SHRs 20-40 mmHg; Category C=SBP in SHRs >40 mmHg.

TABLE 15

| Ex. | Dose, P.O. mpk | Cat. |
|---|---|---|
| 1A | 0.3 | C |
| 2A | 0.3 | A |
| 3A | 0.3 | B |
| 4B | 0.3 | C |
| 7A | 0.3 | B |
| 8B | 3 | B |
| 9A | 1 | B |
| 11B | 0.3 | B |
| 12B | 0.1 | B |
| 13B | 1 | B |
| 17B | 0.3 | A |
| 18A | 0.3 | C |
| 20A | 1 | C |
| 25B | 0.3 | B |
| 33A | 0.3 | C |
| 34A | 0.3 | C |
| 36B | 1 | B |
| 39A | 0.3 | B |
| 41A | 0.3 | B |
| 44B | 1 | B |
| 56A | 3 | B |
| 60A | 0.3 | C |
| 61B | 0.3 | C |
| 65A | 0.3 | C |
| 67B | 0.3 | B |
| 73A | 1 | B |
| 74A | 1 | B |
| 76A | 0.3 | A |
| 77B | 1 | A |
| 78B | 3 | B |
| 79A | 1 | B |
| 85B | 0.3 | C |
| 88B | 1 | C |

TABLE 15-continued

| Ex. | Dose, P.O. mpk | Cat. |
|---|---|---|
| 94A | 1 | C |
| 95B | 0.3 | C |
| 98B | 1 | B |
| 103A | 2 | A |
| 104A | 3 | C |
| 105A | 0.3 | B |
| 106A | 0.3 | C |
| 107A | 3 | C |
| 110A | 3 | B |
| 112A | 3 | A |
| 114A | 1 | B |
| 115A | 1 | B |
| 119A | 1 | B |
| 120A | 1 | B |
| 121B | 1 | B |
| 122B | 1 | B |
| 125A | 3 | A |
| 132B | 1 | A |
| 134A | 1 | B |
| 135A | 1 | B |
| 136B | 3 | B |
| 138B | 1 | C |
| 140B | 1 | A |
| 141A | 1 | B |
| 142A | 0.3 | B |
| 143A | 1 | B |
| 146B | 0.3 | B |
| 151A | 3 | B |
| 152A | 3 | B |
| 154A | 0.3 | B |
| 155B | 1 | B |
| 156B | 0.3 | C |
| 158B | 0.3 | C |
| 160A | 0.3 | B |
| 164A | 2 | B |
| 165A | 3 | B |
| 166B | 3 | B |
| 173A | 1 | A |
| 177A | 1 | C |
| 178A | 1 | B |
| 179B | 0.3 | B |

What is claimed is:

1. A method for treating or preventing systemic sclerosis; the method comprising administering a therapeutically effective amount of a compound having structural Formula I:

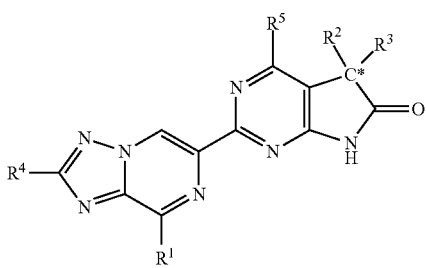

or a pharmaceutically acceptable salt thereof to a patient in need of such treatment, wherein:
C* indicates a potential chiral carbon atom;
$R^1$ is
  (1) hydrogen
  (2) $(C_{1-6})$alkyl,
  (3) halo$(C_{1-6})$alkyl,
  (4) $(C_{1-6})$alkyl-O—,
  (5) halo$(C_{1-6})$alkyl-O—,
  (6) $(C_{1-6})$alkyl-NH—,
  (7) halo$(C_{1-6})$alkyl-NH—,
  (8) —$(C_{1-3})$alkyl-$(C_{3-7})$cycloalkyl,
  (9) —$(C_{1-3})$alkyl-aryl, wherein aryl is unsubstituted or substituted by one, two, or three $R^7$,
  (10) aryl unsubstituted or substituted by one, two, or three $R^7$,
  (11) $(C_{3-7})$cycloalkyl, or
  (12) —$(C_{1-3})$alkyl-heteroaryl wherein the heteroaryl is a 5- or 6-membered ring containing one, two, or three heteroatoms independently selected from the group consisting of N, O, and S, and wherein heteroaryl is unsubstituted or substituted by one, two, or three $R^7$;
$R^2$ is
  (1) $(C_{1-3})$alkyl, or
  (2) $(C_{3-7})$cycloalkyl;
$R^3$ is
  (1) aryl unsubstituted or substituted by one, two, or three $R^6$,
  (2) five- or six-membered heteroaryl containing one, two, or three heteroatoms independently selected from N, O and S, wherein heteroaryl is unsubstituted or substituted by one, two, or three $R^6$,
  (3) $(C_{1-3})$alkyl, or
  (4) $(C_{3-7})$cycloalkyl;
$R^4$ is
  (1) hydrogen,
  (2) $(C_{1-3})$alkyl,
  (3) halo$(C_{1-3})$alkyl, or
  (4) $(C_{3-7})$cycloalkyl;
$R^5$ is
  (1) hydrogen,
  (2) hydroxy,
  (3) —N$(R^{8a})(R^{8b})$,
  (4) —COOH,
  (5) —C(O)NH$_2$,
  (6) $(C_{1-3})$alkyl,
  (7) $(C_{3-7})$cycloalkyl, or
  (8) four- to six-membered monocyclic heterocyclyl containing 1 N heteroatom, wherein the heterocyclyl is unsubstituted or substituted by one to two $R^9$;
each $R^6$ is independently
  (1) $(C_{1-3})$alkyl,
  (2) halo$(C_{1-3})$alkyl,
  (3) $(C_{1-3})$alkoxy,
  (4) halo$(C_{1-3})$alkoxy,
  (5) $(C_{3-7})$cycloalkyl, unsubstituted or substituted by halo,
  (6) halo,
  (7) cyano,
  (8) hydroxy,
  (9) —NH$_2$,
  (10) $(C_{1-3})$alkyl-COOH, or
  (11) $(C_{1-3})$alkyl-COO$(C_{1-4})$alkyl;
each $R^7$ is independently
  (1) $(C_{1-3})$alkoxy,
  (2) halo,
  (3) hydroxy, or
  (4) $(C_{1-3})$alkyl;
$R^{8a}$ and $R^{8b}$ are independently
  (1) hydrogen,
  (2) $(C_{1-3})$alkyl, or
  (3) $(C_{3-7})$cycloalkyl; and R⁹ is
(1) (C₁₋₃)alkyl,
(2) halo(C₁₋₃)alkyl, or
(3) hydroxyl.

2. The method of claim 1, wherein R³ is:
(1) aryl unsubstituted or substituted by one, two, or three R⁶, or
(2) five- or six-membered heteroaryl containing one, two, or three heteroatoms independently selected from N, O and S, wherein heteroaryl is unsubstituted or substituted by one, two, or three R⁶;
in the compound administered to the patient.

3. The method of claim 2, wherein R³ is aryl unsubstituted or substituted by one, two, or three R⁶ in the compound administered to the patient.

4. The method of claim 1, wherein R¹ is (C₁₋₆)alkyl, halo(C₁₋₆)alkyl, or —(C₁₋₃)alkyl-aryl, wherein aryl is unsubstituted or substituted by one, two, or three R⁷ in the compound administered to the patient.

5. The method of claim 1, wherein R⁵ is hydroxyl in the compound administered to the patient.

6. The method of claim 5, wherein R¹ is (C₁₋₆)alkyl, halo(C₁₋₆)alkyl, or —(C₁₋₃)alkyl-aryl, wherein aryl is unsubstituted or substituted by one, two, or three R⁷ in the compound administered to the patient.

7. The method of claim 1, wherein the compound administered to the patient is:
4-amino-5-(4-fluorophenyl)-5-methyl-2-(8-(3,3,4,4,4-pentafluorobutyl)-[1,2,4]triazolo[1,5-a]pyrazin-6-yl)-5H-pyrrolo[2,3-d]pyrimidin-6(7H)-one,
4-amino-5-cyclopropyl-2-(8-(4,4,4-trifluorobutyl)-[1,2,4]triazolo[1,5-a]pyrazin-6-yl)-5-(5-(trifluoromethyl)pyridin-2-yl)-5H-pyrrolo[2,3-d]pyrimidin-6(7H)-one,
4-amino-5-(5-chloropyridin-2-yl)-5-methyl-2-(8-(3,3,4,4,4-pentafluorobutyl)-[1,2,4]triazolo[1,5-a]pyrazin-6-yl)-5H-pyrrolo[2,3-d]pyrimidin-6(7H)-one,
4-amino-5-(5-fluoropyridin-2-yl)-5-methyl-2-(8-(3,3,4,4,4-pentafluorobutyl)-[1,2,4]triazolo[1,5-a]pyrazin-6-yl)-5H-pyrrolo[2,3-d]pyrimidin-6(7H)-one,
4-amino-5-(4-chloro-3-fluorophenyl)-5-methyl-2-(8-(3,3,4,4,4-pentafluorobutyl)-[1,2,4]triazolo[1,5-a]pyrazin-6-yl)-5H-pyrrolo[2,3-d]pyrimidin-6(7H)-one,
4-amino-5-cyclopropyl-5-(3,4-difluorophenyl)-2-(8-(3,3,4,4,4-pentafluorobutyl)-[1,2,4]triazolo[1,5-a]pyrazin-6-yl)-5H-pyrrolo[2,3-d]pyrimidin-6(7H)-one,
4-amino-5-(5-chloropyridin-2-yl)-5-cyclopropyl-2-(8-(3,3,4,4,4-pentafluorobutyl)-[1,2,4]triazolo[1,5-a]pyrazin-6-yl)-5H-pyrrolo[2,3-d]pyrimidin-6(7H)-one,
4-amino-5-cyclopropyl-5-(5-fluoropyridin-3-yl)-2-(8-(3,3,4,4,4-pentafluorobutyl)-[1,2,4]triazolo[1,5-a]pyrazin-6-yl)-5H-pyrrolo[2,3-d]pyrimidin-6(7H)-one,
4-amino-5-(5-fluoropyridin-3-yl)-5-methyl-2-(8-(3,3,4,4,4-pentafluorobutyl)-[1,2,4]triazolo[1,5-a]pyrazin-6-yl)-5H-pyrrolo[2,3-d]pyrimidin-6(7H)-one,
4-amino-5-(4-chlorophenyl)-5-methyl-2-(8-(3,3,4,4,4-pentafluorobutyl)-[1,2,4]triazolo[1,5-a]pyrazin-6-yl)-5H-pyrrolo[2,3-d]pyrimidin-6(7H)-one,
4-amino-5-methyl-2-(8-(3,3,4,4,4-pentafluorobutyl)-[1,2,4]triazolo[1,5-a]pyrazin-6-yl)-5-(pyridin-2-yl)-5H-pyrrolo[2,3-d]pyrimidin-6(7H)-one,
(12) 4-amino-5-methyl-2-(8-(3,3,4,4,4-pentafluorobutyl)-[1,2,4]triazolo[1,5-a]pyrazin-6-yl)-5-phenyl-5H-pyrrolo[2,3-d]pyrimidin-6(7H)-one,
4-amino-5-(6-cyclopropylpyridin-3-yl)-5-methyl-2-(8-(3,3,4,4,4-pentafluorobutyl)-[1,2,4]triazolo[1,5-a]pyrazin-6-yl)-5H-pyrrolo[2,3-d]pyrimidin-6(7H)-one,
4-amino-5-(3-fluorophenyl)-5-methyl-2-(8-(3,3,4,4,4-pentafluorobutyl)-[1,2,4]triazolo[1,5-a]pyrazin-6-yl)-5H-pyrrolo[2,3-d]pyrimidin-6(7H)-one,
4-amino-5-cyclopropyl-2-(8-(3,3,4,4,4-pentafluorobutyl)-[1,2,4]triazolo[1,5-a]pyrazin-6-yl)-5-(5-(trifluoromethyl)pyridin-2-yl)-5H-pyrrolo[2,3-d]pyrimidin-6(7H)-one,
4-amino-5-(6-(1,1-difluoroethyl)pyridin-3-yl)-5-methyl-2-(8-(3,3,4,4,4-pentafluorobutyl)-[1,2,4]triazolo[1,5-a]pyrazin-6-yl)-5H-pyrrolo[2,3-d]pyrimidin-6(7H)-one,
4-amino-5-cyclopropyl-5-(5-methylpyridin-2-yl)-2-(8-(3,3,4,4,4-pentafluorobutyl)-[1,2,4]triazolo[1,5-a]pyrazin-6-yl)-5H-pyrrolo[2,3-d]pyrimidin-6(7H)-one,
6-(4-amino-5-methyl-6-oxo-2-(8-(3,3,4,4,4-pentafluorobutyl)-[1,2,4]triazolo[1,5-a]pyrazin-6-yl)-6,7-dihydro-5H-pyrrolo[2,3-d]pyrimidin-5-yl)nicotinonitrile,
4-amino-5-methyl-5-(5-methylpyridin-2-yl)-2-(8-(3,3,4,4-pentafluorobutyl)-[1,2,4]triazolo[1,5-a]pyrazin-6-yl)-5H-pyrrolo[2,3-d]pyrimidin-6(7H)-one,
4-amino-5-(1-isopropyl-1H-1,2,3-triazol-4-yl)-5-methyl-2-(8-(3,3,4,4,4-pentafluorobutyl)-[1,2,4]triazolo[1,5-a]pyrazin-6-yl)-5H-pyrrolo[2,3-d]pyrimidin-6(7H)-one,
4-amino-5-cyclopropyl-5-(5-methylpyrazin-2-yl)-2-(8-(3,3,4,4,4-pentafluorobutyl)-[1,2,4]triazolo[1,5-a]pyrazin-6-yl)-5H-pyrrolo[2,3-d]pyrimidin-6(7H)-one,
4-amino-5-(5-fluoropyridin-2-yl)-5-methyl-2-(8-(4,4,4-trifluorobutyl)-[1,2,4]triazolo[1,5-a]pyrazin-6-yl)-5H-pyrrolo[2,3-d]pyrimidin-6(7H)-one,
4-amino-5-(4-fluorophenyl)-5-methyl-2-(8-(4,4,4-trifluorobutyl)-[1,2,4]triazolo[1,5-a]pyrazin-6-yl)-5H-pyrrolo[2,3-d]pyrimidin-6(7H)-one,
4-amino-5-methyl-2-(8-(4,4,4-trifluorobutyl)-[1,2,4]triazolo[1,5-a]pyrazin-6-yl)-5-(4-(trifluoromethyl)phenyl)-5H-pyrrolo[2,3-d]pyrimidin-6(7H)-one,
4-amino-5-methyl-2-(8-(4,4,4-trifluorobutyl)-[1,2,4]triazolo[1,5-a]pyrazin-6-yl)-5-(5-(trifluoromethyl)pyridin-2-yl)-5H-pyrrolo[2,3-d]pyrimidin-6(7H)-one,
4-amino-5-(5-chloropyridin-2-yl)-5-methyl-2-(8-(4,4,4-trifluorobutyl)-[1,2,4]triazolo[1,5-a]pyrazin-6-yl)-5H-pyrrolo[2,3-d]pyrimidin-6(7H)-one,
4-amino-5-(5-chloropyridin-2-yl)-5-cyclopropyl-2-(8-(4,4,4-trifluorobutyl)-[1,2,4]triazolo[1,5-a]pyrazin-6-yl)-5H-pyrrolo[2,3-d]pyrimidin-6(7H)-one,
4-amino-5-(4-chloro-3-fluorophenyl)-5-methyl-2-(8-(4,4,4-trifluorobutyl)-[1,2,4]triazolo[1,5-a]pyrazin-6-yl)-5H-pyrrolo[2,3-d]pyrimidin-6(7H)-one,
4-amino-5-(4-chlorophenyl)-5-methyl-2-(8-(4,4,4-trifluorobutyl)-[1,2,4]triazolo[1,5-a]pyrazin-6-yl)-5H-pyrrolo[2,3-d]pyrimidin-6(7H)-one,
4-amino-5-cyclopropyl-5-(4-fluorophenyl)-2-(8-(4,4,4-trifluorobutyl)-[1,2,4]triazolo[1,5-a]pyrazin-6-yl)-5H-pyrrolo[2,3-d]pyrimidin-6(7H)-one,
4-amino-5-(4-chlorophenyl)-5-cyclopropyl-2-(8-(4,4,4-trifluorobutyl)-[1,2,4]triazolo[1,5-a]pyrazin-6-yl)-5H-pyrrolo[2,3-d]pyrimidin-6(7H)-one,
4-amino-5-cyclopropyl-5-(3,4-difluorophenyl)-2-(8-(4,4,4-trifluorobutyl)-[1,2,4]triazolo[1,5-a]pyrazin-6-yl)-5H-pyrrolo[2,3-d]pyrimidin-6(7H)-one,
4-amino-5-(4-chloro-3-fluorophenyl)-5-cyclopropyl-2-(8-(4,4,4-trifluorobutyl)-[1,2,4]triazolo[1,5-a]pyrazin-6-yl)-5H-pyrrolo[2,3-d]pyrimidin-6(7H)-one,
4-amino-5-cyclopropyl-5-(5-fluoropyridin-2-yl)-2-(8-(4,4,4-trifluorobutyl)-[1,2,4]triazolo[1,5-a]pyrazin-6-yl)-5H-pyrrolo[2,3-d]pyrimidin-6(7H)-one, 4-amino-5-cyclopropyl-2-(8-(4,4,4-trifluorobutyl)-[1,2,4]triazolo[1,5-a]pyrazin-6-yl)-5-(4-(trifluoromethyl)phenyl)-5H-pyrrolo[2,3-d]pyrimidin-6(7H)-one, 4-amino-5-methyl-5-(pyridin-2-yl)-2-(8-(4,4,4-trifluorobutyl)-[1,2,4]triazolo[1,5-a]pyrazin-6-yl)-5H-pyrrolo[2,3-d]pyrimidin-6(7H)-one, 4-amino-5-methyl-5-phenyl-2-(8-(4,4,4-trifluorobutyl)-[1,2,4]triazolo[1,5-a]pyrazin-6-yl)-5H-pyrrolo[2,3-d]pyrimidin-6(7H)-one, 4-amino-5-(3,4-difluorophenyl)-5-methyl-2-(8-(4,4,4-trifluorobutyl)-[1,2,4]triazolo[1,5-a]pyrazin-6-yl)-5H-pyrrolo[2,3-d]pyrimidin-6(7H)-one, 4-amino-5-cyclopropyl-5-(5-methoxypyridin-2-yl)-2-(8-(4,4,4-trifluorobutyl)-[1,2,4]triazolo[1,5-a]pyrazin-6-yl)-5H-pyrrolo[2,3-d]pyrimidin-6(7H)-one, 4-amino-5-(5-methoxypyridin-2-yl)-5-methyl-2-(8-(4,4,4-trifluorobutyl)-[1,2,4]triazolo[1,5-a]pyrazin-6-yl)-5H-pyrrolo[2,3-d]pyrimidin-6(7H)-one, 4-amino-5-(5-chloropyrimidin-2-yl)-5-cyclopropyl-2-(8-(4,4,4-trifluorobutyl)-[1,2,4]triazolo[1,5-a]pyrazin-6-yl)-5H-pyrrolo[2,3-d]pyrimidin-6(7H)-one, 4-amino-5-(3-chloro-4-fluorophenyl)-5-methyl-2-(8-(4,4,4-trifluorobutyl)-[1,2,4]triazolo[1,5-a]pyrazin-6-yl)-5H-pyrrolo[2,3-d]pyrimidin-6(7H)-one, 4-amino-5-(5-(difluoromethyl)pyridin-2-yl)-5-methyl-2-(8-(4,4,4-trifluorobutyl)-[1,2,4]triazolo[1,5-a]pyrazin-6-yl)-5H-pyrrolo[2,3-d]pyrimidin-6(7H)-one, 4-amino-5-cyclopropyl-5-(5-(difluoromethyl)pyridin-2-yl)-2-(8-(4,4,4-trifluorobutyl)-[1,2,4]triazolo[1,5-a]pyrazin-6-yl)-5H-pyrrolo[2,3-d]pyrimidin-6(7H)-one, 4-amino-5-(6-(1,1-difluoroethyl)pyridin-3-yl)-5-methyl-2-(8-(4,4,4-trifluorobutyl)-[1,2,4]triazolo[1,5-a]pyrazin-6-yl)-5H-pyrrolo[2,3-d]pyrimidin-6(7H)-one, 4-amino-5-methyl-5-(5-methylpyridin-2-yl)-2-(8-(4,4,4-trifluorobutyl)-[1,2,4]triazolo[1,5-a]pyrazin-6-yl)-5H-pyrrolo[2,3-d]pyrimidin-6(7H)-one, 4-amino-5-cyclopropyl-5-(5-methylpyridin-2-yl)-2-(8-(4,4,4-trifluorobutyl)-[1,2,4]triazolo[1,5-a]pyrazin-6-yl)-5H-pyrrolo[2,3-d]pyrimidin-6(7H)-one, 6-(4-amino-5-methyl-6-oxo-2-(8-(4,4,4-trifluorobutyl)-[1,2,4]triazolo[1,5-a]pyrazin-6-yl)-6,7-dihydro-5H-pyrrolo[2,3-d]pyrimidin-5-yl)nicotinonitrile, 4-amino-5-methyl-5-(6-methyl-5-(trifluoromethyl)pyridin-2-yl)-2-(8-(4,4,4-trifluorobutyl)-[1,2,4]triazolo[1,5-a]pyrazin-6-yl)-5H-pyrrolo[2,3-d]pyrimidin-6(7H)-one, 4-amino-5-methyl-2-(8-(4,4,4-trifluorobutyl)-[1,2,4]triazolo[1,5-a]pyrazin-6-yl)-5-(5-(trifluoromethyl)pyrazin-2-yl)-5H-pyrrolo[2,3-d]pyrimidin-6(7H)-one, 4-amino-5-methyl-2-(8-(4,4,4-trifluorobutyl)-[1,2,4]triazolo[1,5-a]pyrazin-6-yl)-5-(5-(trifluoromethyl)pyrimidin-2-yl)-5H-pyrrolo[2,3-d]pyrimidin-6(7H)-one, 4-amino-5-(4-fluorophenyl)-5-methyl-2-(8-propyl-[1,2,4]triazolo[1,5-a]pyrazin-6-yl)-5H-pyrrolo[2,3-d]pyrimidin-6(7H)-one, 4-amino-5-(4-chlorophenyl)-5-methyl-2-(8-propyl-[1,2,4]triazolo[1,5-a]pyrazin-6-yl)-5H-pyrrolo[2,3-d]pyrimidin-6(7H)-one, 4-amino-5-(5-fluoropyridin-2-yl)-5-methyl-2-(8-propyl-[1,2,4]triazolo[1,5-a]pyrazin-6-yl)-5H-pyrrolo[2,3-d]pyrimidin-6(7H)-one, 5-(5-fluoropyridin-2-yl)-4-hydroxy-5-methyl-2-(8-propyl-[1,2,4]triazolo[1,5-a]pyrazin-6-yl)-5H-pyrrolo[2,3-d]pyrimidin-6(7H)-one, 4-amino-5-cyclopropyl-2-(8-propyl-[1,2,4]triazolo[1,5-a]pyrazin-6-yl)-5-(5-(trifluoromethyl)pyridin-2-yl)-5H-pyrrolo[2,3-d]pyrimidin-6(7H)-one, 4-amino-5-(5-chloropyridin-2-yl)-5-cyclopropyl-2-(8-propyl-[1,2,4]triazolo[1,5-a]pyrazin-6-yl)-5H-pyrrolo[2,3-d]pyrimidin-6(7H)-one, 4-amino-5-cyclopropyl-5-(3,4-difluorophenyl)-2-(8-propyl-[1,2,4]triazolo[1,5-a]pyrazin-6-yl)-5H-pyrrolo[2,3-d]pyrimidin-6(7H)-one, 4-amino-5-cyclopropyl-5-(5-fluoropyridin-2-yl)-2-(8-propyl-[1,2,4]triazolo[1,5-a]pyrazin-6-yl)-5H-pyrrolo[2,3-d]pyrimidin-6(7H)-one, 4-amino-2-(8-butyl-[1,2,4]triazolo[1,5-a]pyrazin-6-yl)-5-(4-fluorophenyl)-5-methyl-5H-pyrrolo[2,3-d]pyrimidin-6(7H)-one, 4-amino-2-(8-butyl-[1,2,4]triazolo[1,5-a]pyrazin-6-yl)-5-(5-fluoropyridin-2-yl)-5-methyl-5H-pyrrolo[2,3-d]pyrimidin-6(7H)-one, 4-amino-2-(8-butyl-[1,2,4]triazolo[1,5-a]pyrazin-6-yl)-5-(4-chloro-3-fluorophenyl)-5-methyl-5H-pyrrolo[2,3-d]pyrimidin-6(7H)-one, 4-amino-2-(8-butyl-[1,2,4]triazolo[1,5-a]pyrazin-6-yl)-5-(4-chlorophenyl)-5-methyl-5H-pyrrolo[2,3-d]pyrimidin-6(7H)-one, 4-amino-2-(8-butyl-[1,2,4]triazolo[1,5-a]pyrazin-6-yl)-5-(3,4-difluorophenyl)-5-methyl-5H-pyrrolo[2,3-d]pyrimidin-6(7H)-one, 4-amino-2-(8-butyl-[1,2,4]triazolo[1,5-a]pyrazin-6-yl)-5-cyclopropyl-5-(3,4-difluorophenyl)-5H-pyrrolo[2,3-d]pyrimidin-6(7H)-one, 4-amino-2-(8-butyl-[1,2,4]triazolo[1,5-a]pyrazin-6-yl)-5-cyclopropyl-5-(5-fluoropyridin-2-yl)-5H-pyrrolo[2,3-d]pyrimidin-6(7H)-one, 4-amino-2-(8-butyl-[1,2,4]triazolo[1,5-a]pyrazin-6-yl)-5-methyl-5-(5-(trifluoromethyl)pyridin-2-yl)-5H-pyrrolo[2,3-d]pyrimidin-6(7H)-one, 4-amino-2-(8-butyl-[1,2,4]triazolo[1,5-a]pyrazin-6-yl)-5-(5-chloropyridin-2-yl)-5-cyclopropyl-5H-pyrrolo[2,3-d]pyrimidin-6(7H)-one, 4-amino-2-(8-butyl-[1,2,4]triazolo[1,5-a]pyrazin-6-yl)-5-(5-chloropyridin-2-yl)-5-methyl-5H-pyrrolo[2,3-d]pyrimidin-6(7H)-one, 4-amino-2-(8-butyl-[1,2,4]triazolo[1,5-a]pyrazin-6-yl)-5-cyclopropyl-5-(5-(trifluoromethyl)pyridin-2-yl)-5H-pyrrolo[2,3-d]pyrimidin-6(7H)-one, 4-amino-2-(8-butyl-[1,2,4]triazolo[1,5-a]pyrazin-6-yl)-5-methyl-5-(5-methylpyridin-2-yl)-5H-pyrrolo[2,3-d]pyrimidin-6(7H)-one, 4-amino-2-(8-butyl-[1,2,4]triazolo[1,5-a]pyrazin-6-yl)-5-cyclopropyl-5-(5-methylpyridin-2-yl)-5H-pyrrolo[2,3-d]pyrimidin-6(7H)-one, 4-amino-5-(4-fluorophenyl)-2-(8-isobutyl-[1,2,4]triazolo[1,5-a]pyrazin-6-yl)-5-methyl-5H-pyrrolo[2,3-d]pyrimidin-6(7H)-one, 4-amino-5-(4-fluorophenyl)-5-methyl-2-(8-(3,3,3-trifluoropropyl)-[1,2,4]triazolo[1,5-a]pyrazin-6-yl)-5H-pyrrolo[2,3-d]pyrimidin-6(7H)-one, 4-amino-5-(4-chloro-3-fluorophenyl)-5-methyl-2-(8-(3,3,3-trifluoropropyl)-[1,2,4]triazolo[1,5-a]pyrazin-6-yl)-5H-pyrrolo[2,3-d]pyrimidin-6(7H)-one, 4-amino-5-(4-chlorophenyl)-5-methyl-2-(8-(3,3,3-trifluoropropyl)-[1,2,4]triazolo[1,5-a]pyrazin-6-yl)-5H-pyrrolo[2,3-d]pyrimidin-6(7H)-one, 4-amino-5-methyl-5-(4-(trifluoromethyl)phenyl)-2-(8-(3,3,3-trifluoropropyl)-[1,2,4]triazolo[1,5-a]pyrazin-6-yl)-5H-pyrrolo[2,3-d]pyrimidin-6(7H)-one, 4-amino-5-methyl-5-(5-(trifluoromethyl)pyridin-2-yl)-2-(8-(3,3,3-trifluoropropyl)-[1,2,4]triazolo[1,5-a]pyrazin-6-yl)-5H-pyrrolo[2,3-d]pyrimidin-6(7H)-one, 4-amino-5-(5-chloropyridin-2-yl)-5-methyl-2-(8-(3,3,3-trifluoropropyl)-[1,2,4]triazolo[1,5-a]pyrazin-6-yl)-5H-pyrrolo[2,3-d]pyrimidin-6(7H)-one), 4-amino-5-cyclopropyl-5-(5-(trifluoromethyl)pyridin-2-yl)-2-(8-(3,3,3-trifluoropropyl)-[1,2,4]triazolo[1,5-a]pyrazin-6-yl)-5H-pyrrolo[2,3-d]pyrimidin-6(7H)-one, 4-amino-5-(5-fluoropyridin-2-yl)-5-methyl-2-(8-(3,3,3-trifluoropropyl)-[1,2,4]triazolo[1,5-a]pyrazin-6-yl)-5H-pyrrolo[2,3-d]pyrimidin-6(7H)-one, 4-amino-5-(5-chloropyridin-2-yl)-5-cyclopropyl-2-(8-(3,3,3-trifluoropropyl)-[1,2,4]triazolo[1,5-a]pyrazin-6-yl)-5H-pyrrolo[2,3-d]pyrimidin-6(7H)-one, 4-amino-5-cyclopropyl-5-(3,4-difluorophenyl)-2-(8-(3,3,3-trifluoropropyl)-[1,2,4]triazolo[1,5-a]pyrazin-6-yl)-5H-pyrrolo[2,3-d]pyrimidin-6(7H)-one, 4-amino-5-(3,4-difluorophenyl)-5-methyl-2-(8-(3,3,3-trifluoropropyl)-[1,2,4]triazolo[1,5-a]pyrazin-6-yl)-5H-pyrrolo[2,3-d]pyrimidin-6(7H)-one, 4-amino-2-(8-(4-fluorobenzyl)-[1,2,4]triazolo[1,5-a]pyrazin-6-yl)-5-(4-fluorophenyl)-5-methyl-5H-pyrrolo[2,3-d]pyrimidin-6(7H)-one, 4-amino-5-(4-fluorophenyl)-2-(8-(3-methoxybenzyl)-[1,2,4]triazolo[1,5-a]pyrazin-6-yl)-5-methyl-5H-pyrrolo[2,3-d]pyrimidin-6(7H)-one, 4-amino-2-(8-(4-fluorobenzyl)-2-methyl-[1,2,4]triazolo[1,5-a]pyrazin-6-yl)-5-(4-fluorophenyl)-5-methyl-5H-pyrrolo[2,3-d]pyrimidin-6(7H)-one, 4-amino-5-(4-fluorophenyl)-5-methyl-2-(2-methyl-8-(3,3,4,4,4-pentafluorobutyl)-[1,2,4]triazolo[1,5-a]pyrazin-6-yl)-5H-pyrrolo[2,3-d]pyrimidin-6(7H)-one, 4-amino-5-(5-fluoropyridin-2-yl)-5-methyl-2-(2-methyl-8-(3,3,4,4,4-pentafluorobutyl)-[1,2,4]triazolo[1,5-a]pyrazin-6-yl)-5H-pyrrolo[2,3-d]pyrimidin-6(7H)-one, 4-amino-5-(4-chloro-3-fluorophenyl)-5-methyl-2-(2-methyl-8-(3,3,4,4,4-pentafluorobutyl)-[1,2,4]triazolo[1,5-a]pyrazin-6-yl)-5H-pyrrolo[2,3-d]pyrimidin-6(7H)-one, 4-amino-5-(4-fluorophenyl)-5-methyl-2-(2-methyl-8-propyl-[1,2,4]triazolo[1,5-a]pyrazin-6-yl)-5H-pyrrolo[2,3-d]pyrimidin-6(7H)-one, 4-amino-5-(5-fluoropyridin-2-yl)-5-methyl-2-(2-methyl-8-propyl-[1,2,4]triazolo[1,5-a]pyrazin-6-yl)-5H-pyrrolo[2,3-d]pyrimidin-6(7H)-one, 4-amino-5-(4-chlorophenyl)-5-methyl-2-(2-methyl-8-propyl-[1,2,4]triazolo[1,5-a]pyrazin-6-yl)-5H-pyrrolo[2,3-d]pyrimidin-6(7H)-one, 2-([1,2,4]triazolo[1,5-a]pyrazin-6-yl)-4-amino-5-(4-chlorophenyl)-5-methyl-5H-pyrrolo[2,3-d]pyrimidin-6(7H)-one, 4-amino-5-(1-cyclopropyl-1H-1,2,3-triazol-4-yl)-5-methyl-2-(8-(3,3,4,4,4-pentafluorobutyl)-[1,2,4]triazolo[1,5-a]pyrazin-6-yl)-5H-pyrrolo[2,3-d]pyrimidin-6(7H)-one, 4-amino-5-cyclopropyl-5-(1-cyclopropyl-1H-1,2,3-triazol-4-yl)-2-(8-(3,3,4,4,4-pentafluorobutyl)-[1,2,4]triazolo[1,5-a]pyrazin-6-yl)-5H-pyrrolo[2,3-d]pyrimidin-6(7H)-one, 4-Amino-5-methyl-5-(5-methyl-1,3,4-oxadiazol-2-yl)-2-(8-(3,3,4,4,4-pentafluorobutyl)-[1,2,4]triazolo[1,5-a]pyrazin-6-yl)-5H-pyrrolo[2,3-d]pyrimidin-6(7H)-one, 4-amino-5-(5-cyclopropyl-1,3,4-oxadiazol-2-yl)-5-methyl-2-(8-(3,3,4,4,4-pentafluorobutyl)-[1,2,4]triazolo[1,5-a]pyrazin-6-yl)-5H-pyrrolo[2,3-d]pyrimidin-6(7H)-one, 4-amino-5-(5-cyclopropyl-1,3,4-oxadiazol-2-yl)-5-methyl-2-(8-(4,4,4-trifluorobutyl)-[1,2,4]triazolo[1,5-a]pyrazin-6-yl)-5H-pyrrolo[2,3-d]pyrimidin-6(7H)-one, 4-amino-5-(5-(difluoromethyl)-1,3,4-oxadiazol-2-yl)-5-methyl-2-(8-(4,4,4-trifluorobutyl)-[1,2,4]triazolo[1,5-a]pyrazin-6-yl)-5H-pyrrolo[2,3-d]pyrimidin-6(7H)-one, 4-amino-5-methyl-2-(8-(4,4,4-trifluorobutyl)-[1,2,4]triazolo[1,5-a]pyrazin-6-yl)-5-(5-(trifluoromethyl)-1,3,4-oxadiazol-2-yl)-5H-pyrrolo[2,3-d]pyrimidin-6(7H)-one, 4-amino-2-(8-butyl-[1,2,4]triazolo[1,5-a]pyrazin-6-yl)-5-methyl-5-(5-(trifluoromethyl)-1,3,4-oxadiazol-2-yl)-5H-pyrrolo[2,3-d]pyrimidin-6(7H)-one, 4-amino-5-(5-cyclopropyl-1,3,4-oxadiazol-2-yl)-5-methyl-2-(2-methyl-8-(3,3,4,4,4-pentafluorobutyl)-[1,2,4]triazolo[1,5-a]pyrazin-6-yl)-5H-pyrrolo[2,3-d]pyrimidin-6(7H)-one, 4-amino-5-cyclopropyl-5-(5-cyclopropyl-1,3,4-oxadiazol-2-yl)-2-(8-(4,4,4-trifluorobutyl)-[1,2,4]triazolo[1,5-a]pyrazin-6-yl)-5H-pyrrolo[2,3-d]pyrimidin-6(7H)-one, 4-amino-2-(8-butyl-[1,2,4]triazolo[1,5-a]pyrazin-6-yl)-5-cyclopropyl-5-(5-(trifluoromethyl)-1,3,4-oxadiazol-2-yl)-5H-pyrrolo[2,3-d]pyrimidin-6(7H)-one, 4-amino-5-cyclopropyl-2-(8-(4,4,4-trifluorobutyl)-[1,2,4]triazolo[1,5-a]pyrazin-6-yl)-5-(5-(trifluoromethyl)-1,3,4-oxadiazol-2-yl)-5H-pyrrolo[2,3-d]pyrimidin-6(7H)-one, 4-amino-5-cyclopropyl-5-(5-cyclopropyl-1,3,4-oxadiazol-2-yl)-2-(8-(3,3,4,4,4-pentafluorobutyl)-[1,2,4]triazolo[1,5-a]pyrazin-6-yl)-5H-pyrrolo[2,3-d]pyrimidin-6(7H)-one, 4-amino-5-cyclopropyl-5-(5-(1-fluorocyclopropyl)-1,3,4-oxadiazol-2-yl)-2-(8-(4,4,4-trifluorobutyl)-[1,2,4]triazolo[1,5-a]pyrazin-6-yl)-5H-pyrrolo[2,3-d]pyrimidin-6(7H)-one, 4-amino-5-(5-(1-fluorocyclopropyl)-1,3,4-oxadiazol-2-yl)-5-methyl-2-(8-(4,4,4-trifluorobutyl)-[1,2,4]triazolo[1,5-a]pyrazin-6-yl)-5H-pyrrolo[2,3-d]pyrimidin-6(7H)-one, 4-amino-5-(5-hydroxypyridin-2-yl)-5-methyl-2-(8-(3,3,4,4,4-pentafluorobutyl)-[1,2,4]triazolo[1,5-a]pyrazin-6-yl)-5,7-dihydro-6H-pyrrolo[2,3-d]pyrimidin-6-one, 4-amino-5-(5-hydroxypyridin-2-yl)-5-methyl-2-(8-(4,4,4-trifluorobutyl)-[1,2,4]triazolo[1,5-a]pyrazin-6-yl)-5H-pyrrolo[2,3-d]pyrimidin-6(7H)-one, 4-amino-5-cyclopropyl-5-(5-hydroxypyridin-2-yl)-2-(8-(4,4,4-trifluorobutyl)-[1,2,4]triazolo[1,5-a]pyrazin-6-yl)-5H-pyrrolo[2,3-d]pyrimidin-6(7H)-one, 4-amino-5-(4-fluorophenyl)-2-(8-(3-hydroxybenzyl)-[1,2,4]triazolo[1,5-a]pyrazin-6-yl)-5-methyl-5H-pyrrolo[2,3-d]pyrimidin-6(7H)-one, 4-amino-5-cyclopropyl-2-(8-(3,3,4,4,4-pentafluorobutyl)-[1,2,4]triazolo[1,5-a]pyrazin-6-yl)-5-(pyridin-2-yl)-5,7-dihydro-6H-pyrrolo[2,3-d]pyrimidin-6-one, 4-amino-5-cyclopropyl-5-(pyridin-2-yl)-2-(8-(4,4,4-trifluorobutyl)-[1,2,4]triazolo[1,5-a]pyrazin-6-yl)-5H-pyrrolo[2,3-d]pyrimidin-6(7H)-one, 4-amino-2-(8-butyl-[1,2,4]triazolo[1,5-a]pyrazin-6-yl)-5-cyclopropyl-5-(pyridin-2-yl)-5H-pyrrolo[2,3-d]pyrimidin-6(7H)-one, 6-(4-amino-5-cyclopropyl-6-oxo-2-(8-(4,4,4-trifluorobutyl)-[1,2,4]triazolo[1,5-a]pyrazin-6-yl)-6,7-dihydro-5H-pyrrolo[2,3-d]pyrimidin-5-yl)nicotinonitrile, 6-(4-amino-5-cyclopropyl-6-oxo-2-(8-(3,3,4,4,4-pentafluorobutyl)-[1,2,4]triazolo[1,5-a]pyrazin-6-yl)-6,7-dihydro-5H-pyrrolo[2,3-d]pyrimidin-5-yl)nicotinonitrile, 5-(4-fluorophenyl)-4-hydroxy-5-methyl-2-(8-(3,3,4,4-pentafluorobutyl)-[1,2,4]triazolo[1,5-a]pyrazin-6-yl)-5H-pyrrolo[2,3-d]pyrimidin-6(7H)-one, 5-(5-chloropyridin-2-yl)-4-hydroxy-5-methyl-2-(8-(3,3,4,4-pentafluorobutyl)-[1,2,4]triazolo[1,5-a]pyrazin-6-yl)-5H-pyrrolo[2,3-d]pyrimidin-6(7H)-one, 5-(4-chloro-3-fluorophenyl)-4-hydroxy-5-methyl-2-(8-(3,3,4,4-pentafluorobutyl)-[1,2,4]triazolo[1,5-a]pyrazin-6-yl)-5H-pyrrolo[2,3-d]pyrimidin-6(7H)-one, 5-(5-fluoropyridin-2-yl)-4-hydroxy-5-methyl-2-(8-(3,3,4,4-pentafluorobutyl)-[1,2,4]triazolo[1,5-a]pyrazin-6-yl)-5H-pyrrolo[2,3-d]pyrimidin-6(7H)-one, 5-cyclopropyl-5-(3,4-difluorophenyl)-4-hydroxy-2-(8-(3,3,4,4-pentafluorobutyl)-[1,2,4]triazolo[1,5-a]pyrazin-6-yl)-5H-pyrrolo[2,3-d]pyrimidin-6(7H)-one, 5-cyclopropyl-5-(5-fluoropyridin-3-yl)-4-hydroxy-2-(8-(3,3,4,4-pentafluorobutyl)-[1,2,4]triazolo[1,5-a]pyrazin-6-yl)-5H-pyrrolo[2,3-d]pyrimidin-6(7H)-one, 5-(5-fluoropyridin-3-yl)-4-hydroxy-5-methyl-2-(8-(3,3,4,4-pentafluorobutyl)-[1,2,4]triazolo[1,5-a]pyrazin-6-yl)-5H-pyrrolo[2,3-d]pyrimidin-6(7H)-one, 5-(4-chlorophenyl)-4-hydroxy-5-methyl-2-(8-(3,3,4,4,4-pentafluorobutyl)-[1,2,4]triazolo[1,5-a]pyrazin-6-yl)-5H-pyrrolo[2,3-d]pyrimidin-6(7H)-one, 4-hydroxy-5-methyl-2-(8-(3,3,4,4,4-pentafluorobutyl)-[1,2,4]triazolo[1,5-a]pyrazin-6-yl)-5-(pyridin-2-yl)-5H-pyrrolo[2,3-d]pyrimidin-6(7H)-one, 4-hydroxy-5-methyl-2-(8-(3,3,4,4,4-pentafluorobutyl)-[1,2,4]triazolo[1,5-a]pyrazin-6-yl)-5-phenyl-5H-pyrrolo[2,3-d]pyrimidin-6(7H)-one, 5-(3-fluorophenyl)-4-hydroxy-5-methyl-2-(8-(3,3,4,4,4-pentafluorobutyl)-[1,2,4]triazolo[1,5-a]pyrazin-6-yl)-5,7-dihydro-6H-pyrrolo[2,3-d]pyrimidin-6-one, 4-hydroxy-5-methyl-5-(5-methylpyridin-2-yl)-2-(8-(3,3,4,4,4-pentafluorobutyl)-[1,2,4]triazolo[1,5-a]pyrazin-6-yl)-5H-pyrrolo[2,3-d]pyrimidin-6(7H)-one, 6-(4-hydroxy-5-methyl-6-oxo-2-(8-(3,3,4,4,4-pentafluorobutyl)-[1,2,4]triazolo[1,5-a]pyrazin-6-yl)-6,7-dihydro-5H-pyrrolo[2,3-d]pyrimidin-5-yl)nicotinonitrile, 5-(4-chloro-3-fluorophenyl)-4-hydroxy-5-methyl-2-(2-methyl-8-(3,3,4,4,4-pentafluorobutyl)-[1,2,4]triazolo[1,5-a]pyrazin-6-yl)-5H-pyrrolo[2,3-d]pyrimidin-6(7H)-one, 5-(4-fluorophenyl)-4-hydroxy-5-methyl-2-(2-methyl-8-(3,3,4,4,4-pentafluorobutyl)-[1,2,4]triazolo[1,5-a]pyrazin-6-yl)-5H-pyrrolo[2,3-d]pyrimidin-6(7H)-one, 5-(5-chloropyridin-2-yl)-4-hydroxy-5-methyl-2-(8-(4,4,4-trifluorobutyl)-[1,2,4]triazolo[1,5-a]pyrazin-6-yl)-5H-pyrrolo[2,3-d]pyrimidin-6(7H)-one, 5-(4-fluorophenyl)-4-hydroxy-5-methyl-2-(8-(4,4,4-trifluorobutyl)-[1,2,4]triazolo[1,5-a]pyrazin-6-yl)-5H-pyrrolo[2,3-d]pyrimidin-6(7H)-one, 5-(5-fluoropyridin-2-yl)-4-hydroxy-5-methyl-2-(8-(4,4,4-trifluorobutyl)-[1,2,4]triazolo[1,5-a]pyrazin-6-yl)-5H-pyrrolo[2,3-d]pyrimidin-6(7H)-one, 4-hydroxy-5-methyl-2-(8-(4,4,4-trifluorobutyl)-[1,2,4]triazolo[1,5-a]pyrazin-6-yl)-5-(4-(trifluoromethyl)phenyl)-5H-pyrrolo[2,3-d]pyrimidin-6(7H)-one, 5-(4-chloro-3-fluorophenyl)-4-hydroxy-5-methyl-2-(8-(4,4,4-trifluorobutyl)-[1,2,4]triazolo[1,5-a]pyrazin-6-yl)-5H-pyrrolo[2,3-d]pyrimidin-6(7H)-one, 5-cyclopropyl-5-(4-fluorophenyl)-4-hydroxy-2-(8-(4,4,4-trifluorobutyl)-[1,2,4]triazolo[1,5-a]pyrazin-6-yl)-5H-pyrrolo[2,3-d]pyrimidin-6(7H)-one, 5-(4-chlorophenyl)-5-cyclopropyl-4-hydroxy-2-(8-(4,4,4-trifluorobutyl)-[1,2,4]triazolo[1,5-a]pyrazin-6-yl)-5H-pyrrolo[2,3-d]pyrimidin-6(7H)-one, 5-cyclopropyl-5-(3,4-difluorophenyl)-4-hydroxy-2-(8-(4,4,4-trifluorobutyl)-[1,2,4]triazolo[1,5-a]pyrazin-6-yl)-5H-pyrrolo[2,3-d]pyrimidin-6(7H)-one, 5-(4-chlorophenyl)-4-hydroxy-5-methyl-2-(8-(4,4,4-trifluorobutyl)-[1,2,4]triazolo[1,5-a]pyrazin-6-yl)-5H-pyrrolo[2,3-d]pyrimidin-6(7H)-one, 4-hydroxy-5-methyl-5-phenyl-2-(8-(4,4,4-trifluorobutyl)-[1,2,4]triazolo[1,5-a]pyrazin-6-yl)-5H-pyrrolo[2,3-d]pyrimidin-6(7H)-one, 5-cyclopropyl-4-hydroxy-2-(8-(4,4,4-trifluorobutyl)-[1,2,4]triazolo[1,5-a]pyrazin-6-yl)-5-(4-(trifluoromethyl)phenyl)-5H-pyrrolo[2,3-d]pyrimidin-6(7H)-one, 4-hydroxy-5-methyl-5-(pyridin-2-yl)-2-(8-(4,4,4-trifluorobutyl)-[1,2,4]triazolo[1,5-a]pyrazin-6-yl)-5H-pyrrolo[2,3-d]pyrimidin-6(7H)-one, 5-(3,4-difluorophenyl)-4-hydroxy-5-methyl-2-(8-(4,4,4-trifluorobutyl)-[1,2,4]triazolo[1,5-a]pyrazin-6-yl)-5H-pyrrolo[2,3-d]pyrimidin-6(7H)-one, 5-(3-chloro-4-fluorophenyl)-4-hydroxy-5-methyl-2-(8-(4,4,4-trifluorobutyl)-[1,2,4]triazolo[1,5-a]pyrazin-6-yl)-5,7-dihydro-6H-pyrrolo[2,3-d]pyrimidin-6-one 4-hydroxy-5-(5-methoxypyridin-2-yl)-5-methyl-2-(8-(4,4,4-trifluorobutyl)-[1,2,4]triazolo[1,5-a]pyrazin-6-yl)-5H-pyrrolo[2,3-d]pyrimidin-6(7H)-one, 4-hydroxy-5-methyl-5-(5-methylpyridin-2-yl)-2-(8-(4,4,4-trifluorobutyl)-[1,2,4]triazolo[1,5-a]pyrazin-6-yl)-5H-pyrrolo[2,3-d]pyrimidin-6(7H)-one, 5-cyclopropyl-5-(5-fluoropyridin-2-yl)-4-hydroxy-2-(8-(4,4,4-trifluorobutyl)-[1,2,4]triazolo[1,5-a]pyrazin-6-yl)-5,7-dihydro-6H-pyrrolo[2,3-d]pyrimidin-6-one, 5-(4-fluorophenyl)-4-hydroxy-5-methyl-2-(8-(3,3,3-trifluoropropyl)-[1,2,4]triazolo[1,5-a]pyrazin-6-yl)-5H-pyrrolo[2,3-d]pyrimidin-6(7H)-one, 5-(4-chlorophenyl)-4-hydroxy-5-methyl-2-(8-(3,3,3-trifluoropropyl)-[1,2,4]triazolo[1,5-a]pyrazin-6-yl)-5H-pyrrolo[2,3-d]pyrimidin-6(7H)-one, 5-(4-chloro-3-fluorophenyl)-4-hydroxy-5-methyl-2-(8-(3,3,3-trifluoropropyl)-[1,2,4]triazolo[1,5-a]pyrazin-6-yl)-5H-pyrrolo[2,3-d]pyrimidin-6(7H)-one, 2-(8-butyl-[1,2,4]triazolo[1,5-a]pyrazin-6-yl)-5-(4-fluorophenyl)-4-hydroxy-5-methyl-5H-pyrrolo[2,3-d]pyrimidin-6(7H)-one, 2-(8-butyl-[1,2,4]triazolo[1,5-a]pyrazin-6-yl)-5-(5-fluoropyridin-2-yl)-4-hydroxy-5-methyl-5H-pyrrolo[2,3-d]pyrimidin-6(7H)-one, 2-(8-butyl-[1,2,4]triazolo[1,5-a]pyrazin-6-yl)-5-(4-chloro-3-fluorophenyl)-4-hydroxy-5-methyl-5H-pyrrolo[2,3-d]pyrimidin-6(7H)-one, 2-(8-butyl-[1,2,4]triazolo[1,5-a]pyrazin-6-yl)-5-(4-chlorophenyl)-4-hydroxy-5-methyl-5H-pyrrolo[2,3-d]pyrimidin-6(7H)-one, 2-(8-butyl-[1,2,4]triazolo[1,5-a]pyrazin-6-yl)-5-(3,4-difluorophenyl)-4-hydroxy-5-methyl-5H-pyrrolo[2,3-d]pyrimidin-6(7H)-one, 2-(8-butyl-[1,2,4]triazolo[1,5-a]pyrazin-6-yl)-4-hydroxy-5-methyl-5-(5-(trifluoromethyl)pyridin-2-yl)-5H-pyrrolo[2,3-d]pyrimidin-6(7H)-one, 2-(8-butyl-[1,2,4]triazolo[1,5-a]pyrazin-6-yl)-5-(5-chloropyridin-2-yl)-4-hydroxy-5-methyl-5H-pyrrolo[2,3-d]pyrimidin-6(7H)-one, 2-(8-butyl-[1,2,4]triazolo[1,5-a]pyrazin-6-yl)-4-hydroxy-5-methyl-5-(5-methylpyridin-2-yl)-5H-pyrrolo[2,3-d]pyrimidin-6(7H)-one, 2-(8-(4-fluorobenzyl)-[1,2,4]triazolo[1,5-a]pyrazin-6-yl)-5-(4-fluorophenyl)-4-hydroxy-5-methyl-5H-pyrrolo[2,3-d]pyrimidin-6(7H)-one, 5-(4-fluorophenyl)-4-hydroxy-2-(8-isobutyl-[1,2,4]triazolo[1,5-a]pyrazin-6-yl)-5-methyl-5H-pyrrolo[2,3-d]pyrimidin-6(7H)-one, 5-(4-chlorophenyl)-4-hydroxy-5-methyl-2-(8-propyl-[1,2,4]triazolo[1,5-a]pyrazin-6-yl)-5H-pyrrolo[2,3-d]pyrimidin-6(7H)-one, 5-(4-fluorophenyl)-4-hydroxy-5-methyl-2-(8-propyl-[1,2,4]triazolo[1,5-a]pyrazin-6-yl)-5H-pyrrolo[2,3-d]pyrimidin-6(7H)-one, 5-(4-chloro-3-fluorophenyl)-4-hydroxy-5-methyl-2-(8-propyl-[1,2,4]triazolo[1,5-a]pyrazin-6-yl)-5H-pyrrolo[2,3-d]pyrimidin-6(7H)-one, 5-cyclopropyl-5-(3,4-difluorophenyl)-4-hydroxy-2-(8-propyl-[1,2,4]triazolo[1,5-a]pyrazin-6-yl)-5H-pyrrolo[2,3-d]pyrimidin-6(7H)-one, 5-(4-chlorophenyl)-4-hydroxy-5-methyl-2-(2-methyl-8-propyl-[1,2,4]triazolo[1,5-a]pyrazin-6-yl)-5H-pyrrolo[2,3-d]pyrimidin-6(7H)-one, 5-(3,4-difluorophenyl)-4-hydroxy-5-methyl-2-(8-(3,3,4,4,4-pentafluorobutyl)-[1,2,4]triazolo[1,5-a]pyrazin-6-yl)-5,7-dihydro-6H-pyrrolo[2,3-d]pyrimidin-6-one, 5-(2-fluorophenyl)-4-hydroxy-5-methyl-2-(8-(3,3,4,4,4-pentafluorobutyl)-[1,2,4]triazolo[1,5-a]pyrazin-6-yl)-5,7-dihydro-6H-pyrrolo[2,3-d]pyrimidin-6-one, 2-(8-butyl-[1,2,4]triazolo[1,5-a]pyrazin-6-yl)-5-(3-fluorophenyl)-4-hydroxy-5-methyl-5,7-dihydro-6H-pyrrolo[2,3-d]pyrimidin-6-one, 5-(4-Fluorophenyl)-5-methyl-2-(8-(3,3,4,4,4-pentafluorobutyl)-[1,2,4]triazolo[1,5-a]pyrazin-6-yl)-5H-pyrrolo[2,3-d]pyrimidin-6(7H)-one, 5-(4-fluorophenyl)-2-(8-isobutyl-[1,2,4]triazolo[1,5-a]pyrazin-6-yl)-5-methyl-5H-pyrrolo[2,3-d]pyrimidin-6(7H)-one, 5-(4-fluorophenyl)-5-methyl-2-(8-(3,3,3-trifluoropropyl)-[1,2,4]triazolo[1,5-a]pyrazin-6-yl)-5H-pyrrolo[2,3-d]pyrimidin-6(7H)-one, 5-(5-chloropyridin-2-yl)-5-methyl-2-(8-(3,3,4,4,4-pentafluorobutyl)-[1,2,4]triazolo[1,5-a]pyrazin-6-yl)-5H-pyrrolo[2,3-d]pyrimidin-6(7H)-one, 5-(5-fluoropyridin-2-yl)-5-methyl-2-(8-(4,4,4-trifluorobutyl)-[1,2,4]triazolo[1,5-a]pyrazin-6-yl)-5H-pyrrolo[2,3-d]pyrimidin-6(7H)-one, 5-(4-fluorophenyl)-5-methyl-6-oxo-2-(8-(3,3,4,4,4-pentafluorobutyl)-[1,2,4]triazolo[1,5-a]pyrazin-6-yl)-6,7-dihydro-5H-pyrrolo[2,3-d]pyrimidine-4-carboxamide, 5-cyclopropyl-6-oxo-2-(8-(3,3,4,4,4-pentafluorobutyl)-[1,2,4]triazolo[1,5-a]pyrazin-6-yl)-5-(5-(trifluoromethyl)pyridin-2-yl)-6,7-dihydro-5H-pyrrolo[2,3-d]pyrimidine-4-carboxamide, 5-methyl-6-oxo-2-(8-(4,4,4-trifluorobutyl)-[1,2,4]triazolo[1,5-a]pyrazin-6-yl)-5-(5-(trifluoromethyl)pyridin-2-yl)-6,7-dihydro-5H-pyrrolo[2,3-d]pyrimidine-4-carboxamide, 4-amino-5-cyclopropyl-2-(8-(4,4,4-trifluorobutyl)-[1,2,4]triazolo[1,5-a]pyrazin-6-yl)-5-(5-(trifluoromethyl)pyrimidin-2-yl)-5,7-dihydro-6H-pyrrolo[2,3-d]pyrimidin-6-one, or 4-hydroxy-5-(5-(difluoromethyl)pyridin-2-yl)-5-methyl-2-(8-(4,4,4-trifluorobutyl)-[1,2,4]triazolo[1,5-a]pyrazin-6-yl)-5H-pyrrolo[2,3-d]pyrimidin-6(7H)-one, or a pharmaceutically acceptable salt thereof.

8. The method of claim 1 further comprising one or more additional active agents selected from camphor, menthol, a topical emollient, a methotrexate, chlorambucil, mycophenolate mofetil, cyclosporine, FK506, cyclophosphamide, a statin, a tyrosine kinase inhibitor, an angiotensin converting enzyme inhibitor, an angiotensin II receptor antagonist, a calcium channel blocker, omeprazole, D-penicillamine, interferon alfa, interferon gamma, aspirin, pancrealipase, a fat soluble vitamin, pulmozyme, ivacaftor, vacaftor, gentamycin, aztronam, colistin, tobramycin, a fluoroquinoline, piperacillin, chloramphenicol, sulfamethoxazole, trimethoprim, cephalexin, ceftazidime, nintedanib, N-acetylcysteine, azathioprine, tocilizumab, or pirfenidone.

9. The method of claim 1, wherein the compound administered to the patient is

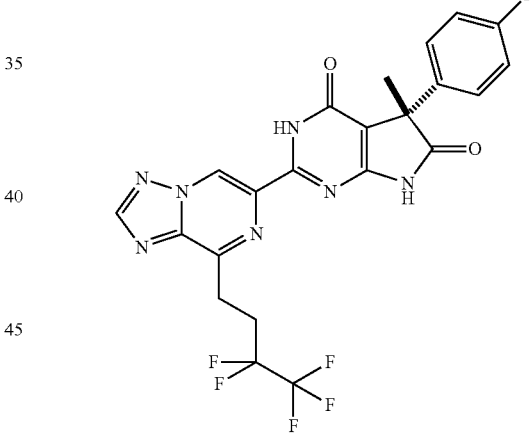

or a pharmaceutically acceptable salt thereof.

* * * * *